US012699318B2

(12) United States Patent
Fukushima et al.

(10) Patent No.: US 12,699,318 B2
(45) Date of Patent: Aug. 4, 2026

(54) ONIUM SALT, RESIST COMPOSITION, AND PATTERNING PROCESS

(71) Applicant: SHIN-ETSU CHEMICAL CO., LTD., Tokyo (JP)

(72) Inventors: Masahiro Fukushima, Joetsu (JP); Jun Hatakeyama, Joetsu (JP); Tomomi Watanabe, Joetsu (JP); Kazuhiro Katayama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 595 days.

(21) Appl. No.: 18/349,364

(22) Filed: Jul. 10, 2023

(65) Prior Publication Data

US 2024/0036466 A1 Feb. 1, 2024

(30) Foreign Application Priority Data

Jul. 12, 2022 (JP) ................................ 2022-111933

(51) Int. Cl.

| | |
|---|---|
| ***C07C 65/21*** | (2006.01) |
| ***C07C 25/18*** | (2006.01) |
| ***C07C 65/26*** | (2006.01) |
| ***C07C 205/57*** | (2006.01) |
| ***C07C 211/63*** | (2006.01) |
| ***C07C 381/12*** | (2006.01) |
| ***C07D 327/08*** | (2006.01) |
| ***C07D 333/76*** | (2006.01) |
| ***G03F 7/004*** | (2006.01) |
| ***G03F 7/038*** | (2006.01) |
| ***G03F 7/039*** | (2006.01) |

(52) U.S. Cl.

CPC ............ *G03F 7/0045* (2013.01); *C07C 25/18* (2013.01); *C07C 65/26* (2013.01); *C07C 205/57* (2013.01); *C07C 211/63* (2013.01); *C07C 381/12* (2013.01); *C07D 327/08* (2013.01); *C07D 333/76* (2013.01); *G03F 7/0382* (2013.01); *G03F 7/0392* (2013.01); *C07C 65/21* (2013.01); *C07C 2601/08* (2017.05); *C07C 2601/14* (2017.05); *C07C 2602/42* (2017.05); *C07C 2603/66* (2017.05); *C07C 2603/74* (2017.05)

(58) Field of Classification Search

None

See application file for complete search history.

(56) References Cited

U.S. PATENT DOCUMENTS

2006/0228648 A1 10/2006 Ohsawa et al.
2007/0231708 A1 10/2007 Matsumaru et al.
2007/0231738 A1 10/2007 Kaneko et al.
2008/0085469 A1 4/2008 Ohsawa et al.
2008/0090172 A1 4/2008 Hatakeyama et al.
2008/0118860 A1 5/2008 Harada et al.
2008/0153030 A1 6/2008 Kobayashi et al.
2008/0241736 A1 10/2008 Kobayashi et al.
2009/0246694 A1 10/2009 Ohsawa et al.
2010/0035185 A1 2/2010 Hagiwara et al.
2010/0209827 A1 8/2010 Ohashi et al.
2012/0045724 A1 2/2012 Ohsawa et al.
2012/0100486 A1 4/2012 Sagehashi et al.
2013/0084529 A1 4/2013 Hatakeyama et al.
2013/0089820 A1 4/2013 Hatakeyama et al.
2014/0199629 A1 7/2014 Ohashi et al.
2017/0031243 A1 2/2017 Hatakeyama et al.
2018/0335696 A1 11/2018 Hatakeyama et al.
2019/0204735 A1 7/2019 Nagamine et al.
(Continued)

FOREIGN PATENT DOCUMENTS

JP 2006-045311 A 2/2006
JP 3790649 B 6/2006
(Continued)

OTHER PUBLICATIONS

Korean Office Action in application No. 10-2023-0089329 issued on Nov. 13, 2025.
(Continued)

*Primary Examiner* — Mark F. Huff
*Assistant Examiner* — Richard David Champion
(74) *Attorney, Agent, or Firm* — Harness, Dickey & Pierce, PLC

(57) ABSTRACT

Provided is a novel onium salt used for a resist composition that has high sensitivity and excellent resolution, improved LWR and CDU, and that can inhibit collapse of a resist pattern for both of positive-type and negative-type resists in lithography: an onium salt represented by the following general formula (1), (1)

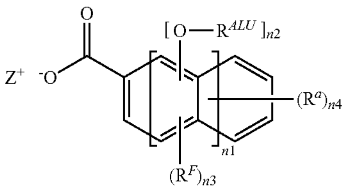

wherein $R^{ALU}$ represents any one of a tertiary ether, tertiary carbonate, or acetal formed together with the adjacent oxygen atom and having a cyclic structure; $R^F$ represents any one of a fluorine atom, a fluorine-containing alkyl group having 1 to 6 carbon atoms, and a nitro group; $R^a$ represents a hydrocarbyl group having 1 to 20 carbon atoms; n1 represents an integer of 0 or 1; n2 and n3 represent an integer of 1 or 2; one of $R^F$ and one of —O—$R^{ALU}$ are bonded to carbon atoms adjacent to each other; n4 represents an integer of 0 to 3; and $Z^+$ represents an onium cation.

20 Claims, No Drawings

(56) References Cited

U.S. PATENT DOCUMENTS

| | | | |
|---|---|---|---|
| 2019/0391488 A1 | 12/2019 | Nishikori et al. | |
| 2020/0174369 A1* | 6/2020 | Yoshii | G03F 7/2004 |
| 2020/0183275 A1 | 6/2020 | Kojima et al. | |
| 2020/0393755 A1 | 12/2020 | Nemoto et al. | |
| 2021/0188770 A1 | 6/2021 | Fujiwara et al. | |
| 2021/0278763 A1 | 9/2021 | Hatakeyama et al. | |
| 2023/0375925 A1* | 11/2023 | Yoshimura | G03F 7/029 |
| 2024/0329530 A1* | 10/2024 | Nagamine | G03F 7/0392 |

FOREIGN PATENT DOCUMENTS

| | | | |
|---|---|---|---|
| JP | 2006-178317 | A | 7/2006 |
| JP | 2007-114431 | A | 5/2007 |
| JP | 2007-145797 | A | 6/2007 |
| JP | 2007-297590 | A | 11/2007 |
| JP | 2008-106045 | A | 5/2008 |
| JP | 2008-111103 | A | 5/2008 |
| JP | 2008-122932 | A | 5/2008 |
| JP | 2008-158339 | A | 7/2008 |
| JP | 2008-239918 | A | 10/2008 |
| JP | 2009-007327 | A | 1/2009 |
| JP | 2009-258695 | A | 11/2009 |
| JP | 2010-215608 | A | 9/2010 |
| JP | 2012-041320 | A | 3/2012 |
| JP | 2012-106986 | A | 6/2012 |
| JP | 2012-153644 | A | 8/2012 |
| JP | 2013-080033 | A | 5/2013 |
| JP | 2013-083821 | A | 5/2013 |
| JP | 2014-133723 | A | 7/2014 |
| JP | 2017-026980 | A | 2/2017 |
| JP | 2018-197853 | A | 12/2018 |
| JP | 2019-120760 | A | 7/2019 |
| JP | 2020-091312 | A | 6/2020 |
| JP | 2020-091404 | A | 6/2020 |
| JP | 2020-203984 | A | 12/2020 |
| KR | 10-2021-0075020 | A | 6/2021 |
| KR | 10-2021-0109454 | A | 9/2021 |
| WO | 2018/159560 | A1 | 9/2018 |
| WO | 2020246566 | A1 | 12/2020 |

OTHER PUBLICATIONS

Kishikawa, et al.; Assessment of trade-off between resist resolution and sensitivity for optimization of hyper-NA immersion lithography; Optical Microlithography XX, edited by Donis G. Flagello, Proc. of SPIE vol. 6520, 65203L, (2007) 0277-786X/07/$18 • doi: 10.1117/12.711420; published 2007.

* cited by examiner

ONIUM SALT, RESIST COMPOSITION, AND PATTERNING PROCESS

TECHNICAL FIELD

The present invention relates to an onium salt, a resist composition, and a patterning process.

BACKGROUND ART

As higher integration and higher speed of LSI have been achieved, a pattern rule has been rapidly miniaturized. This is because a high-speed communication with 5G and artificial intelligence (AI) have become widespread, and a high-performance device to process them has been required. As the latest microfabrication technique, 5-nm node devices are industrially manufactured using lithography with extreme ultraviolet ray (EUV) having a wavelength of 13.5 nm. Furthermore, investigation using the EUV lithography is progressed for a 3-nm node device, next generation, and a 2-nm node device, next to the next generation.

The miniaturization in progress causes a problem of blurring an image due to acid diffusion. To achieve resolution with a fine pattern of 45 nm or finer in size, not only improvement of a dissolution contrast, conventionally proposed, but also importance of controlling the acid diffusion is proposed (Non Patent Document 1). However, since a chemically amplified resist material enhances sensitivity and contrast by utilizing the acid diffusion, inhibiting the acid diffusion to the utmost limit with lowering a temperature or shortening a time of post exposure bake (PEB) considerably deteriorates the sensitivity and the contrast.

Pointed out is a triangle trade-off relationship between sensitivity, resolution, and edge roughness. Although inhibiting the acid diffusion is required in order to improve the resolution, shortening a distance of the acid diffusion deteriorates the sensitivity.

It is effective that an acid generator to generate a bulky acid is added to inhibit the acid diffusion. Accordingly, proposed is containing a repeating unit derived from an onium salt having a polymerizable unsaturated bond into a polymer. In this case, the polymer also functions as an acid generator (polymer-bound acid generator). Patent Document 1 proposes a sulfonium salt or iodonium salt having a polymerizable unsaturated bond to generate a specific sulfonic acid. Patent Document 2 proposes a sulfonium salt in which a sulfonic acid is directly bonded to a main chain.

With an acid-labile group used for a (meth)acrylate polymer for an ArF resist material, using a photoacid generator to generate a sulfonic acid having an α-position substituted with a fluorine atom proceeds a deprotection reaction. An acid generator to generate a sulfonic acid or a carboxylic acid having an α-position not substituted with a fluorine atom does not proceed the deprotection reaction. Mixing the sulfonium salt or iodonium salt to generate a sulfonic acid having an α-position not substituted with a fluorine atom with the sulfonium salt or iodonium salt to generate the sulfonic acid having an α-position substituted with a fluorine atom proceeds ion exchange between the sulfonium salt or iodonium salt to generate the sulfonic acid having an α-position not substituted with a fluorine atom and the sulfonic acid having an α-position substituted with a fluorine atom. The photo-generated sulfonic acid having an α-position substituted with a fluorine atom is returned to the sulfonium salt or the iodonium salt with the ion exchange, and thereby the sulfonium salt or iodonium salt of the sulfonic acid or a carboxylic acid having an α-position not substituted with a fluorine atom functions as a quencher. Proposed is a resist material using a sulfonium salt or iodonium salt to generate a carboxylic acid as a quencher (Patent Document 3).

Various sulfonium salt quenchers to generate a carboxylic acid are proposed. Specifically proposed are sulfonium salts of salicylic acid or a (3-hydroxycarboxylic acid (Patent Document 4), a salicylic acid derivative (Patent Documents 5 and 6), fluorosalicylic acid (Patent Document 7), and hydroxynaphthoic acid (Patent Document 8). In particular, salicylic acid has an effect of inhibiting the acid diffusion with an intramolecular hydrogen bond between the carboxylic acid and the hydroxy group.

Meanwhile, it is pointed out that aggregation of the quencher deteriorates critical dimension uniformity of a resist pattern. Preventing the aggregation of the quencher in a resist film to uniformize the distribution is promising to increase the critical dimension uniformity of a pattern after development.

With the requirement of further miniaturization, there is a problem of swelling by a developer during, in particular, alkaline development in a positive-type resist to cause pattern collapse in fine patterning. For such a problem with miniaturization, development of a novel resist material is important, and desired is development of an onium salt quencher having good sensitivity, sufficiently inhibiting the acid diffusion, having excellent solvent solubility, and effectively inhibiting the pattern collapse.

CITATION LIST

Patent Literature

Patent Document 1: JP 2006-045311 A

Patent Document 2: JP 2006-178317 A

Patent Document 3: JP 2007-114431 A

Patent Document 4: WO 2018/159560

Patent Document 5: JP 2020-203984 A

Patent Document 6: JP 2020-91404 A

Patent Document 7: JP 2020-91312 A

Patent Document 8: JP 2019-120760 A

Non Patent Literature

Non Patent Document 1: SPIE Vol. 6520 65203L-1 (2007)

SUMMARY OF INVENTION

Technical Problem

The present invention has been made in view of the above circumstances. An object of the present invention is to provide a novel onium salt used for a resist composition that has high sensitivity and excellent resolution, improved LWR (roughness) and CDU (critical dimension uniformity), and that can inhibit collapse of a resist pattern for both of positive-type and negative-type resists in far-ultraviolet lithography and EUV lithography.

Solution to Problem

To solve the above problem, the present invention provides an onium salt represented by the following general formula (1), (1)

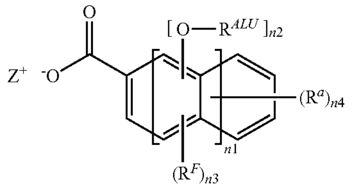

wherein $R^{ALU}$ represents any one of a tertiary ether, tertiary carbonate, or acetal formed together with the adjacent oxygen atom, having a cyclic structure, and optionally having a heteroatom; $R^F$ represents any one of a fluorine atom, a fluorine-containing alkyl group having 1 to 6 carbon atoms, and a nitro group; $R^a$ represents a hydrocarbyl group having 1 to 20 carbon atoms and optionally having a heteroatom; n1 represents an integer of 0 or 1; n2 and n3 represent an integer of 1 or 2; when n2 and n3 represent 1, $R^F$ and —O—$R^{ALU}$ are bonded to carbon atoms adjacent to each other, and when any one or both of n2 and n3 represent 2, one of $R^F$ and one of —O—$R^{ALU}$ are bonded to carbon atoms adjacent to each other; n4 represents an integer of 0 to 3; when n4≥2, a plurality of $R^a$ are optionally bonded to each other to form a cyclic structure together with the carbon atoms to which these are bonded; and $Z^+$ represents an onium cation.

Such an onium salt is useful as a novel onium salt used for a resist composition that has high sensitivity and excellent resolution, improved LWR and CDU, and that can inhibit collapse of a resist pattern with both of positive-type and negative-type resists in the lithography.

The structure of $R^{ALU}$ in the general formula (1) is preferably represented by the following general formula (ALU-1) or (ALU-2), (ALU-1)

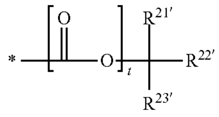

(ALU-2)

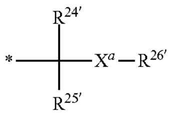

wherein in the formula (ALU-1), $R^{21'}$, $R^{22'}$, and $R^{23'}$ each independently represent a hydrocarbyl group having 1 to 12 carbon atoms and optionally having a heteroatom, any two of $R^{21'}$, $R^{22'}$, and $R^{23'}$ being optionally bonded to each other to form a ring; when $R^{21'}$, $R^{22'}$, and $R^{23'}$ are not bonded to each other to form a ring, at least one of them has a cyclic structure; "t" represents an integer of 0 or 1; in the formula (ALU-2), $R^{24'}$ and $R^{25'}$ each independently represent a hydrogen atom or a hydrocarbyl group having 1 to 10 carbon atoms; $R^{26'}$ represents a hydrocarbyl group having 1 to 20 carbon atoms, or is optionally bonded to $R^{24'}$ or $R^{25'}$ each other to form a heterocyclic group having 3 to 20 carbon atoms together with $X^a$ and the carbon atom to which these groups are bonded; —$CH_2$— contained in the hydrocarbyl group and the heterocyclic group is optionally substituted with —O— or —S—; $X^a$ represents an oxygen atom or a sulfur atom; and "*" represents a bond to the adjacent oxygen atom.

Such an onium salt more favorably serves as an acid diffusion inhibitor contained in a resist composition.

$R^F$ in the general formula (1) preferably represents any one of a fluorine atom or a fluorine-containing alkyl group having 1 to 6 carbon atoms.

Such an onium salt further favorably serves as an acid diffusion inhibitor contained in a resist composition.

$Z^+$ in the general formula (1) preferably represents an onium cation represented by any one of the following general formulae (Cation-1) to (Cation-3), (Cation-1)

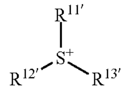

(Cation-2)

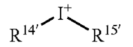

(Cation-3)

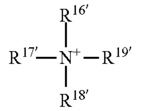

wherein in the formulae (Cation-1) to (Cation-3), $R^{11'}$ to $R^{19'}$ each independently represent a saturated or unsaturated, linear, branched, or cyclic hydrocarbyl group having 1 to 30 carbon atoms and optionally having a heteroatom.

Such an onium salt particularly favorably serves as an acid diffusion inhibitor contained in a resist composition.

The present invention also provides an acid diffusion inhibitor comprising the above onium salt.

The inventive onium salt is useful as an acid diffusion inhibitor.

The present invention also provides a resist composition comprising the above acid diffusion inhibitor.

The resist composition comprising the above acid diffusion inhibitor is a favorable resist composition.

The resist composition preferably further comprises an acid generator to generate an acid.

Such an acid generator allows the above onium salt to function as the acid diffusion inhibitor, and allows the inventive resist composition to function.

The acid generator preferably generates a sulfonic acid, an imide acid, or a methide acid.

Such an acid generator is more preferable as the acid generator.

The resist composition preferably further comprises an organic solvent.

Such a resist composition can dissolve each component, and improves coatability of the composition.

The resist composition preferably further comprises a base polymer.

Such a resist composition is more preferable as the resist composition.

The base polymer preferably comprises a repeating unit represented by the following general formula (a1) and/or a repeating unit represented by the general formula (a2), (a1)

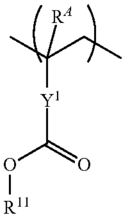

(a2)

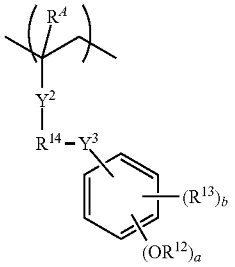

wherein $R^A$ each independently represents a hydrogen atom or a methyl group; $Y^1$ represents a single bond, a phenylene group, a naphthylene group, or a linking group having 1 to 12 carbon atoms and having at least one selected from an ester bond and a lactone ring; $Y^2$ represents a single bond or an ester bond; $Y^3$ represents a single bond, an ether bond, or an ester bond; $R^{11}$ and $R^{12}$ each independently represent an acid-labile group; $R^{13}$ represents a fluorine atom, a trifluoromethyl group, a cyano group, or a saturated hydrocarbyl group having 1 to 6 carbon atoms; $R^{14}$ represents a single bond or an alkanediyl group having 1 to 6 carbon atoms, and a part of carbon atoms therein is optionally substituted with an ether bond or an ester bond; "a" represents 1 or 2; "b" represents an integer of 0 to 4, and $1 \leq a+b \leq 5$.

Such a resist composition has the acid-labile group, and is preferable as a positive-type resist composition.

The resist composition is preferably a chemically amplified positive-type resist composition.

The inventive resist composition can function as a chemically amplified positive-type resist composition.

The base polymer also preferably has no acid-labile group.

Such a resist composition has no acid-labile group, and is preferable as a negative-type resist composition.

The resist composition is preferably a chemically amplified negative-type resist composition.

The inventive resist composition can function as a chemically amplified negative-type resist composition.

The base polymer preferably further comprises at least one selected from repeating units represented by the following general formulae (f1) to (f3), (f1)

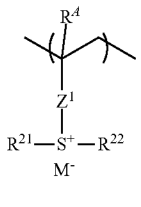

-continued (f2)

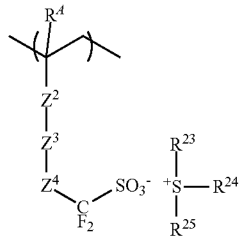

(f3)

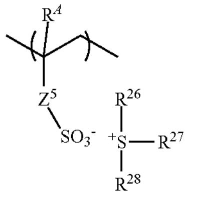

wherein $R^A$ each independently represents a hydrogen atom or a methyl group; $Z^1$ represents a single bond, an aliphatic hydrocarbylene group having 1 to 6 carbon atoms, a phenylene group, a naphthylene group, an ester bond, a group having 7 to 18 carbon atoms obtained by combining these groups, $-O-Z^{11}-$, $-C(=O)-O-Z^{11}-$, or $-C(=O)-NH-Z^{11}-$; $Z^{11}$ represents an aliphatic hydrocarbylene group having 1 to 6 carbon atoms, a phenylene group, a naphthylene group, or a group having 7 to 18 carbon atoms obtained by combining these groups, $Z^{11}$ optionally having a carbonyl group, an ester bond, an ether bond, or a hydroxy group; $Z^2$ represents a single bond or an ester bond; $Z^3$ represents a single bond, $-Z^{31}-C(=O)-O-$, $-Z^{31}-O-$, or $-Z^{31}-O-C(=O)-$; $Z^{31}$ represents a hydrocarbylene group having 1 to 12 carbon atoms, a phenylene group, or a group having 7 to 18 carbon atoms obtained by combining these groups, $Z^{31}$ optionally having a carbonyl group, an ester bond, an ether bond, an iodine atom, or a bromine atom; $Z^4$ represents a methylene group, a 2,2,2-trifluoro-1,1-ethanediyl group, or a carbonyl group; $Z^5$ represents a single bond, a methylene group, an ethylene group, a phenylene group, a fluorinated phenylene group, a phenylene group substituted with a trifluoromethyl group, $-O-Z^{51}-$, $-C(=O)-O-Z^{51}-$, or $-C(=O)-NH-Z^{51}-$; $Z^{51}$ represents an aliphatic hydrocarbylene group having 1 to 6 carbon atoms, a phenylene group, a fluorinated phenylene group, a phenylene group substituted with a trifluoromethyl group, or a combination thereof, $Z^{51}$ optionally having a carbonyl group, an ester bond, an ether bond, a halogen atom, and/or a hydroxy group; $R^{21}$ to $R^{28}$ each independently represent a halogen atom or a hydrocarbyl group having 1 to 20 carbon atoms and optionally having a heteroatom; $R^{23}$ and $R^{24}$ or $R^{26}$ and $R^{27}$ are optionally bonded to each other to form a ring together with the sulfur atom to which these groups are bonded; and $M^-$ represents a non-nucleophilic counterion.

Such a repeating unit has a function as an acid generator in the base polymer.

The resist composition preferably further comprises a surfactant.

Such a resist composition can improve or regulate the coatability of the resist composition.

The present invention also provides a patterning process, comprising steps of: forming a resist film on a substrate by using the above resist composition; exposing the resist film to high-energy ray; and developing the exposed resist film by using a developer.

Such a patterning process can form a good pattern.

KrF excimer laser light, ArF excimer laser light, electron beam, or extreme ultraviolet ray having a wavelength of 3 to 15 nm can be used as the high-energy ray.

Using such high-energy ray can form a better pattern.

Advantageous Effects of Invention

The inventive novel onium salt favorably functions as the acid diffusion inhibitor (quencher) in a resist composition and has high sensitivity and excellent dissolution contrast, and as a result, the inventive novel onium salt can construct a pattern profile with a small LWR and CDU, excellent rectangularity, and high resolution. The inventive novel onium salt can inhibit swelling of a resist pattern during alkaline development, form a pattern hardly collapsed, and provide a resist composition using the inventive novel onium salt and having excellence for fine patterning, and a patterning process using this resist composition.

DESCRIPTION OF EMBODIMENTS

There have been demands for development of an onium salt quencher that has good sensitivity, sufficiently regulated acid diffusion, and excellent solvent solubility, and that effectively inhibits pattern collapse.

The present inventors have made earnest study to achieve the above object, and consequently found that a resist composition containing an onium salt having a specific structure as an acid diffusion inhibitor has excellent sensitivity and resolution of a resist film, reduced LWR of a line pattern and CDU of a hole pattern, and inhibits swelling during development, which is extremely effective for precise fine patterning. This finding has led to complete the present invention.

Specifically, the present invention is an onium salt represented by the following general formula (1), (1)

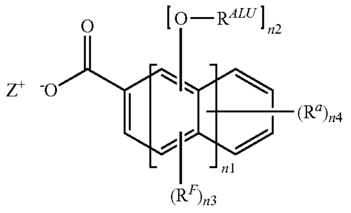

wherein $R^{ALU}$ represents any one of a tertiary ether, tertiary carbonate, or acetal formed together with the adjacent oxygen atom, having a cyclic structure, and optionally having a heteroatom; $R^F$ represents any one of a fluorine atom, a fluorine-containing alkyl group having 1 to 6 carbon atoms, and a nitro group; $R^a$ represents a hydrocarbyl group having 1 to 20 carbon atoms and optionally having a heteroatom; n1 represents an integer of 0 or 1; n2 and n3 represent an integer of 1 or 2; when n2 and n3 represent 1, $R^F$ and —O—$R^{ALU}$ are bonded to carbon atoms adjacent to each other, and when any one or both of n2 and n3 represent 2, one of $R^F$ and one of —O—$R^{ALU}$ are bonded to carbon atoms adjacent to each other; n4 represents an integer of 0 to 3; when n4≥2, a plurality of $R^a$ are optionally bonded to each other to form a cyclic structure together with the carbon atoms to which these are bonded; and $Z^+$ represents an onium cation.

Hereinafter, the present invention will be described in detail, but the present invention is not limited thereto.

Onium Salt

The inventive onium salt is represented by the following general formula (1), (1)

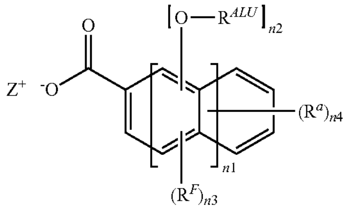

wherein $R^{ALU}$ represents any one of a tertiary ether, tertiary carbonate, or acetal formed together with the adjacent oxygen atom, having a cyclic structure, and optionally having a heteroatom; $R^F$ represents any one of a fluorine atom, a fluorine-containing alkyl group having 1 to 6 carbon atoms, and a nitro group; $R^a$ represents a hydrocarbyl group having 1 to 20 carbon atoms and optionally having a heteroatom; n1 represents an integer of 0 or 1; n2 and n3 represent an integer of 1 or 2; when n2 and n3 represent 1, $R^F$ and —O—$R^{ALU}$ are bonded to carbon atoms adjacent to each other, and when any one or both of n2 and n3 represent 2, one of $R^F$ and one of —O—$R^{ALU}$ are bonded to carbon atoms adjacent to each other; n4 represents an integer of 0 to 3; when n4≥2, a plurality of $R^a$ are optionally bonded to each other to form a cyclic structure together with the carbon atoms to which these are bonded; and $Z^+$ represents an onium cation.

In the general formula (1), $R^{ALU}$ represents any one of a tertiary ether, tertiary carbonate, or acetal formed together with the adjacent oxygen atom and having a cyclic structure. Specifically, $R^{ALU}$ is preferably represented by the following general formula (ALU-1) or (ALU-2), (ALU-1)

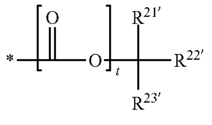

(ALU-2)

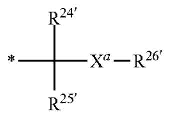

In the general formula (ALU-1), $R^{21'}$, $R^{22'}$, and $R^{23'}$ each independently represent a hydrocarbyl group having 1 to 12, preferably 1 to 10, carbon atoms, and any two of $R^{21'}$, $R^{22'}$, and $R^{23'}$ are optionally bonded to each other to form a ring. When $R^{21'}$, $R^{22'}$, and $R^{23'}$ are not bonded to each other to form a ring, at least one of them has a cyclic structure, preferably an alicyclic structure having 3 to 30 carbon atoms or an aromatic cyclic structure having 6 to 30 carbon atoms. "t" represents an integer of 0 or 1. In the formula (ALU-2), $R^{24'}$ and $R^{25'}$ each independently represent a hydrogen atom or a hydrocarbyl group having 1 to 10 carbon atoms. $R^{26'}$ represents a hydrocarbyl group having 1 to 20 carbon atoms, or is optionally bonded to $R^{24'}$ or $R^{25'}$ each other to form a heterocyclic group having 3 to 20 carbon atoms together with $X^a$ and the carbon atom to which these groups are bonded. —$CH_2$— contained in the hydrocarbyl group and the heterocyclic group is optionally substituted with —O— or —S—. $X^a$ represents an oxygen atom or a sulfur atom. "*" represents a bond to the adjacent oxygen atom.

Specific examples of the structure represented by the general formula (ALU-1) include the following structures, but the structure is not limited thereto.

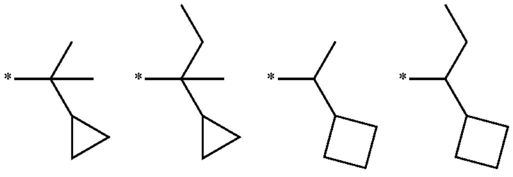

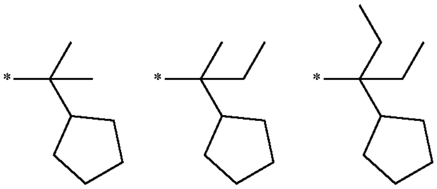

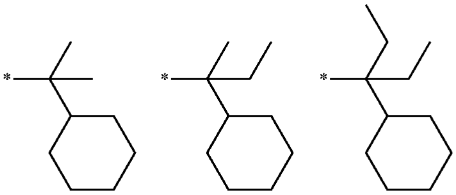

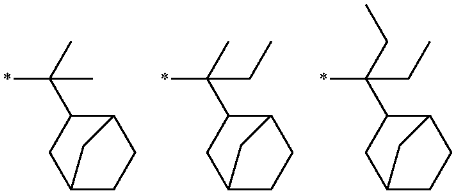

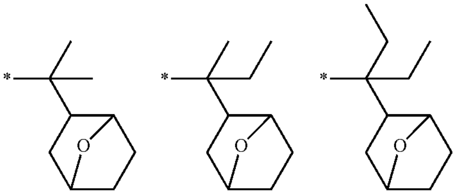

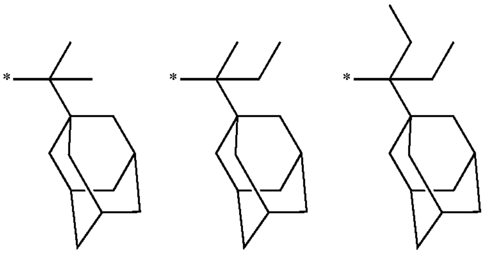

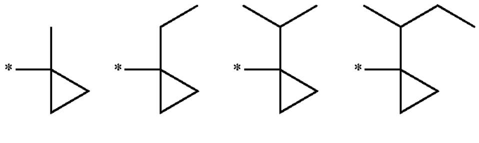

-continued

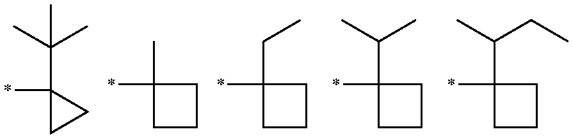

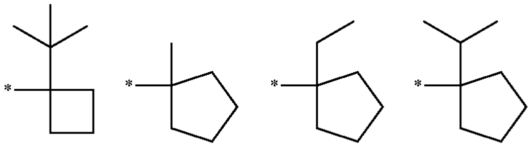

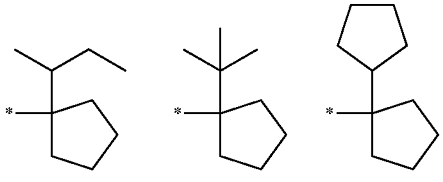

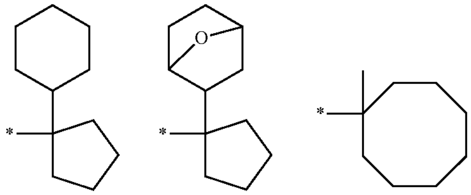

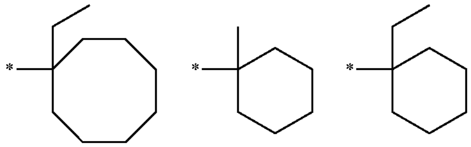

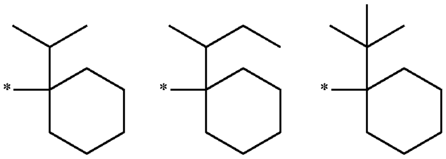

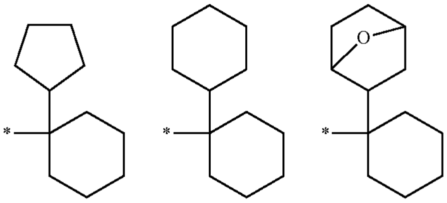

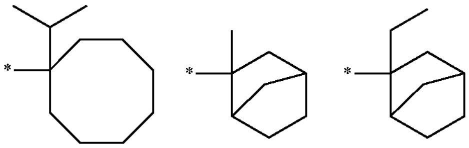

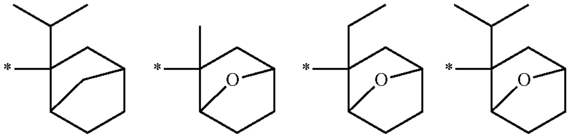

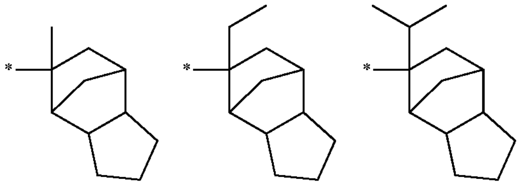

-continued
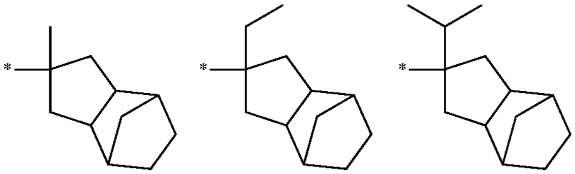
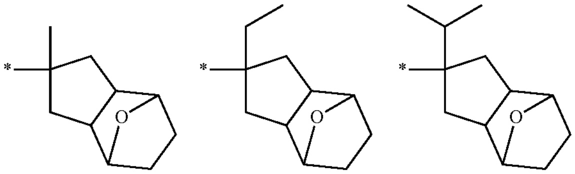
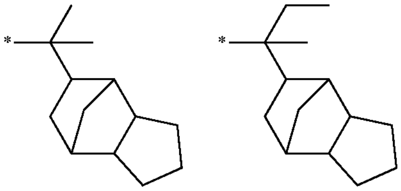
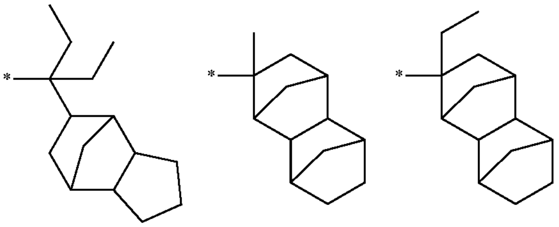
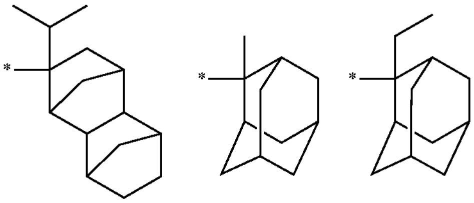
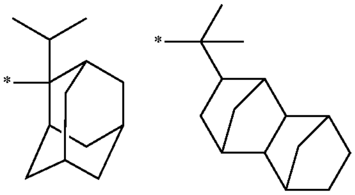
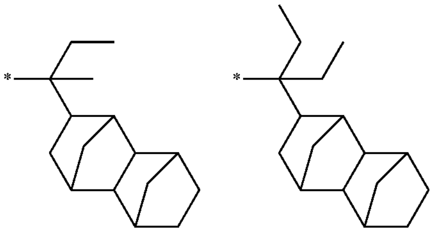
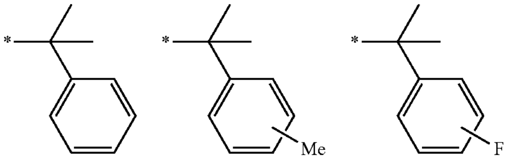
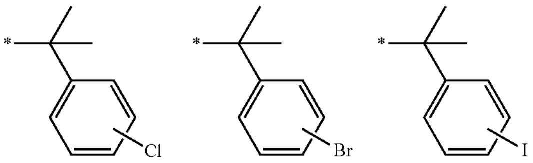
-continued
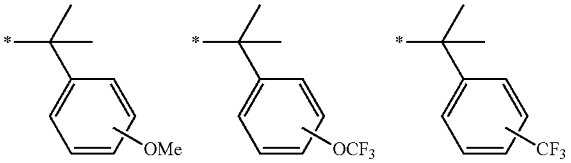
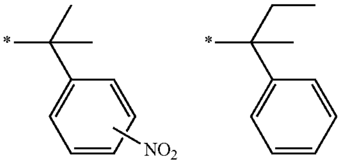
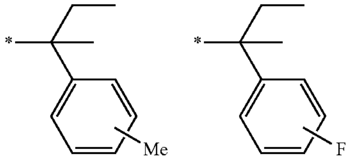
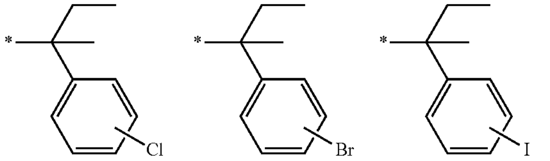
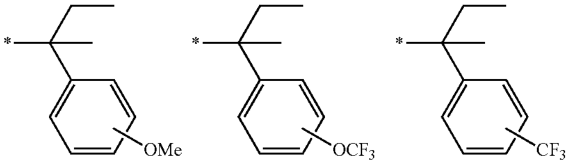
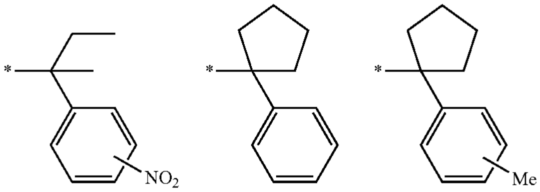
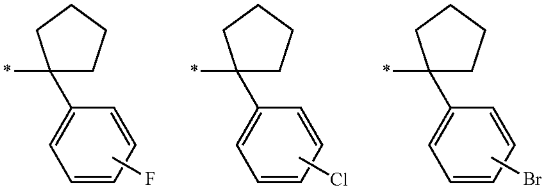
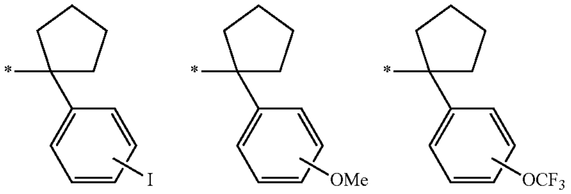
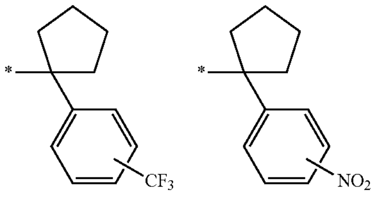

-continued
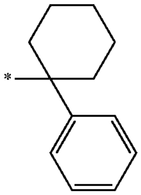
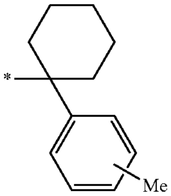
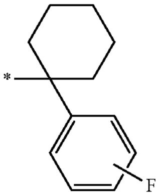
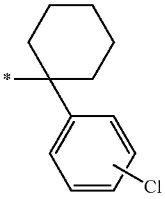
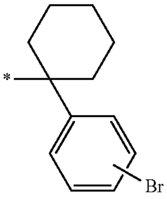
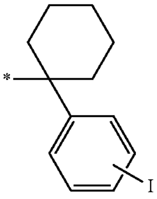
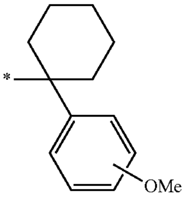
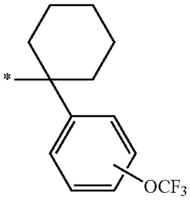
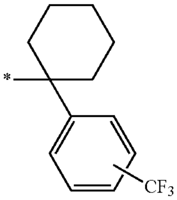
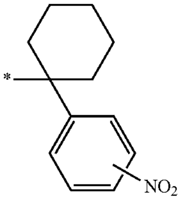
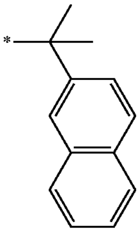
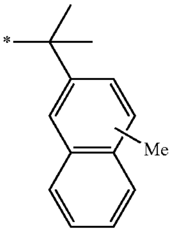
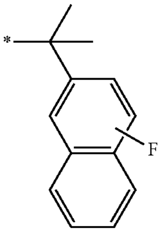
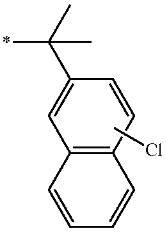
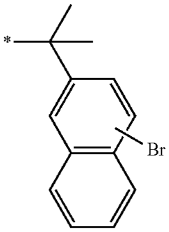
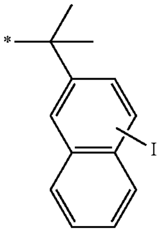
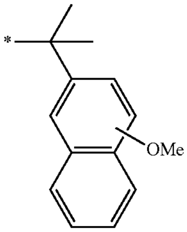
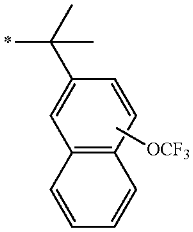
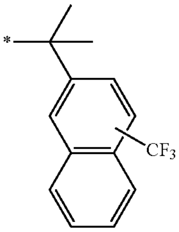
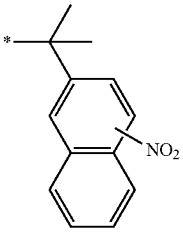
-continued
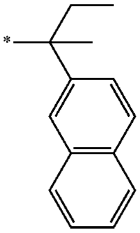
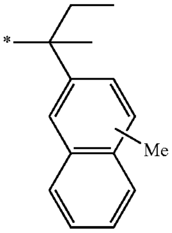
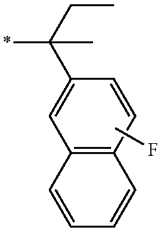
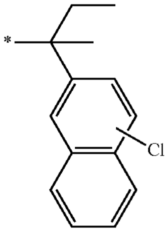
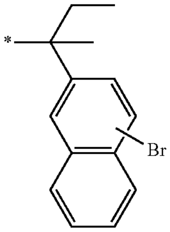
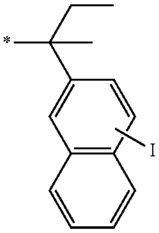
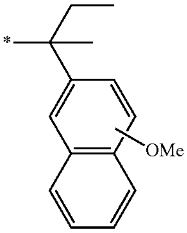
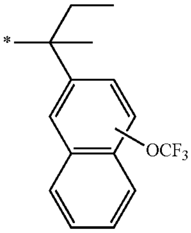
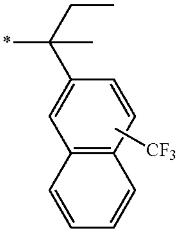
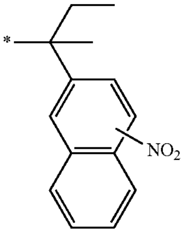
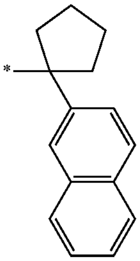
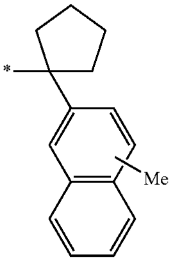
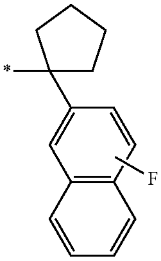
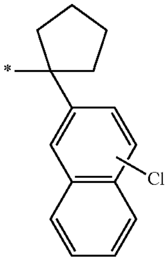
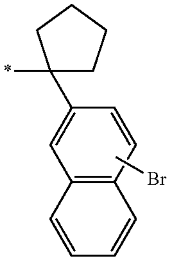
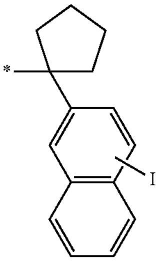
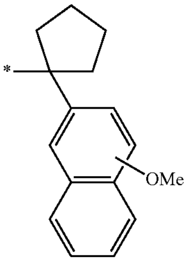
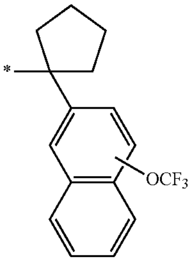

-continued
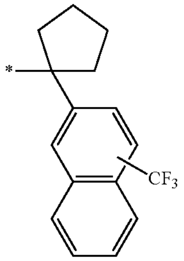
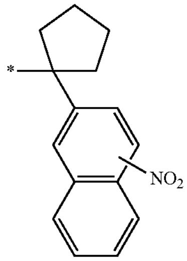
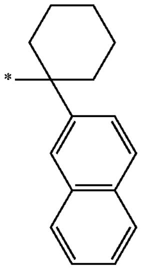
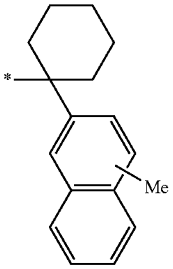
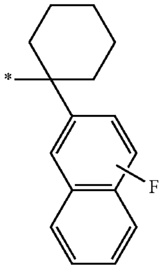
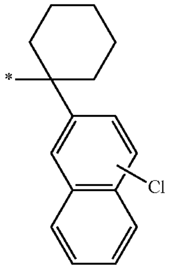
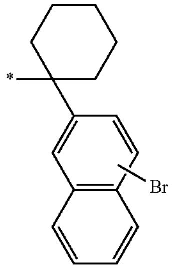
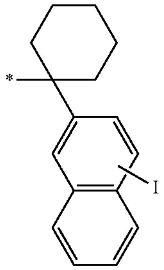
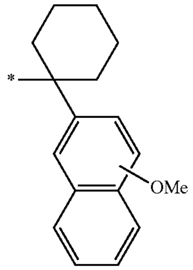
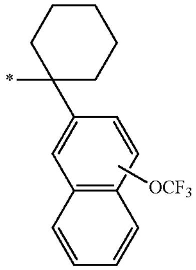
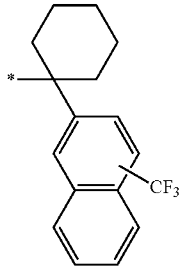
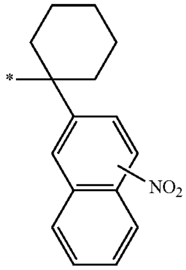
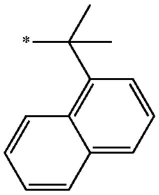
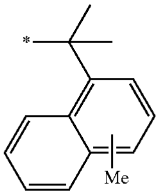
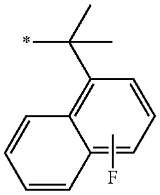
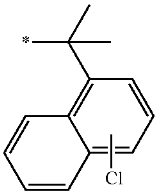
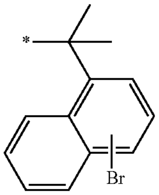
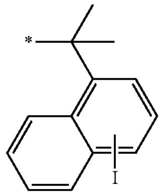
-continued
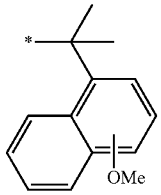
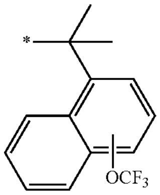
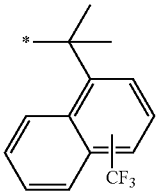
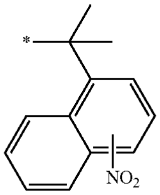
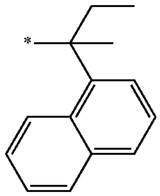
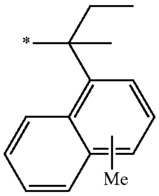
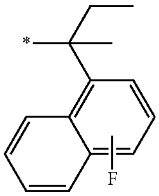
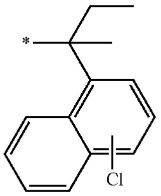
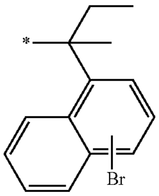
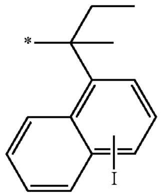
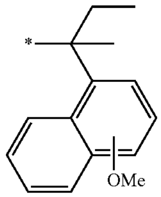
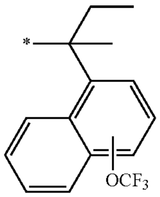
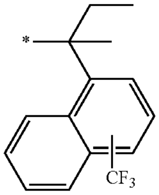
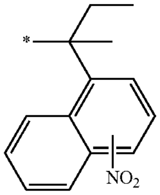
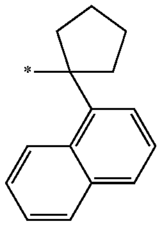
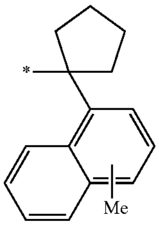
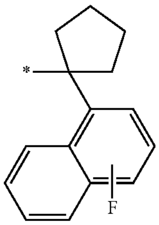
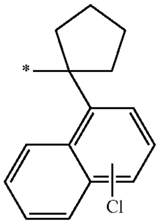
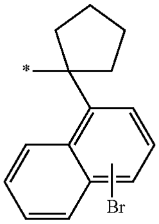
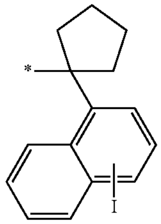

-continued
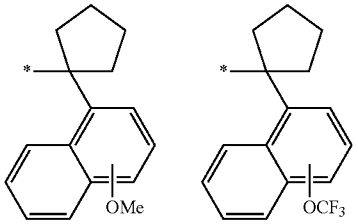
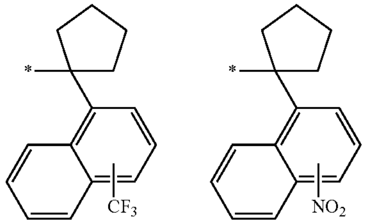
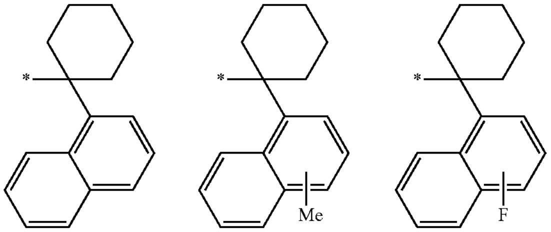
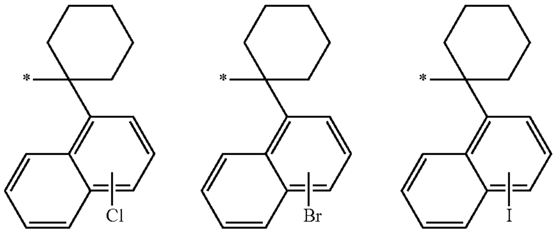
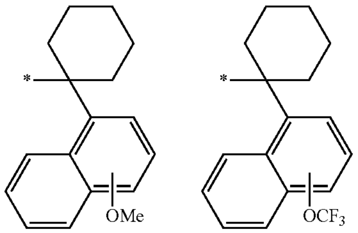
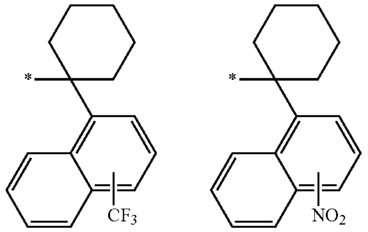
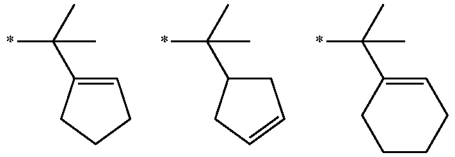
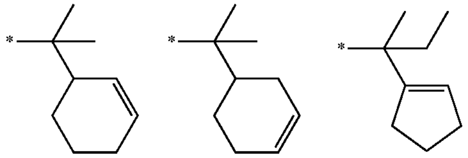
-continued
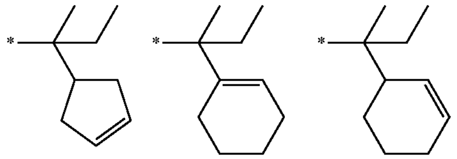
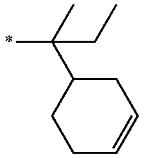
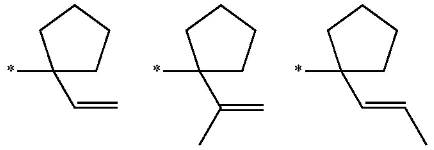
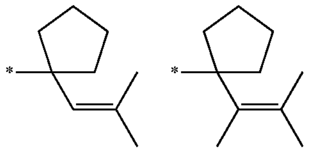
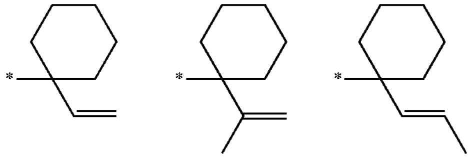
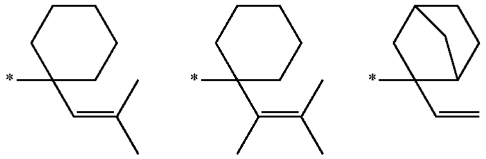
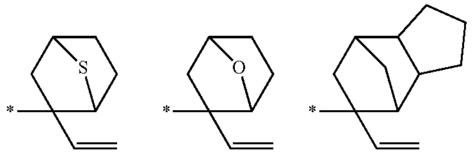
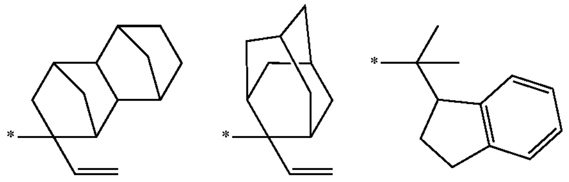
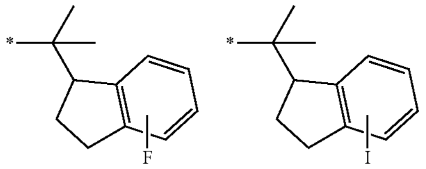
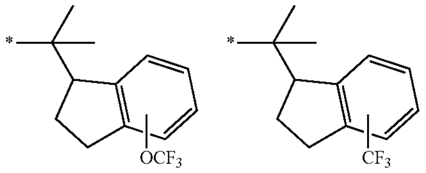

-continued
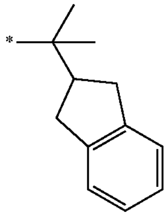
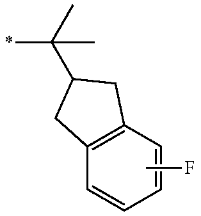
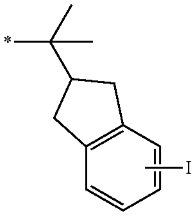
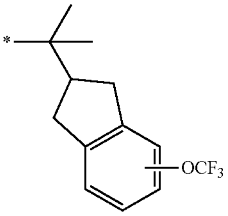
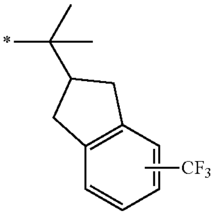
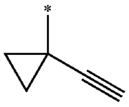
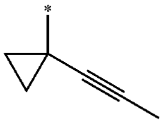
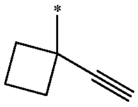
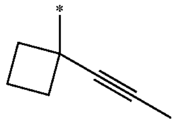
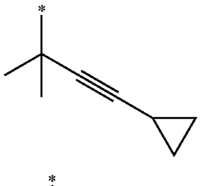
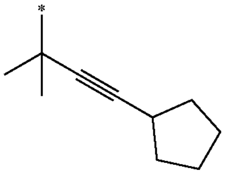
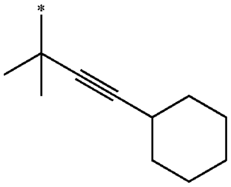
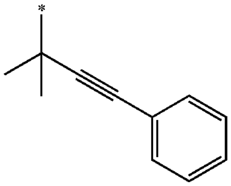
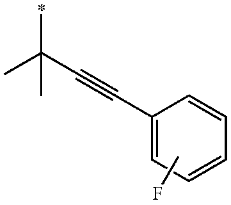
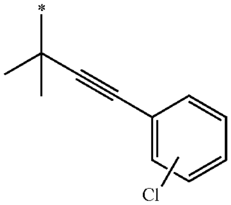
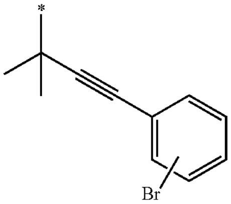
-continued
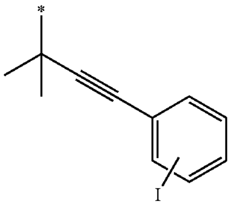
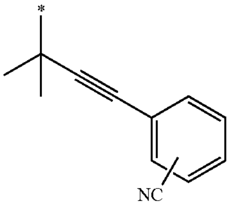
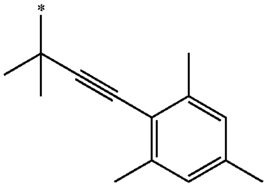
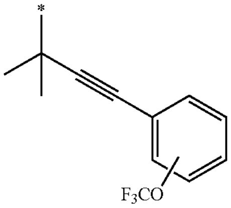
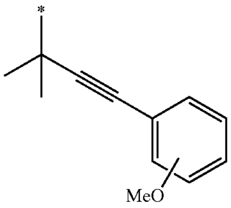
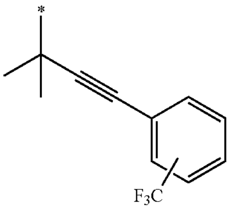
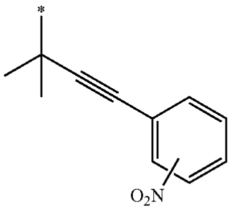
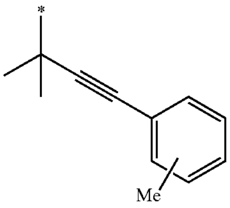
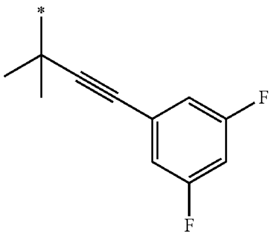
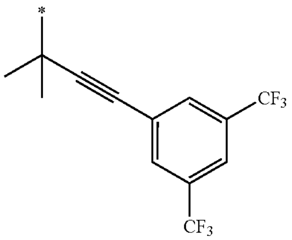
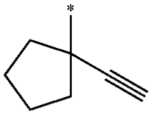
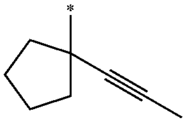
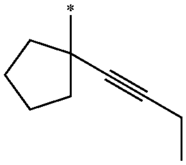
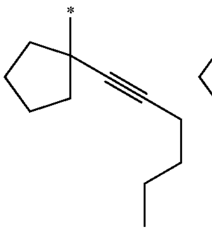
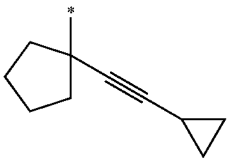
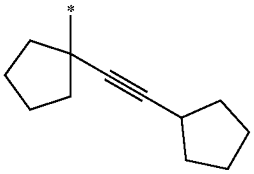
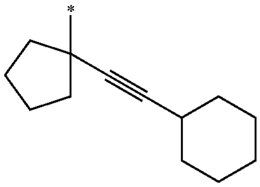

-continued
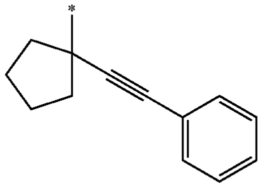
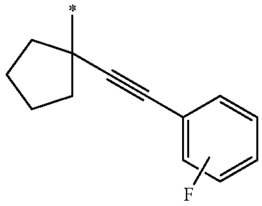
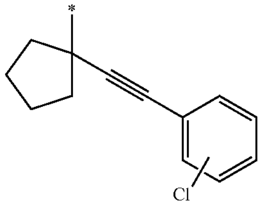
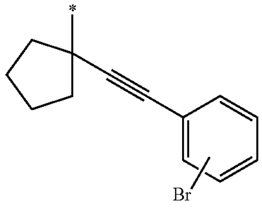
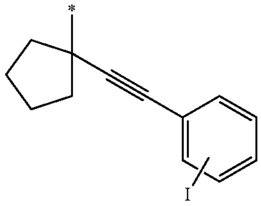
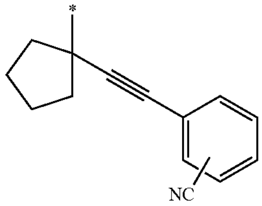
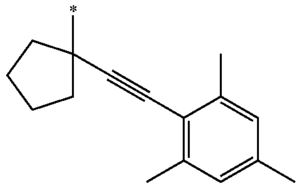
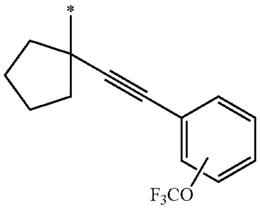
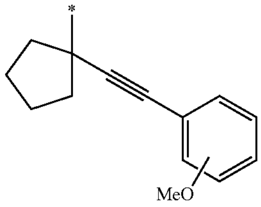
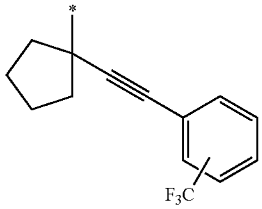
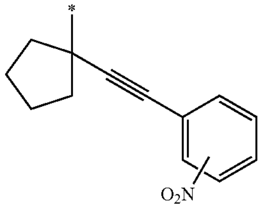
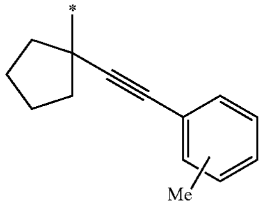
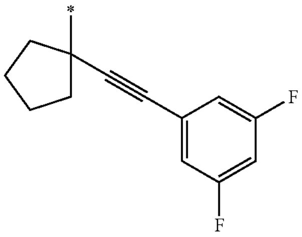
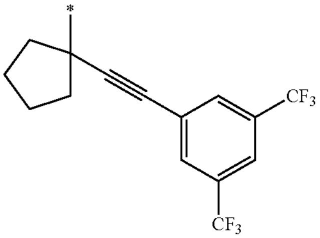
-continued
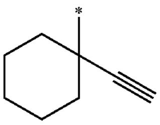
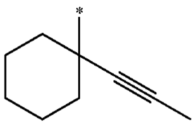
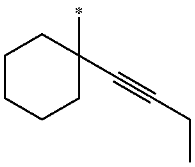
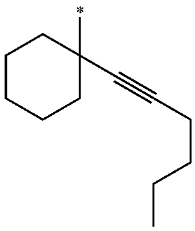
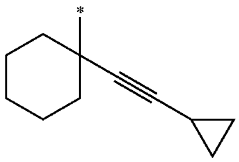
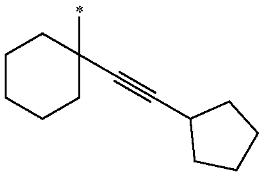
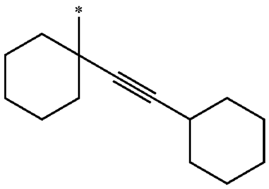
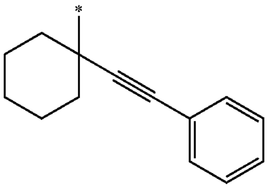
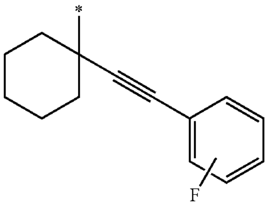
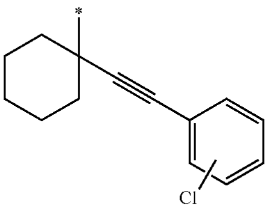
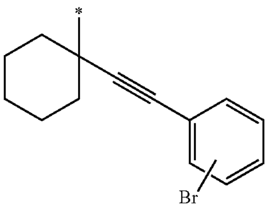
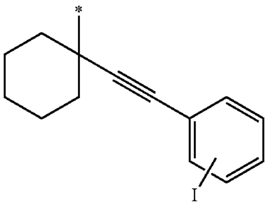
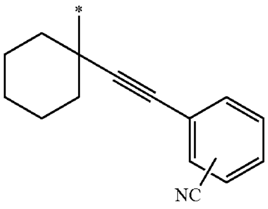
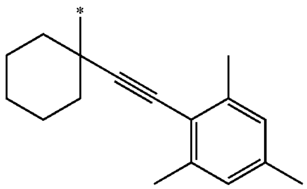
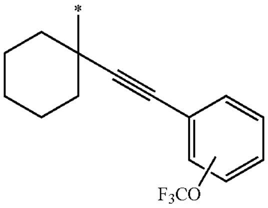
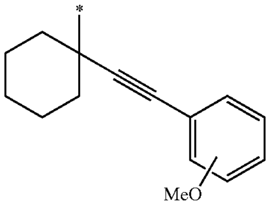

-continued
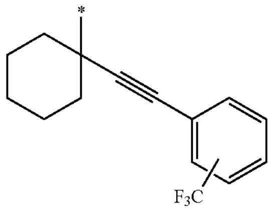
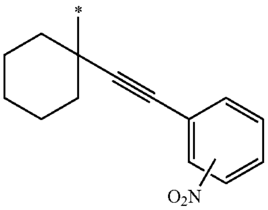
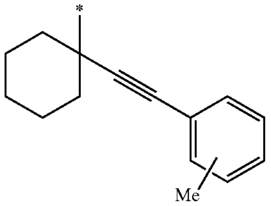
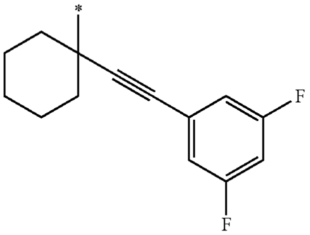
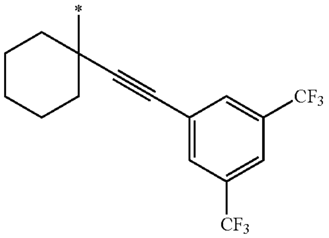
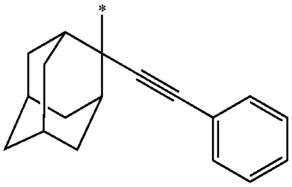
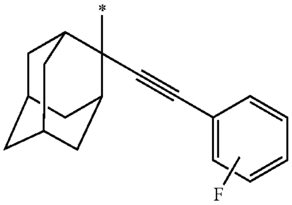
Specific examples of the structure represented by the general formula (ALU-2) include the following structures, but the structure is not limited thereto.
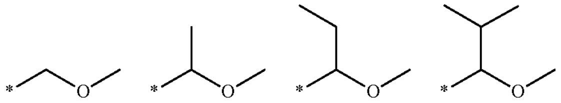
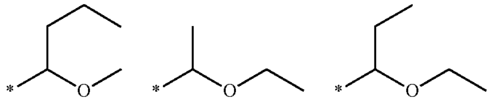
-continued
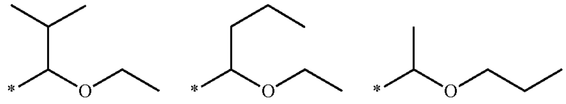
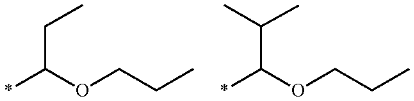
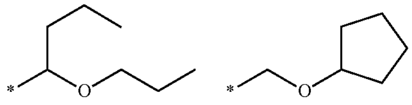
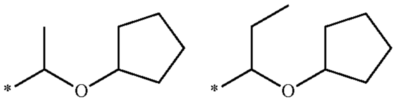
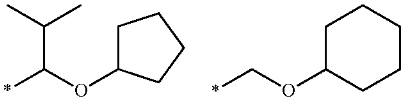
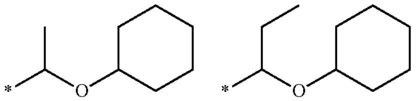
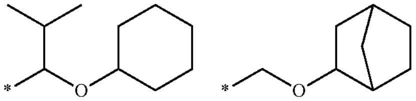
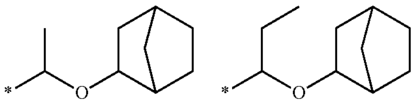
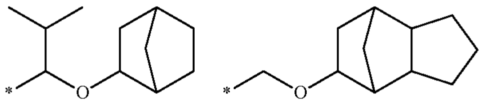
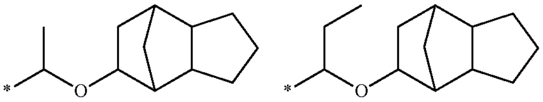
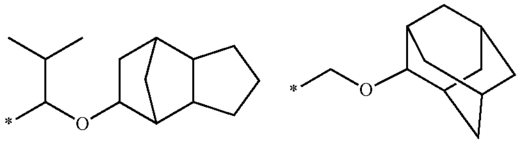
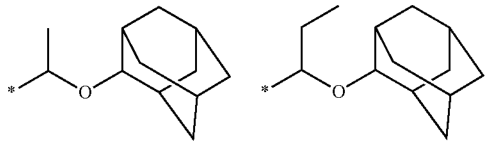
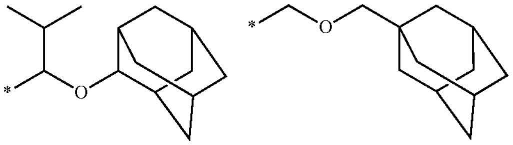
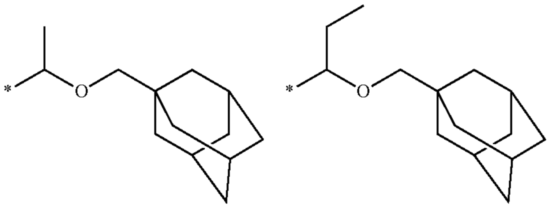

-continued

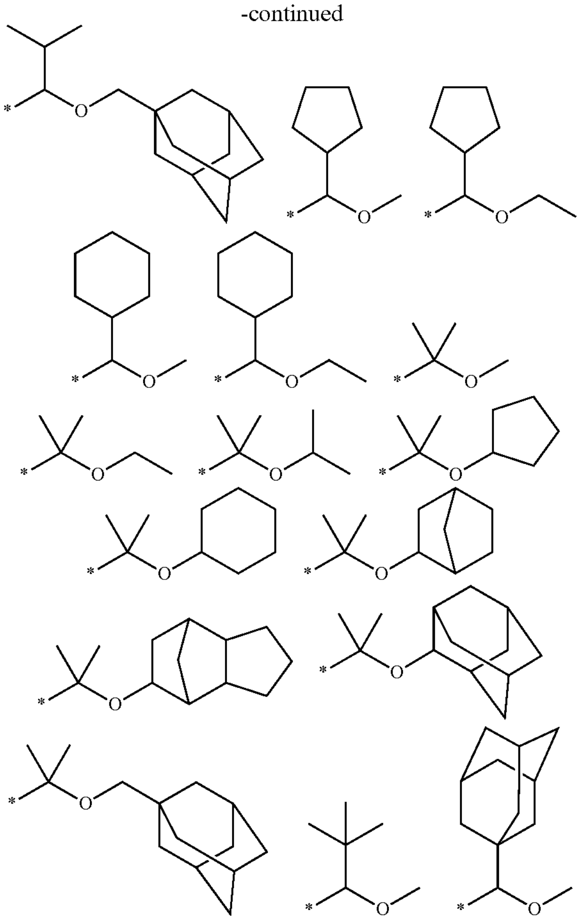

In the general formula (1), $R^F$ represents any one of a fluorine atom, a fluorine-containing alkyl group having 1 to 6 carbon atoms, and a nitro group. Among these, a fluorine atom and a fluorine-containing alkyl group having 1 to 6 carbon atoms are preferable from the viewpoint of the solvent solubility and acidity of a conjugate acid of an anion of the onium salt. As the fluorine-containing alkyl group having 1 to 6 carbon atoms, a trifluoromethyl group is preferable.

In the general formula (1), $R^F$ and —O—$R^{ALU}$ are necessarily bonded to carbon atoms adjacent to each other. Specifically, when n2 and n3 represent 1, $R^F$ and —O—$R^{ALU}$ are bonded to carbon atoms adjacent to each other. When any one or both of n2 and n3 represent 2, one of $R^F$ and one of —O—$R^{ALU}$ are bonded to carbon atoms adjacent to each other. The adjacent bonds increases acidity of an aromatic alcohol generated by eliminating the acid-labile group from —O—$R^{ALU}$ to increase solubility in an alkaline developer and improve the effect of inhibiting swelling.

In the general formula (1), $R^a$ represents a hydrocarbyl group having 1 to 20 carbon atoms and optionally having a heteroatom. A part or all of hydrogen atoms in the hydrocarbyl group are optionally substituted with a halogen atom, and —$CH_2$— constituting the hydrocarbyl group is optionally substituted with —O— or —C(=O)—. The hydrocarbyl group may be a saturated or unsaturated group, and may be any of linear, branched, and cyclic groups. Specific examples thereof include: alkyl groups having 1 to 20 carbon atoms, such as a methyl group, an ethyl group, an n-propyl group, an isopropyl group, an n-butyl group, and a tert-butyl group; cyclic saturated hydrocarbyl groups having 3 to 20 carbon atoms, such as a cyclopropyl group, a cyclopentyl group, a cyclohexyl group, a cyclopropylmethyl group, a 4-methylcyclohexyl group, a cyclohexylmethyl group, a norbornyl group, and an adamantyl group; alkenyl groups having 2 to 20 carbon atoms, such as a vinyl group, an allyl group, a propenyl group, a butenyl group, and a hexenyl group; cyclic unsaturated hydrocarbyl groups having 3 to 20 carbon atoms, such as a cyclohexenyl group; aryl groups having 6 to 20 carbon atoms, such as a phenyl group and a naphthyl group; aralkyl groups having 7 to 20 carbon atoms, such as a benzyl group, a 1-phenylethyl group, and a 2-phenylethyl group; and groups obtained by combining these groups. A part or all of hydrogen atoms in the hydrocarbyl group are optionally substituted with a group having a heteroatom such as an oxygen atom, a sulfur atom, a nitrogen atom, and a halogen atom. A part of —$CH_2$— constituting the hydrocarbyl group is optionally substituted with a group having a heteroatom such as an oxygen atom, a sulfur atom, and a nitrogen atom. As a result, optionally contained are a hydroxy group, a cyano group, a fluorine atom, a chlorine atom, a bromine atom, an iodine atom, a carbonyl group, an ether bond, an ester bond, a sulfonate ester bond, a carbonate bond, a lactone ring, a sultone ring, a carboxylic anhydride, a haloalkyl group, etc.

In the general formula (1), n1 represents an integer of 0 or 1. n1=0 represents a benzene ring and n1=1 represents a naphthalene ring. From the viewpoint of the solvent solubility, n1=0 representing a benzene ring is preferable.

In the general formula (1), n2 and n3 represent an integer of 1 or 2. From the viewpoint of availability of a starting material, n2 and n3 each preferably represent an integer of 1.

In the general formula (1), n4 represents an integer of 0 to 3. When n4≥2, a plurality of $R^a$ are optionally bonded to each other to form a cyclic structure together with the carbon atoms to which these groups are bonded. When the cyclic structure is formed, specific examples of the cyclic structure include five-membered ring and six-membered ring structures.

Examples of the anion of the onium salt represented by the general formula (1) include the following anions, but the anion is not limited thereto. The substitution position of the substituents on the aromatic ring is also not limited thereto as long as the groups labeled with n2 and n3 are present adjacent to each other.

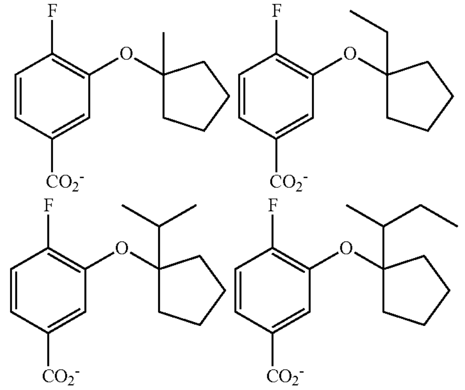

-continued
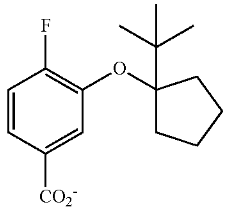
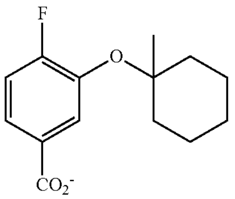
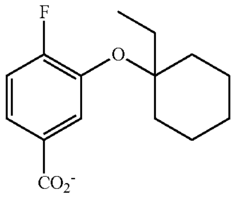
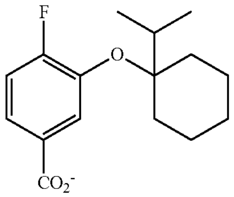
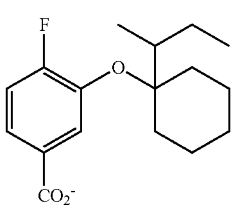
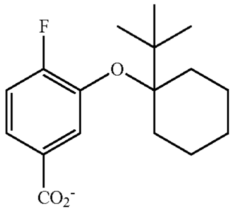
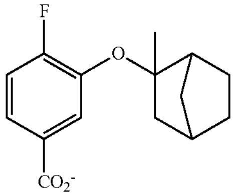
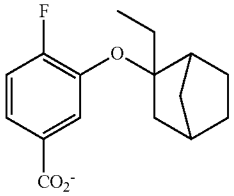
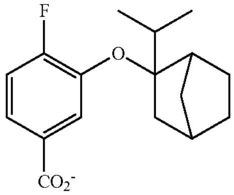
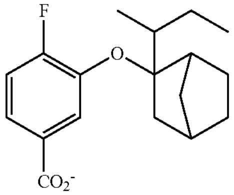
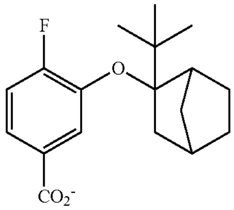
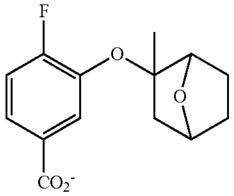
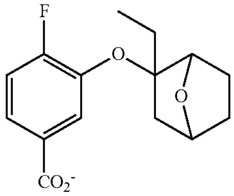
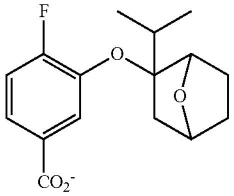
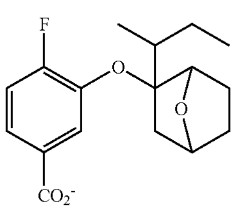
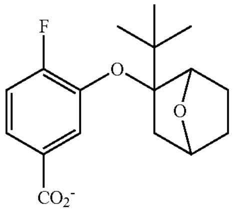
-continued
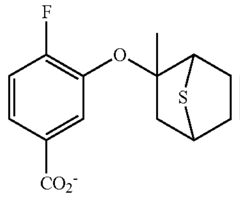
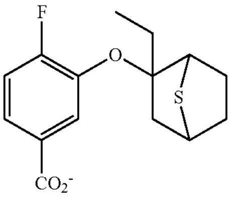
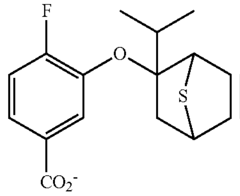
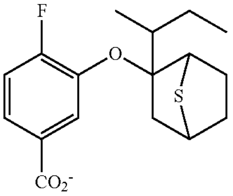
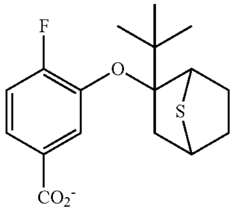
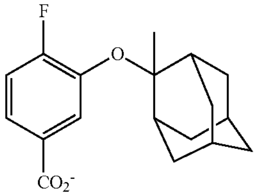
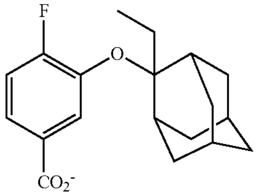
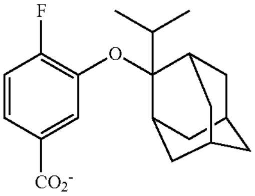
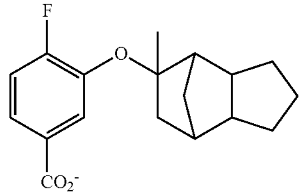
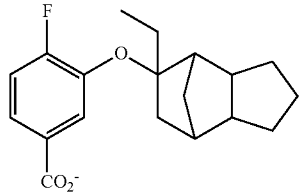
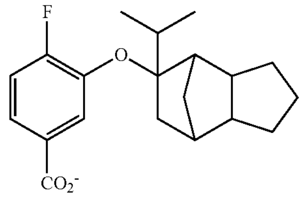
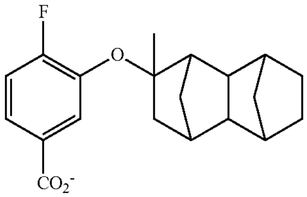

-continued
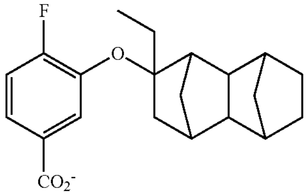
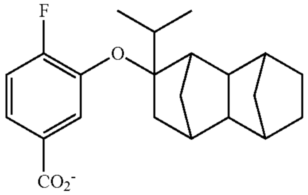
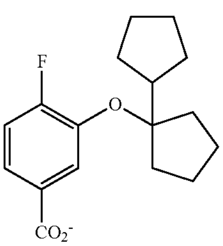
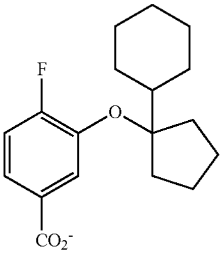
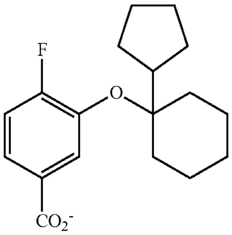
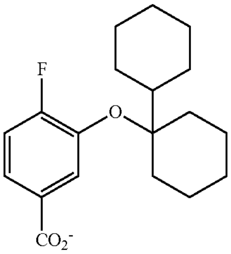
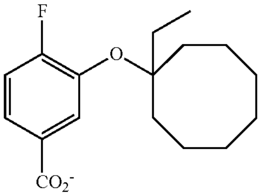
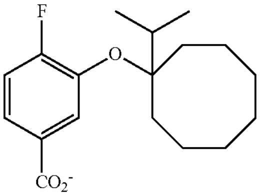
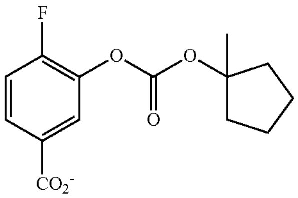
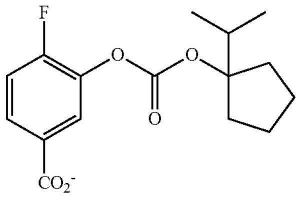
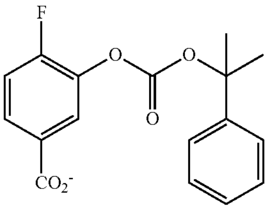
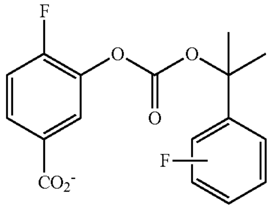
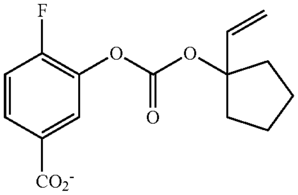
-continued
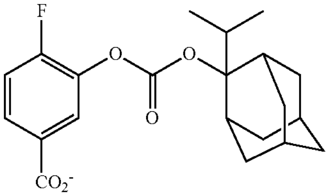
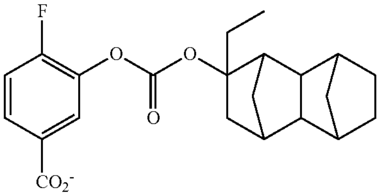
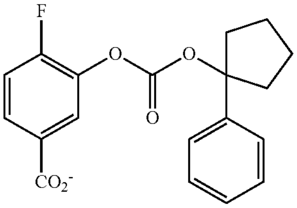
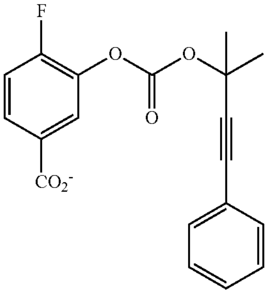
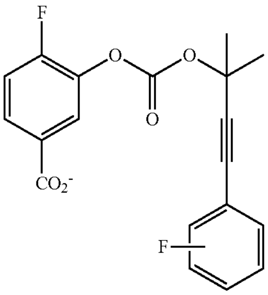
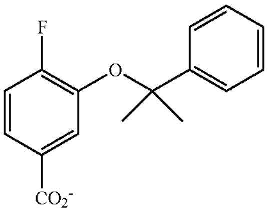
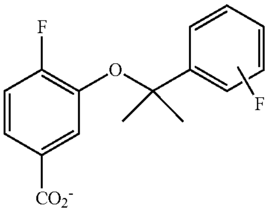
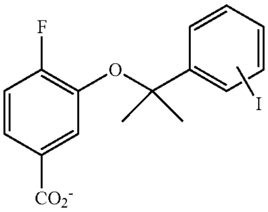
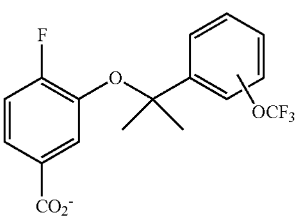
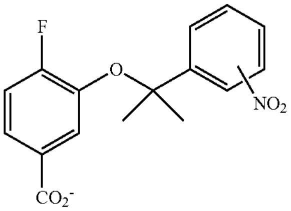
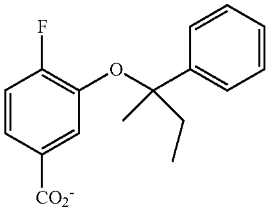

-continued
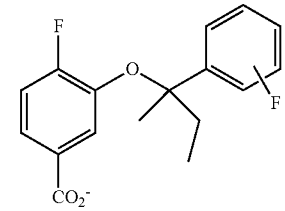
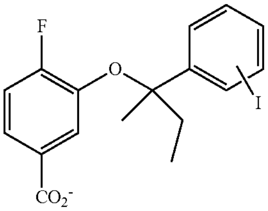
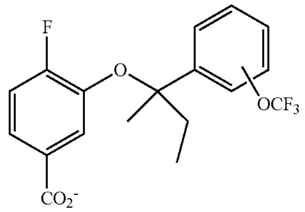
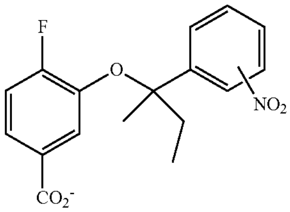
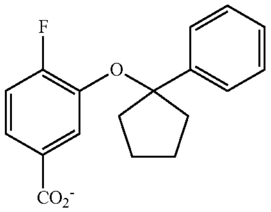
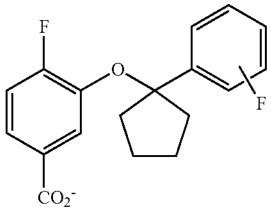
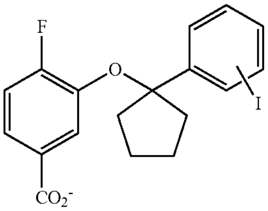
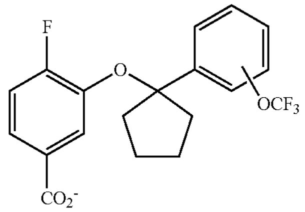
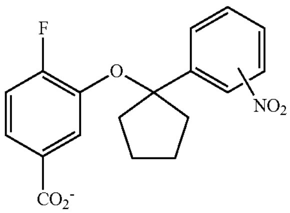
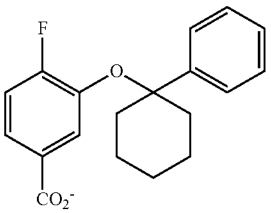
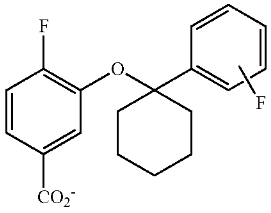
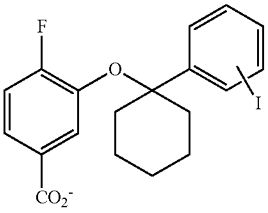
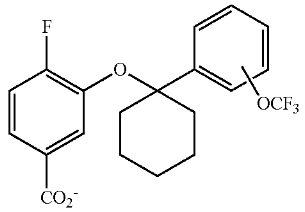
-continued
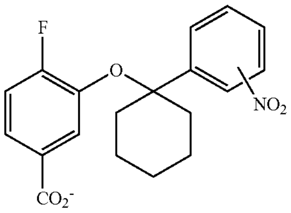
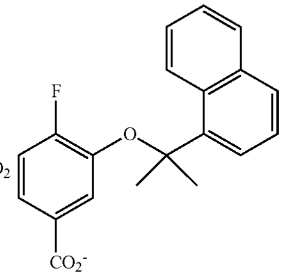
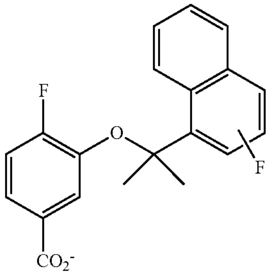
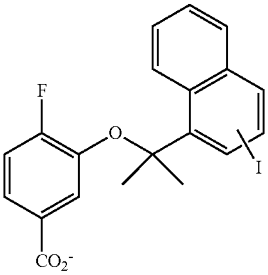
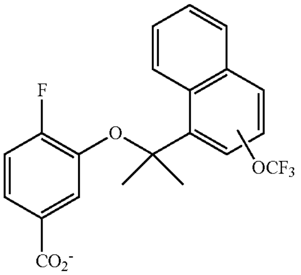
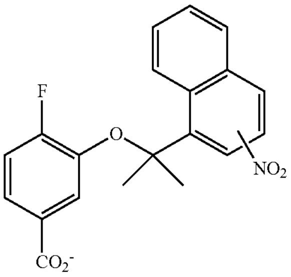
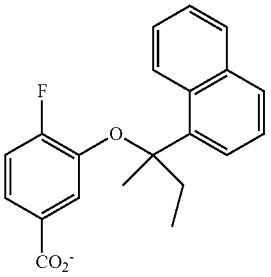
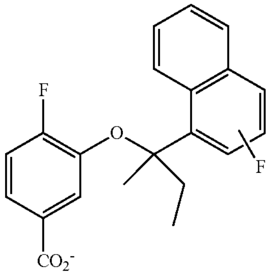
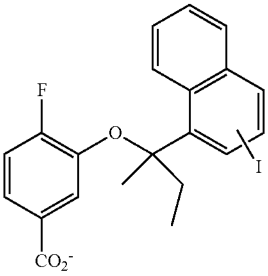
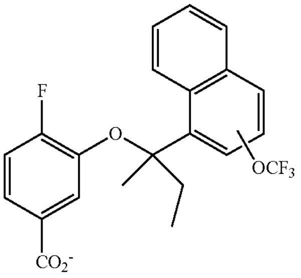

-continued
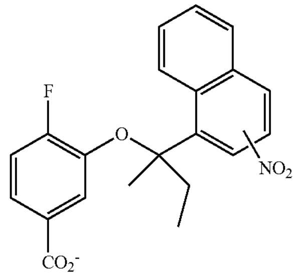
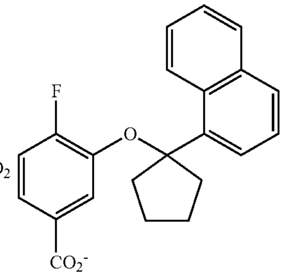
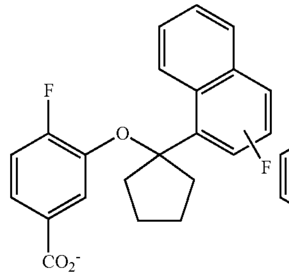
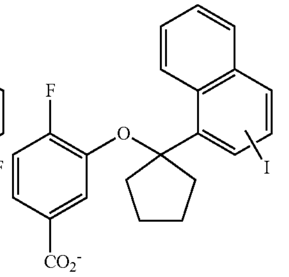
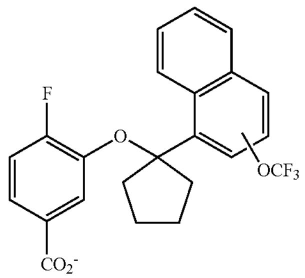
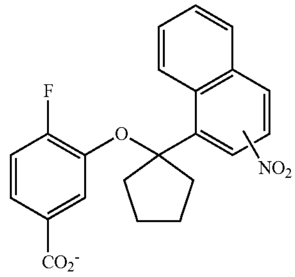
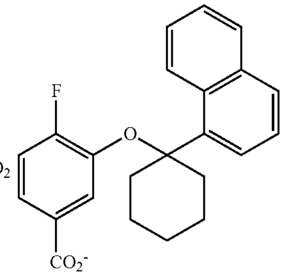
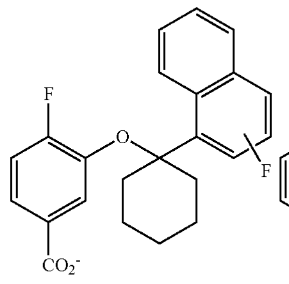
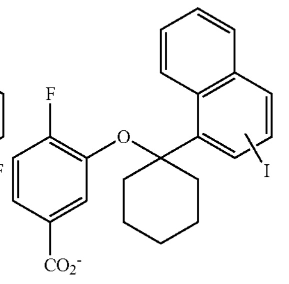
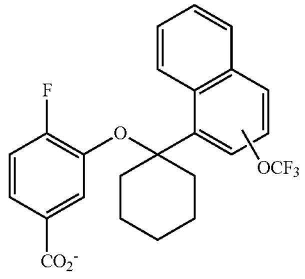
-continued
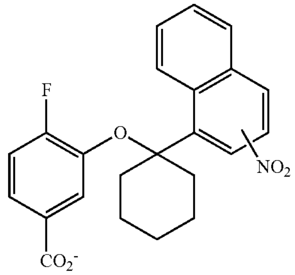
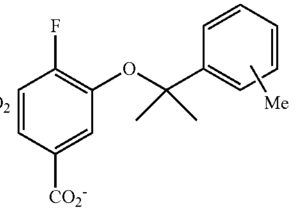
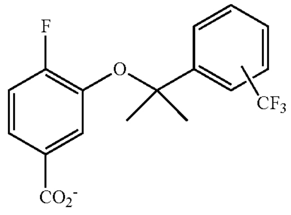
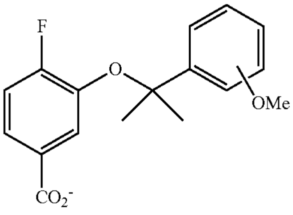
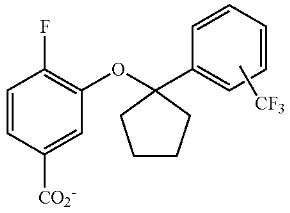
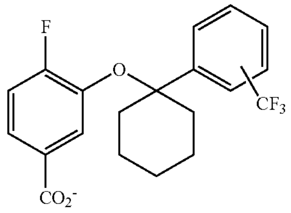
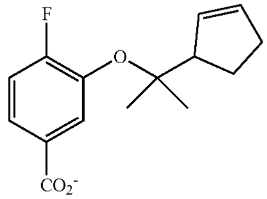
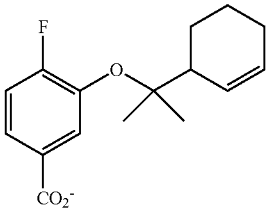
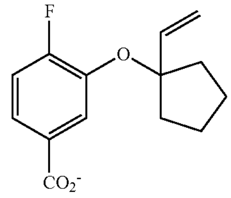
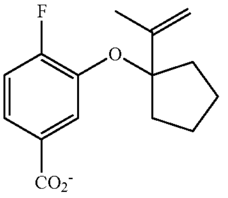
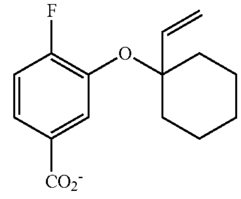
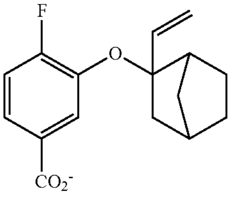
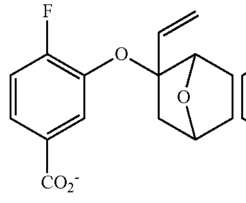
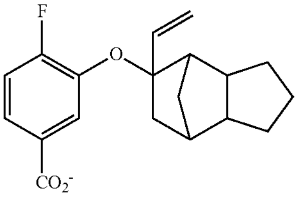
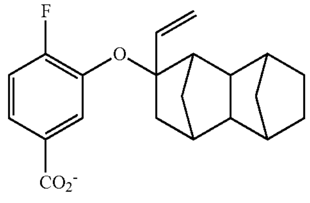
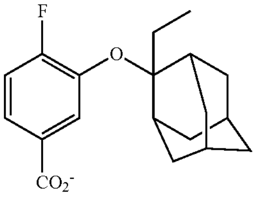

-continued
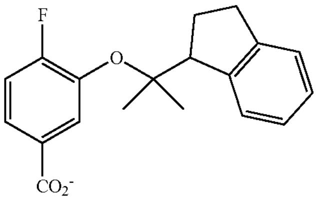
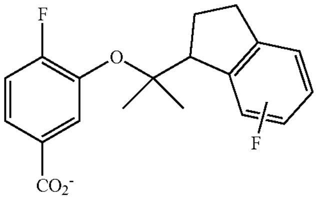
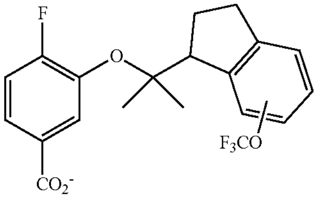
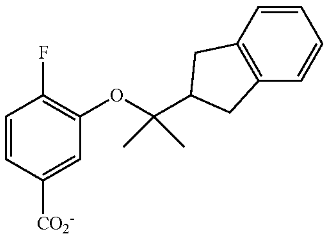
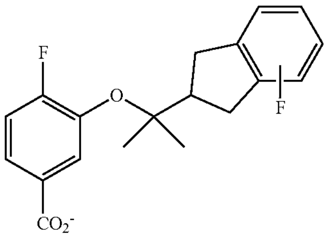
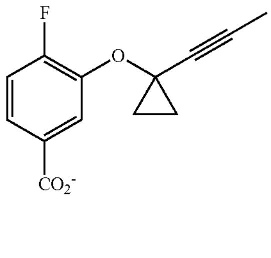
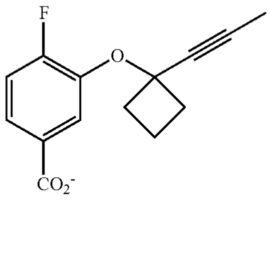
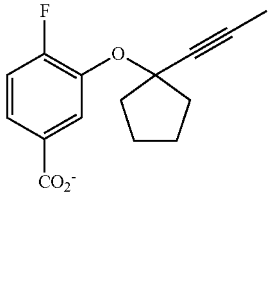
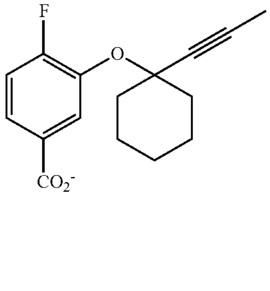
-continued
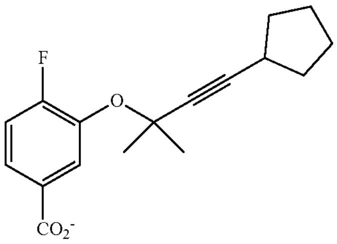
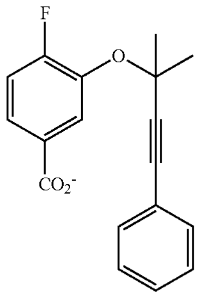
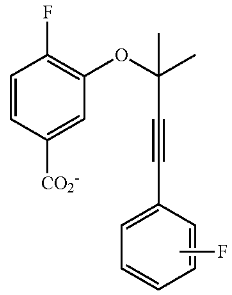
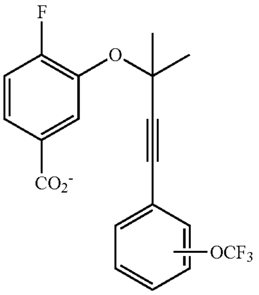
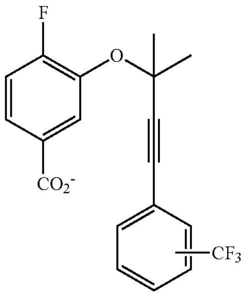
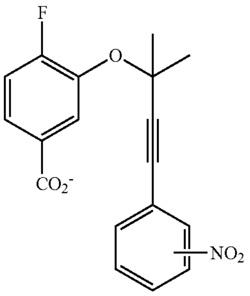
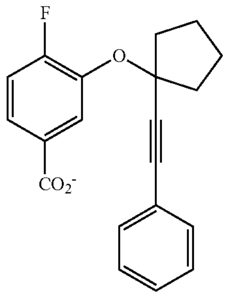
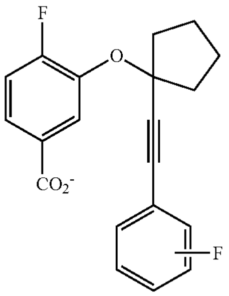
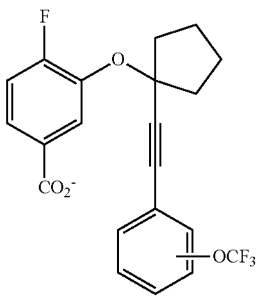
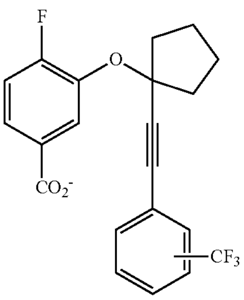

-continued
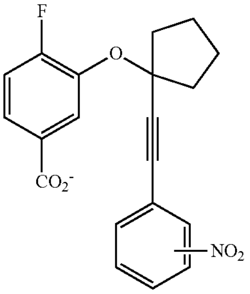
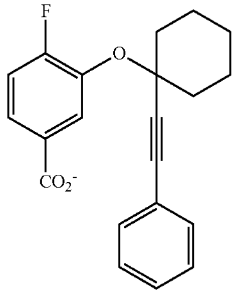
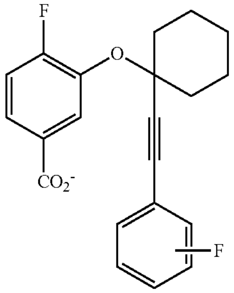
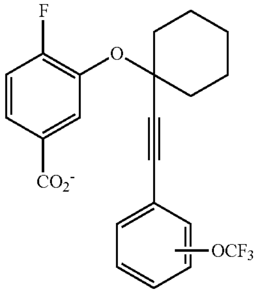
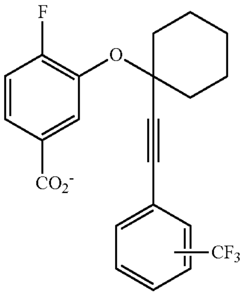
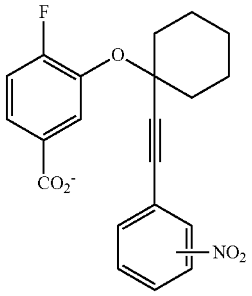
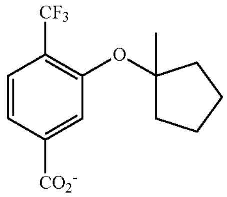
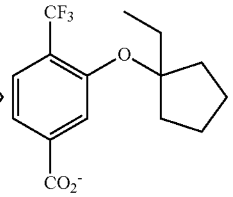
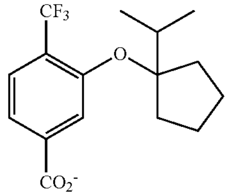
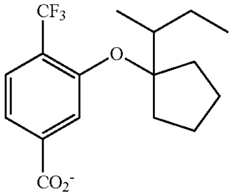
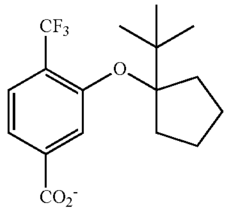
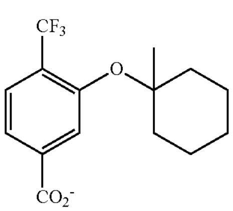
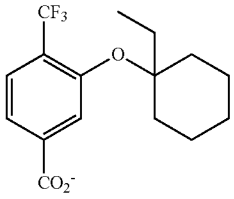
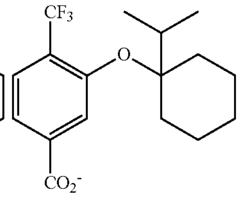
-continued
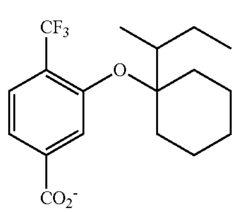
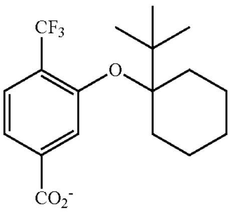
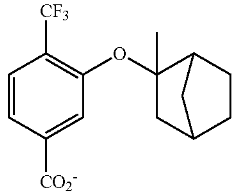
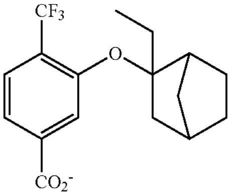
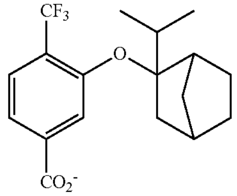
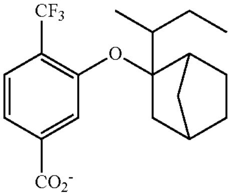
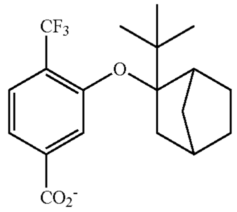
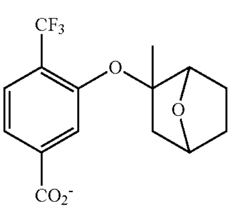
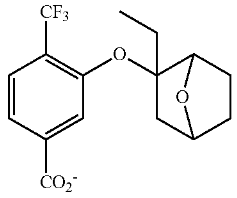
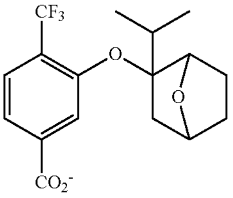
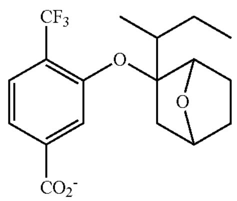
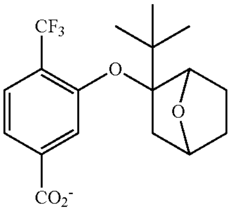
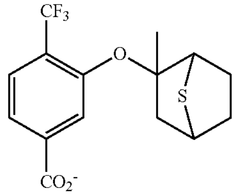
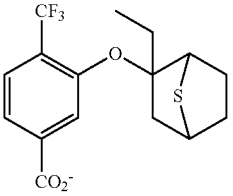
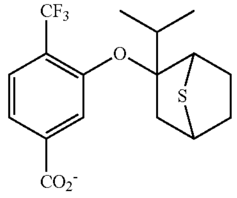
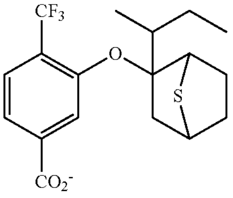

-continued
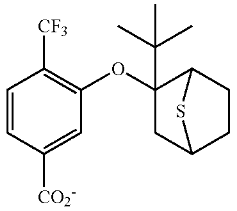
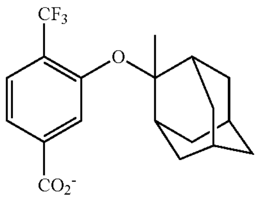
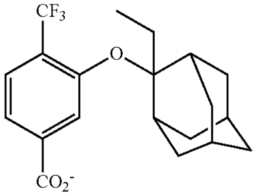
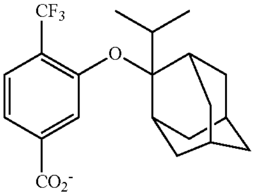
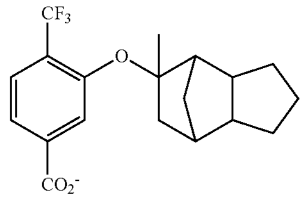
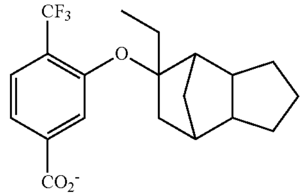
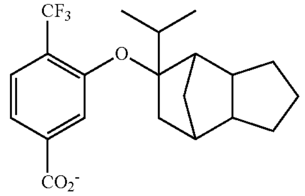
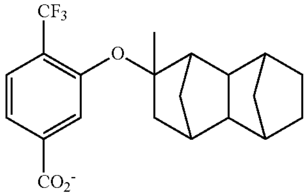
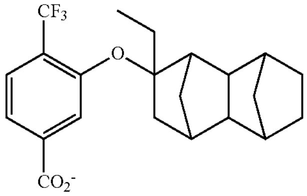
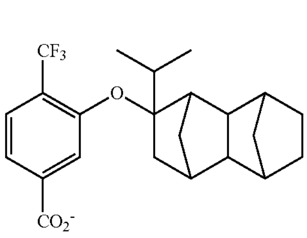
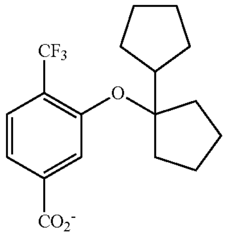
-continued
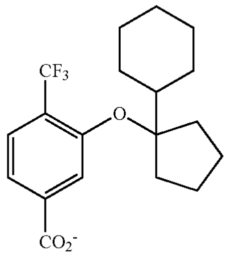
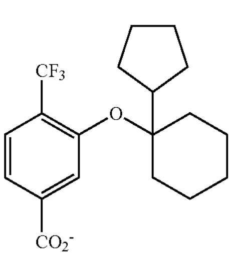
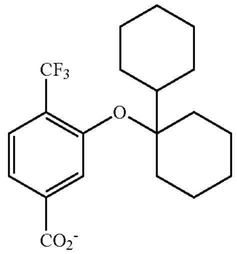
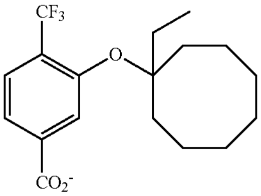
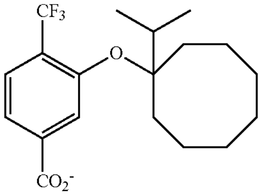
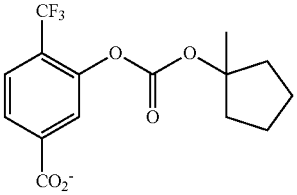
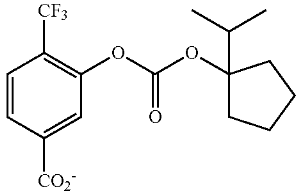
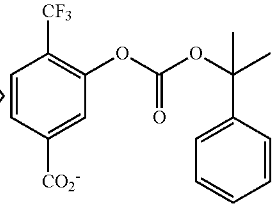
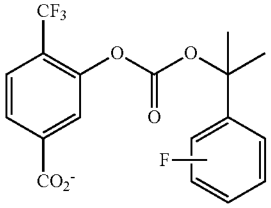
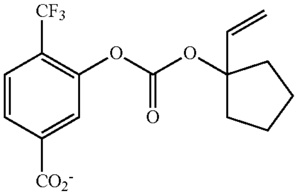
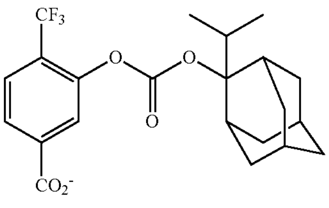
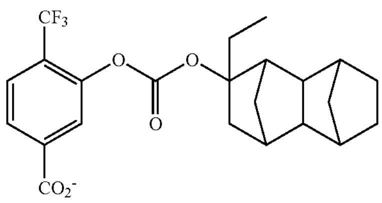

-continued
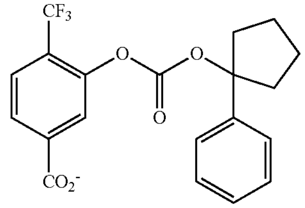
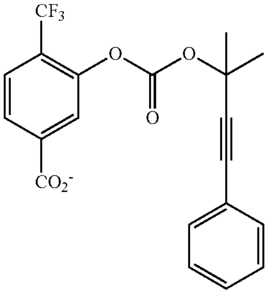
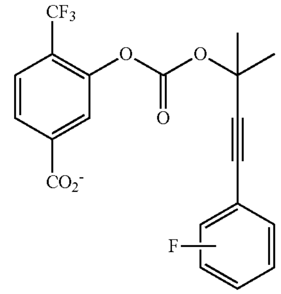
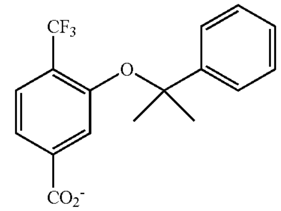
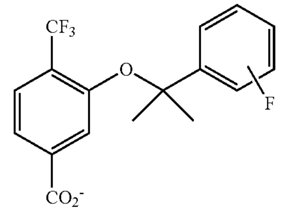
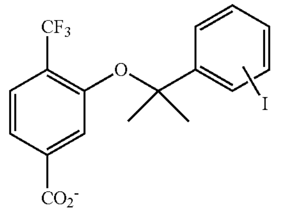
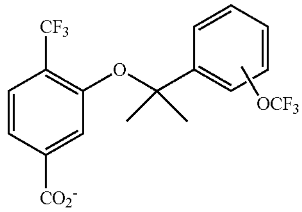
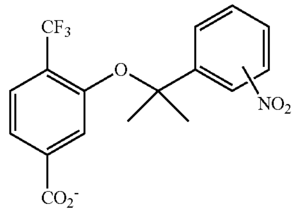
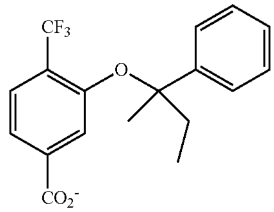
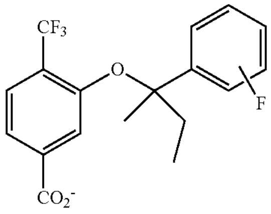
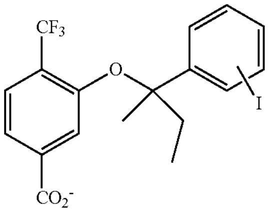
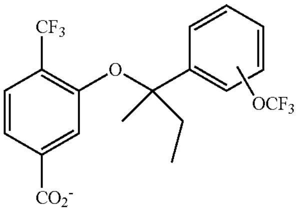
-continued
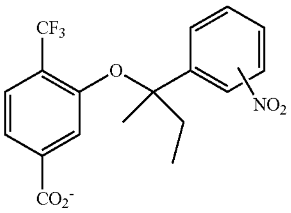
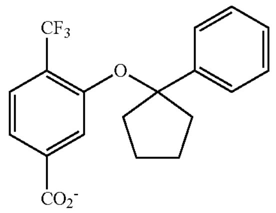
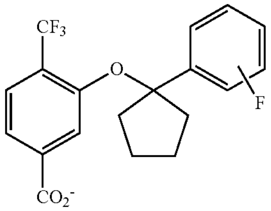
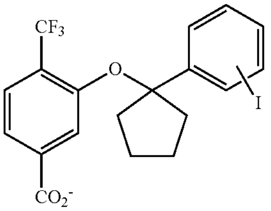
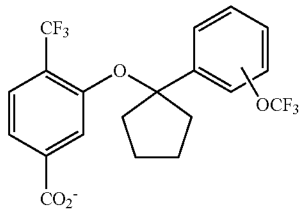
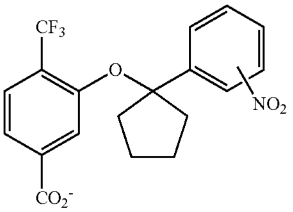
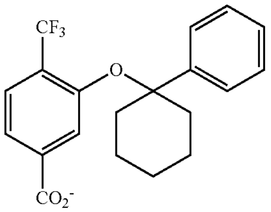
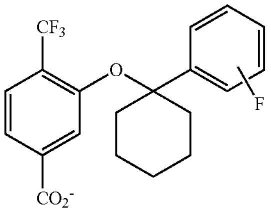
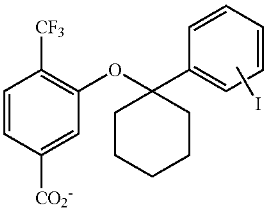
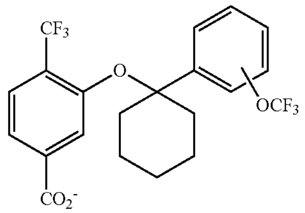
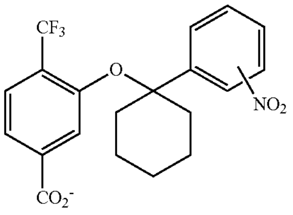
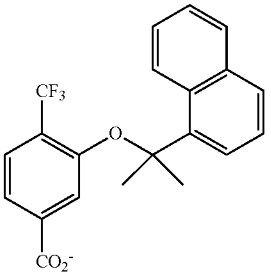

-continued
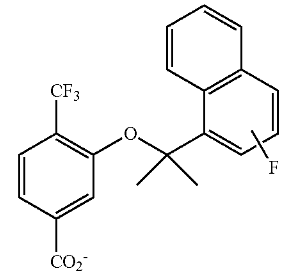
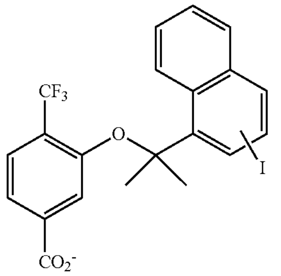
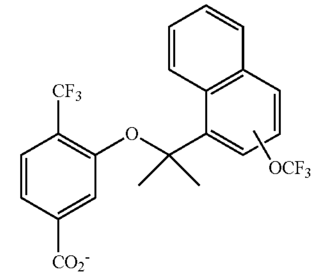
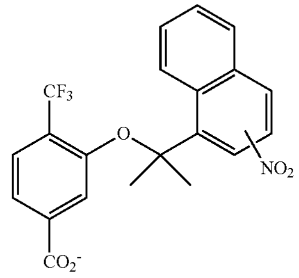
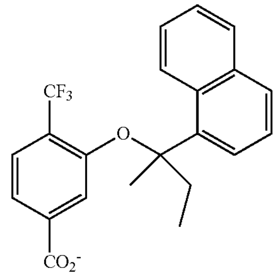
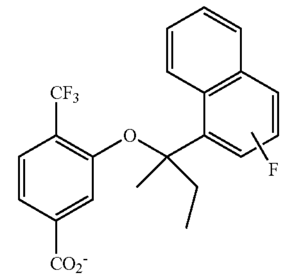
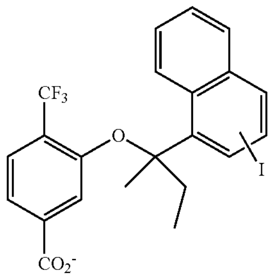
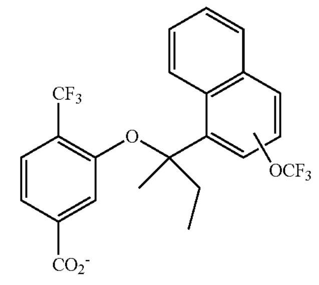
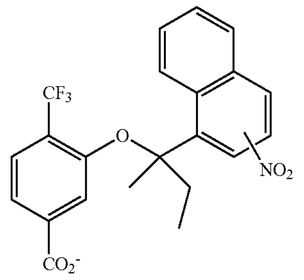
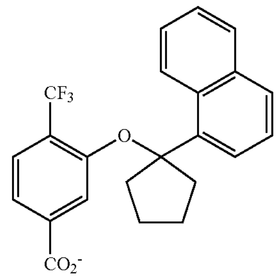
-continued
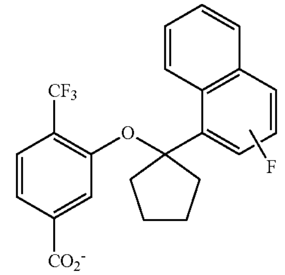
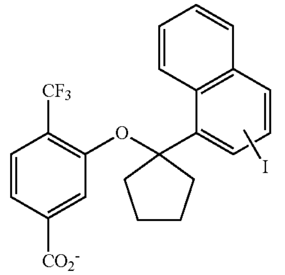
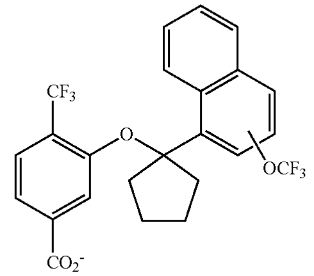
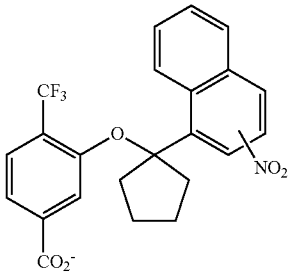
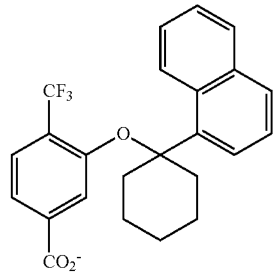
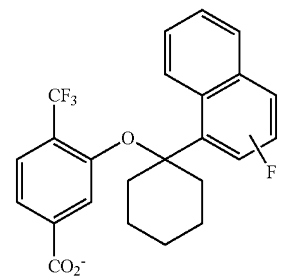
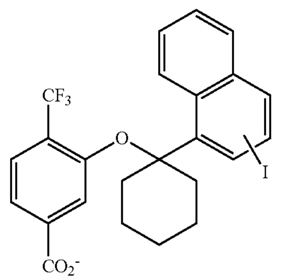
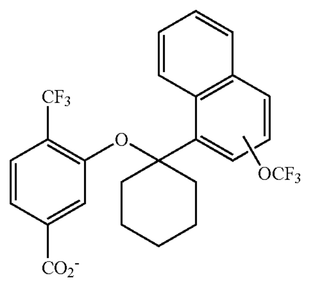
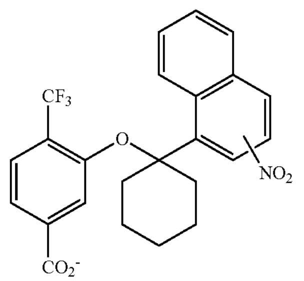
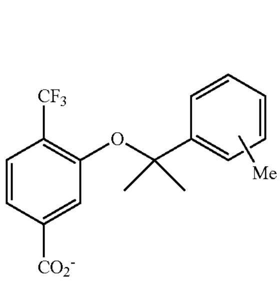

-continued
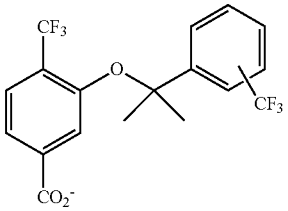
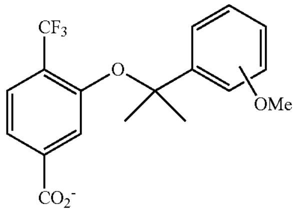
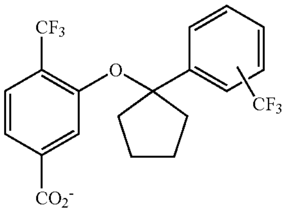
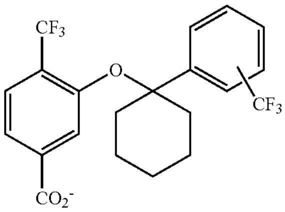
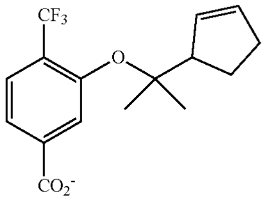
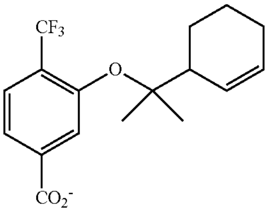
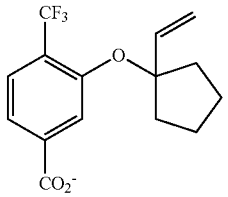
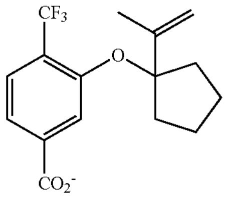
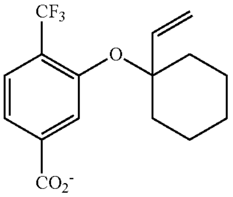
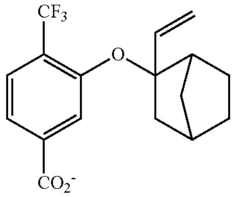
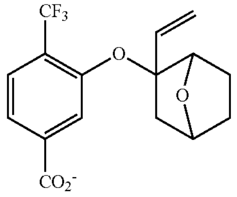
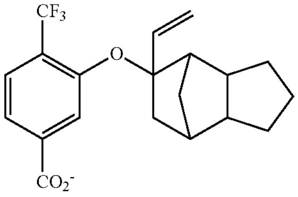
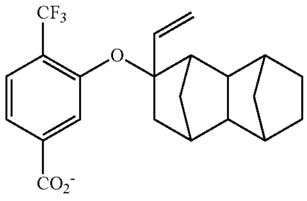
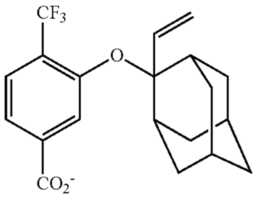
-continued
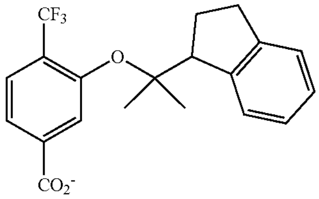
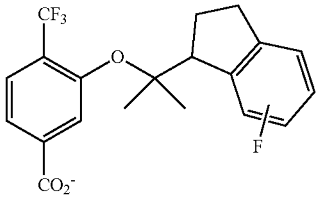
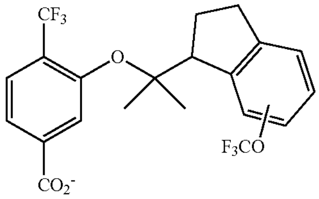
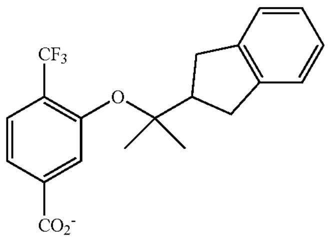
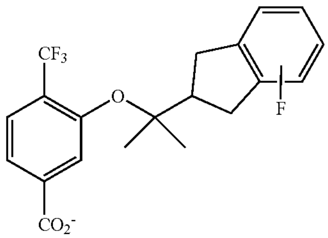
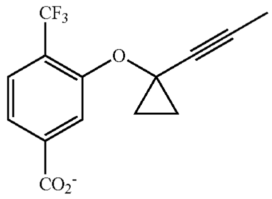
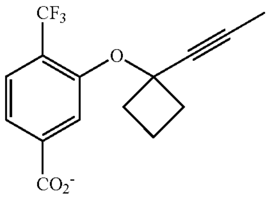
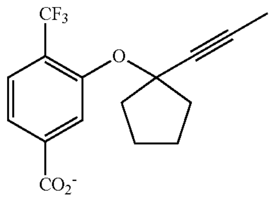
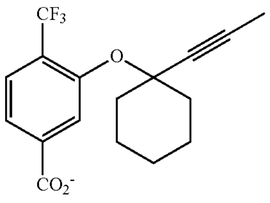

-continued
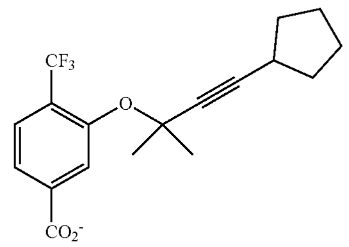
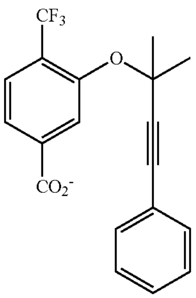
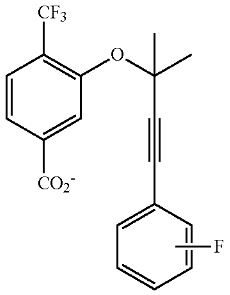
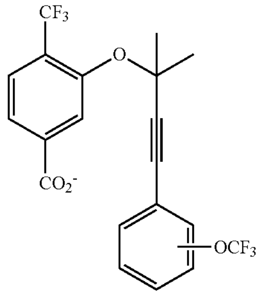
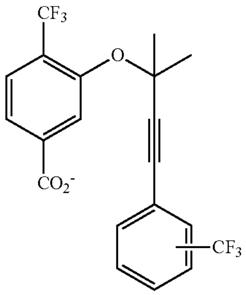
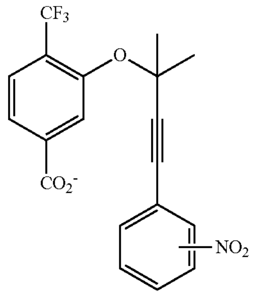
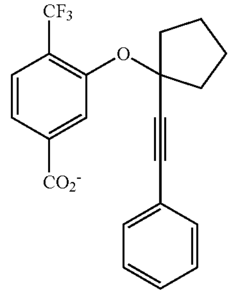
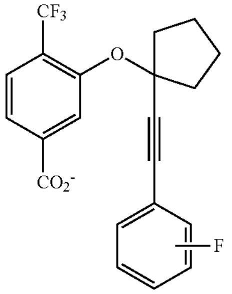
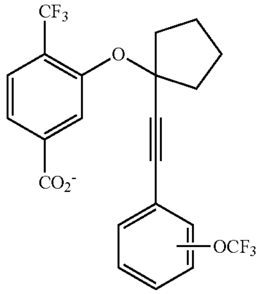
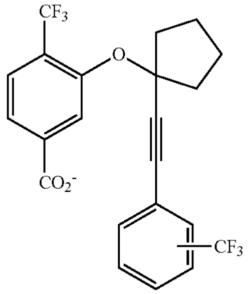
-continued
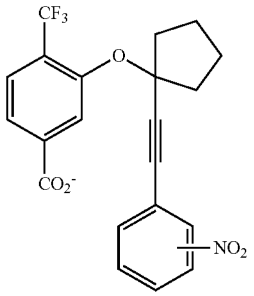
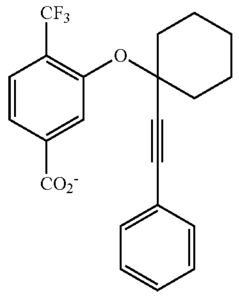
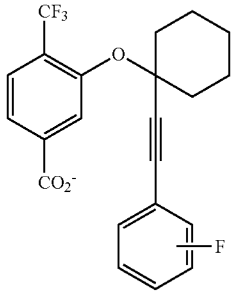
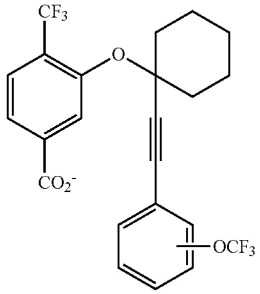
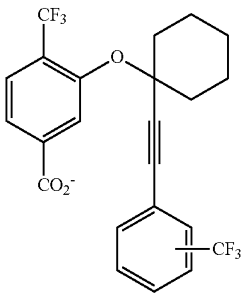
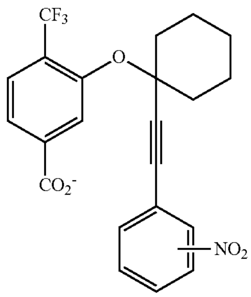
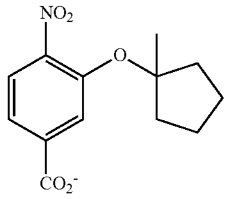
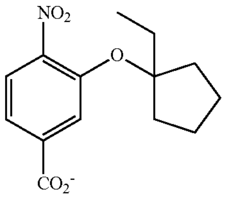
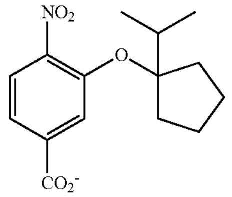
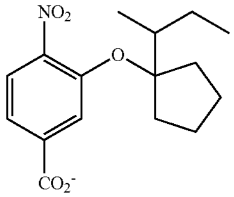
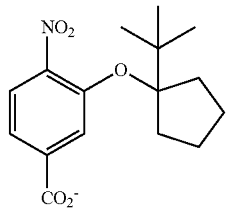
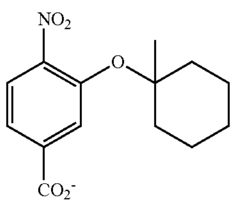
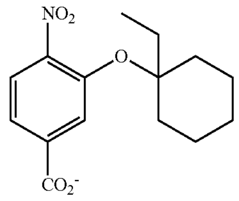
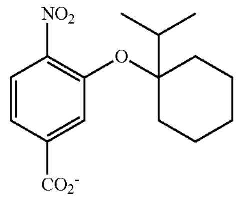

-continued
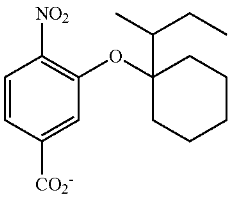
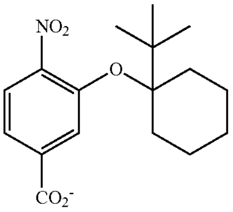
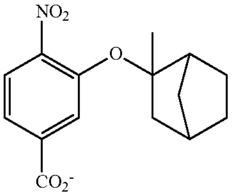
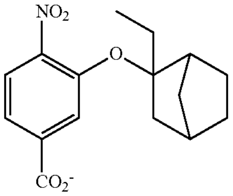
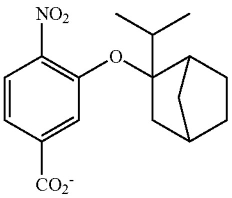
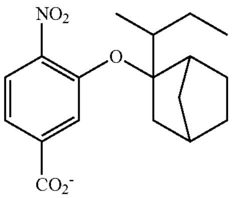
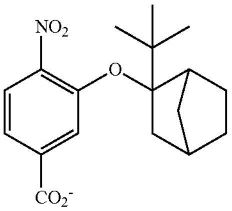
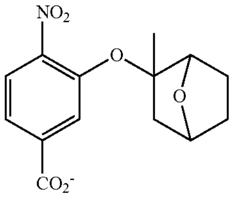
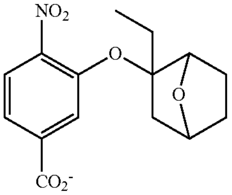
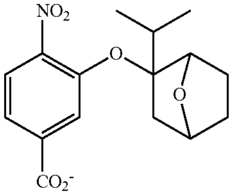
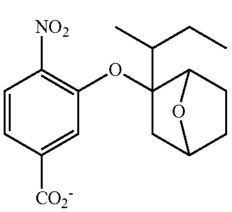
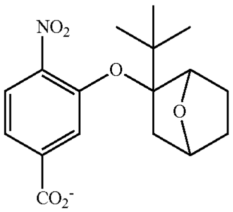
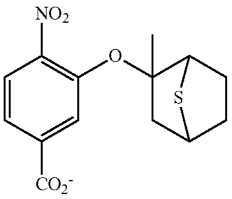
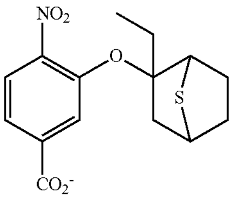
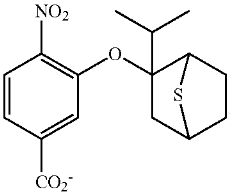
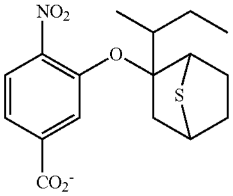
-continued
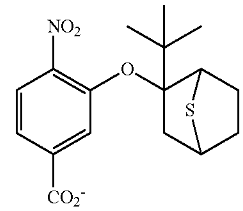
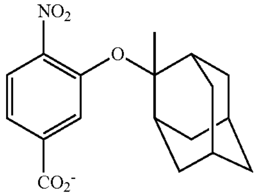
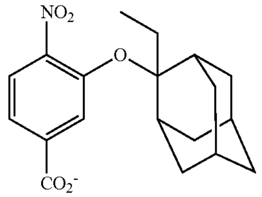
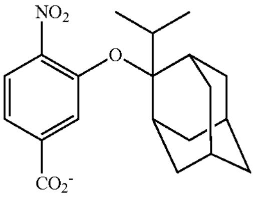
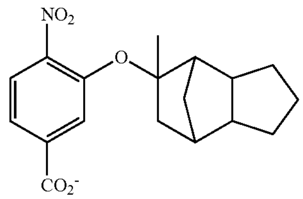
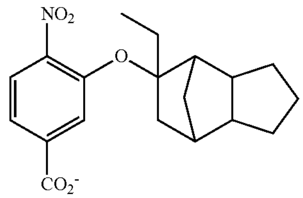
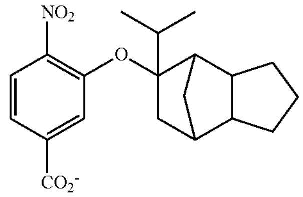
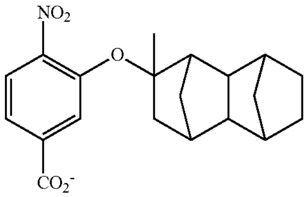
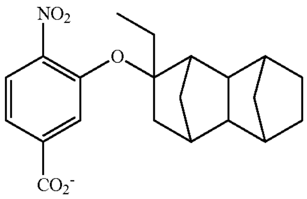
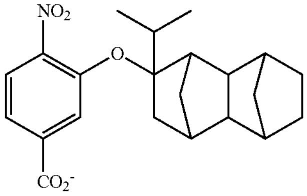

-continued
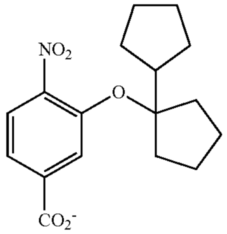
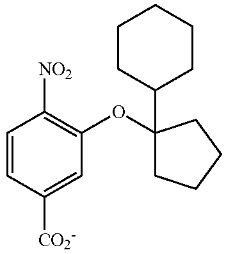
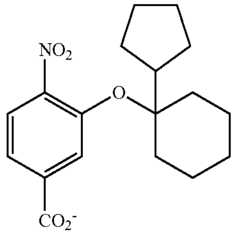
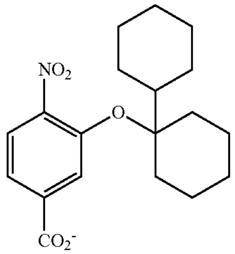
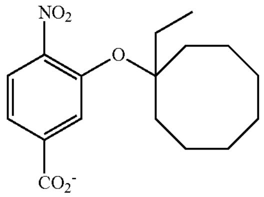
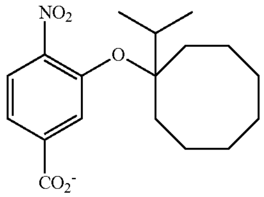
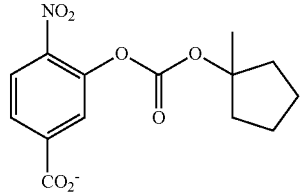
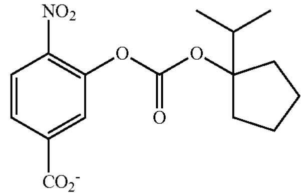
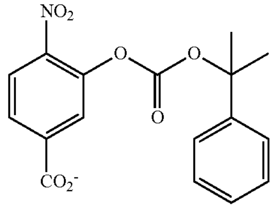
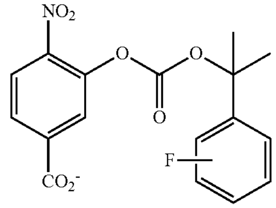
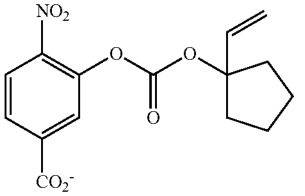
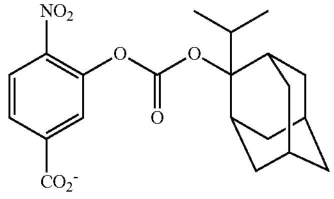
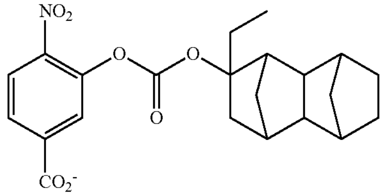
-continued
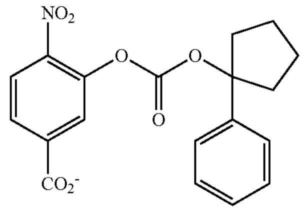
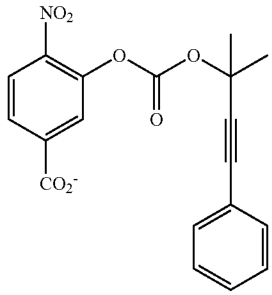
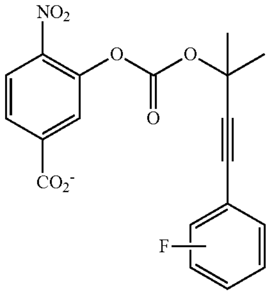
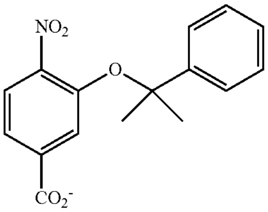
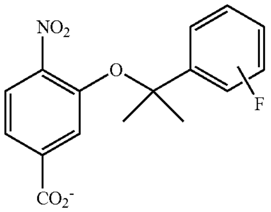
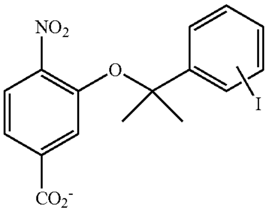
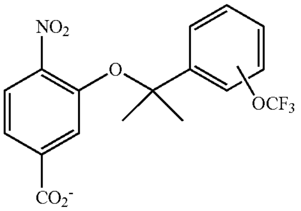
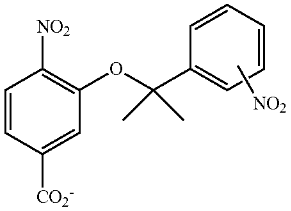
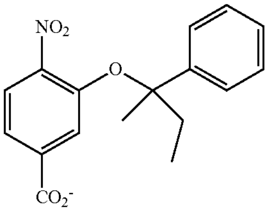
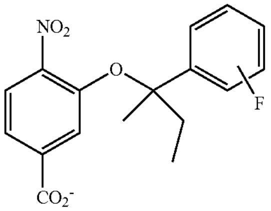
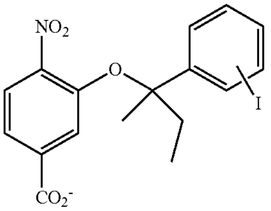
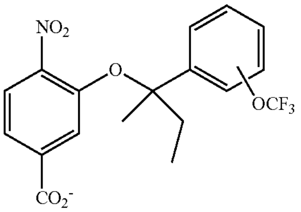

-continued
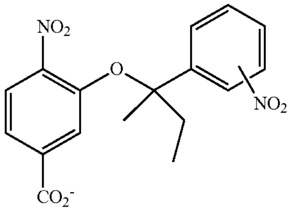
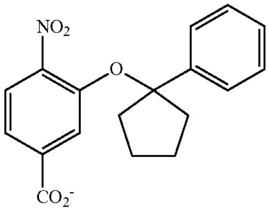
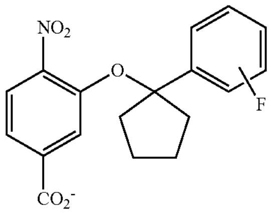
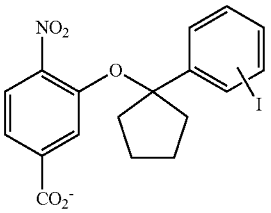
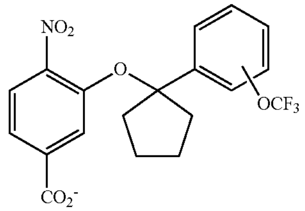
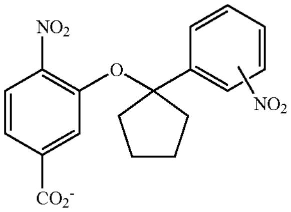
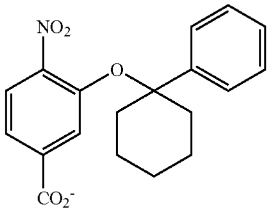
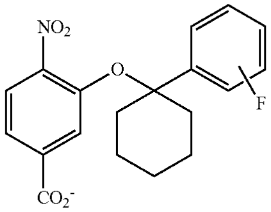
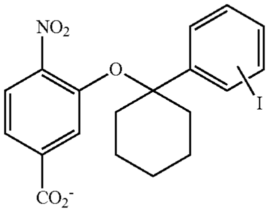
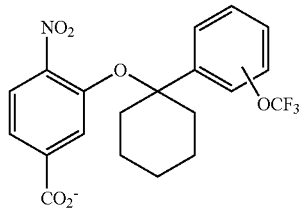
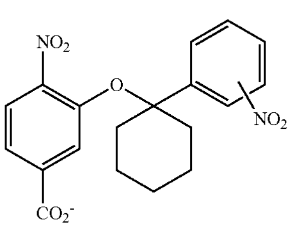
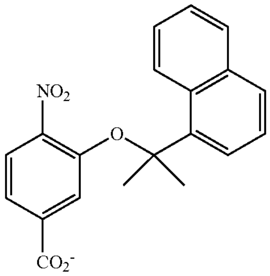
-continued
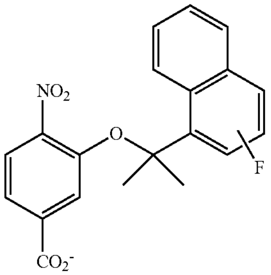
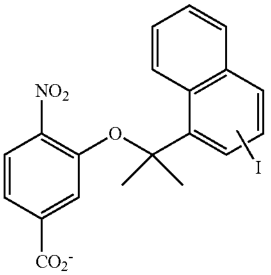
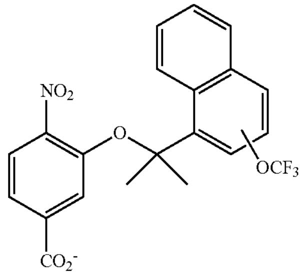
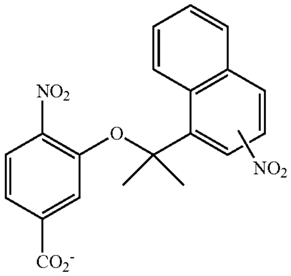
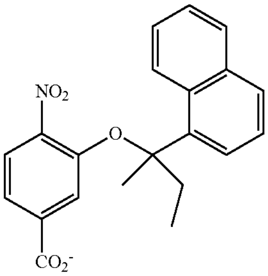
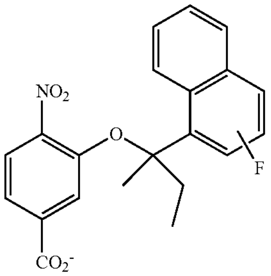
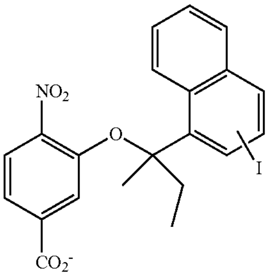
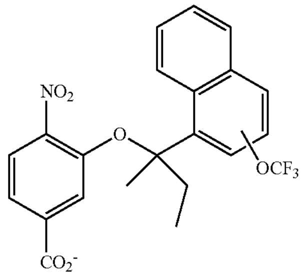
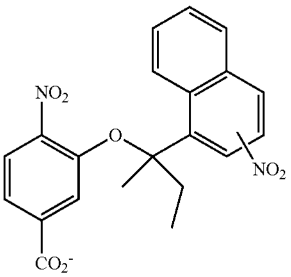
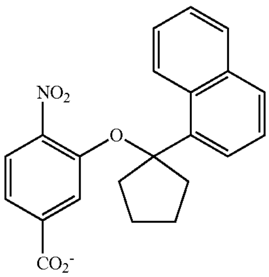

-continued
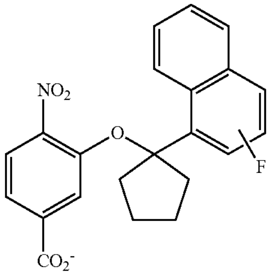
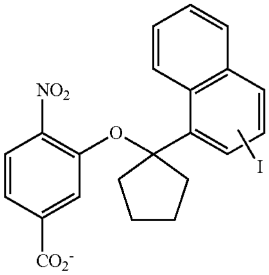
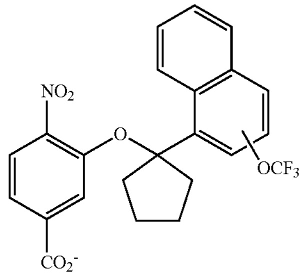
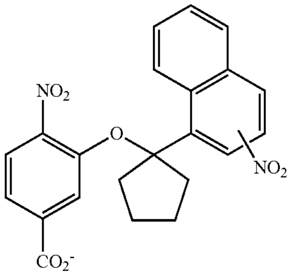
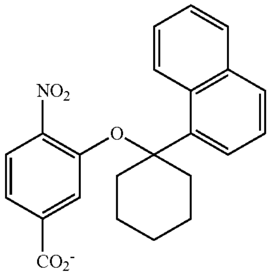
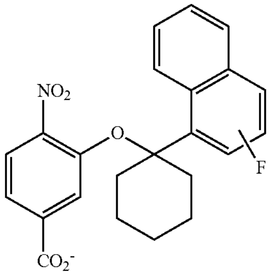
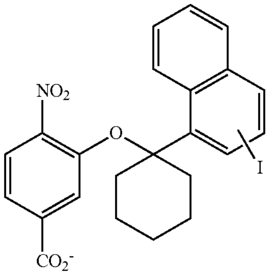
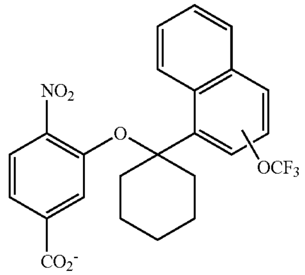
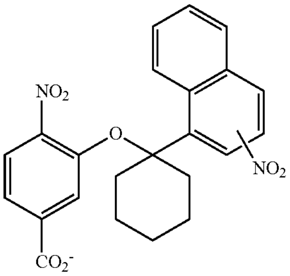
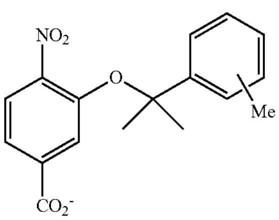
-continued
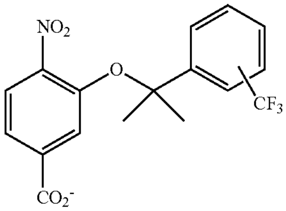
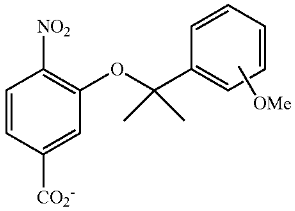
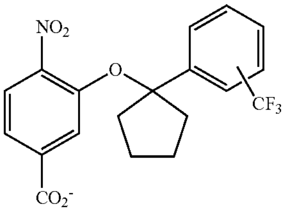
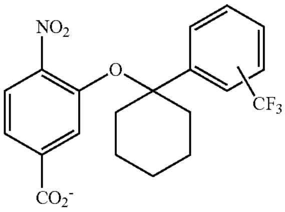
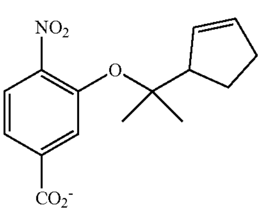
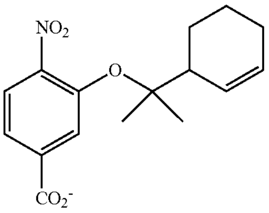
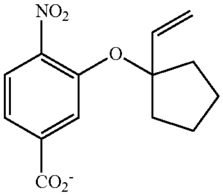
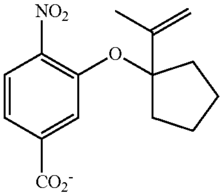
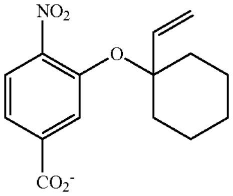
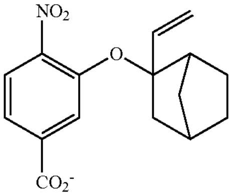
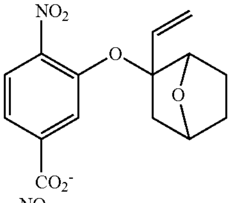
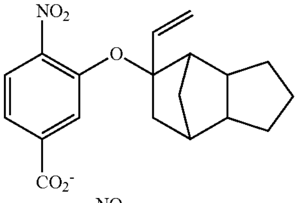
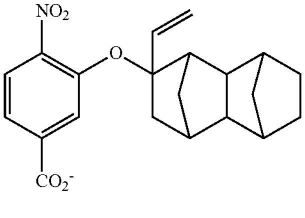
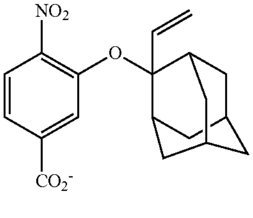

-continued
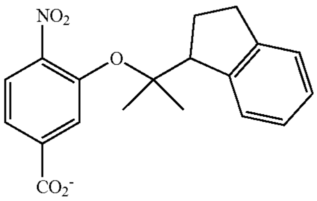
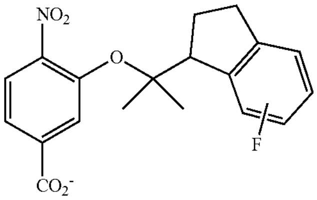
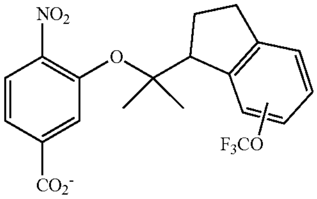
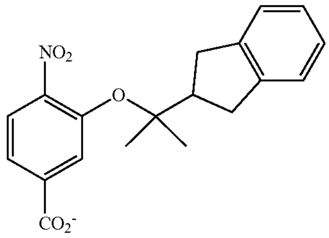
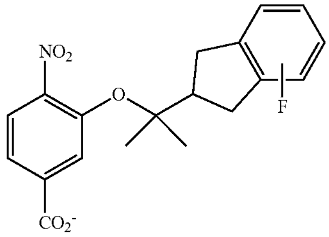
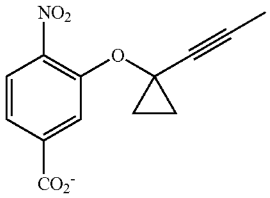
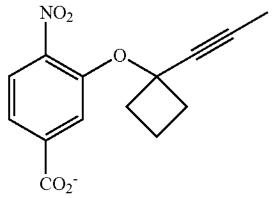
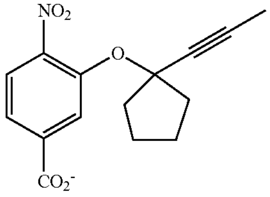
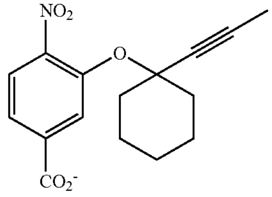
-continued
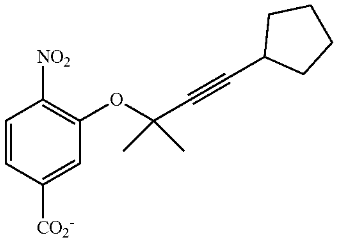
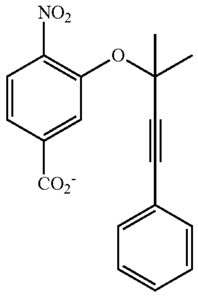
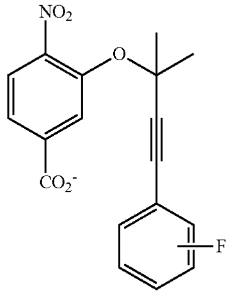
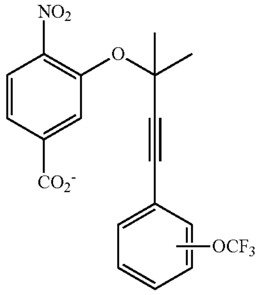
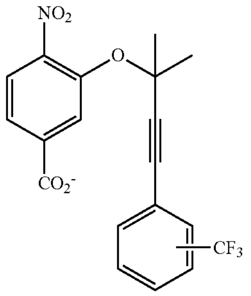
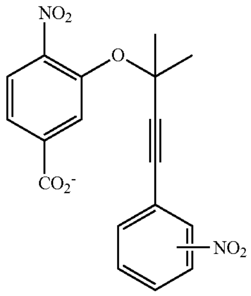
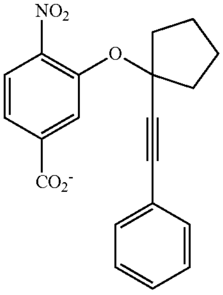
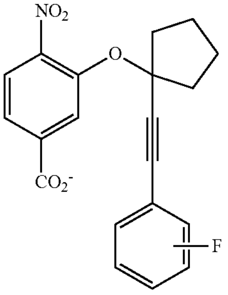
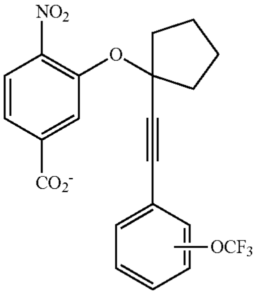
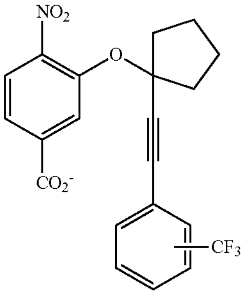

-continued
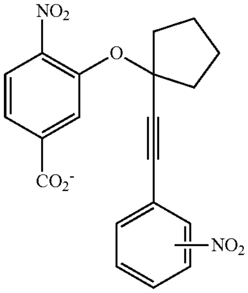
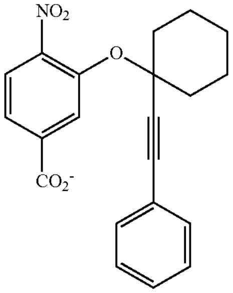
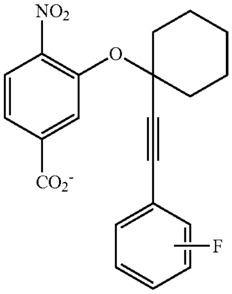
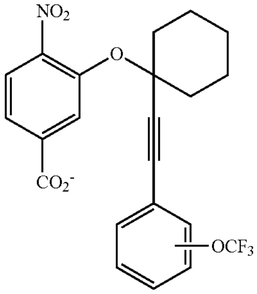
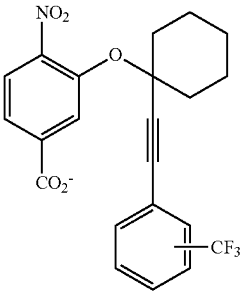
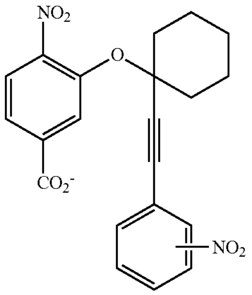
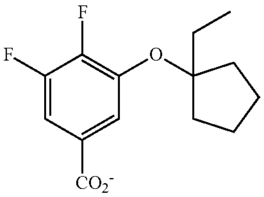
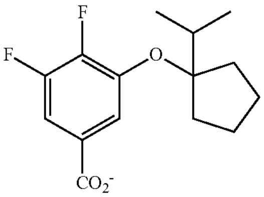
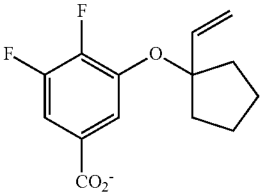
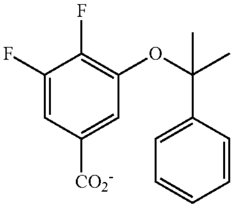
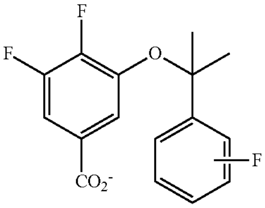
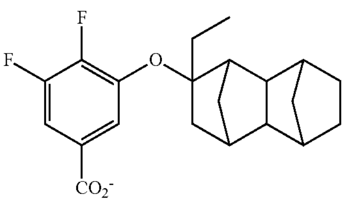
-continued
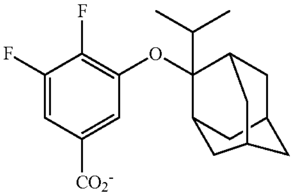
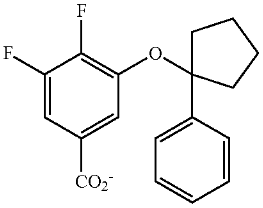
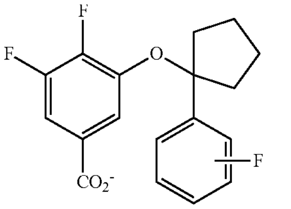
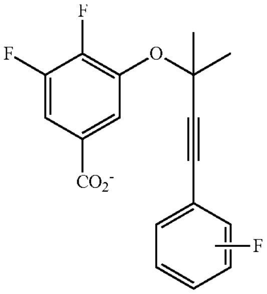
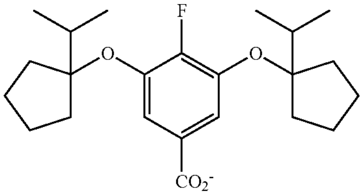
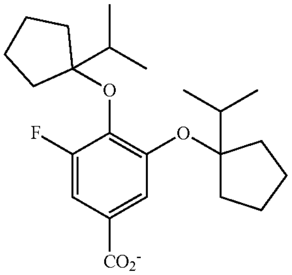
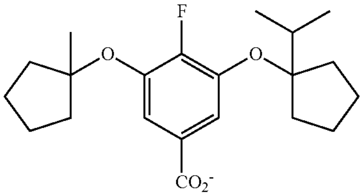
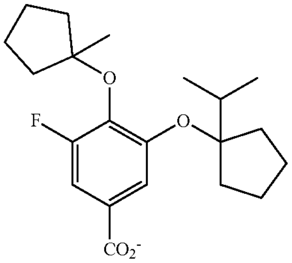
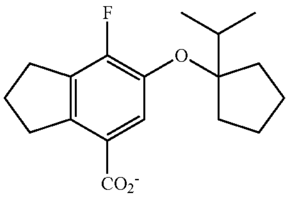

-continued
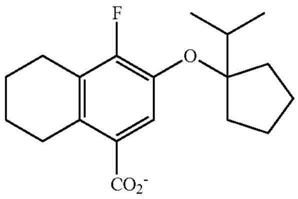
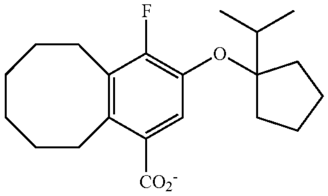
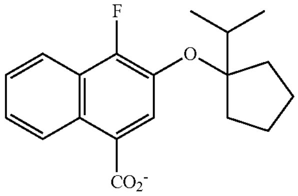
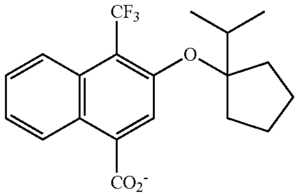
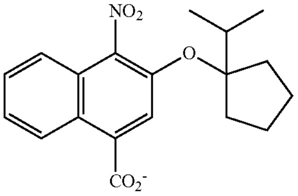
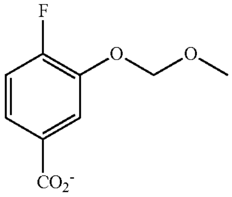
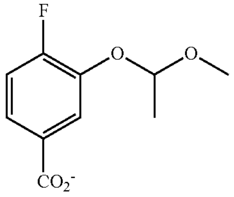
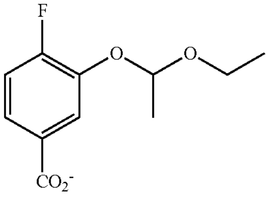
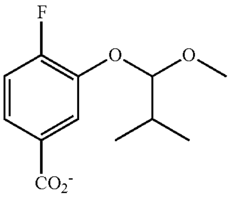
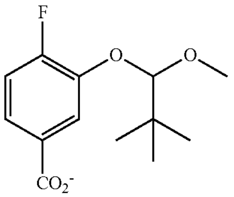
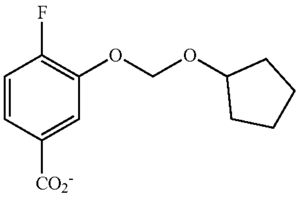
-continued
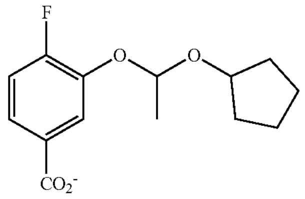
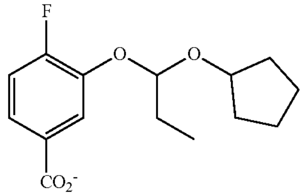
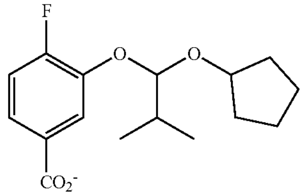
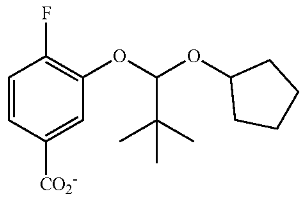
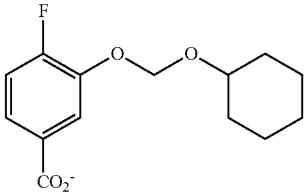
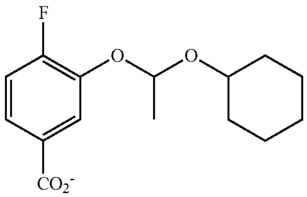
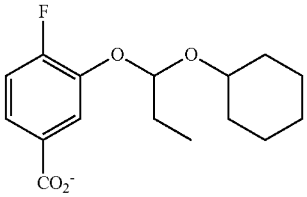
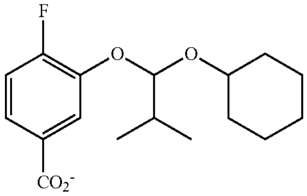

-continued
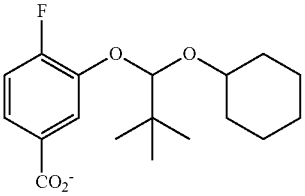
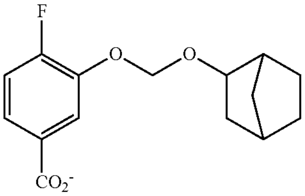
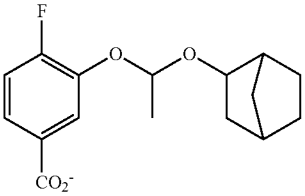
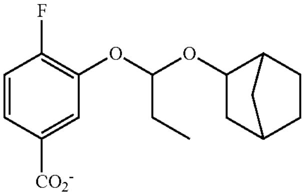
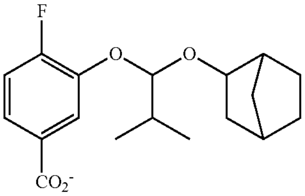
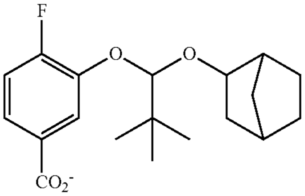
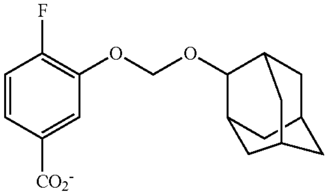
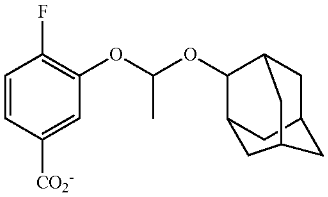
-continued
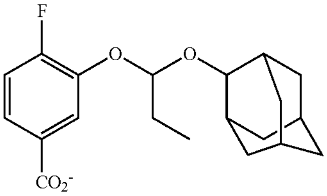
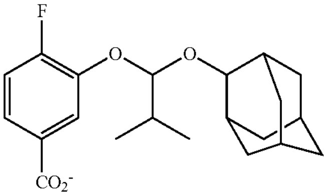
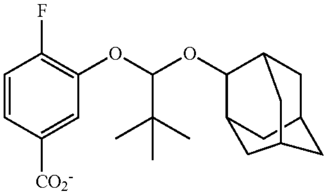
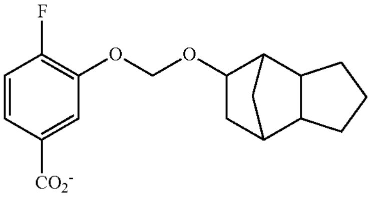
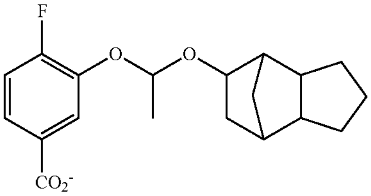
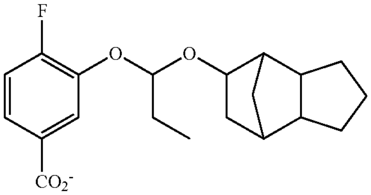
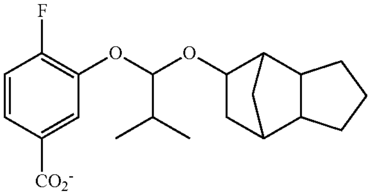
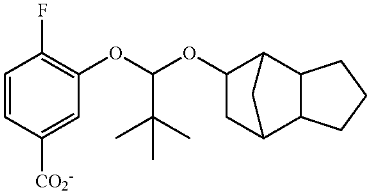

-continued
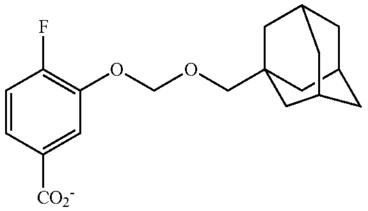
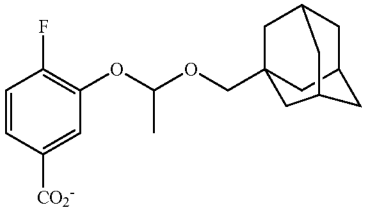
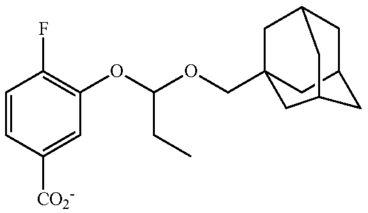
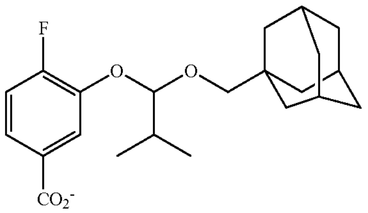
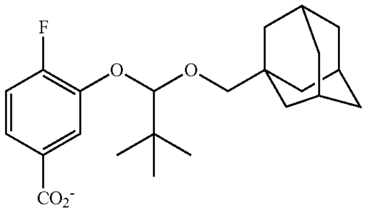
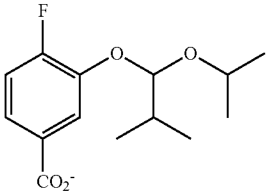
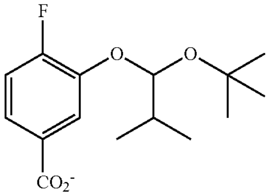
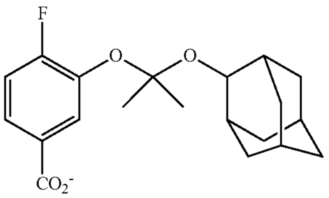
-continued
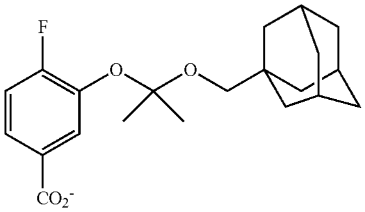
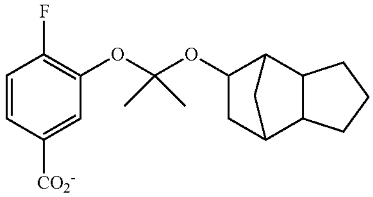
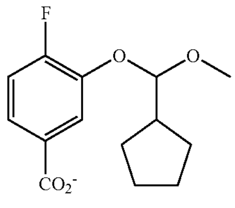
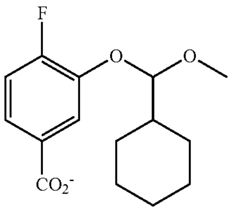
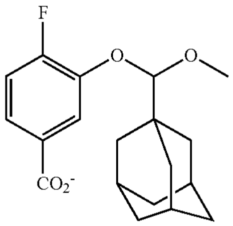
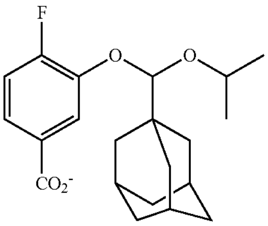
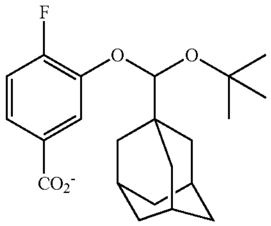
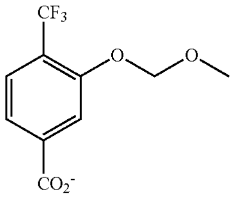
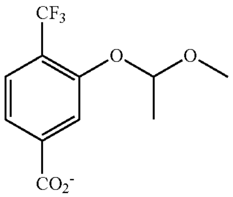
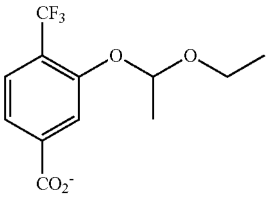
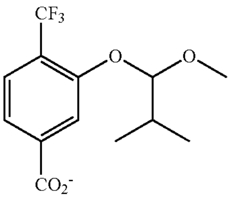
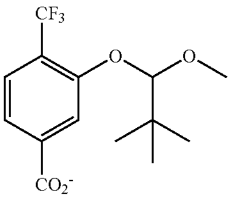
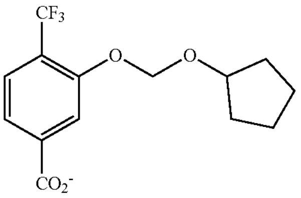

-continued
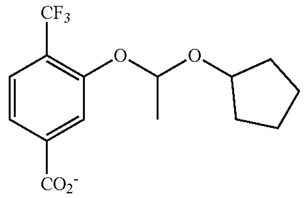
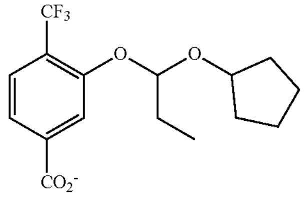
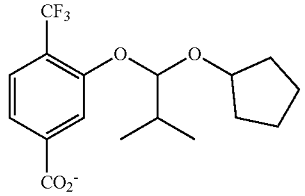
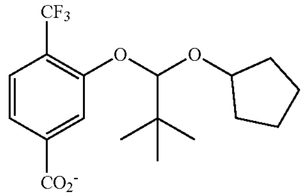
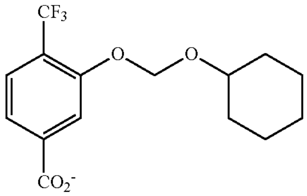
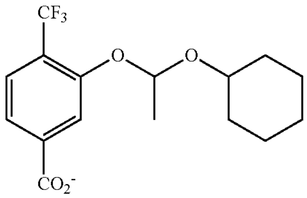
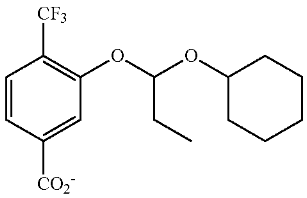
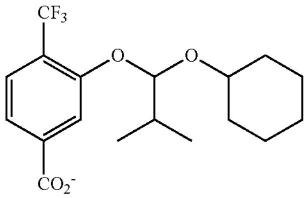
-continued
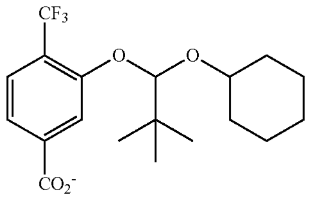
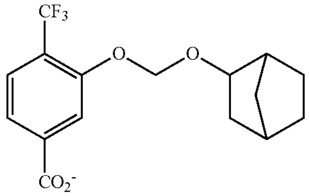
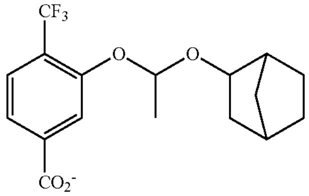
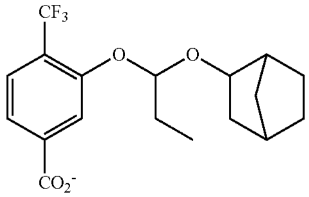
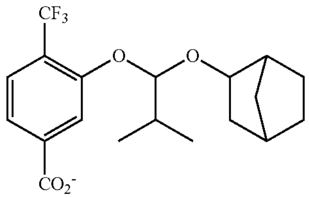
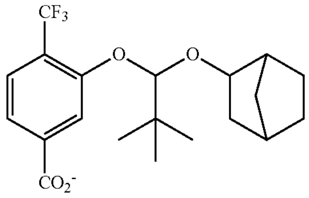
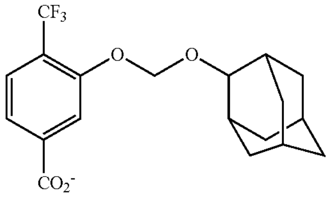
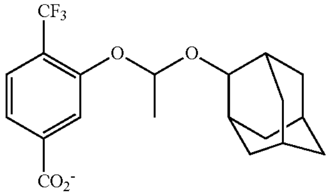

-continued
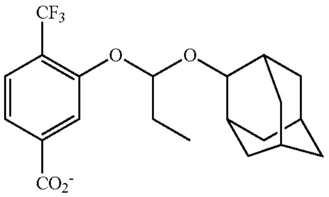
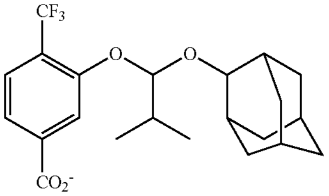
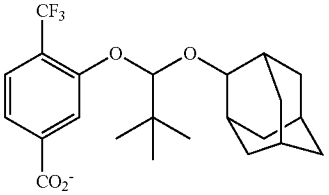
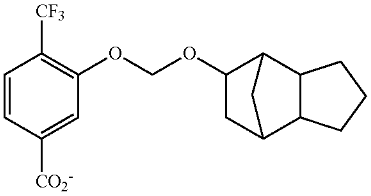
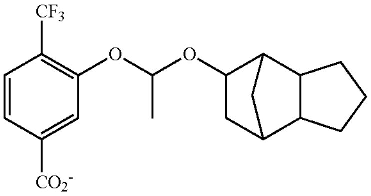
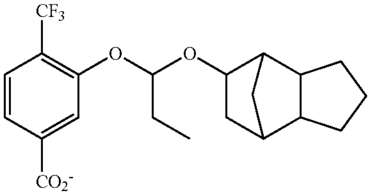
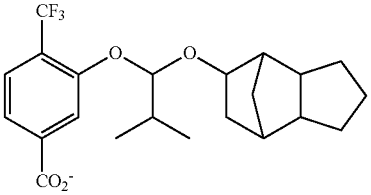
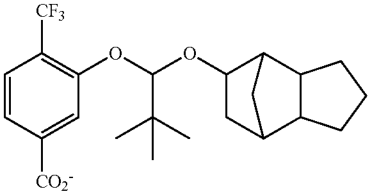
-continued
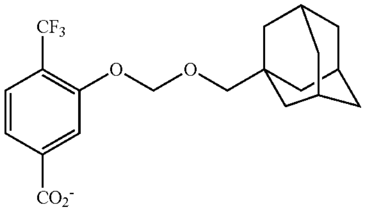
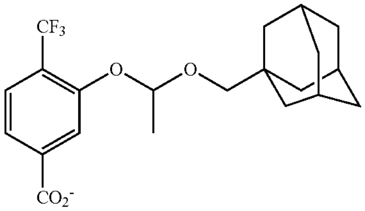
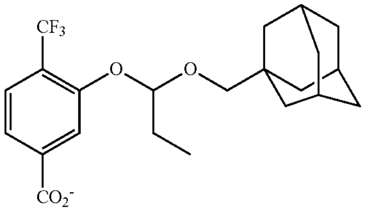
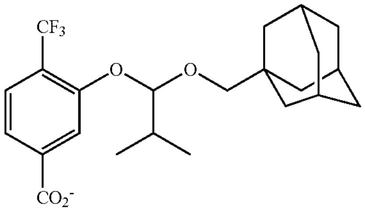
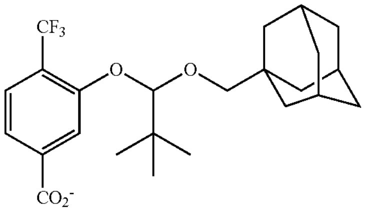
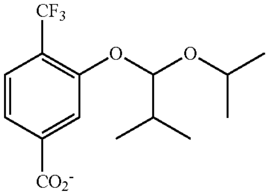
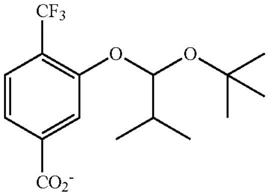
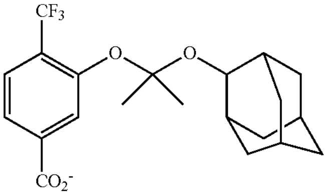

-continued
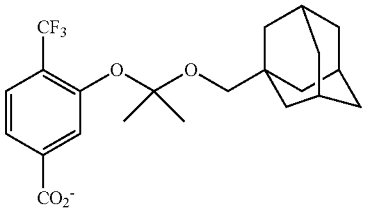
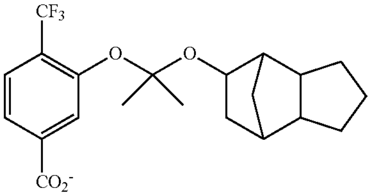
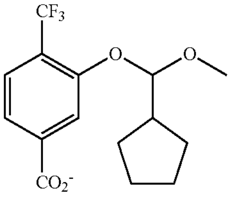
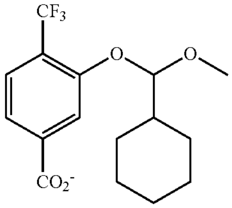
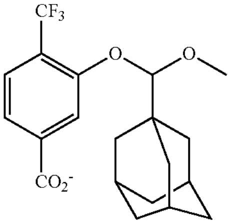
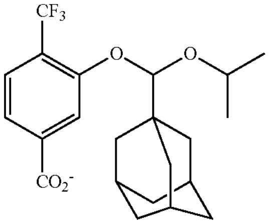
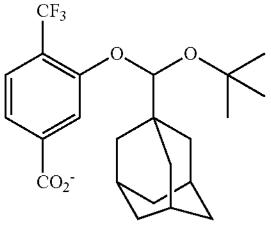
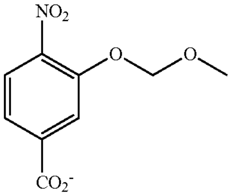
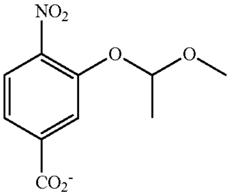
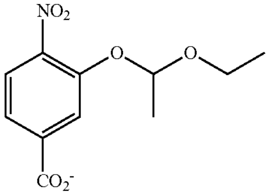
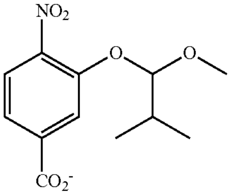
-continued
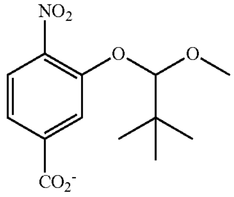
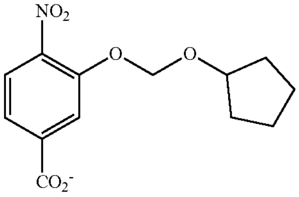
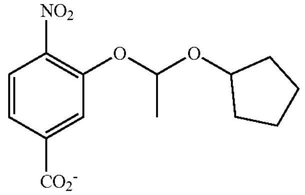
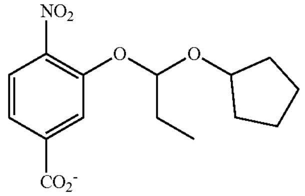
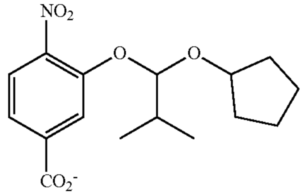
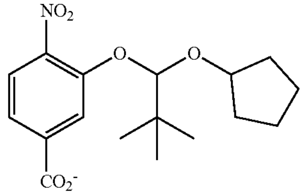
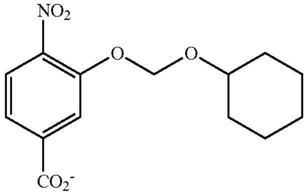
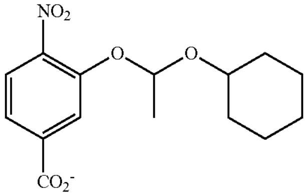
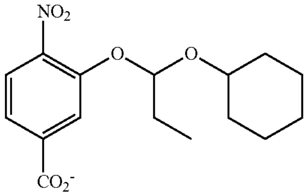

-continued
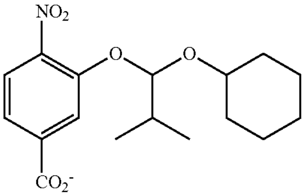
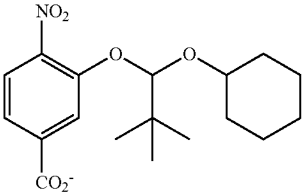
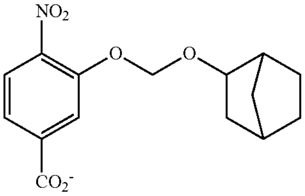
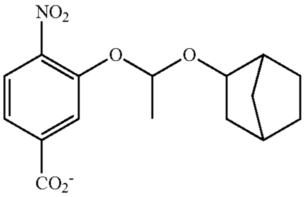
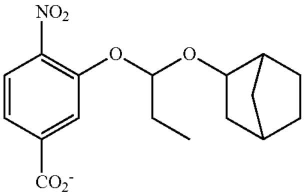
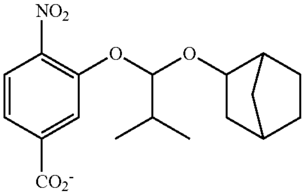
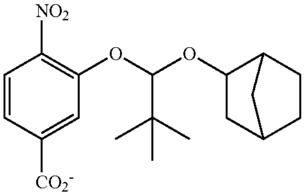
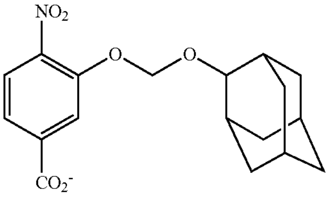
-continued
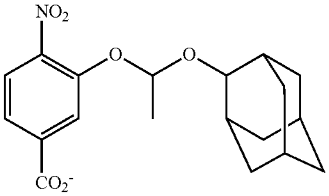
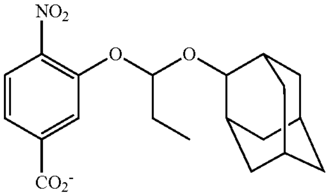
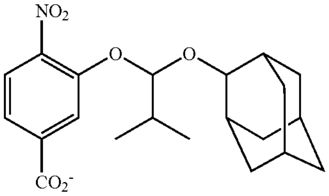
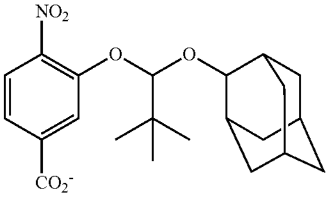
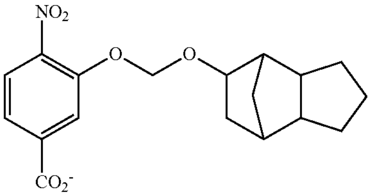
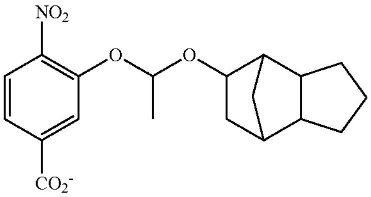
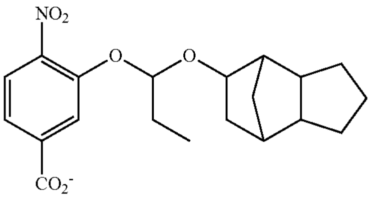
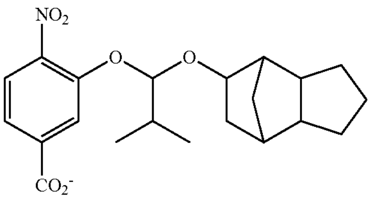

-continued
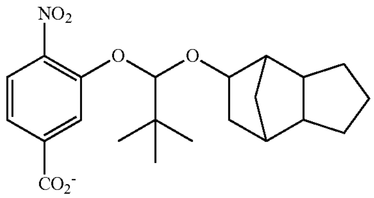
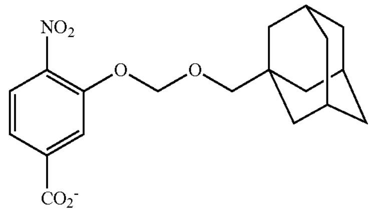
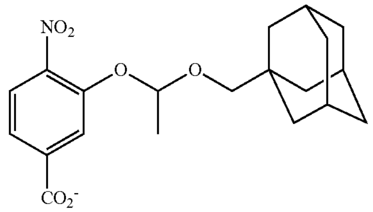
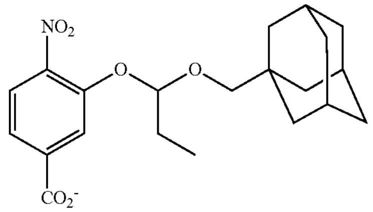
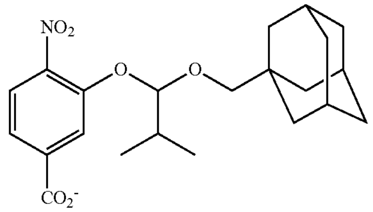
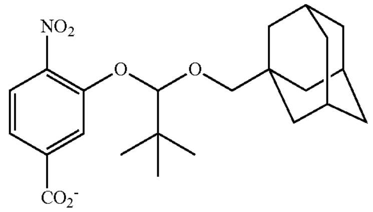
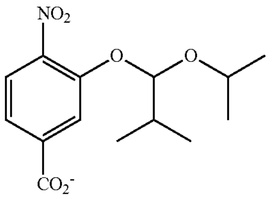
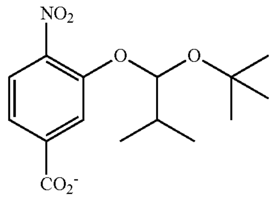
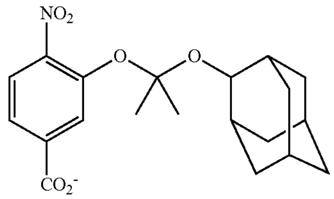
-continued
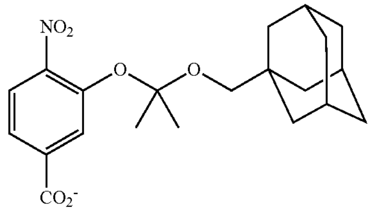
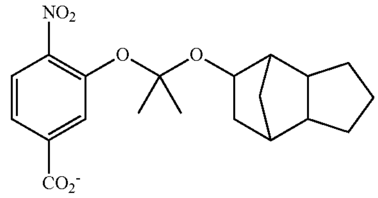
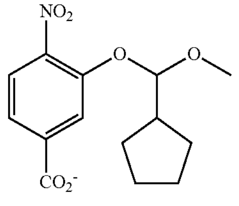
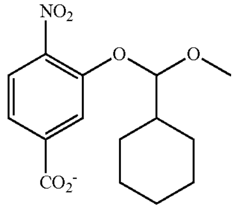
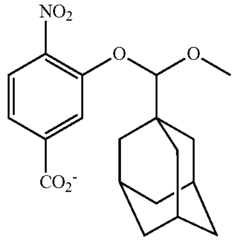
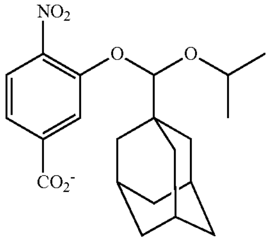
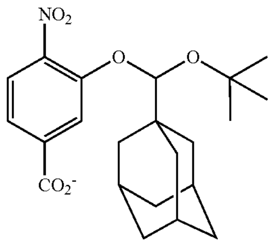
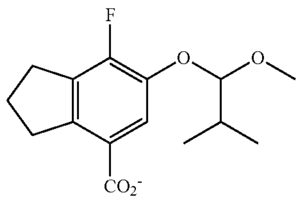
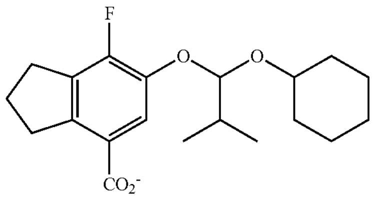
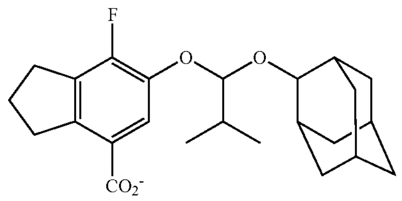
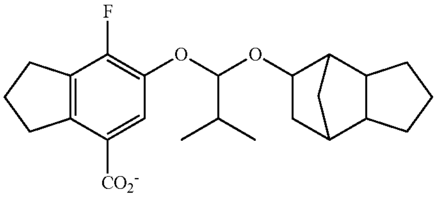

-continued

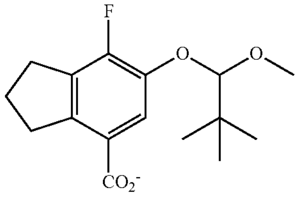

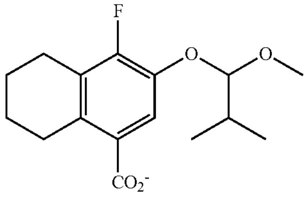

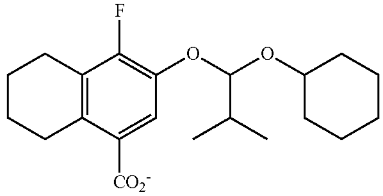

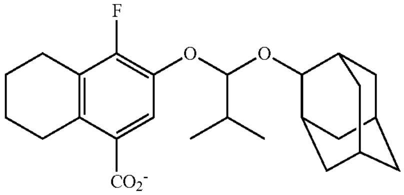

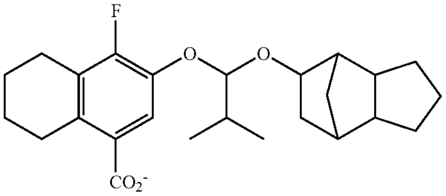

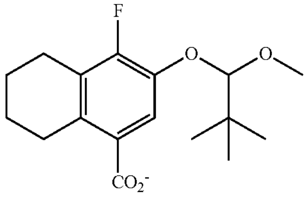

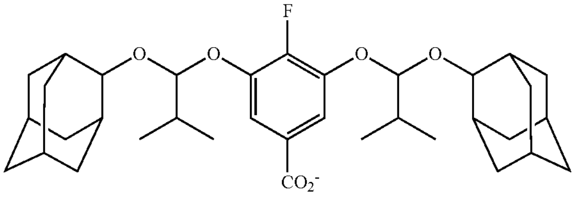

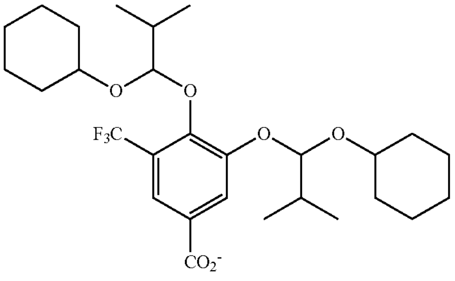

-continued

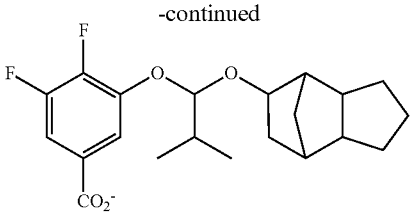

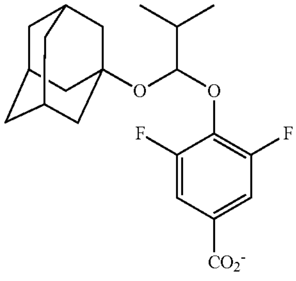

In the general formula (1), $Z^+$ represents an onium cation. Specific examples thereof include a sulfonium cation, an iodonium cation, an ammonium cation, and a phosphonium cation. A sulfonium cation, iodonium cation, and ammonium cation represented below are preferable.

$Z^+$ in the general formula (1) is represented by any one of the following general formulae (Cation-1) to (Cation-3).

(Cation-1)

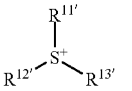

(Cation-2)

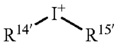

(Cation-3)

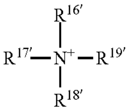

In the general formulae (Cation-1) to (Cation-3), $R^{11'}$ to $R^{19'}$ each independently represent a hydrocarbyl group having 1 to 30 carbon atoms and optionally having a heteroatom. The hydrocarbyl group may be a saturated or unsaturated group, and may be any of linear, branched, and cyclic groups. Specific examples thereof include: alkyl groups, such as a methyl group, an ethyl group, an n-propyl group, an isopropyl group, an n-butyl group, and a tert-butyl group; cyclic saturated hydrocarbyl groups, such as a cyclopropyl group, a cyclopentyl group, a cyclohexyl group, a cyclopropylmethyl group, a 4-methylcyclohexyl group, a cyclohexylmethyl group, a norbornyl group, and an adamantyl group; alkenyl groups, such as a vinyl group, an allyl group, a propenyl group, a butenyl group, and a hexenyl group; cyclic unsaturated hydrocarbyl groups, such as cyclohexenyl group; aryl groups, such as a phenyl group, a naphthyl group, and a thienyl group; aralkyl groups, such as a benzyl group, a 1-phenylethyl group, and a 2-phenylethyl group; and groups obtained by combining these groups. The hydrocarbyl group is preferably an aryl group. A part of hydrogen atoms in the hydrocarbyl group is optionally substituted with a group having a heteroatom such as an oxygen atom, a sulfur atom, a nitrogen atom, and a halogen atom. Between carbon atoms of these groups, a group having a heteroatom such as an oxygen atom, a sulfur atom, and a nitrogen atom is optionally interposed. As a result, optionally contained are a hydroxy group, a cyano group, a carbonyl group, an ether bond, an ester bond, a sulfonate ester bond, a carbonate bond, a lactone ring, a sultone ring, a carboxylic anhydride, a haloalkyl group, etc.

$R^{11'}$ and $R^{12'}$ are optionally bonded to each other to form a ring together with the sulfur atom to which these groups are bonded. In this case, examples of the sulfonium cation represented by the formula (Cation-1) include the following cations.

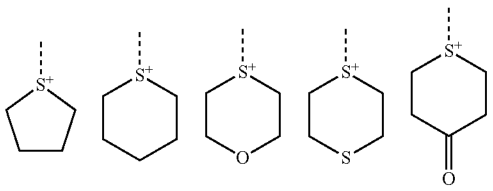

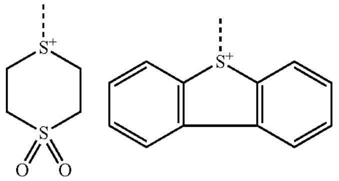

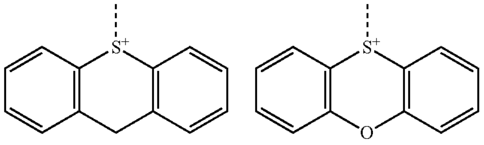

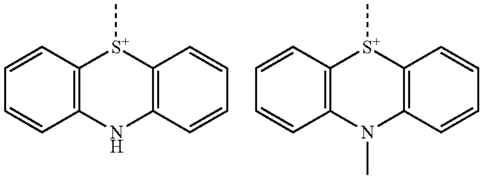

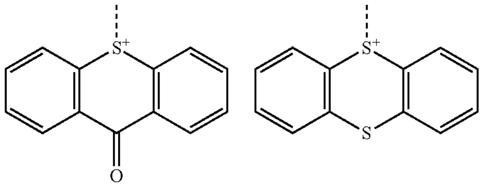

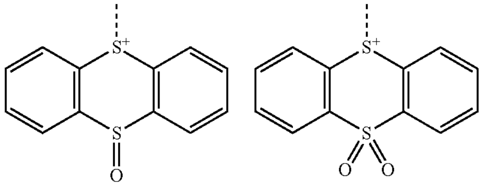

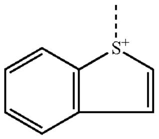

In the formulae, a broken line represents an attachment point to $R^{13}$.

Examples of the cation of the sulfonium salt represented by the formula (Cation-1) include the following cations, but the cation is not limited thereto.

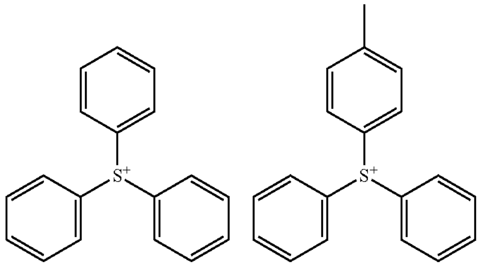

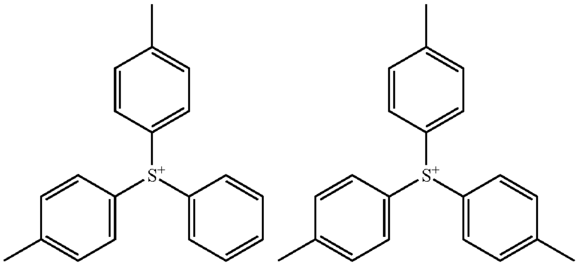

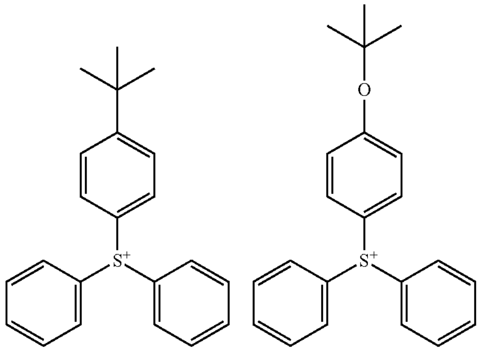

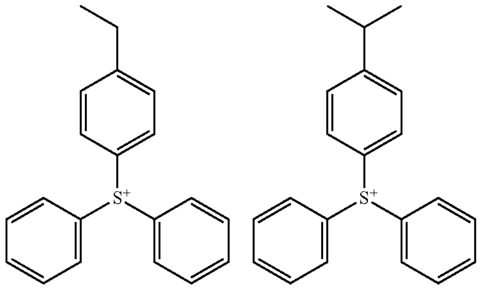

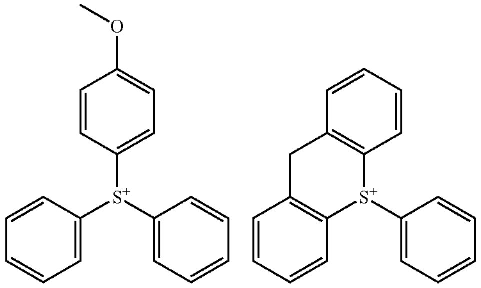

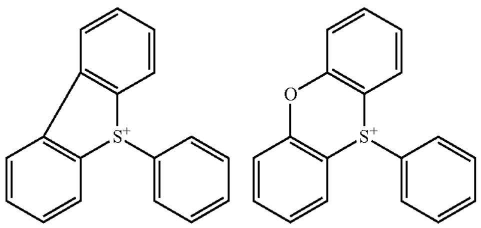

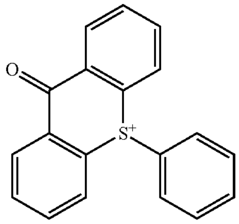
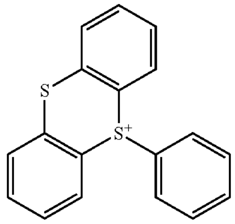
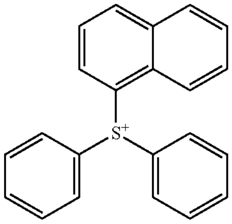
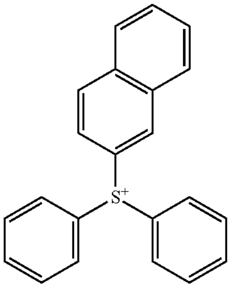
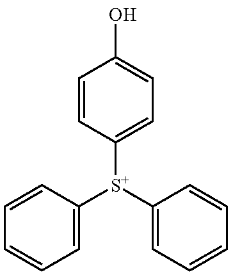
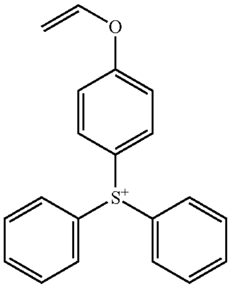
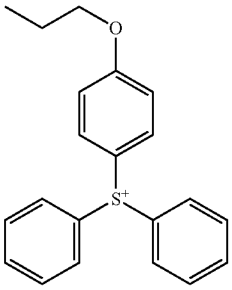
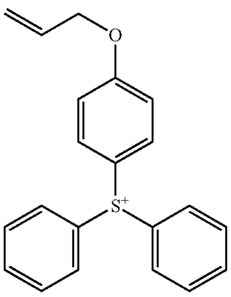
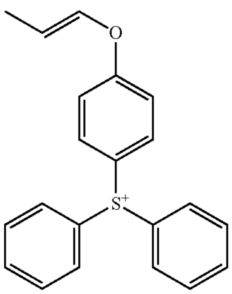
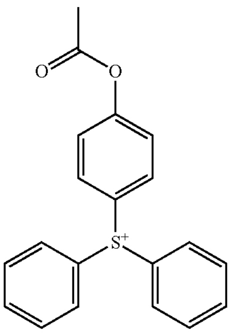
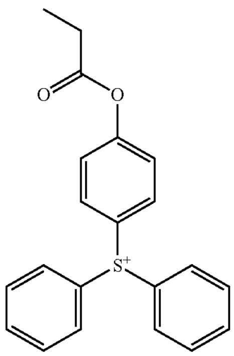
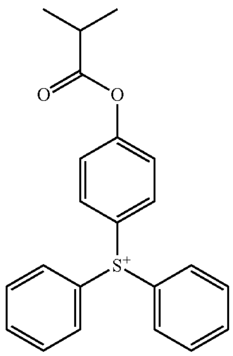
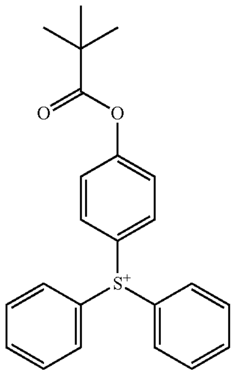
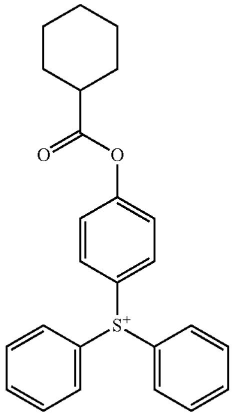
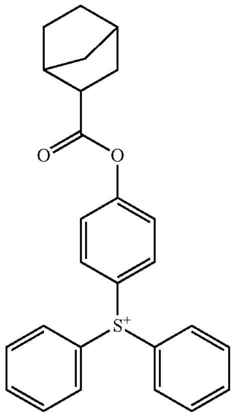
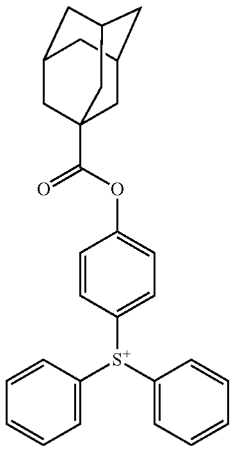
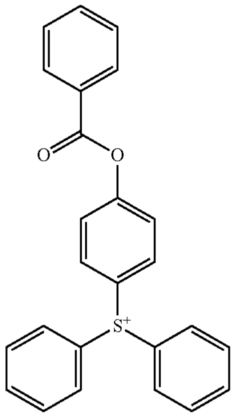
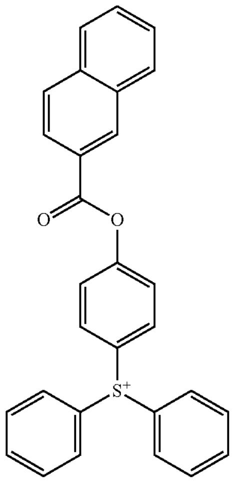

-continued
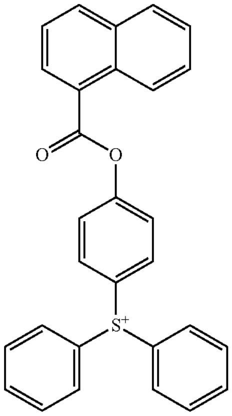
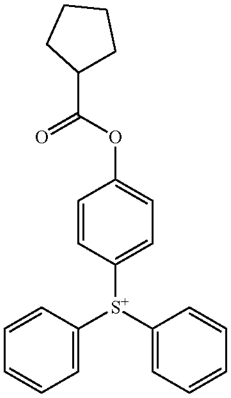
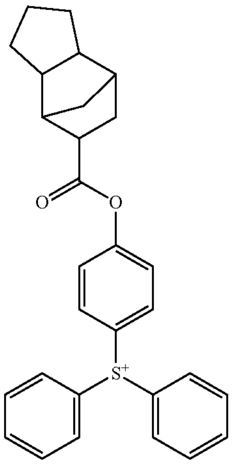
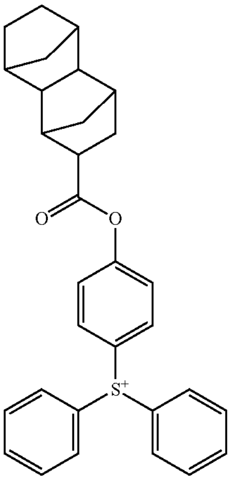
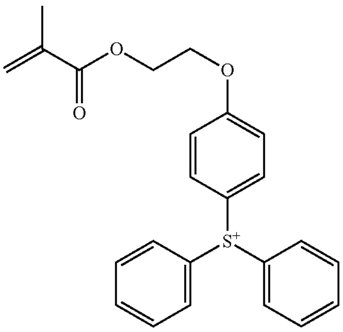
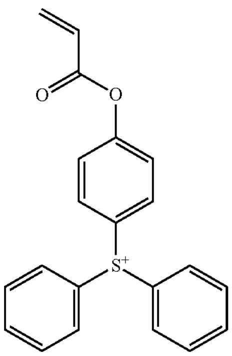
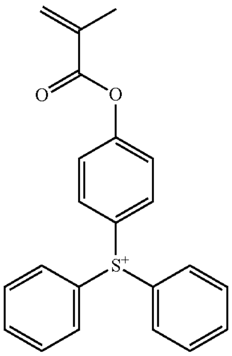
-continued
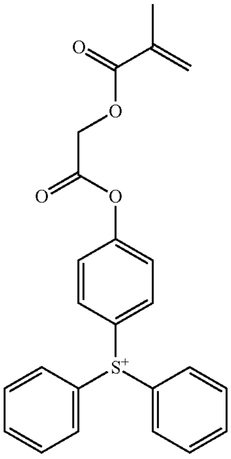
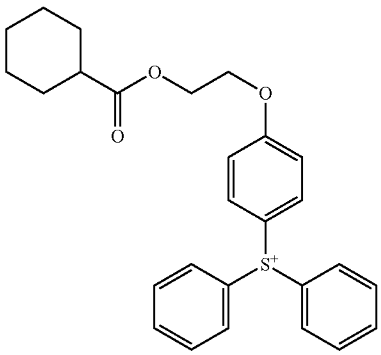
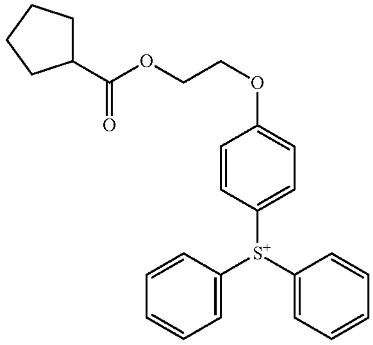
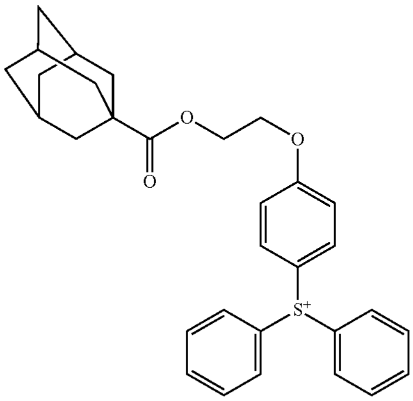

-continued
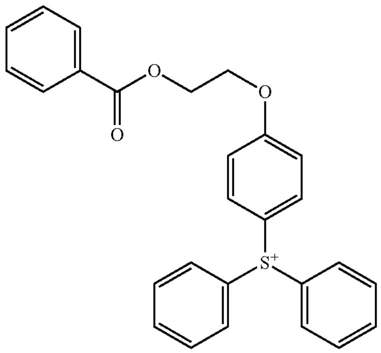
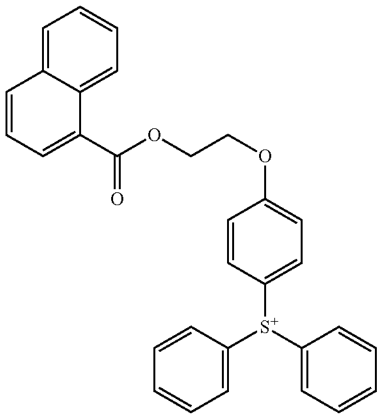
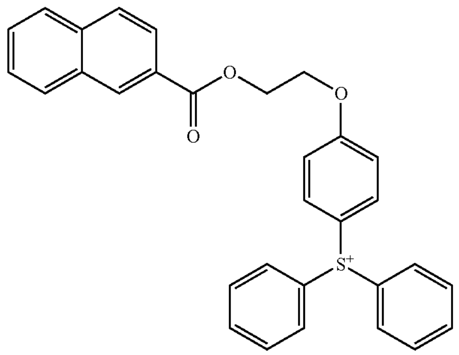
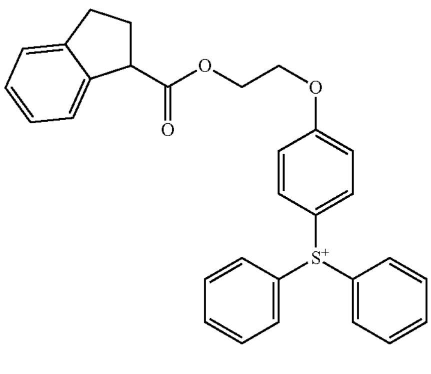
-continued
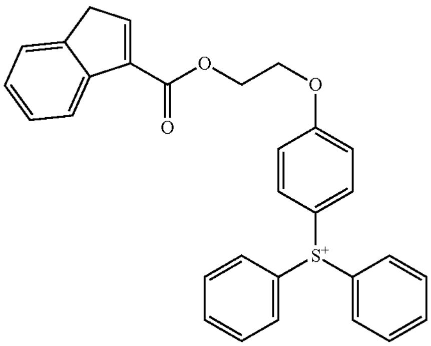
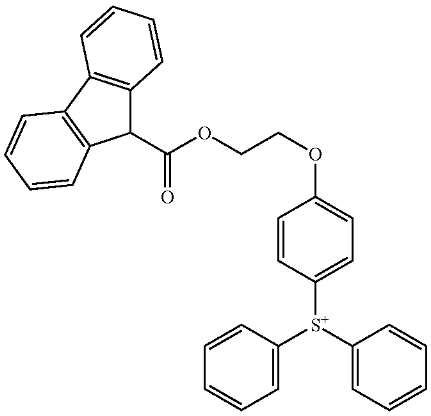
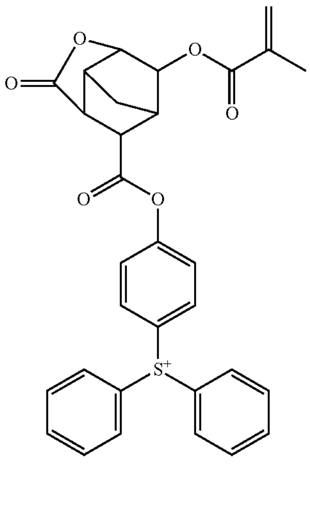
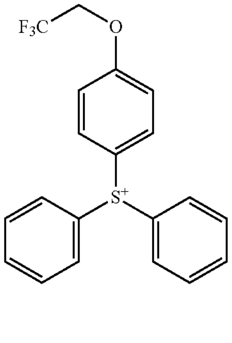
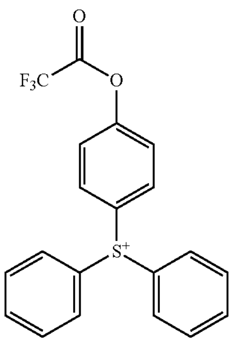
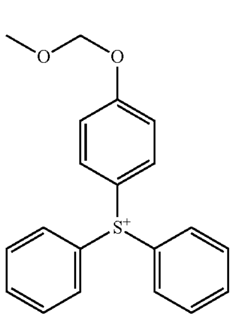

-continued
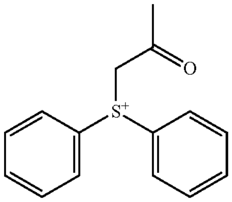
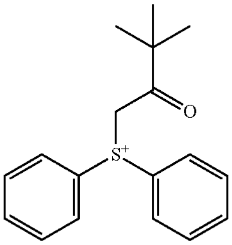
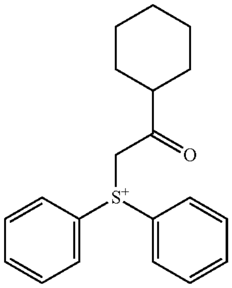
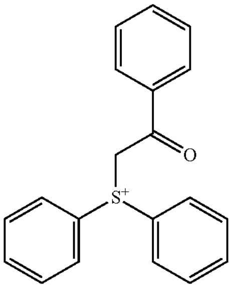
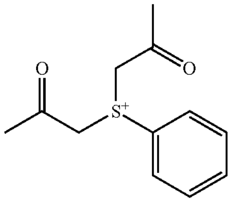
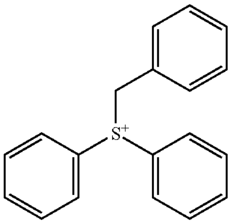
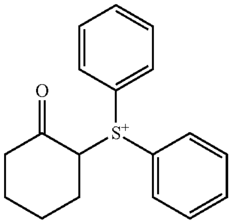
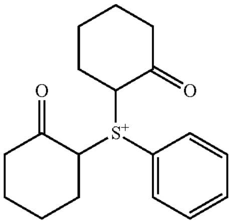
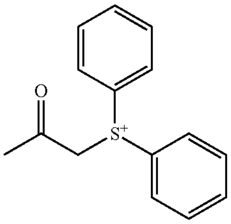
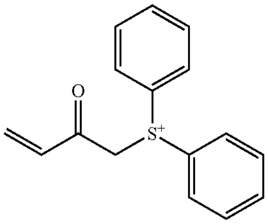
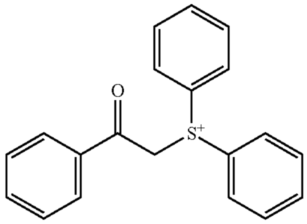
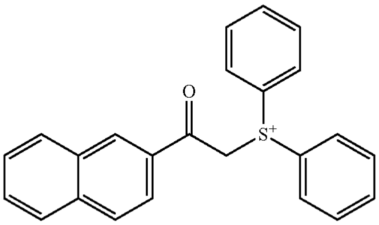
-continued
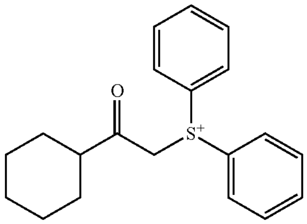
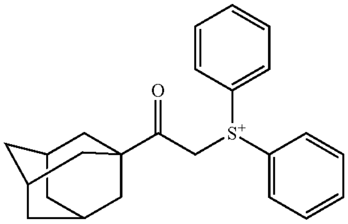
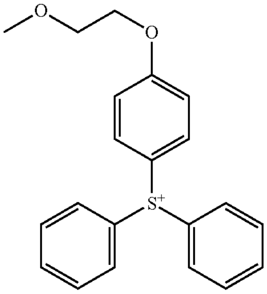
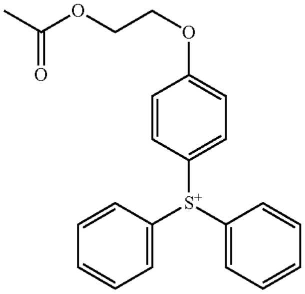
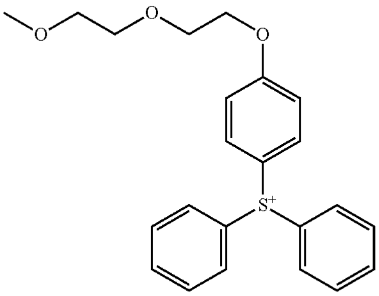
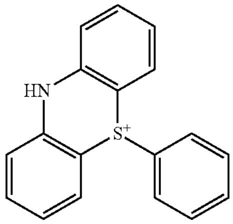
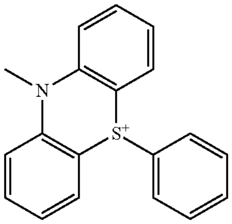
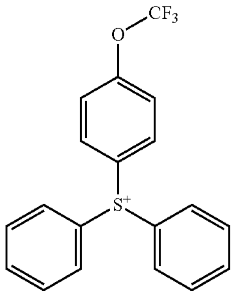
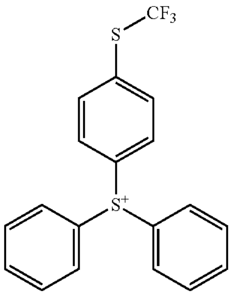

-continued
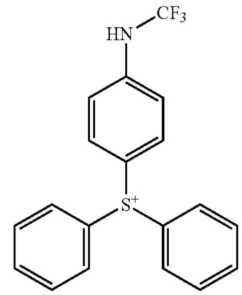
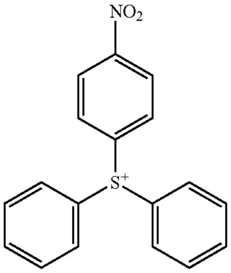
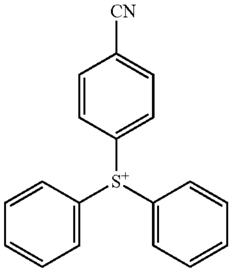
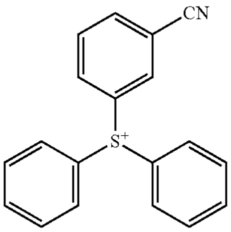
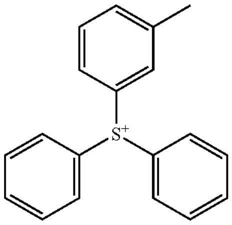
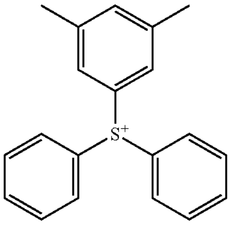
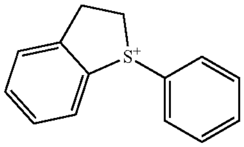
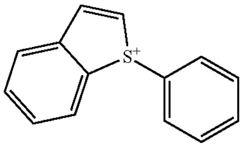
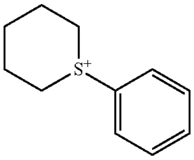
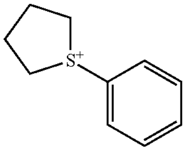
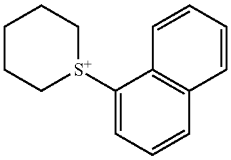
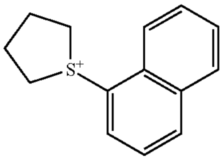
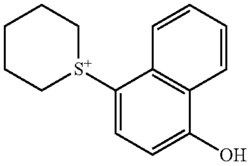
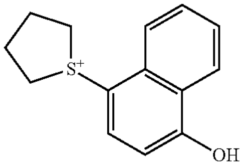
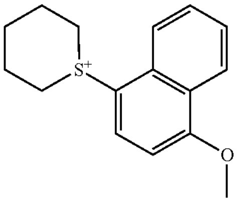
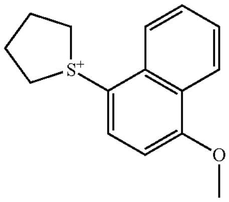
-continued
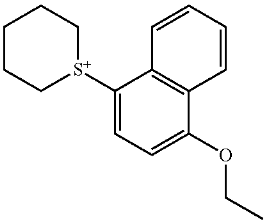
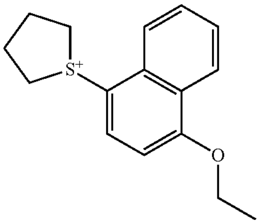
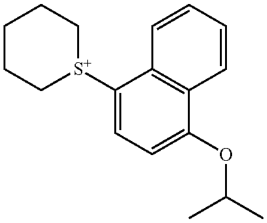
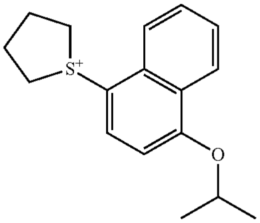
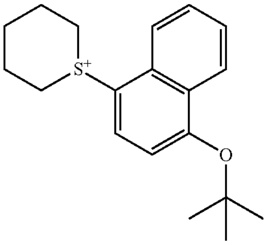
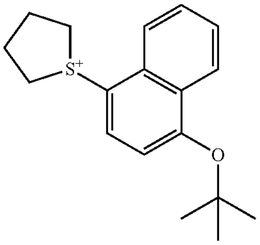
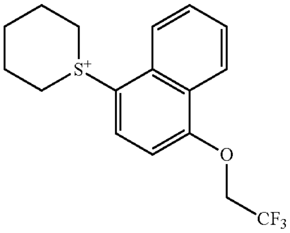
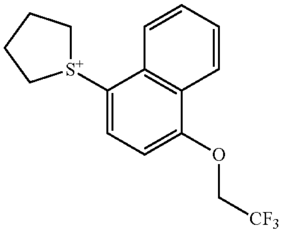
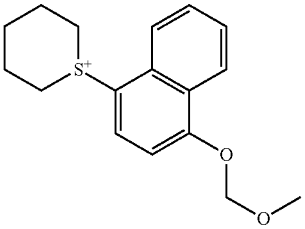
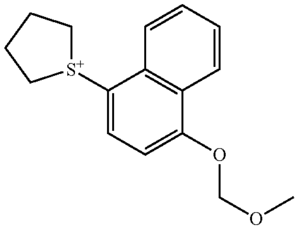
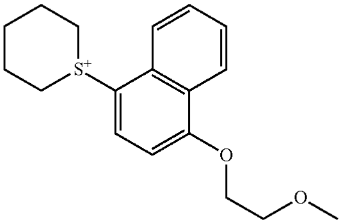

-continued
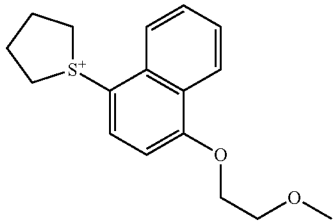
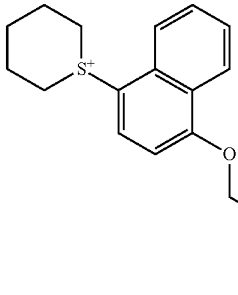
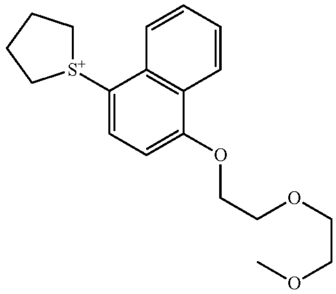
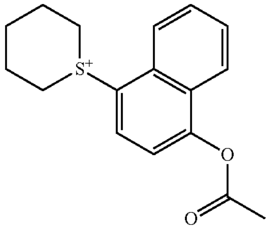
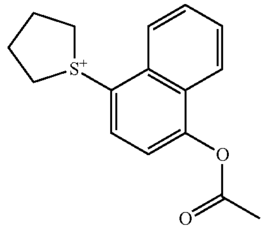
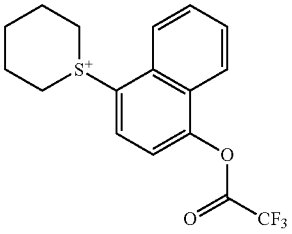
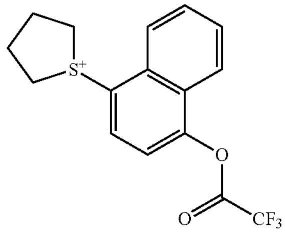
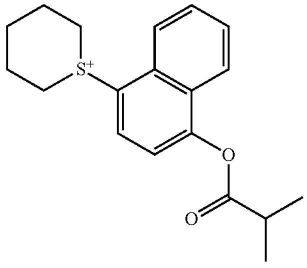
-continued
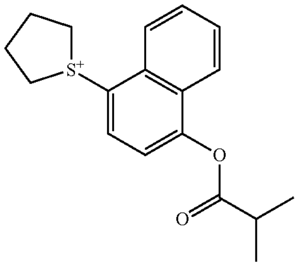
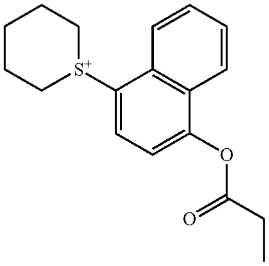
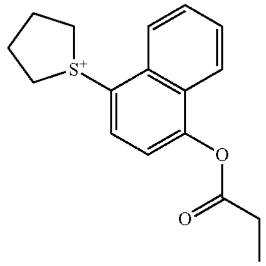
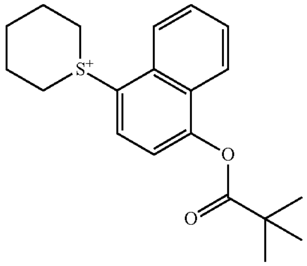
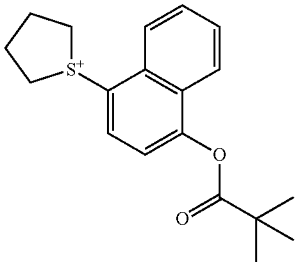
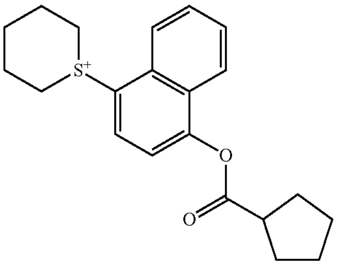
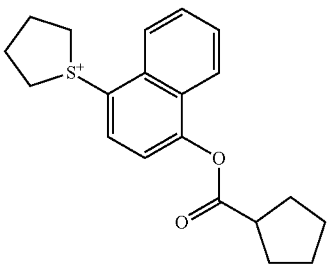

-continued
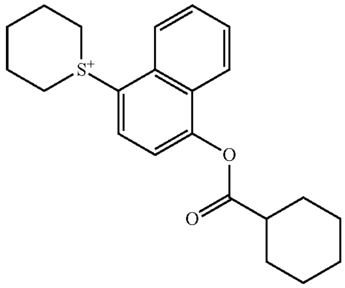
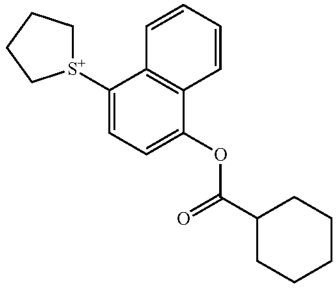
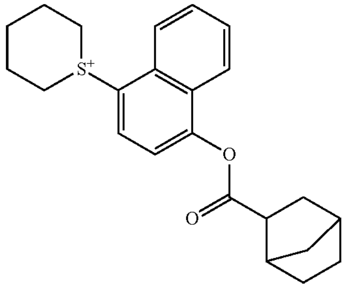
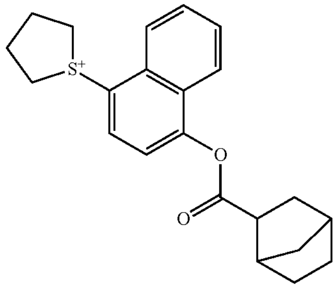
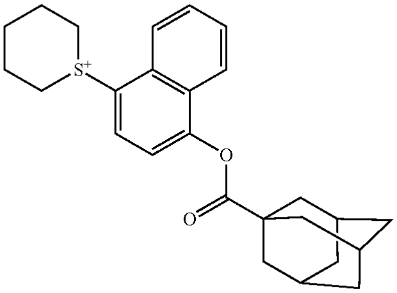
-continued
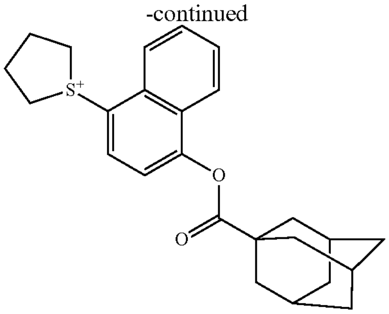
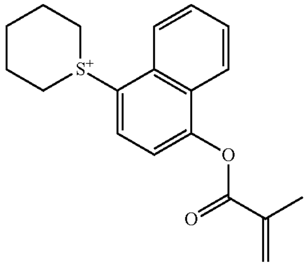
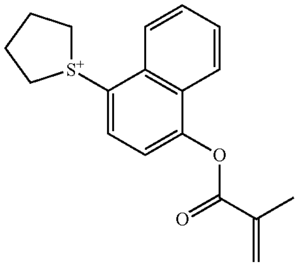
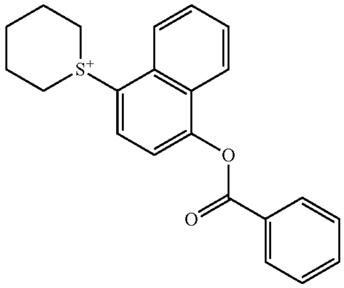
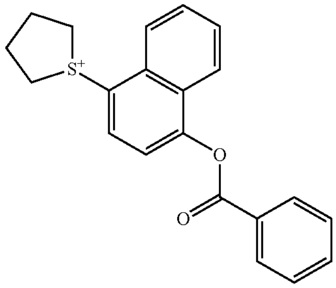
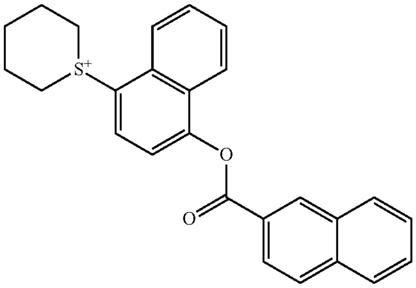

-continued
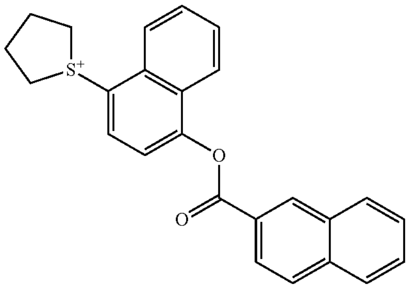
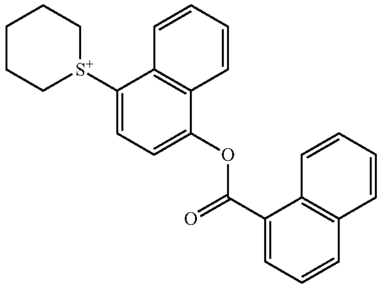
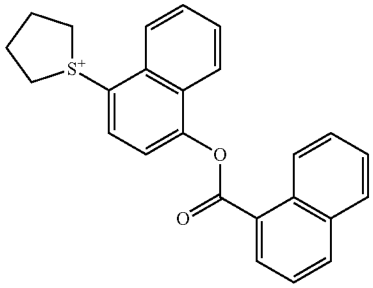
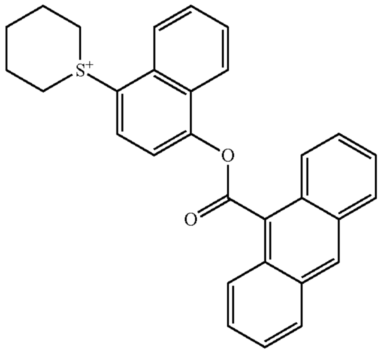
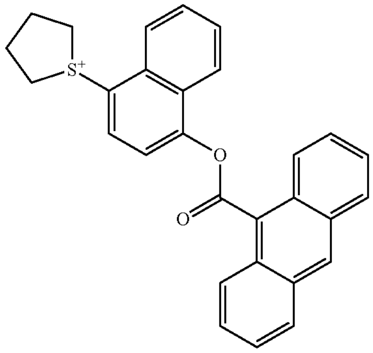
-continued
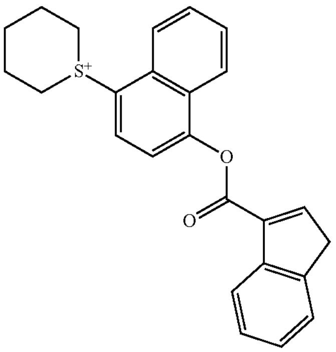
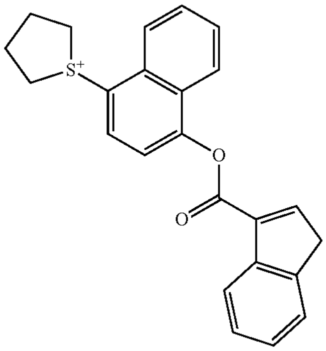
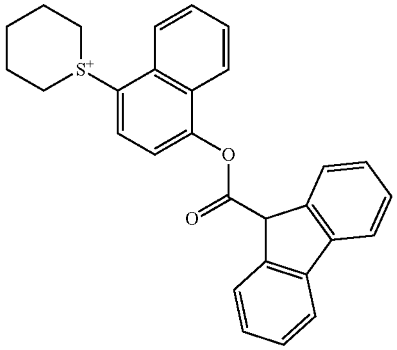
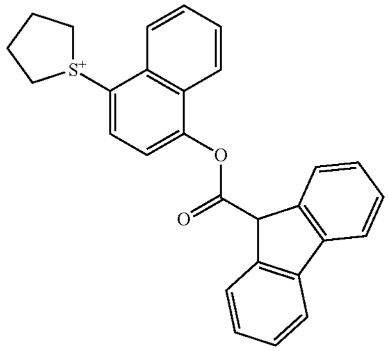
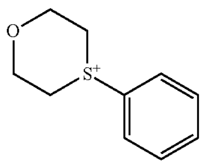
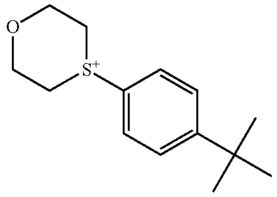

-continued
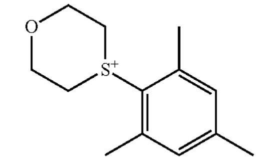
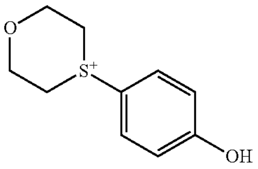
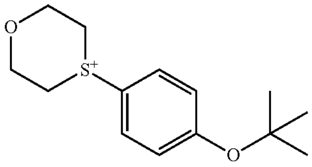
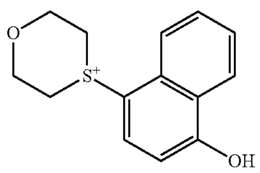
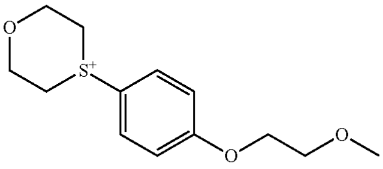
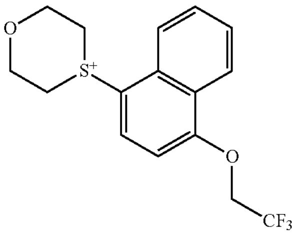
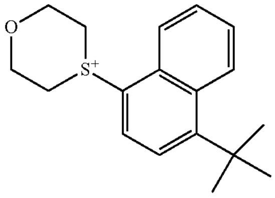
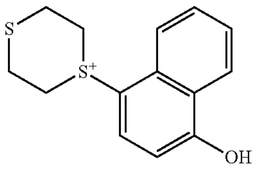
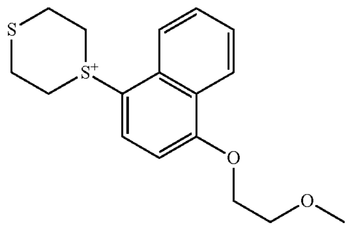
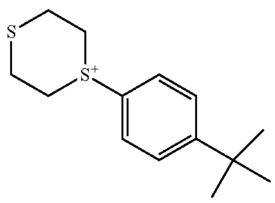
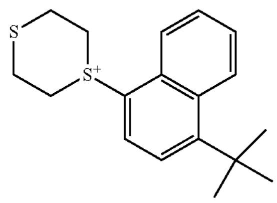
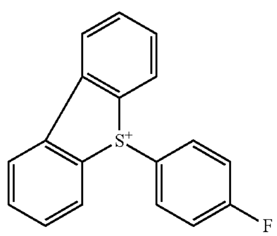
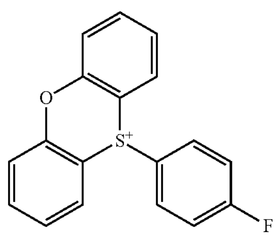
-continued
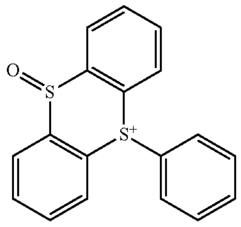
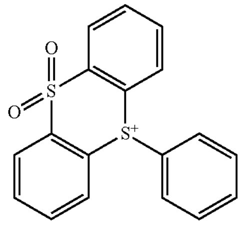
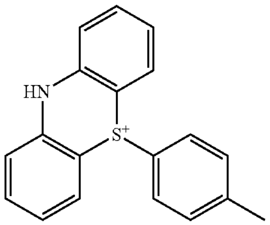
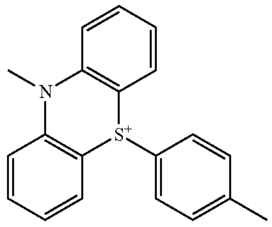
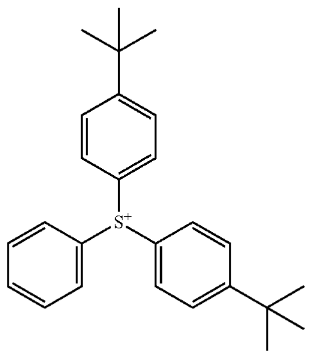
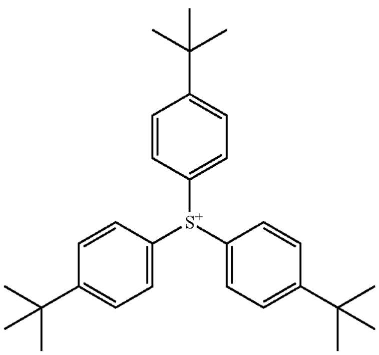
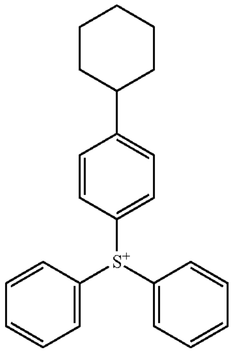

-continued
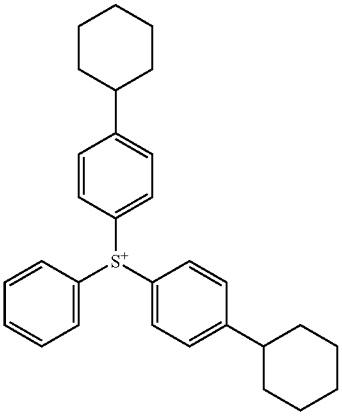
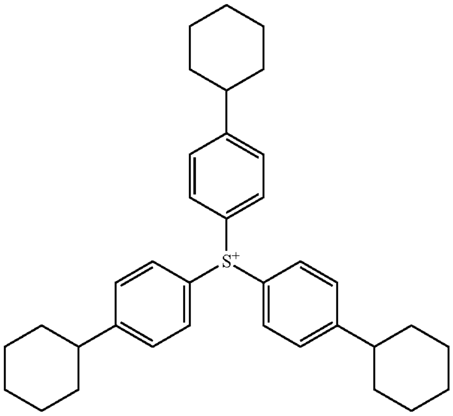
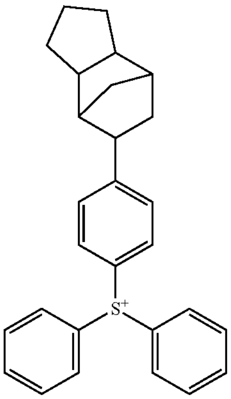
-continued
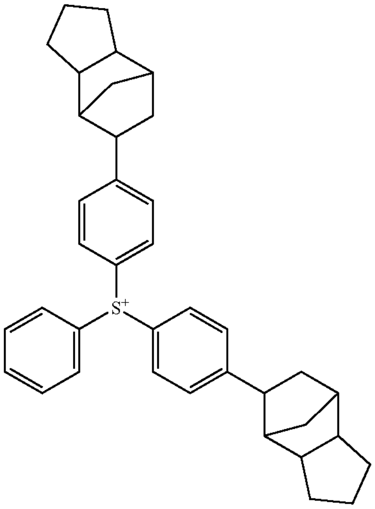
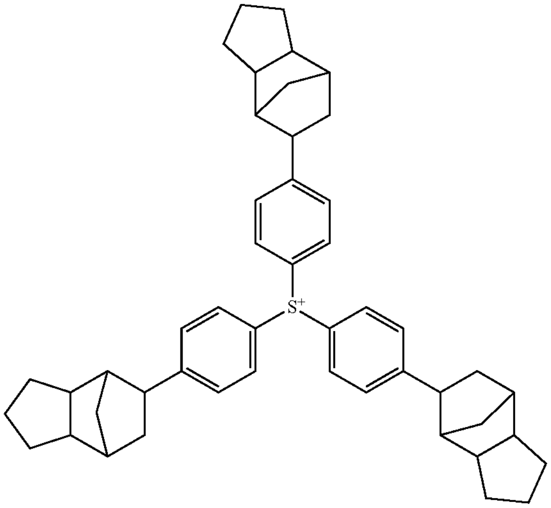
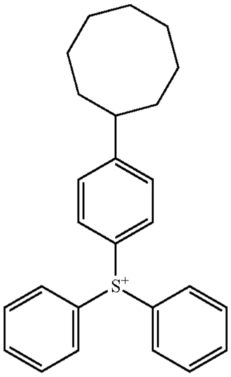

-continued
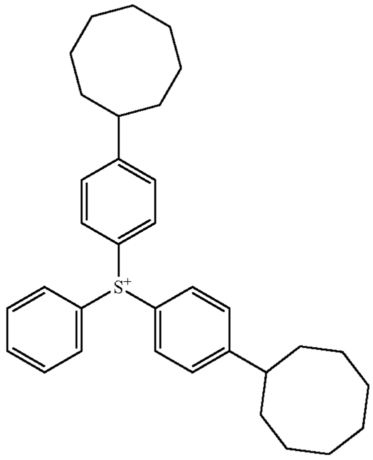
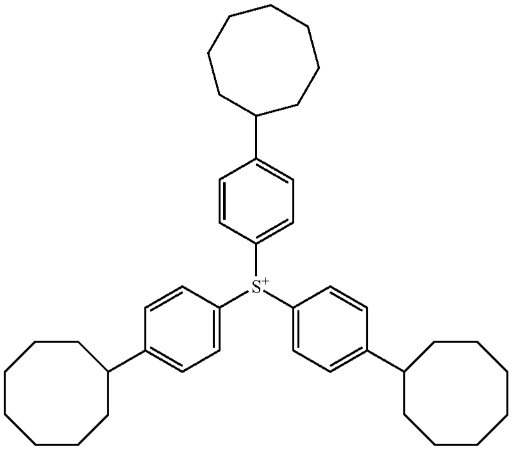
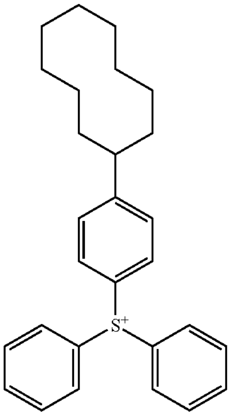
-continued
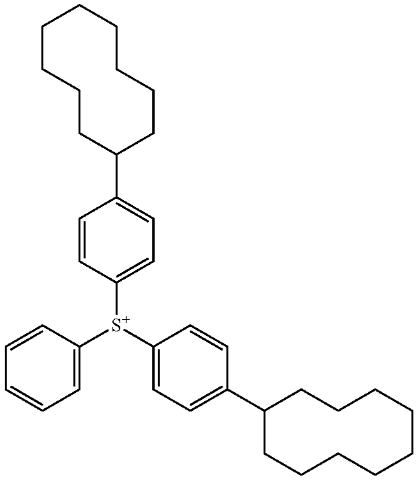
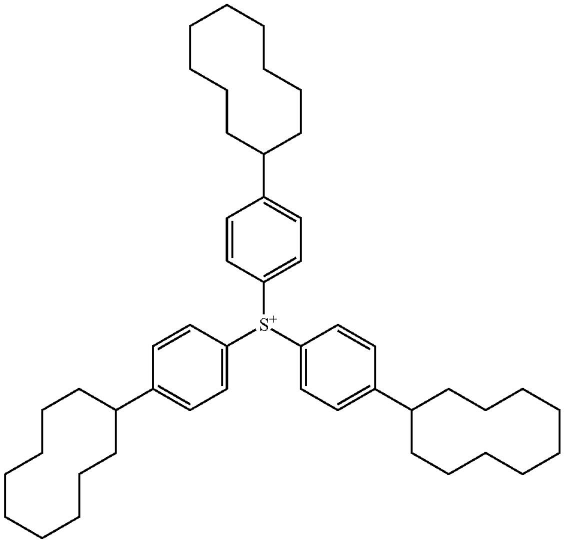
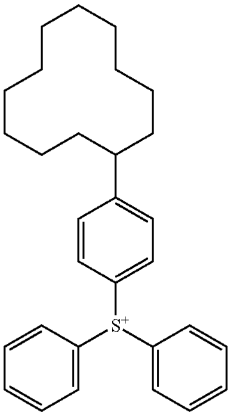

-continued
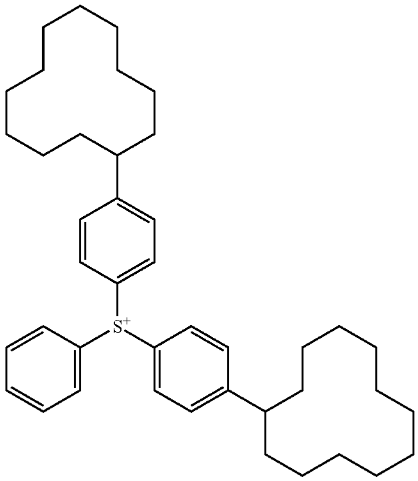
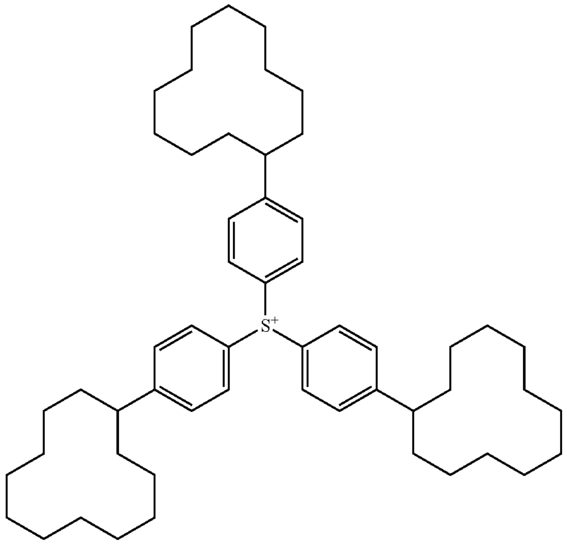
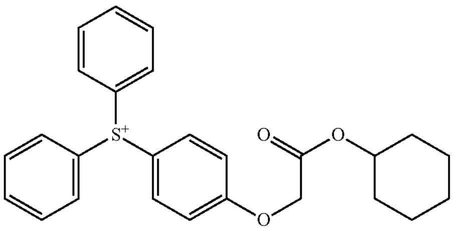
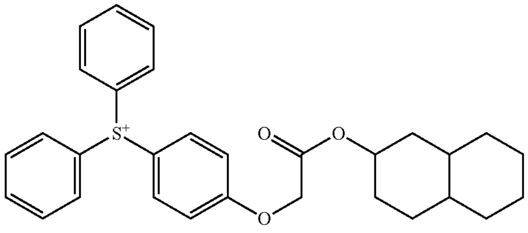
-continued
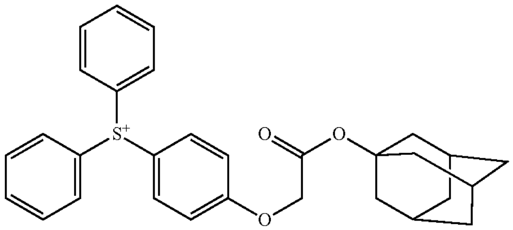
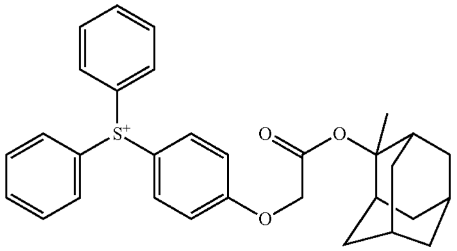
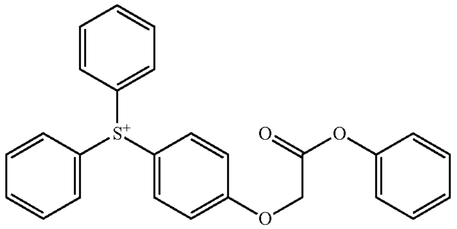
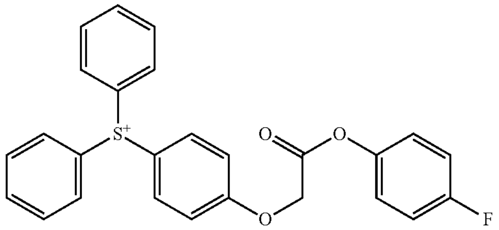
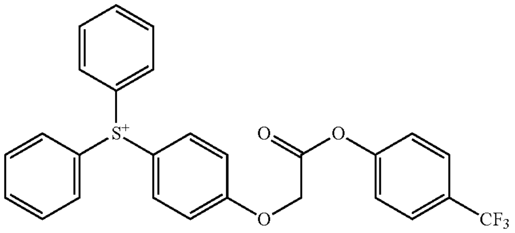
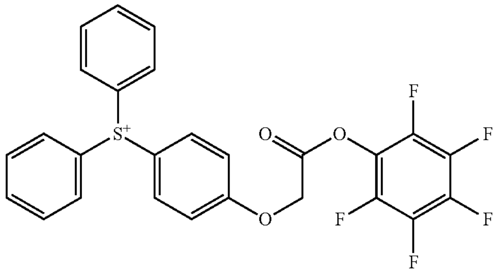 [SMILES: O=C(COc1ccc([S+](c2ccccc2)c2ccccc2)cc1)Oc1c(F)c(F)c(F)c(F)c1F]

-continued
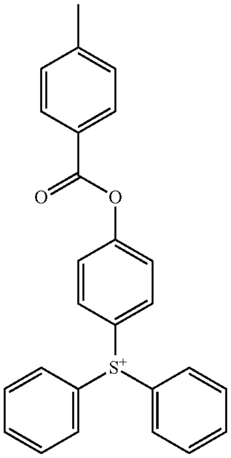
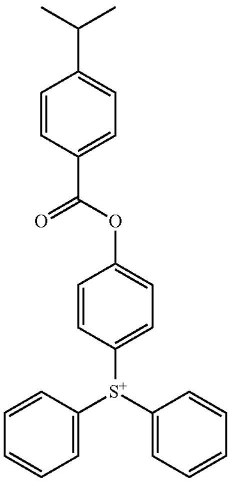
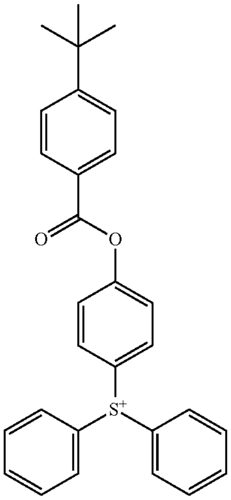
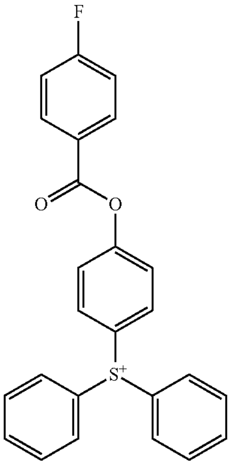
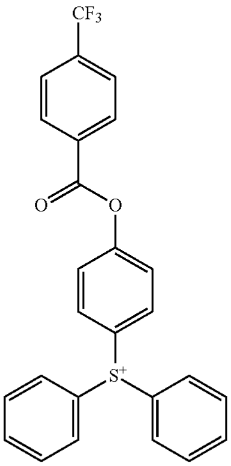
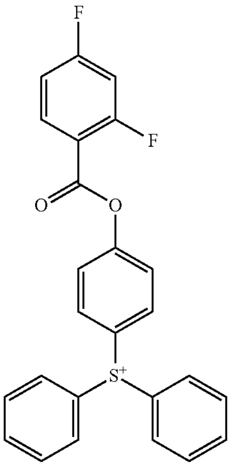
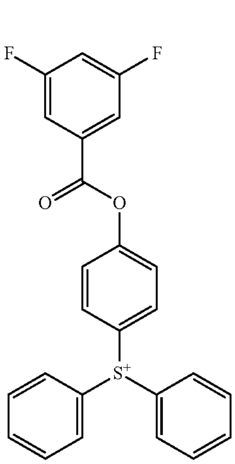
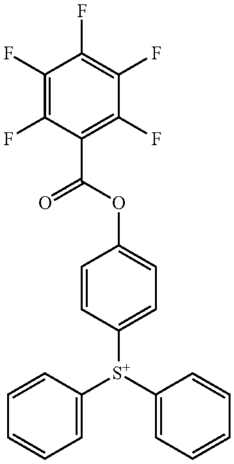
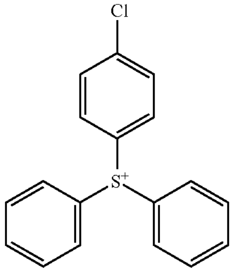
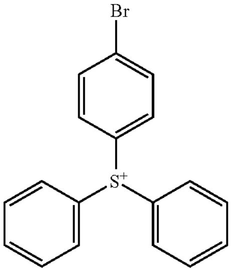
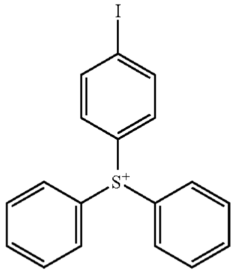
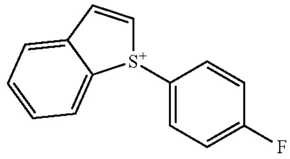
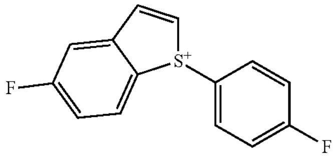
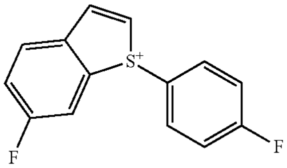
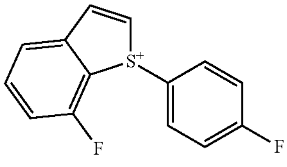
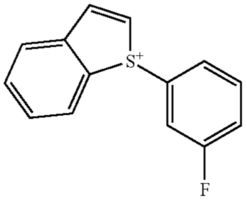
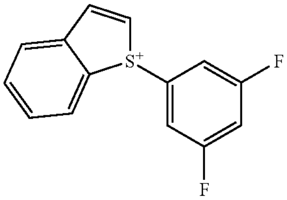
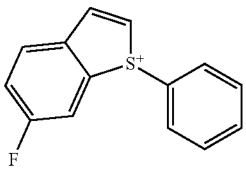
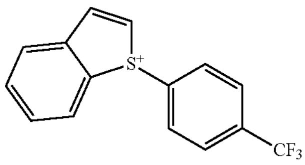

-continued
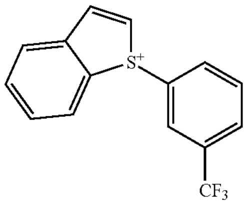
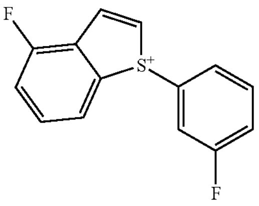
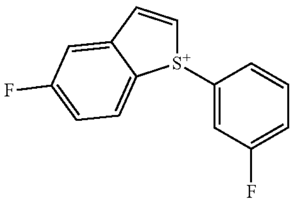
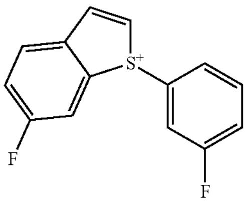
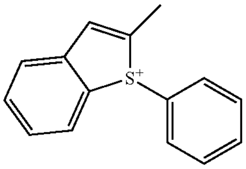
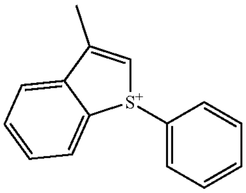
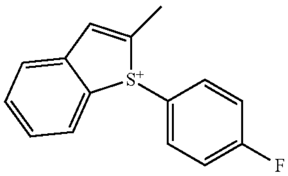
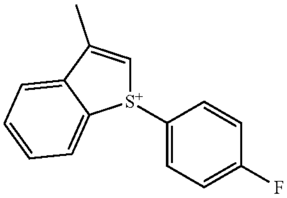
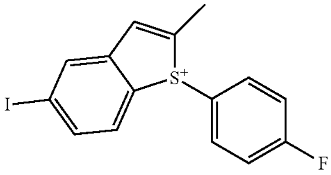
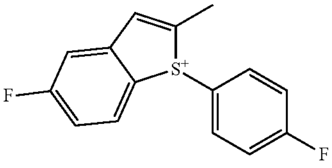
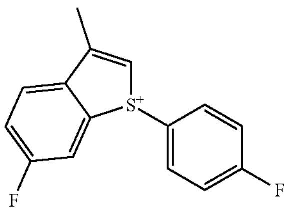
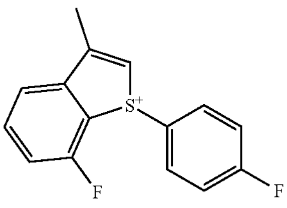
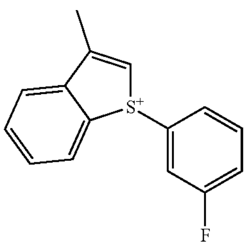
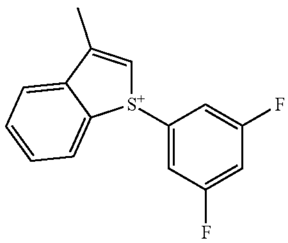
-continued
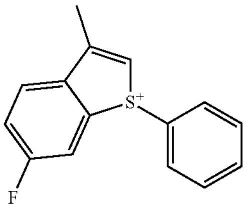
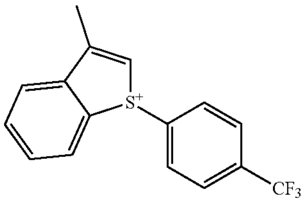
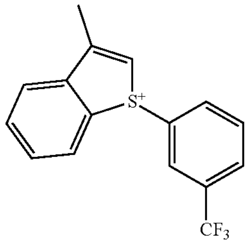
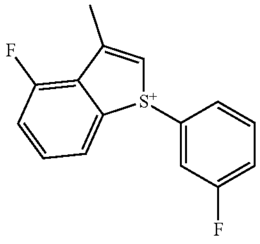
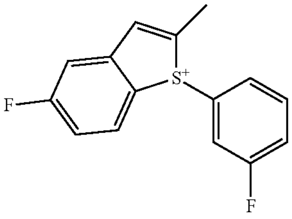
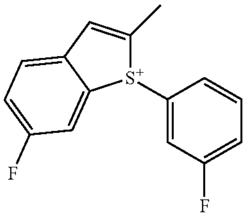
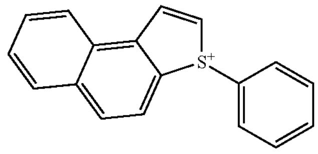
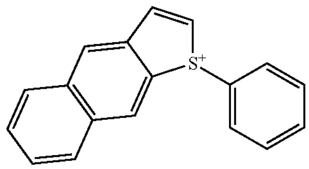
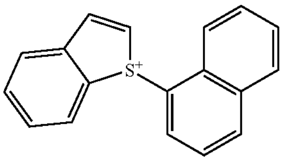
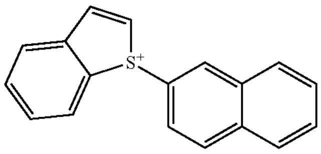
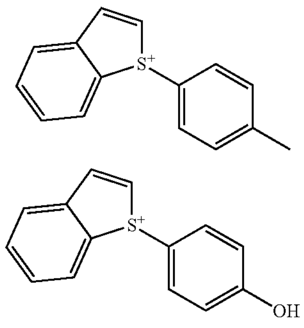

-continued
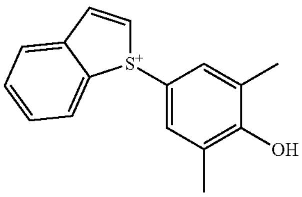
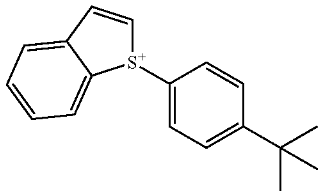
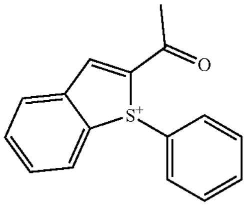
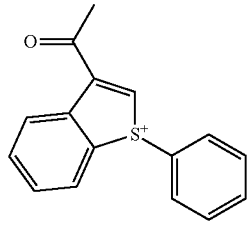
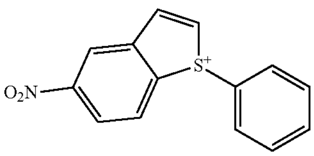
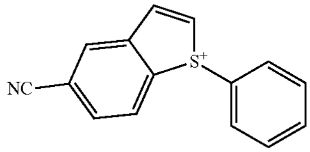
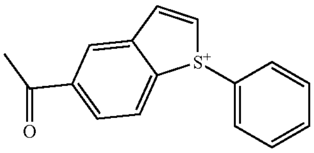
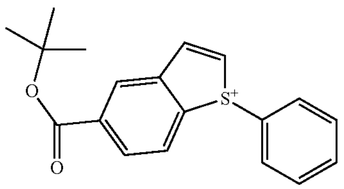
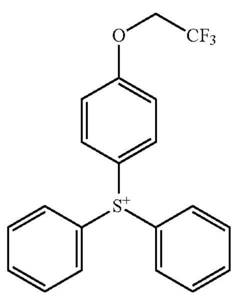
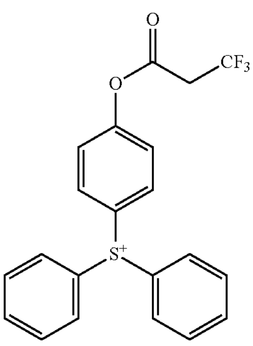
-continued
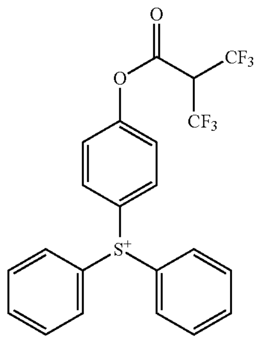
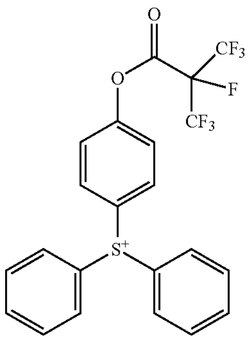
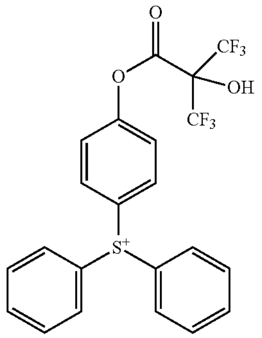
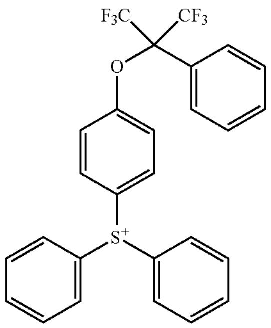
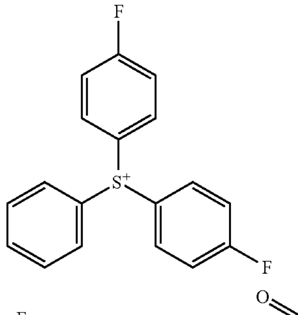
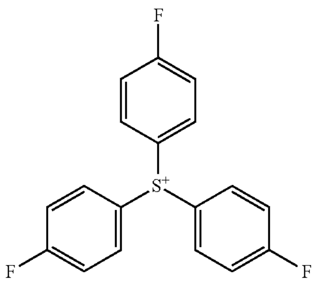
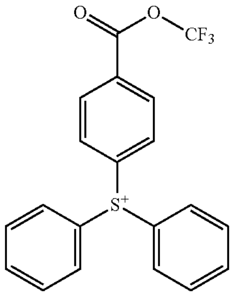
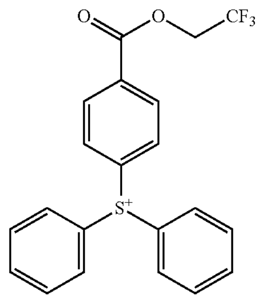
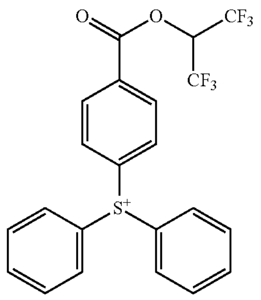

-continued
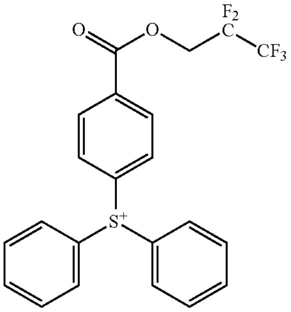
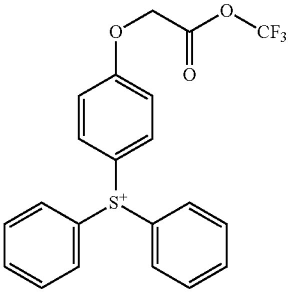
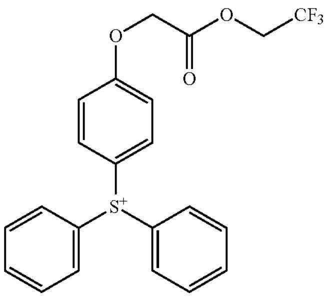
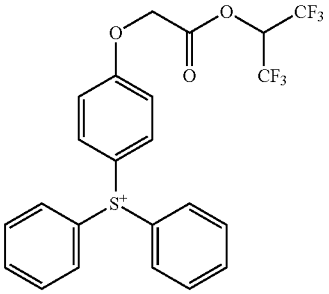
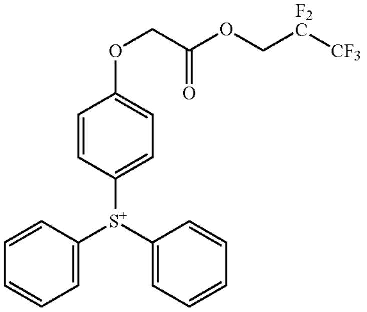
-continued
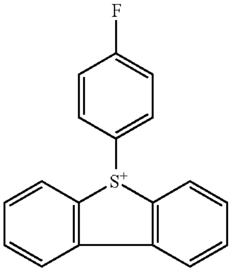
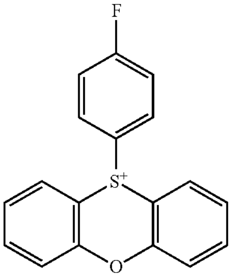
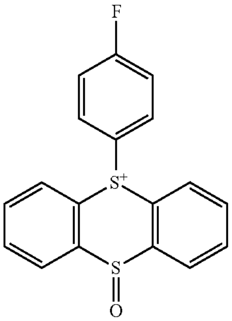
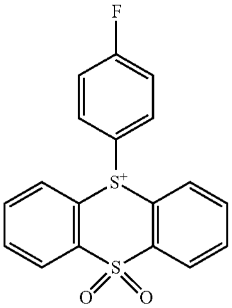
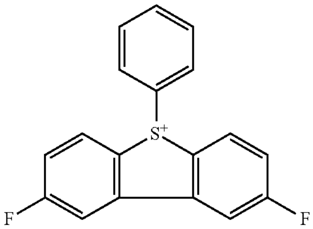
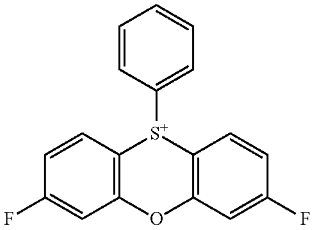
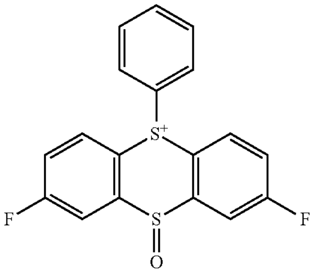
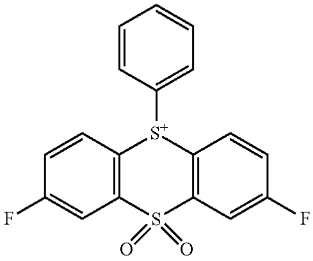

-continued
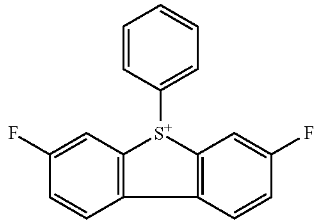
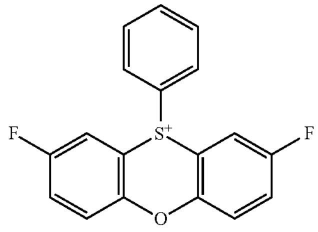
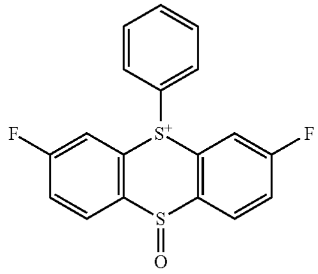
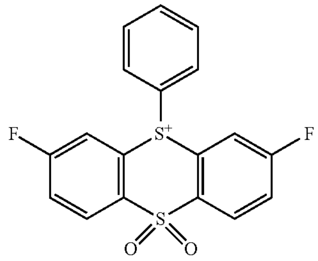
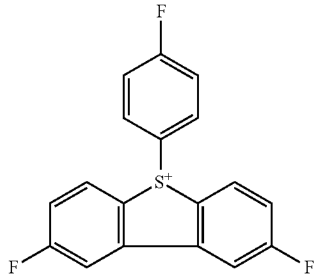
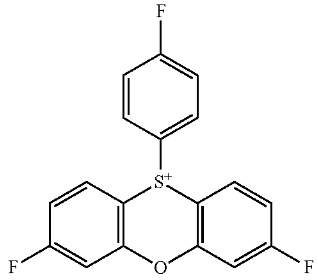
-continued
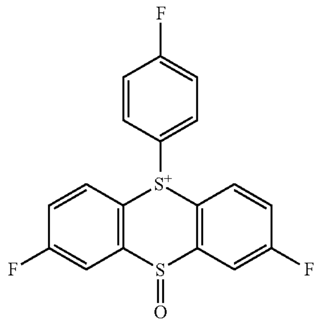
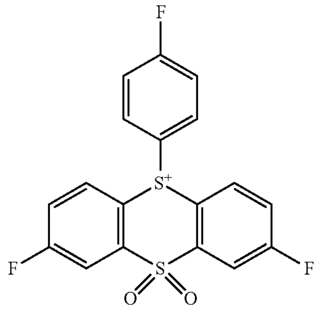
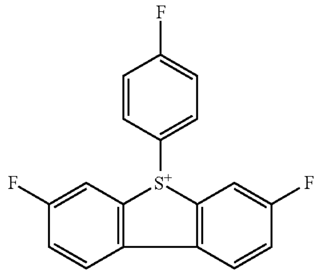
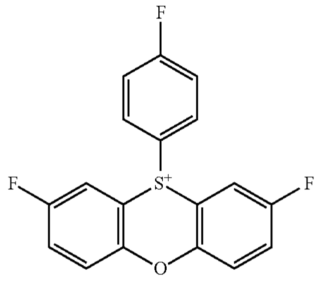
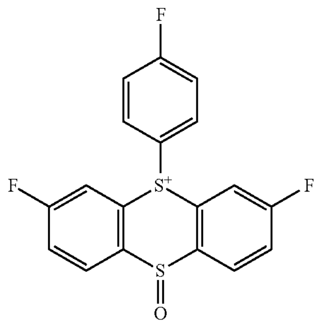

-continued
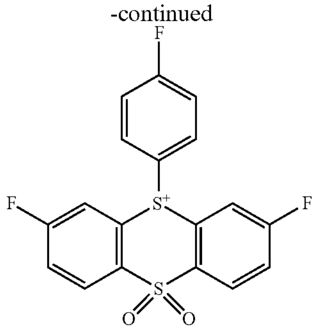
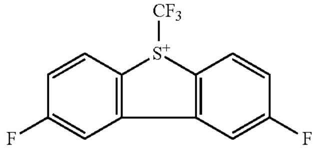
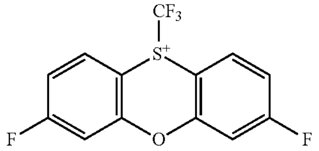
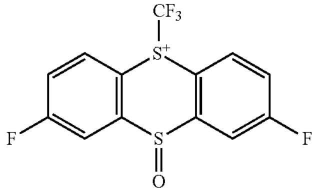
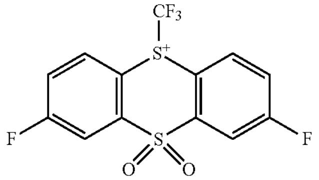
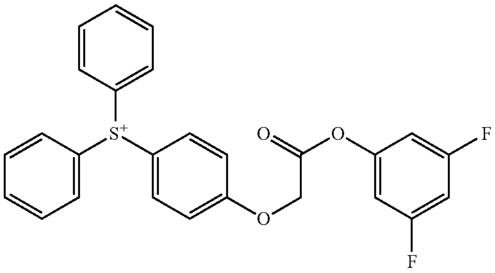
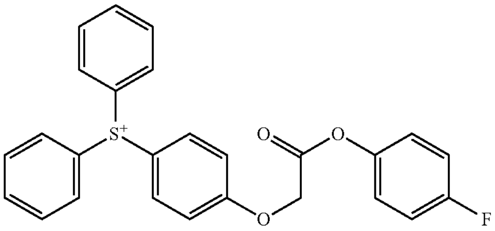
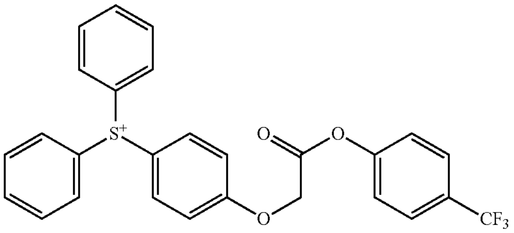
-continued
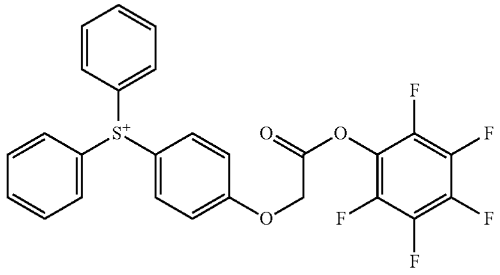
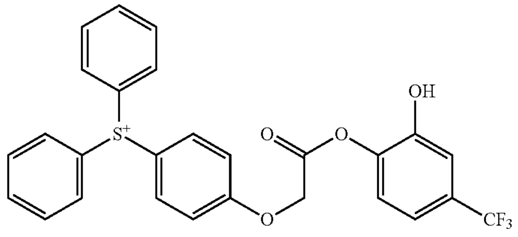
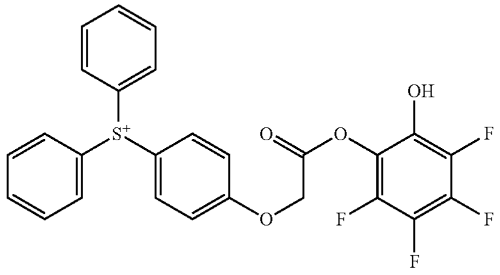
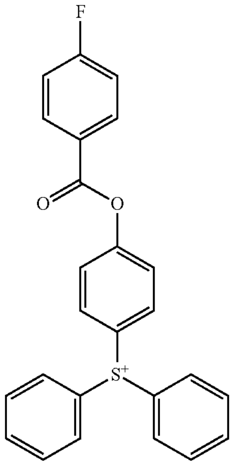
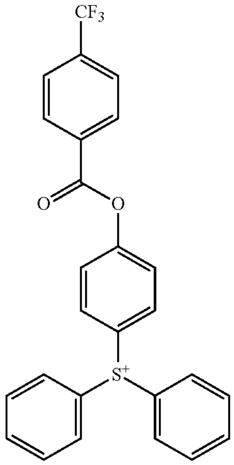
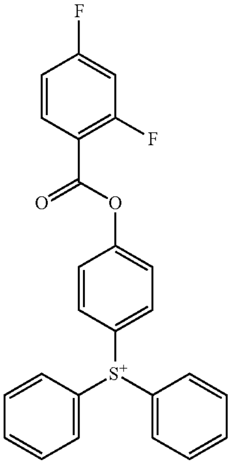
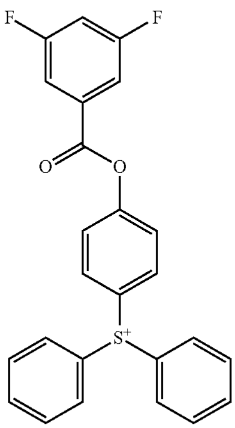

-continued
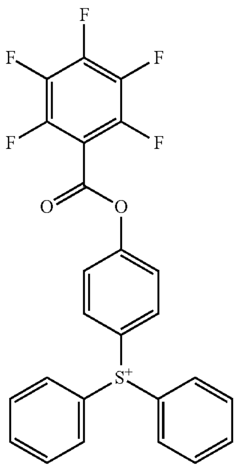
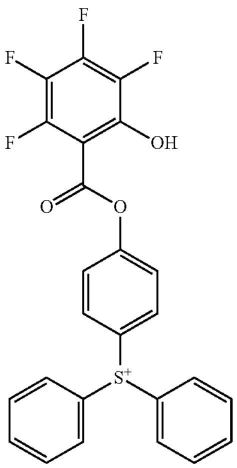
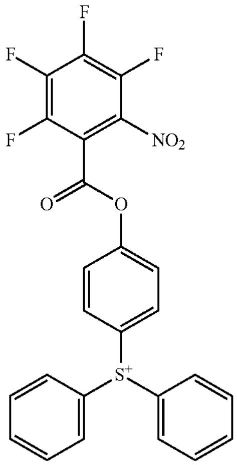
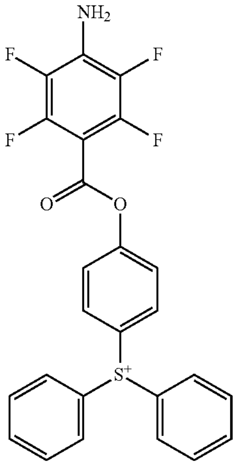
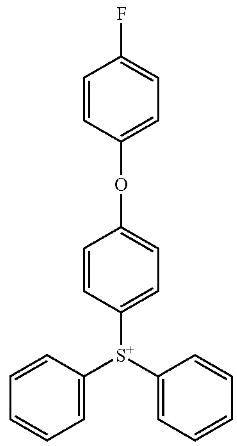
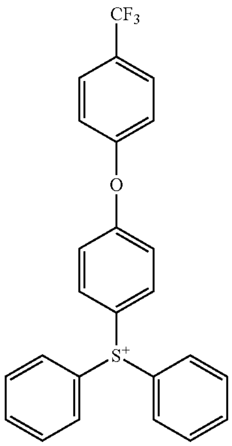
-continued
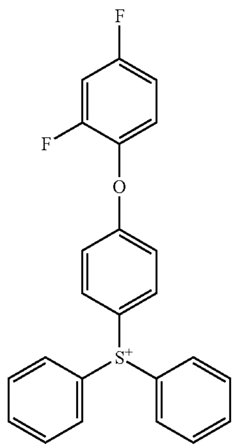
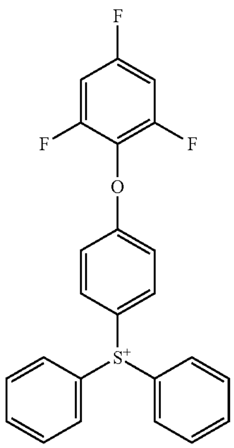
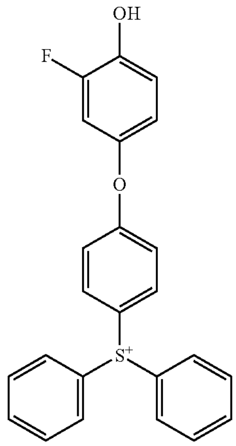
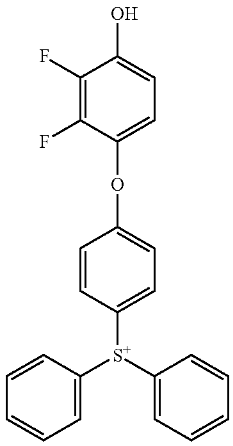
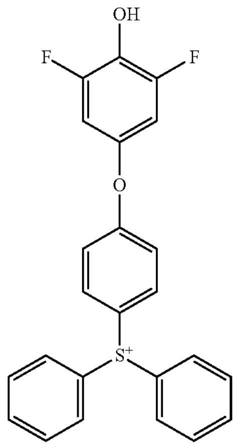
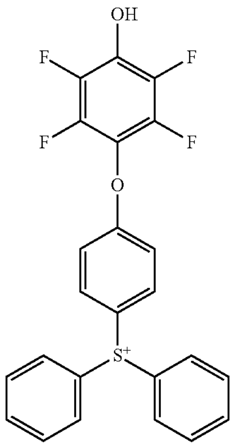
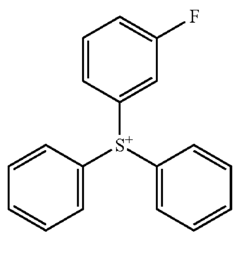
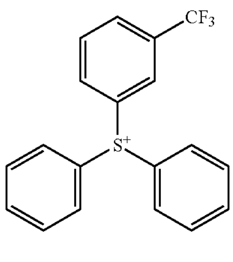

-continued
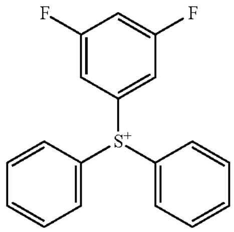
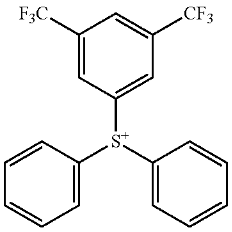
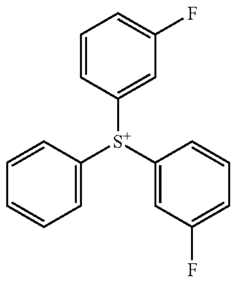
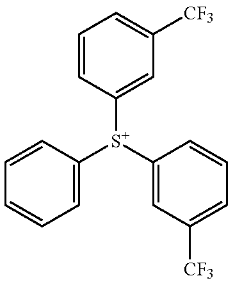
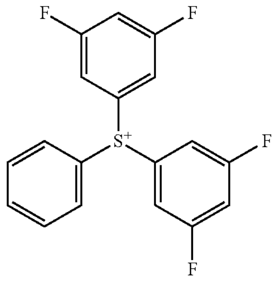
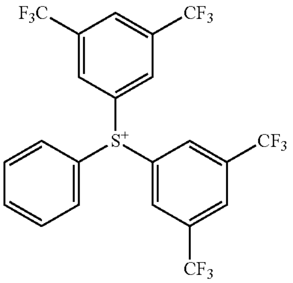
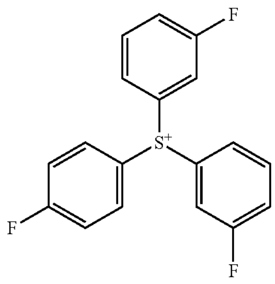
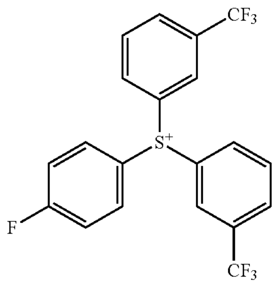
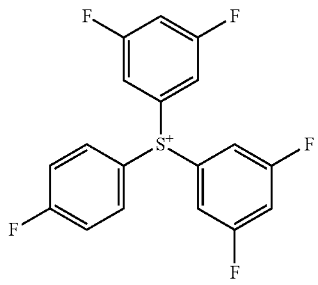
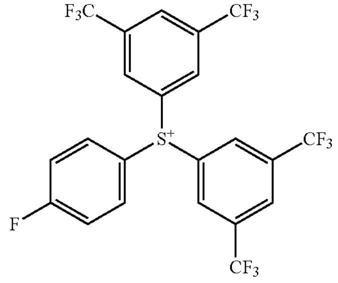
-continued
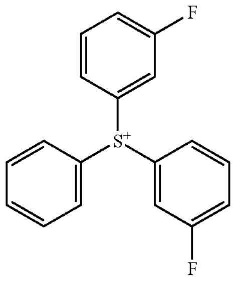
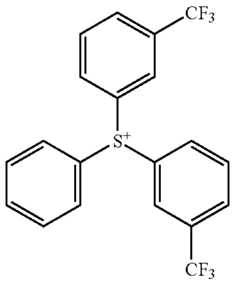
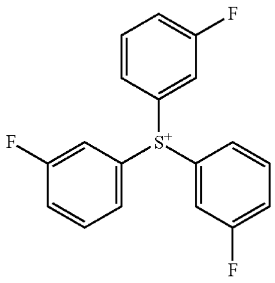
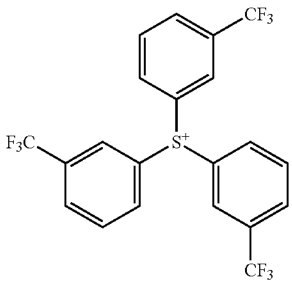
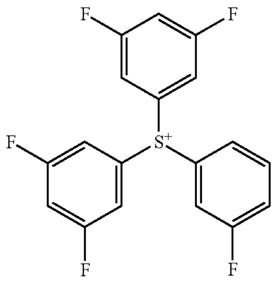
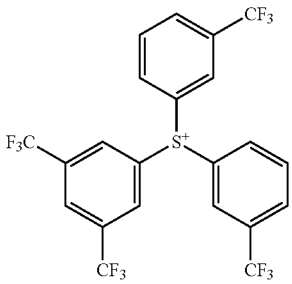
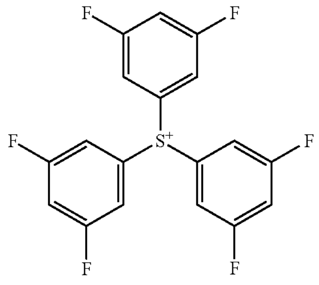
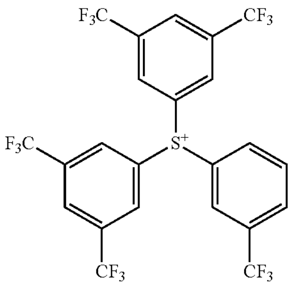
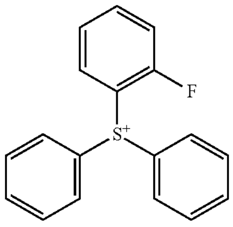
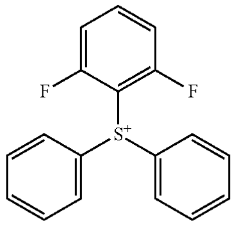

-continued
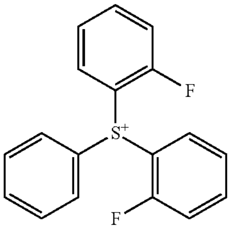
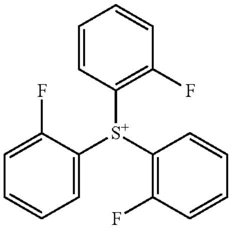
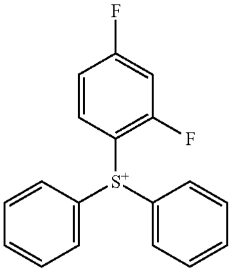
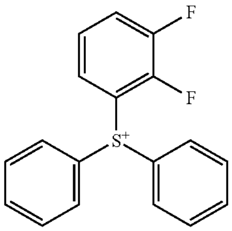
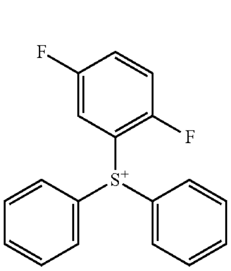
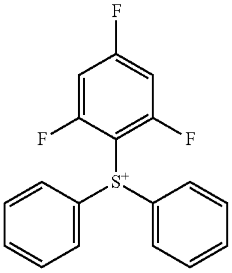
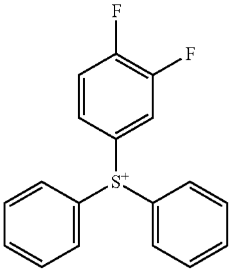
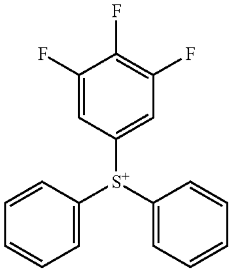
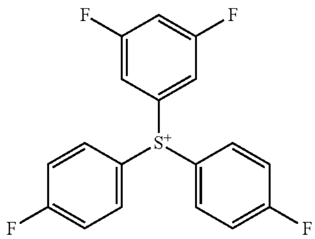
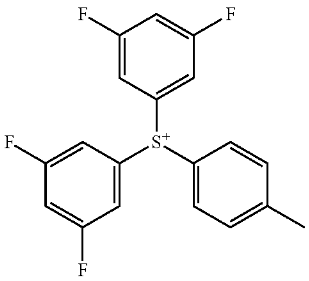
-continued
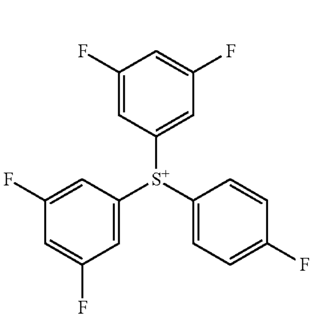
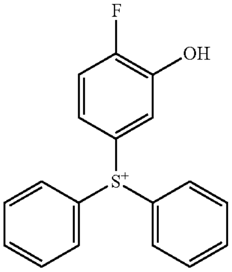
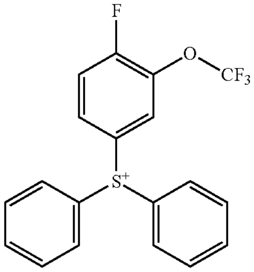
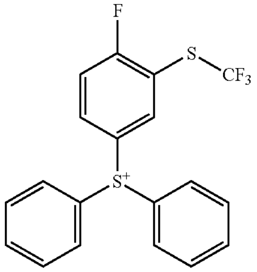
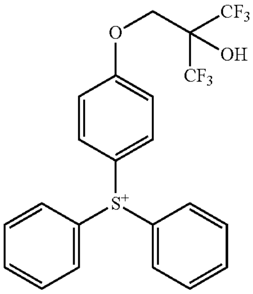
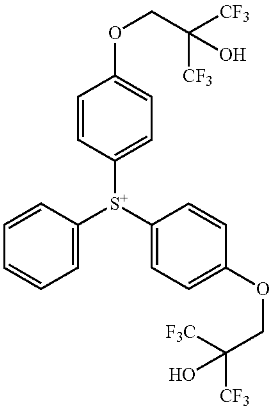
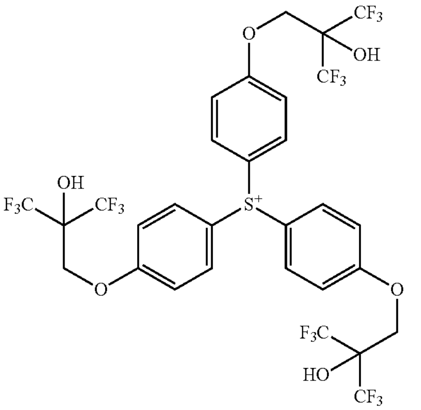
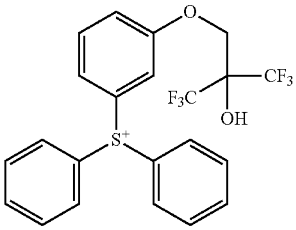

-continued
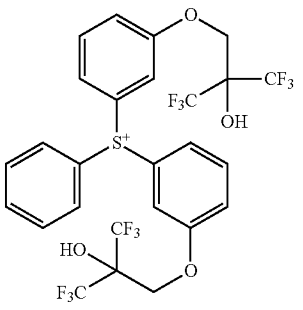
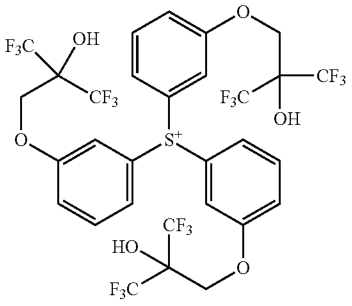
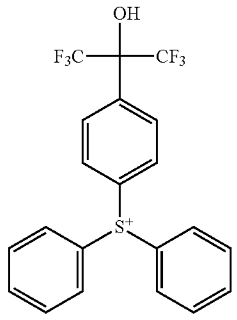
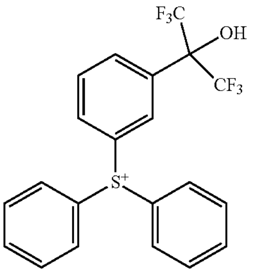
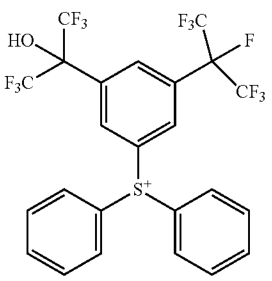
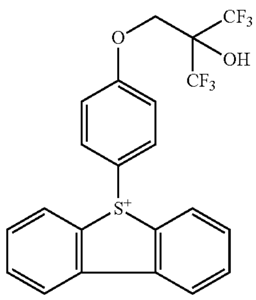
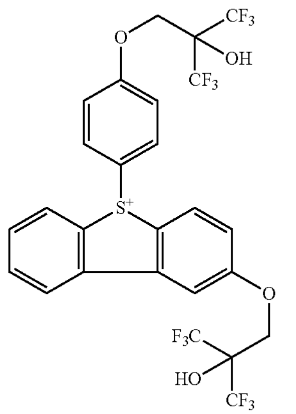
-continued
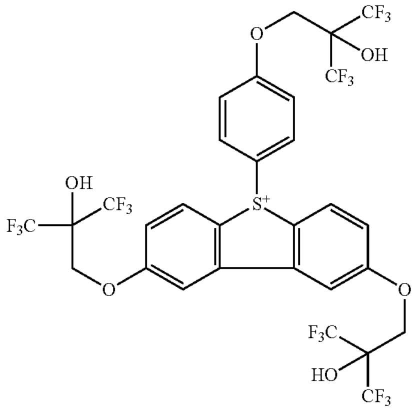
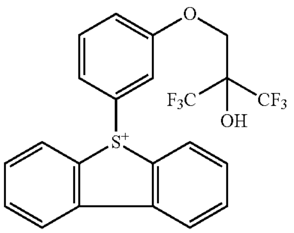
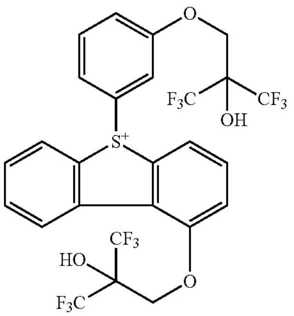
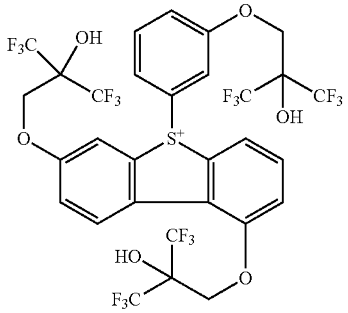
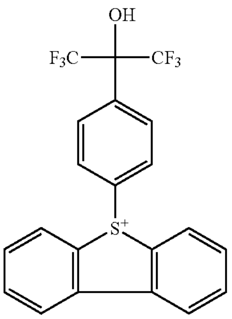
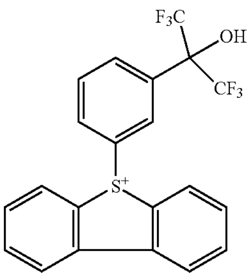

-continued
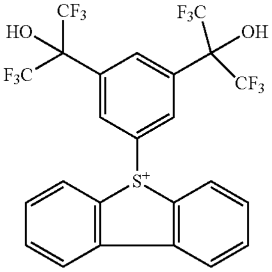
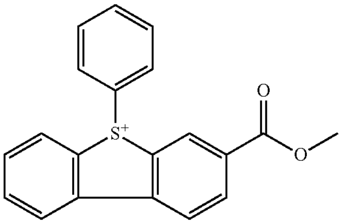
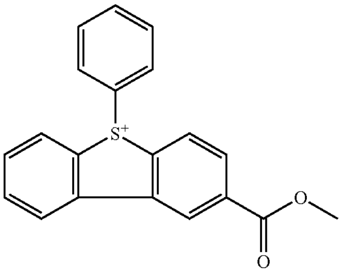
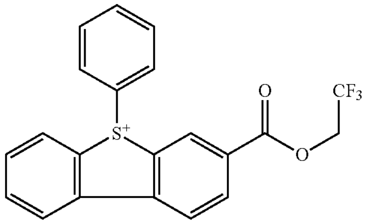
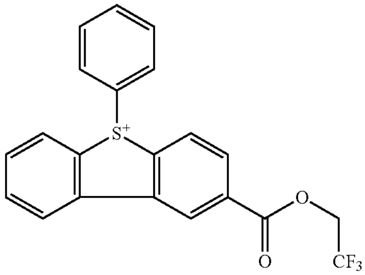
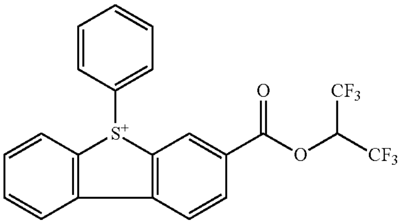
-continued
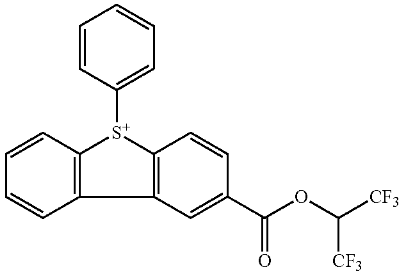
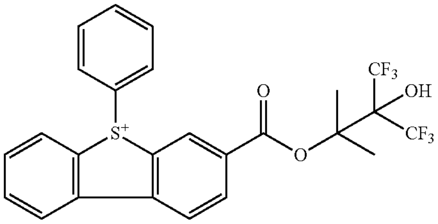
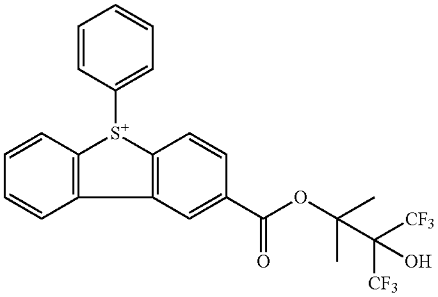
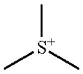
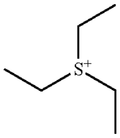
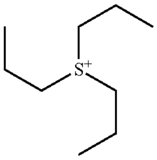
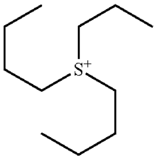
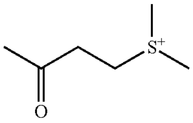
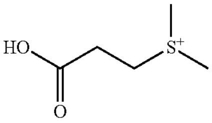
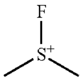
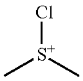
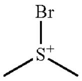
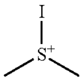
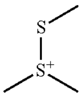
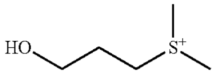
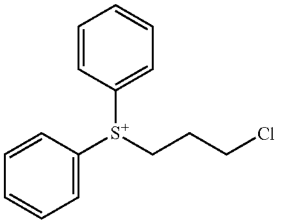
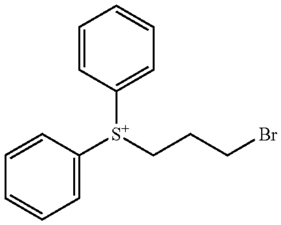
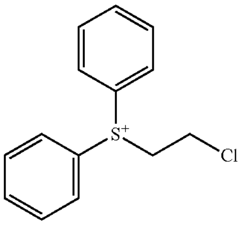

-continued
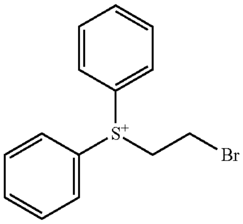
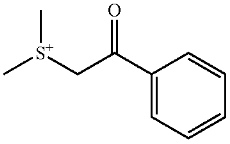
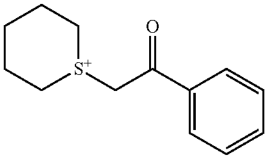
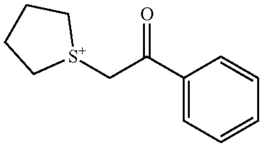
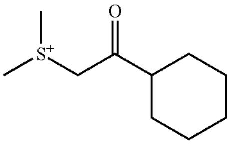
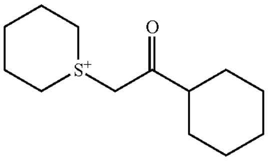
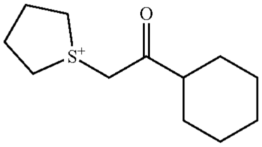
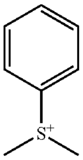
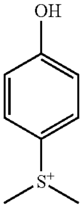
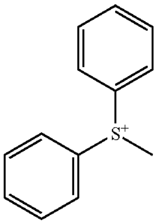
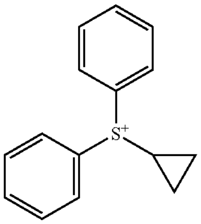
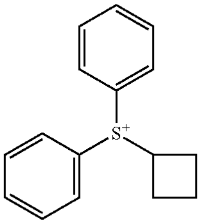
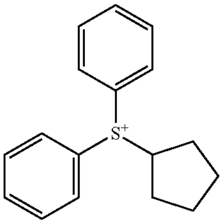
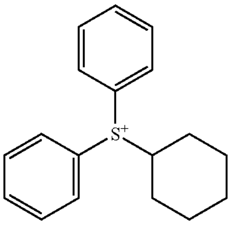
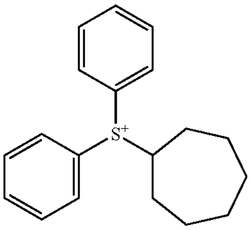
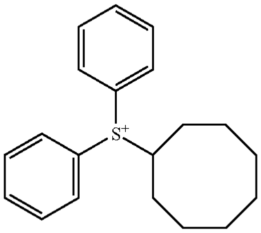
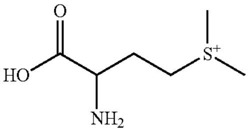
-continued
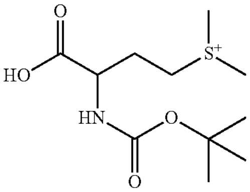
Examples of the iodonium cation represented by the general formula (Cation-2) include the following cations, but the cation is not limited thereto.
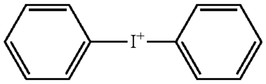
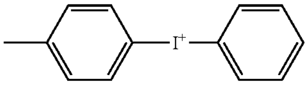
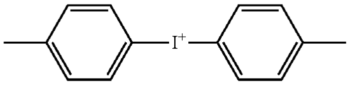
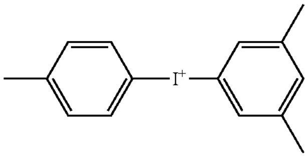
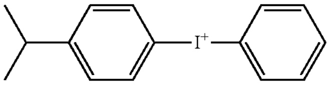
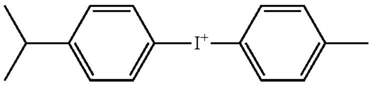
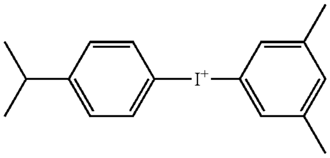
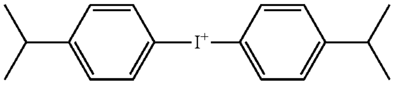
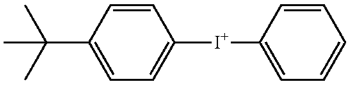
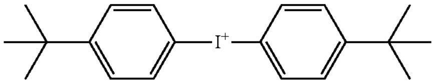
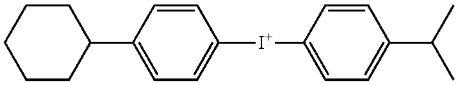
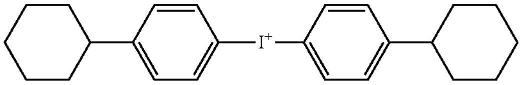
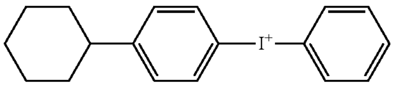
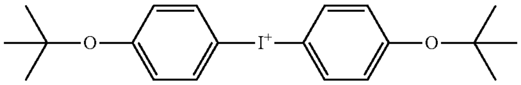

-continued
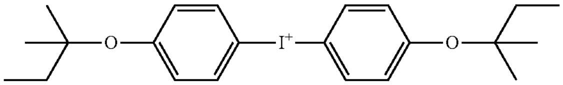
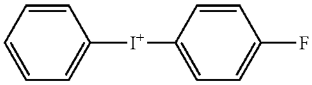
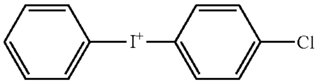
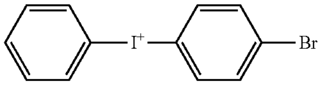
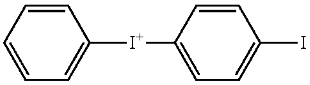
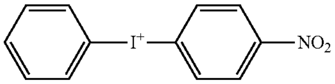
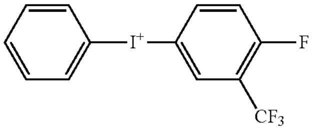
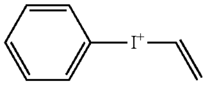
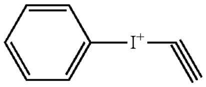
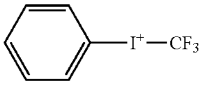
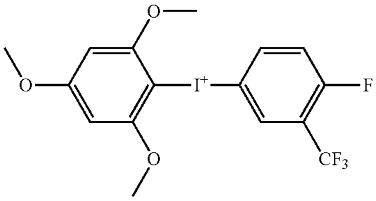
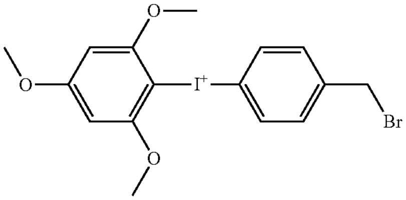
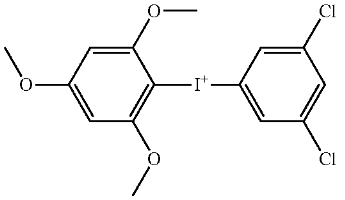
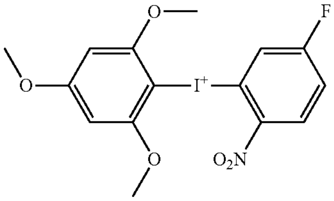
-continued
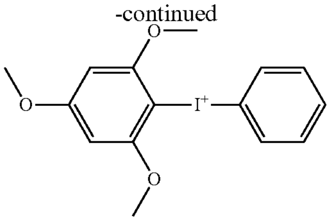
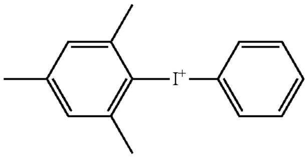
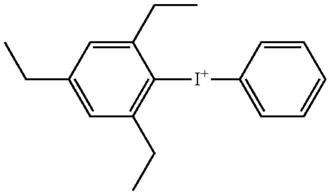
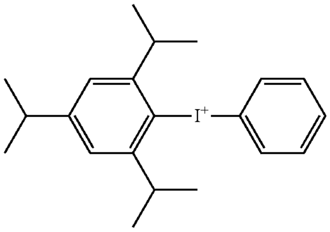
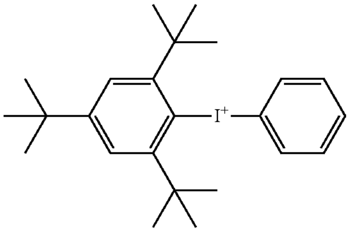
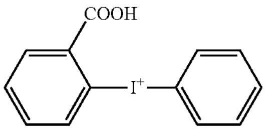
Examples of the ammonium cation represented by the general formula (Cation-3) include the following cations, but the cation is not limited thereto.
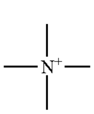
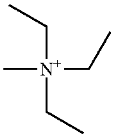
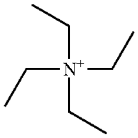
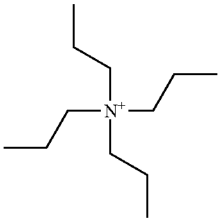
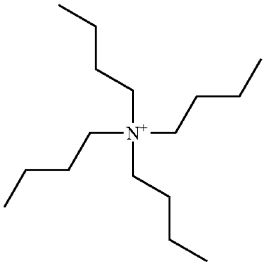

-continued

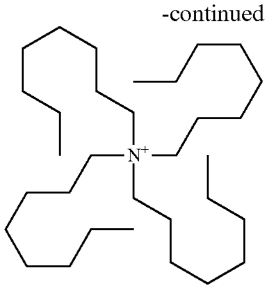

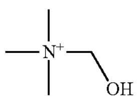

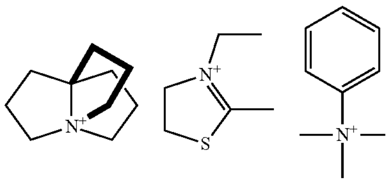

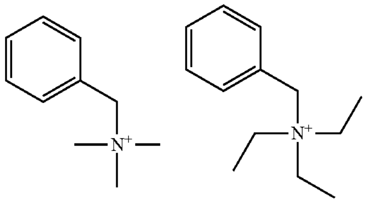

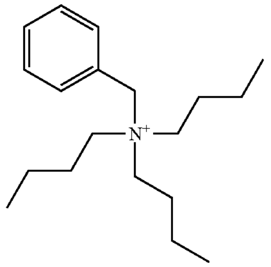

Examples of specific structures of the inventive onium salt include any combination of the aforementioned anions and cations.

The inventive onium salt can be synthesized by, for example, ion-exchanging a hydrochloride salt or carbonate salt having the onium cation with a corresponding benzoic acid derivative.

When both the inventive onium salt and an onium salt to generate a strong acid, such as an α-fluorinated sulfonic acid, imide acid, or methide acid (hereinafter, these acids are collectively defined as "strong acid") are present, the corresponding carboxylic acid and strong acid are generated with light irradiation. Meanwhile, many undecomposed onium salts are present in the low exposure-dose portion. The strong acid functions as a catalyst to cause a deprotection reaction of the base resin, but the inventive onium salt hardly causes a deprotection reaction. The strong acid is ion-exchanged with the remained sulfonium carboxylate salt to form an onium salt of the strong acid. Instead, the carboxylic acid is released. In other words, the ion exchange neutralizes the strong acid with the onium carboxylate salt. That is, the inventive onium salt functions as a quencher (acid diffusion inhibitor). This onium salt quencher typically tends to reduce LWR of a resist pattern compared with a quencher using an amine compound.

The salt exchange between the strong acid and the onium carboxylate salt is unlimitedly repeated. The place where the strong acid is generated with exposure in the final stage differs from the place where the strong acid-generating onium salt is originally present. It is presumed that the cycle of the acid generation with light and the salt exchange is repeated many times to uniformize acid generating points, resulting in reduction of LWR of a resist pattern after the development.

As noted above, the inventive onium salt functions as an acid diffusion inhibitor of a resist composition, and the acid diffusion inhibitor comprising the inventive onium salt is preferably contained in a resist composition.

The content of the inventive onium salt in the resist composition is preferably 0.001 to 50 parts by mass, and more preferably 0.01 to 40 parts by mass, relative to 100 parts by mass of the base polymer described later. The inventive onium salt may be used singly, or may be used in combination of two or more kinds thereof.

Base Polymer

The inventive resist material may comprise a base polymer. The base polymer has a repeating unit having an acid-labile group in a case of the positive-type resist material. The repeating unit having an acid-labile group is preferably a repeating unit represented by the following general formula (a1) (hereinafter, also referred to as the repeating unit a1) and/or a repeating unit represented by the following general formula (a2) (hereinafter, also referred to as the repeating unit a2).

(a1)

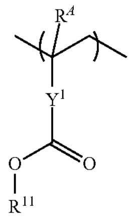

(a2)

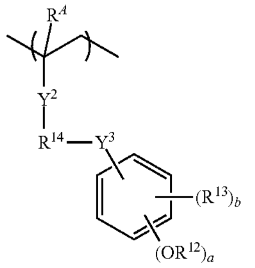

In the general formulae (a1) and (a2), $R^A$ each independently represents a hydrogen atom or a methyl group. $Y^1$ represents a single bond, a phenylene group, a naphthylene group, or a linking group having 1 to 12 carbon atoms and having at least one selected from an ester bond and a lactone ring. $Y^2$ represents a single bond or an ester bond. $Y^3$ represents a single bond, an ether bond, or an ester bond. $R^{11}$ and $R^{12}$ each independently represent an acid-labile group. When the base polymer comprises both the repeating unit a1 and the repeating unit a2, $R^{11}$ and $R^{12}$ may be same as or different from each other. $R^{13}$ represents a fluorine atom, a trifluoromethyl group, a cyano group, or a saturated hydrocarbyl group having 1 to 6 carbon atoms. $R^{14}$ represents a single bond or an alkanediyl group having 1 to 6 carbon atoms, and a part of carbon atoms therein is optionally substituted with an ether bond or an ester bond. "a" represents 1 or 2, "b" represents an integer of 0 to 4, and $1 \leq a+b \leq 5$.

Examples of a monomer to yield the repeating unit a1 include the following monomers, but the monomer is not limited thereto. In the following formulae, $R^A$ and $R^{11}$ represent the same as above.

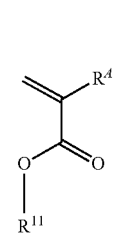
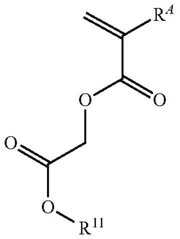
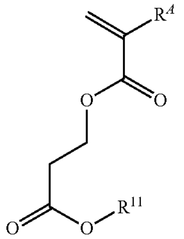
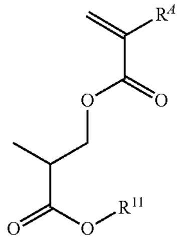
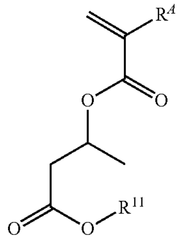
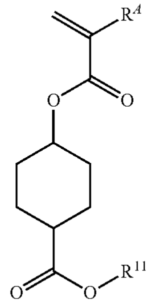
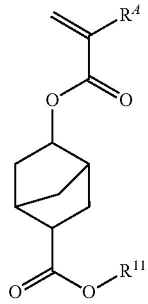
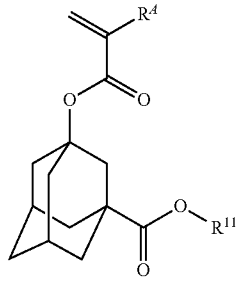
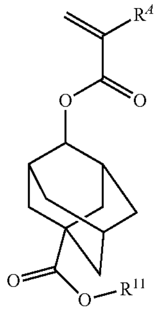
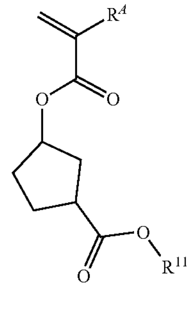
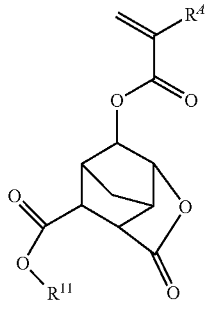
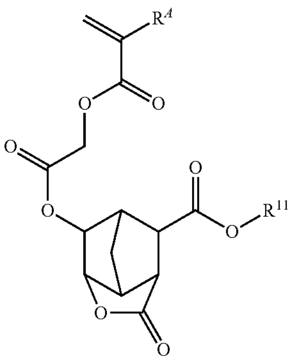
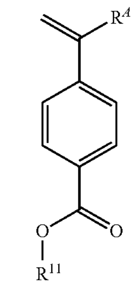
-continued
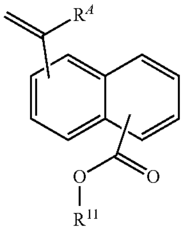
Examples of a monomer to yield the repeating unit a2 include the following monomers, but the monomer is not limited thereto. In the following formulae, $R^A$ and $R^{12}$ represent the same as above.
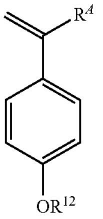
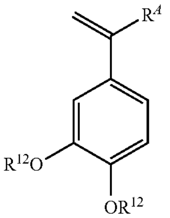
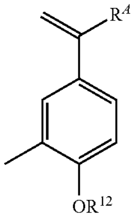
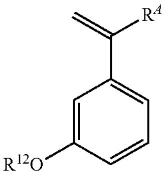
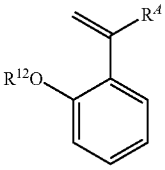
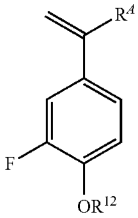
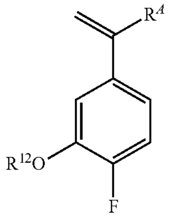
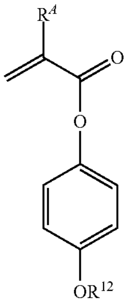
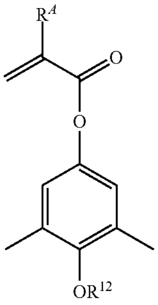
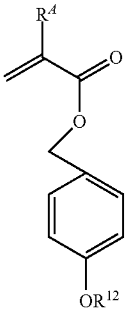
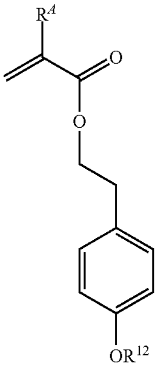
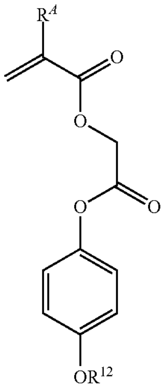

-continued

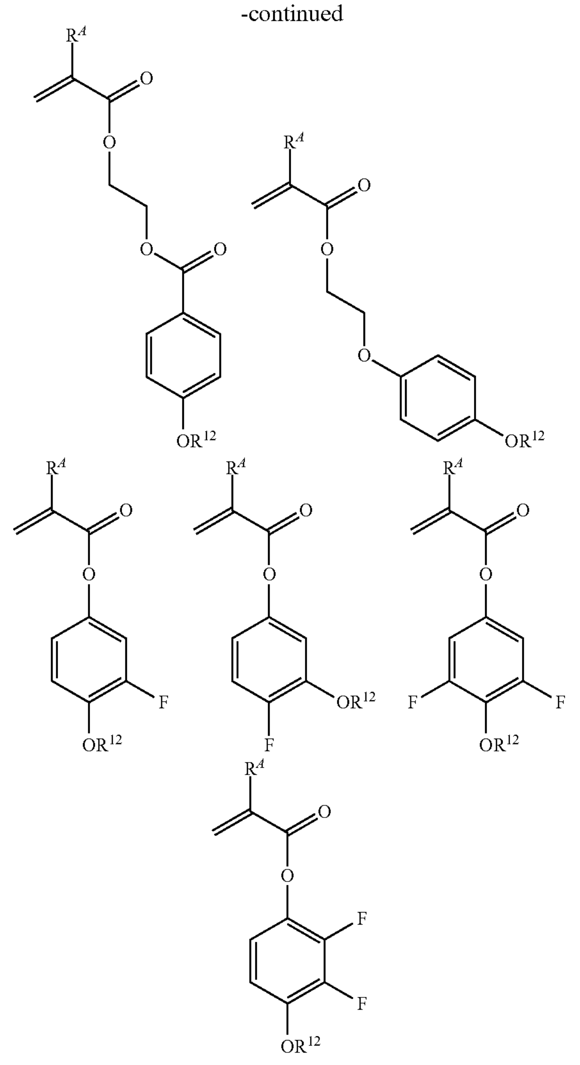

Examples of the acid-labile group represented by $R^{ALU}$, $R^{11}$, and $R^{12}$ in the general formulae (1), (a1), and (a2) include groups described in JP 2013-80033 A and JP 2013-83821 A.

Typical examples of the acid-labile group include groups represented by the following formulae (AL-1) to (AL-3).

(AL-1)

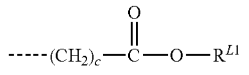

(AL-2)

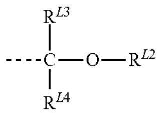

(AL-3)

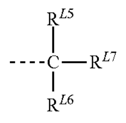

In the formulae, a broken line represents an attachment point.

In the general formulae (AL-1) and (AL-2), $R^{L1}$ and $R^{L2}$ each independently represent a hydrocarbyl group having 1 to 40 carbon atoms and optionally having a heteroatom such as an oxygen atom, a sulfur atom, a nitrogen atom, and a fluorine atom. The hydrocarbyl group may be a saturated or unsaturated group, and may be any of linear, branched, and cyclic groups. The hydrocarbyl group is preferably a saturated hydrocarbyl group having 1 to 40 carbon atoms, and more preferably a saturated hydrocarbyl group having 1 to 20 carbon atoms.

In the general formula (AL-1), "c" represents an integer of 0 to 10, and preferably an integer of 1 to 5.

In the general formula (AL-2), $R^{L3}$ and $R^{L4}$ each independently represent a hydrogen atom or a hydrocarbyl group having 1 to 20 carbon atoms and optionally having a heteroatom such as an oxygen atom, a sulfur atom, a nitrogen atom, and a fluorine atom. The hydrocarbyl group may be a saturated or unsaturated group, and may be any of linear, branched, and cyclic groups. The hydrocarbyl group is preferably a saturated hydrocarbyl group having 1 to 20 carbon atoms. Any two of $R^{L2}$, $R^{L3}$, and $R^{L4}$ are optionally bonded to each other to form a ring having 3 to 20 carbon atoms together with the carbon atom or the carbon atom and oxygen atom to which these groups are bonded. The ring is preferably a ring having 4 to 16 carbon atoms, and particularly preferably an aliphatic ring.

In the formula (AL-3), $R^{L5}$, $R^{L6}$, and $R^{L7}$ each independently represent a hydrocarbyl group having 1 to 20 carbon atoms and optionally having a heteroatom such as an oxygen atom, a sulfur atom, a nitrogen atom, and a fluorine atom. The hydrocarbyl group may be a saturated or unsaturated group, and may be any of linear, branched, and cyclic groups. The hydrocarbyl group is preferably a saturated hydrocarbyl group having 1 to 20 carbon atoms. Any two of $R^{L5}$, $R^{L6}$ and $R^{L7}$ are optionally bonded to each other to form a ring having 3 to 20 carbon atoms together with the carbon atom to which these groups are bonded. The ring is preferably a ring having 4 to 16 carbon atoms, and particularly preferably an aliphatic ring.

When the base polymer in the resist material has the repeating unit a1 or a2, the resist material is a chemically amplified positive-type resist material.

The base polymer in the resist material also preferably has no acid-labile group. In this case, the resist material is a chemically amplified negative-type resist material.

The base polymer may have a repeating unit b having a phenolic hydroxy group as an adhesive group. Examples of a monomer to yield the repeating unit b include the following monomers, but the monomer is not limited thereto. In the following formulae, $R^A$ represents the same as above.

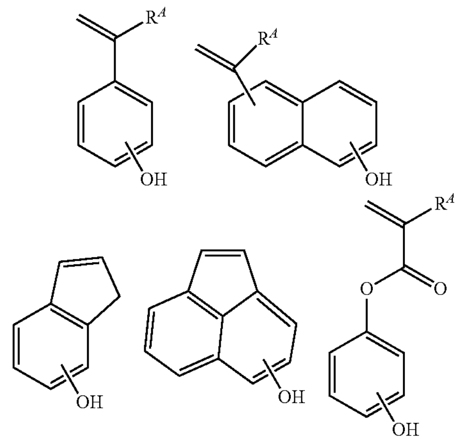

-continued
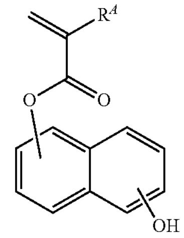
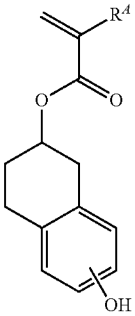
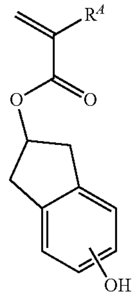
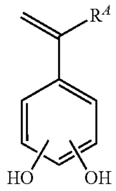
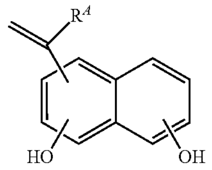
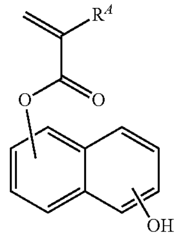
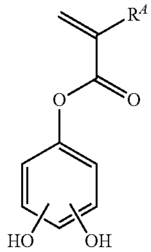
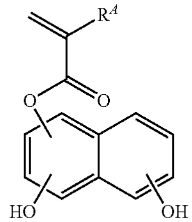
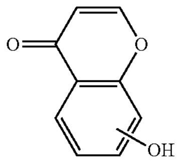
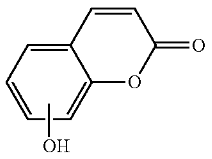
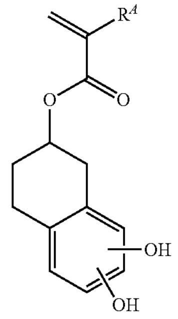
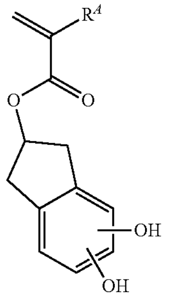
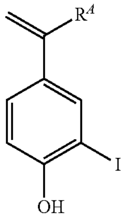
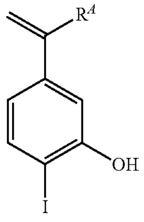
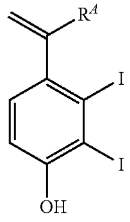
-continued
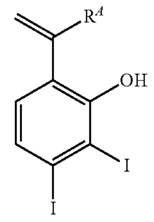
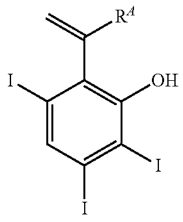
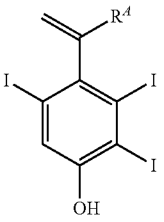
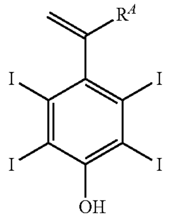
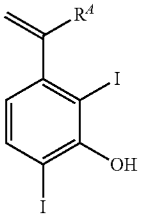
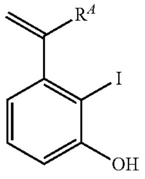
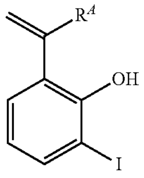
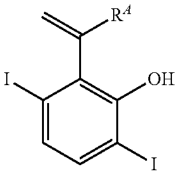
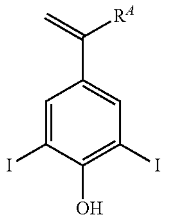
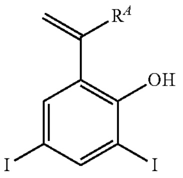
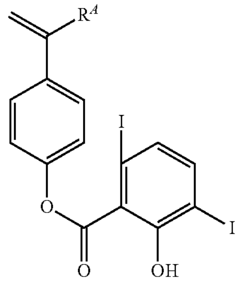
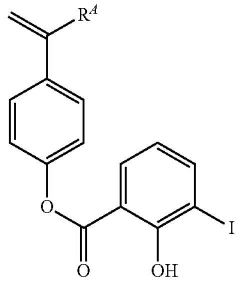
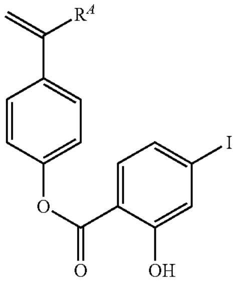
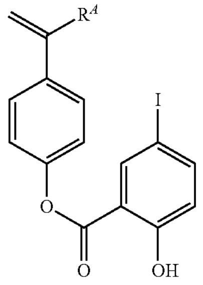
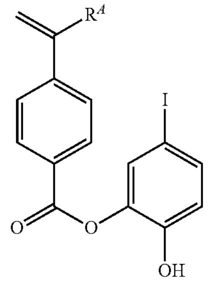
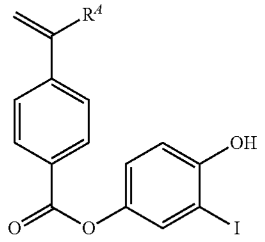

-continued

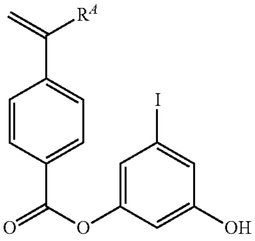

The base polymer may have a repeating unit c having, as another adhesive group, a hydroxy group other than a phenolic hydroxy group, a lactone ring, a sultone ring, an ether bond, an ester bond, a sulfonate ester bond, a carbonyl group, a sulfonyl group, a cyano group, and/or a carboxy group. Examples of a monomer to yield the repeating unit c include the following monomers, but the monomer is not limited thereto. In the following formulae, $R^A$ represents the same as above.

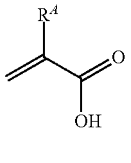
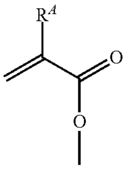
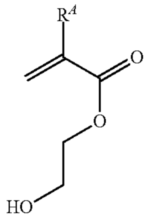
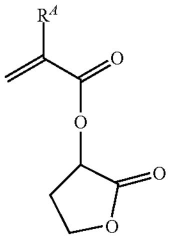
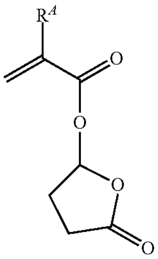
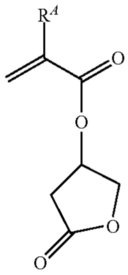
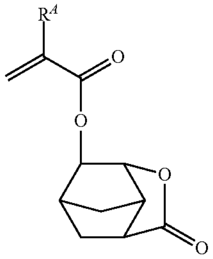
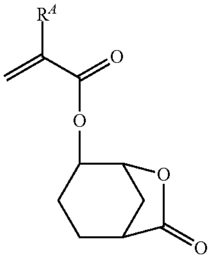
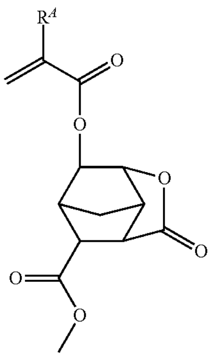
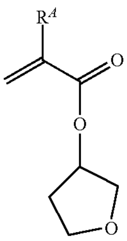
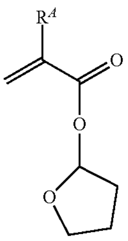

-continued

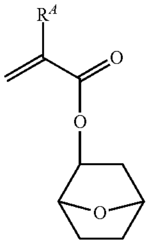
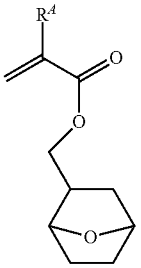
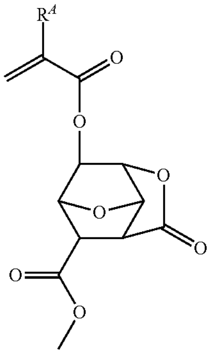
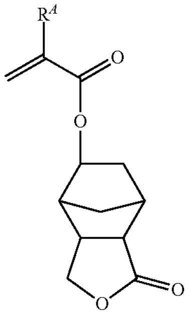
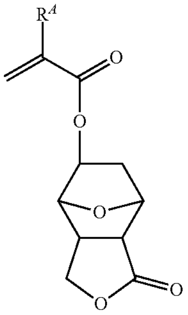
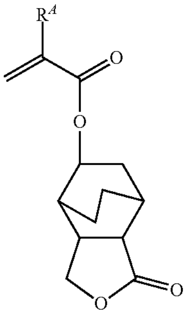
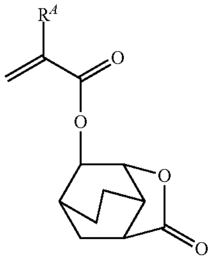
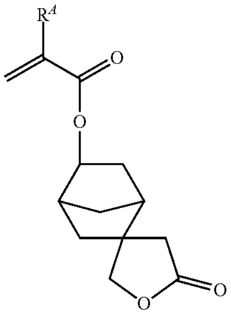
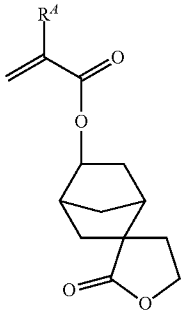
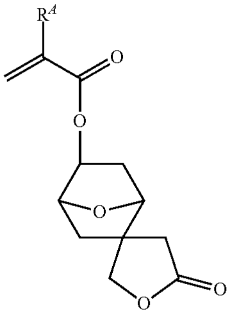
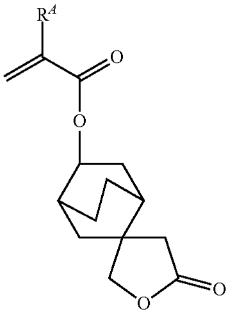

-continued
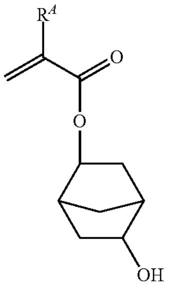
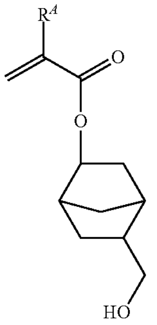
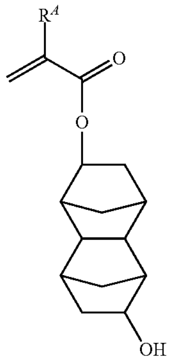
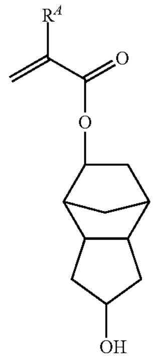
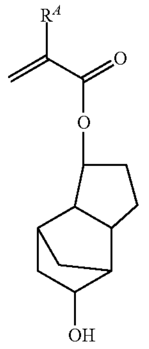
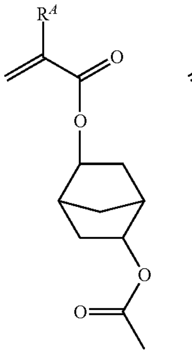
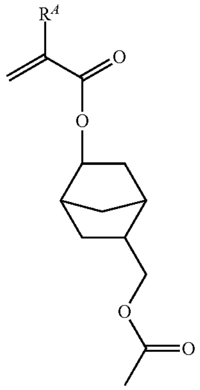
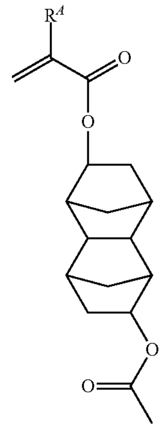
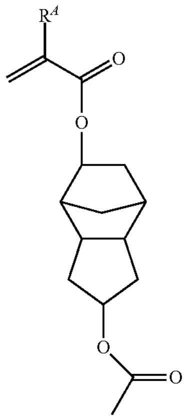
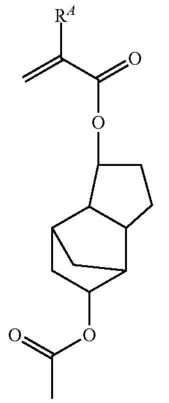
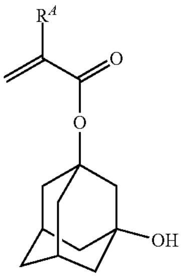
-continued
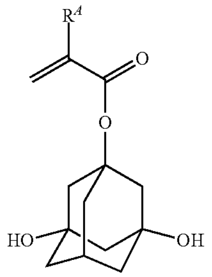
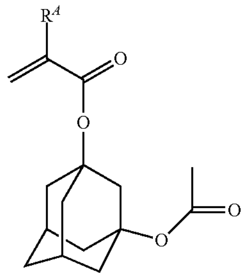
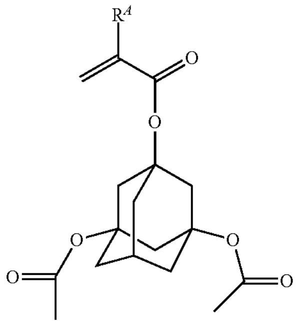
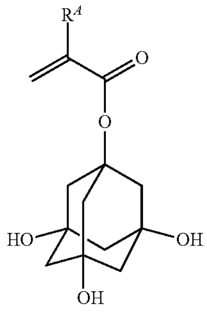
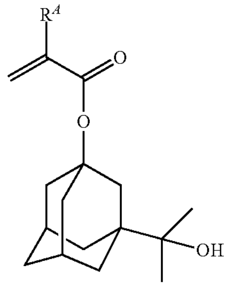
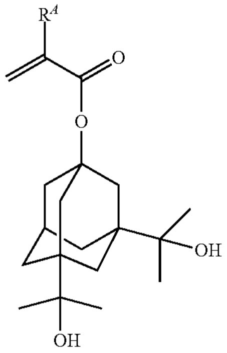
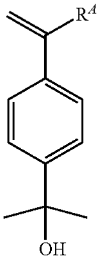
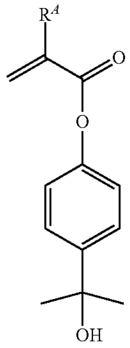
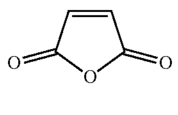
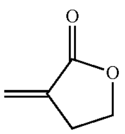
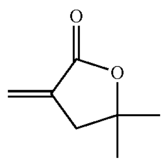
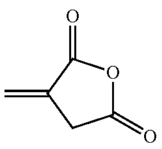
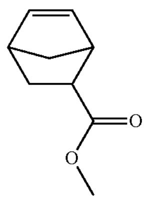
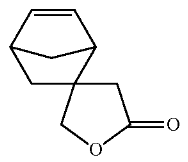
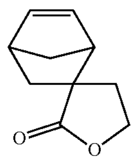

-continued
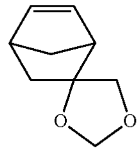
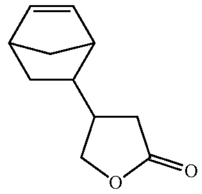
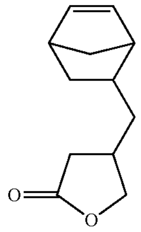
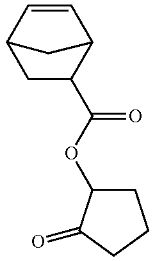
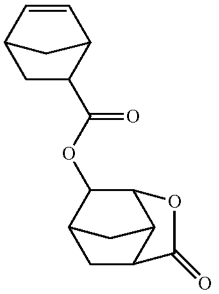
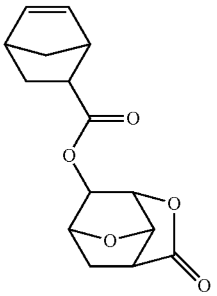
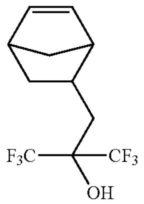
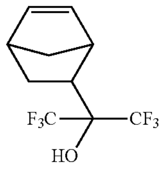
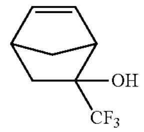
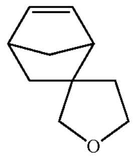
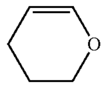
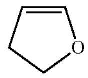
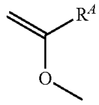
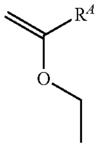
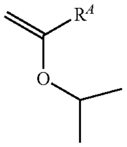
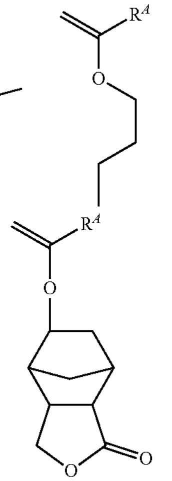
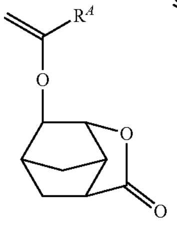
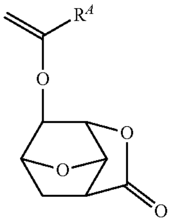
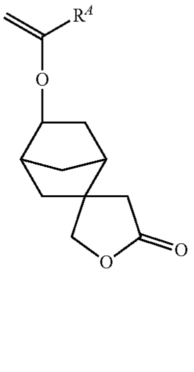
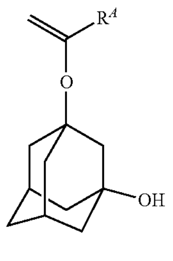
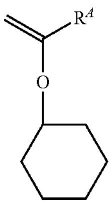
-continued
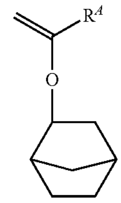
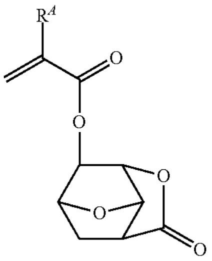
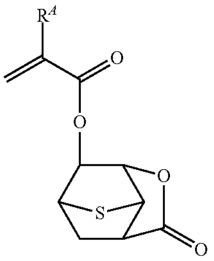
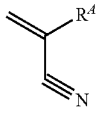
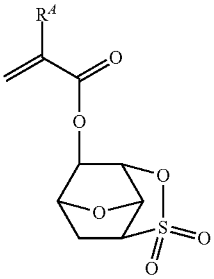
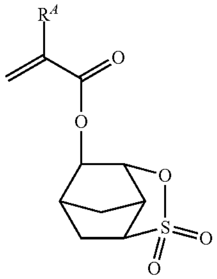
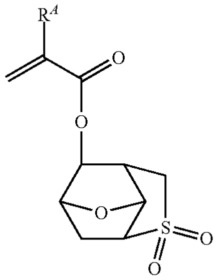
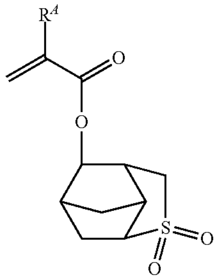
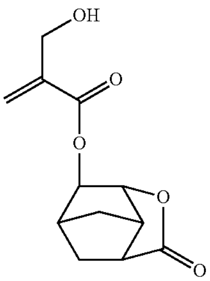
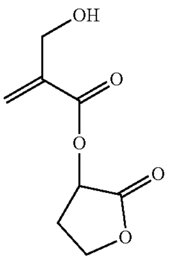
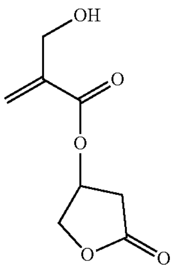
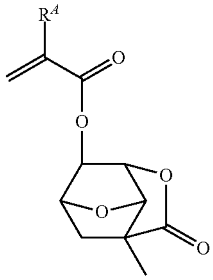
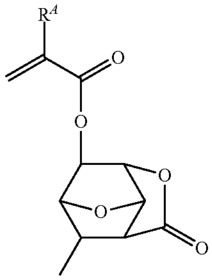
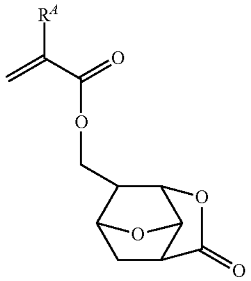
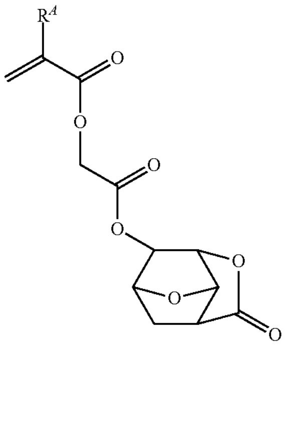

-continued
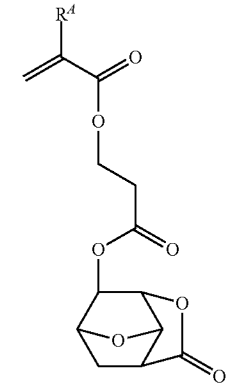
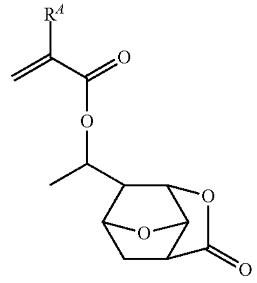
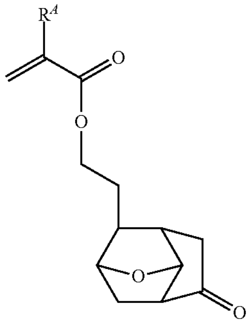
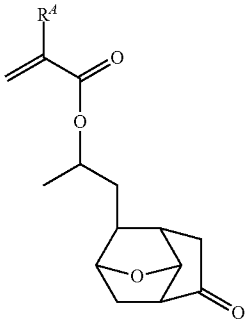
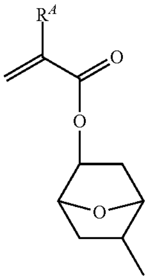
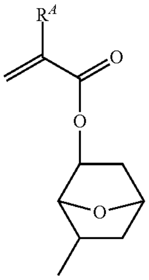
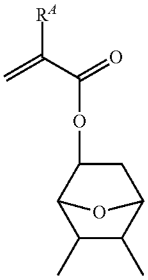
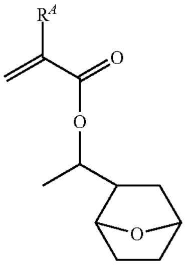
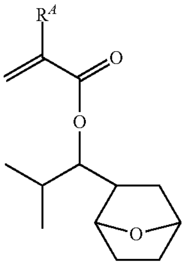
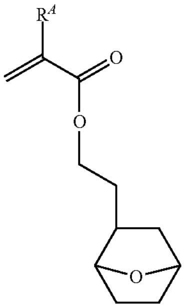
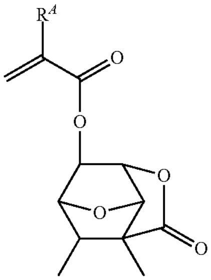
-continued
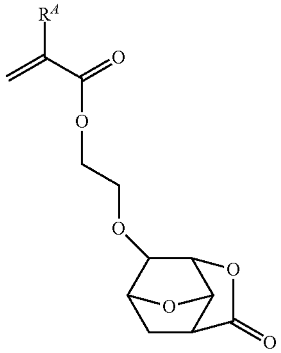
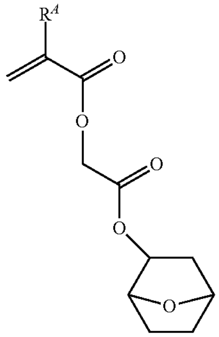
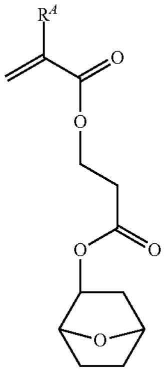
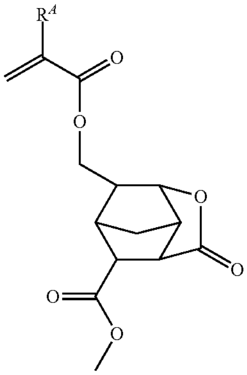
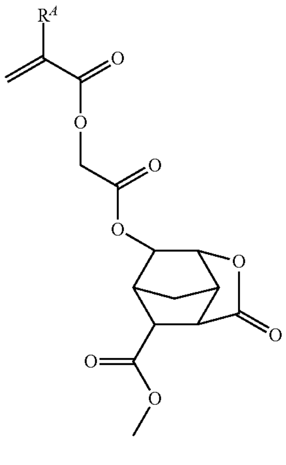
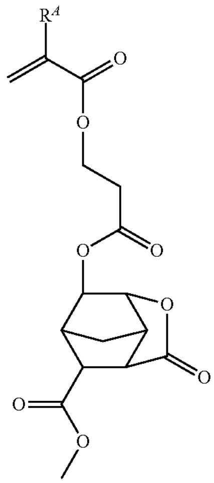
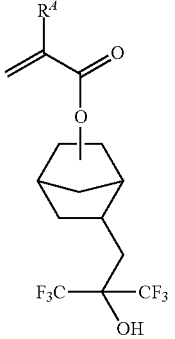
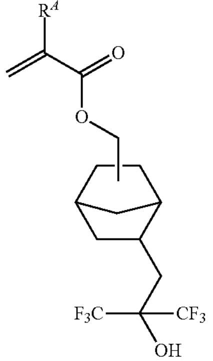

-continued
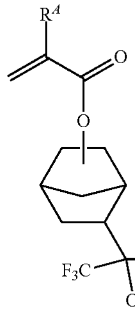
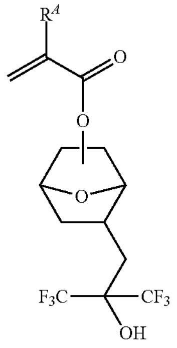
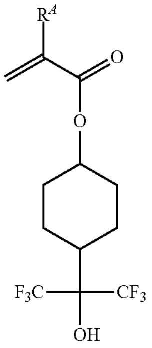
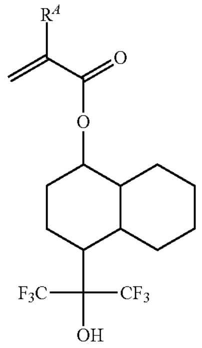
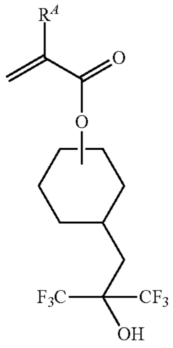
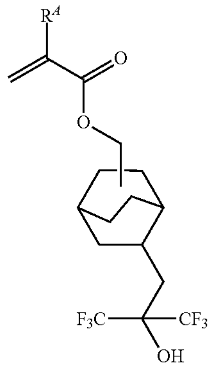
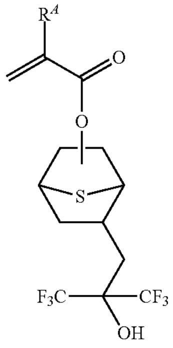
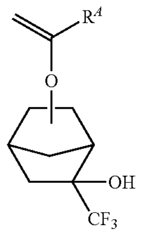
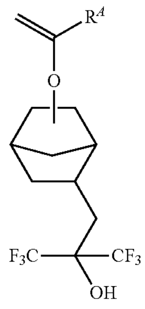
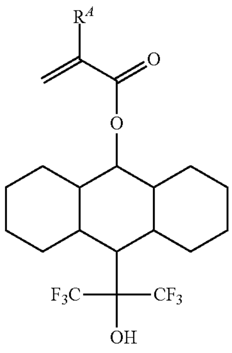
-continued
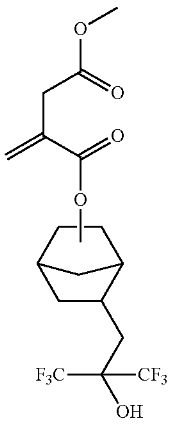
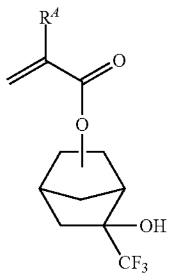
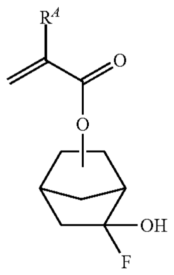
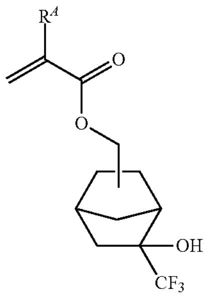
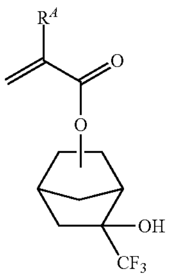
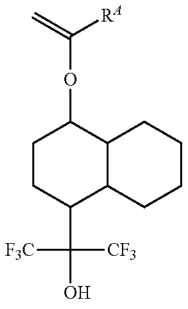
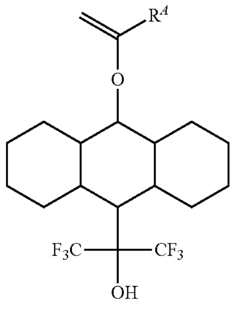
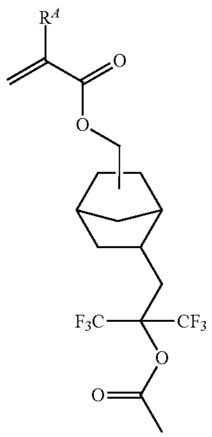
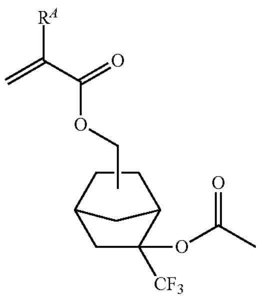

-continued
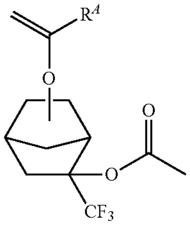
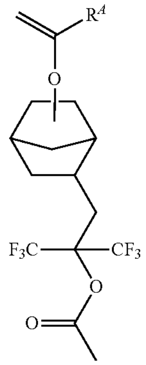
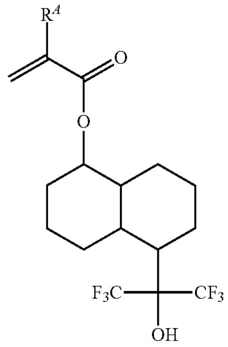
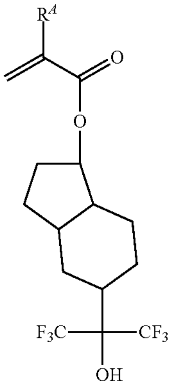
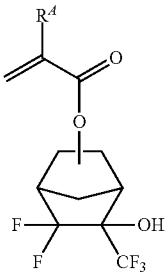
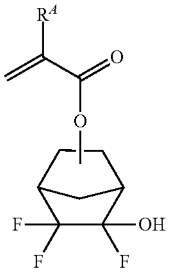
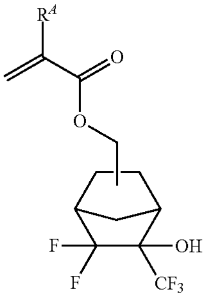
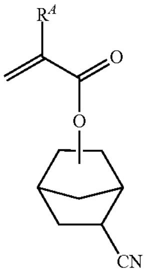
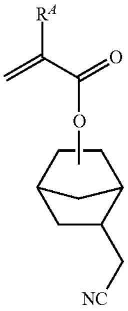
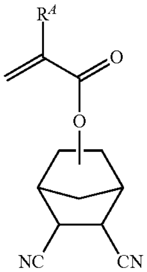
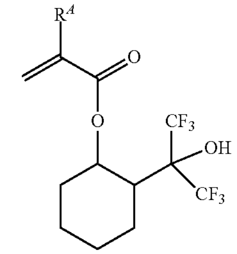
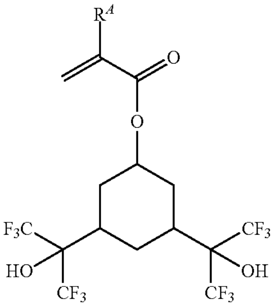
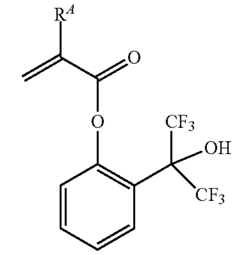
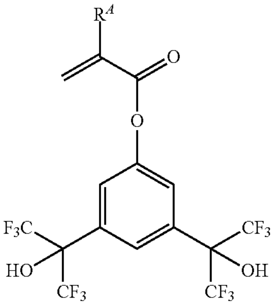
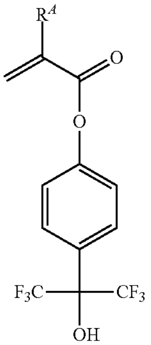
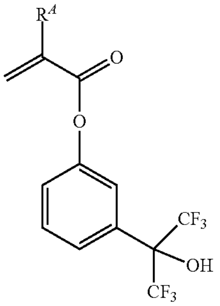
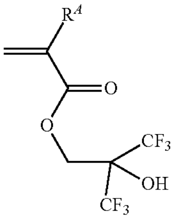
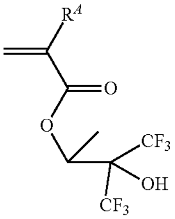
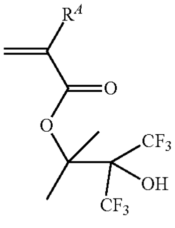
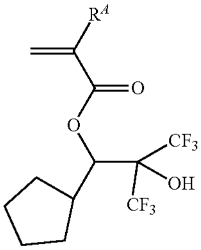
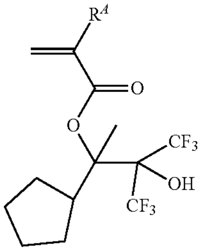
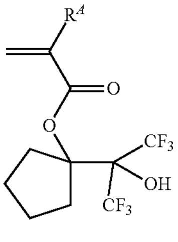
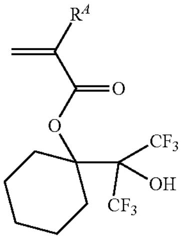
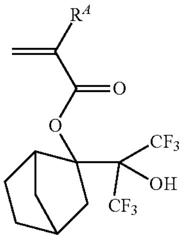
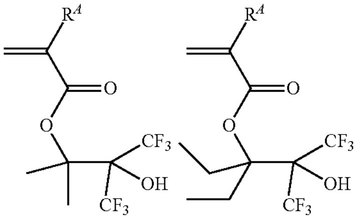

-continued
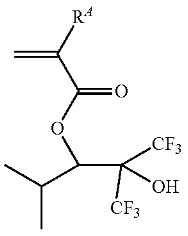
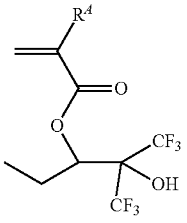
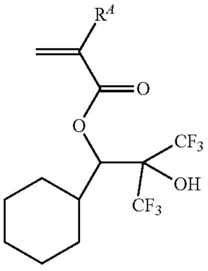
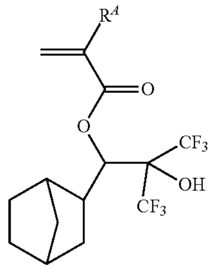
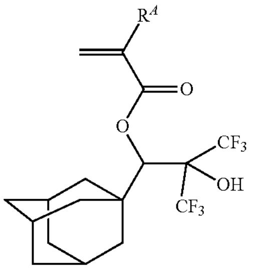
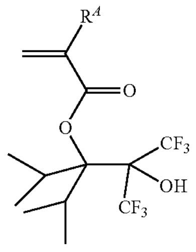
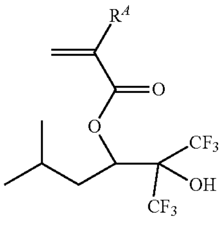
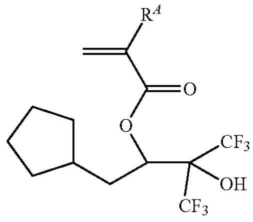
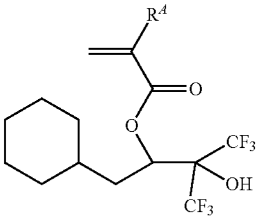
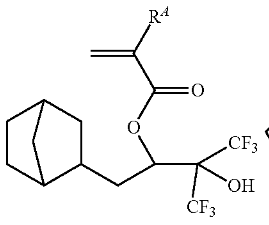
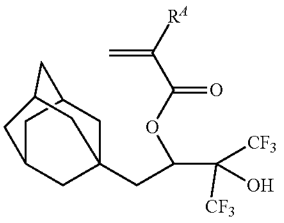
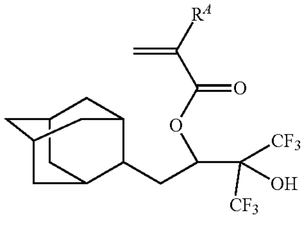
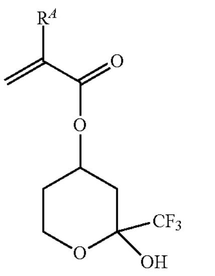
-continued
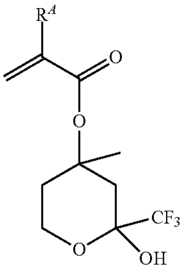
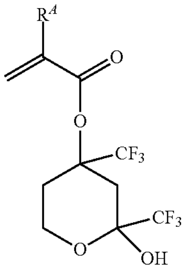
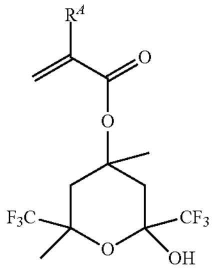
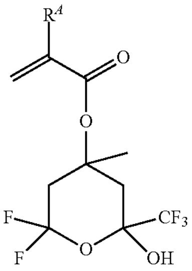
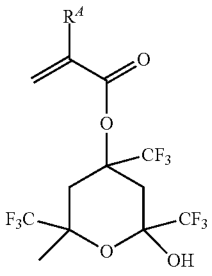
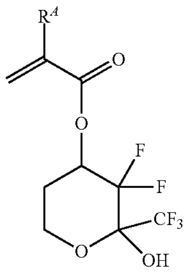
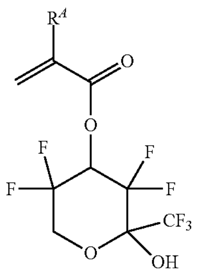
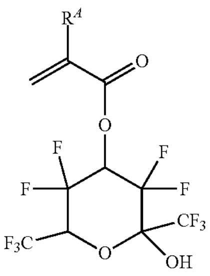
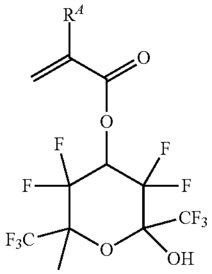
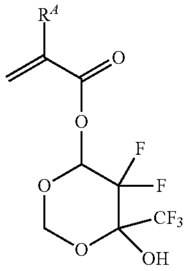
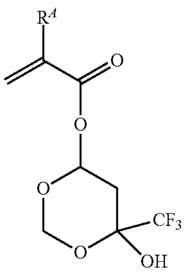
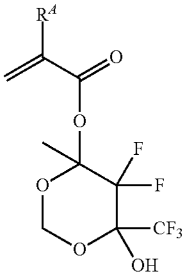
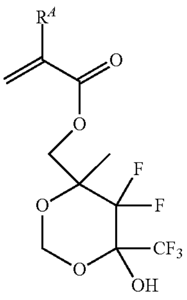

-continued
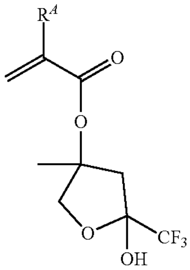
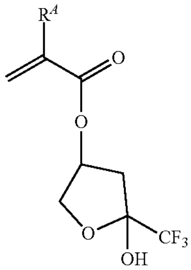
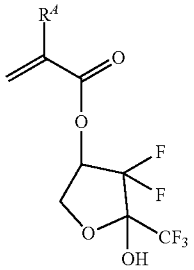
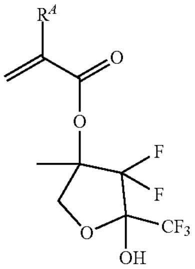
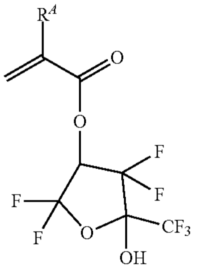
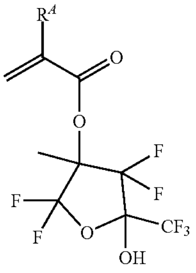
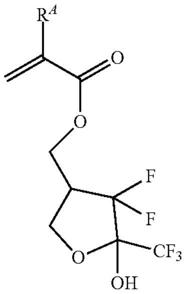
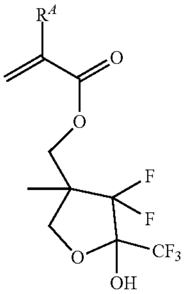
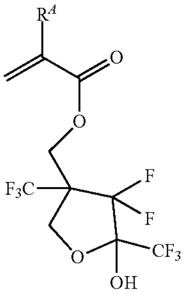
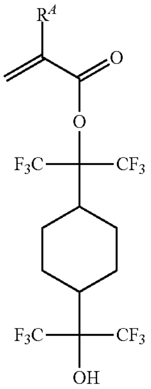
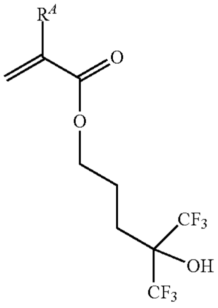
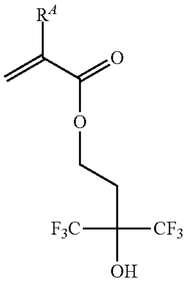
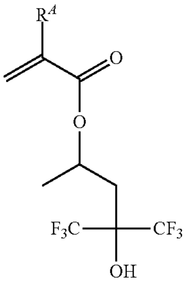
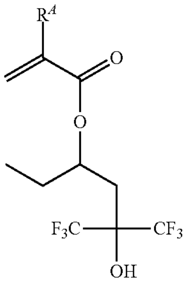
-continued
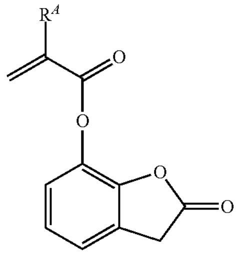
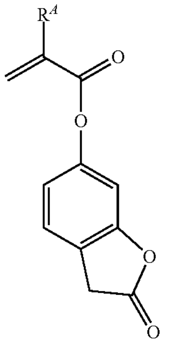
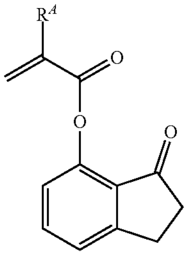
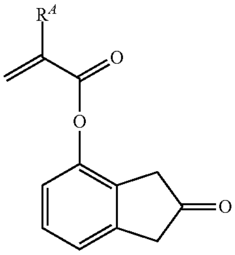
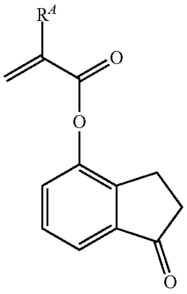
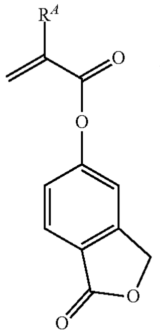
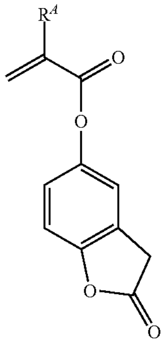
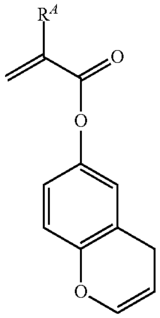
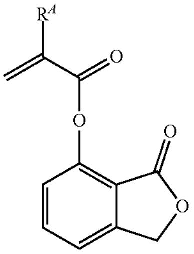
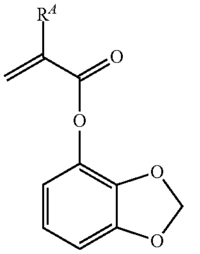
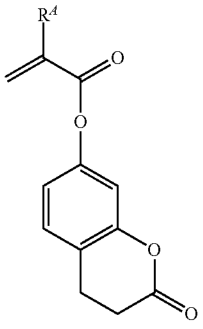
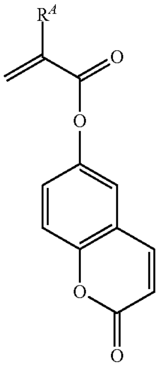
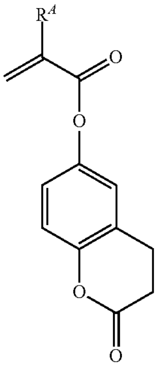

-continued
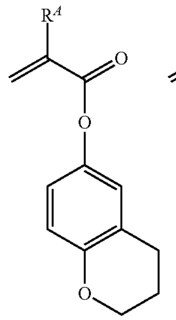
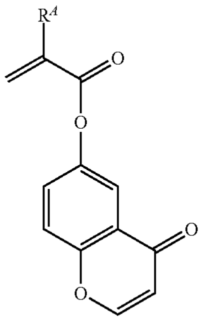
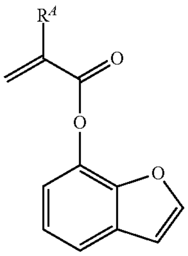
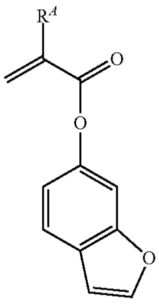
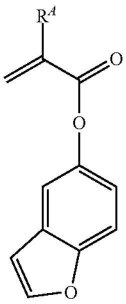
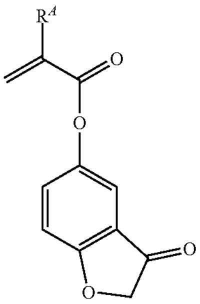
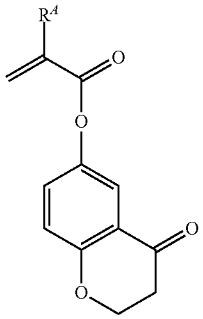
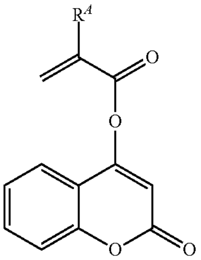
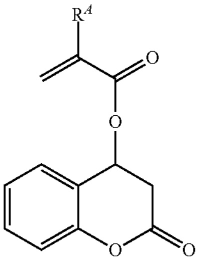
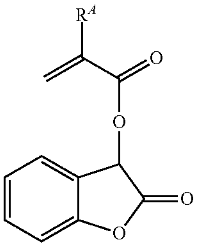
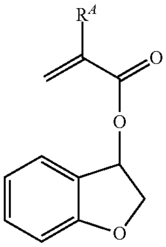
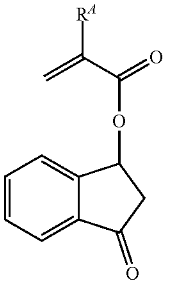
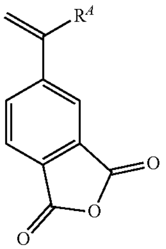
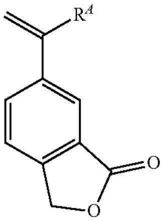
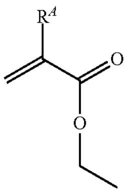
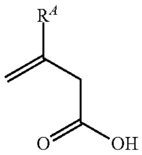
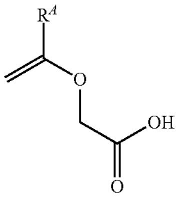
-continued
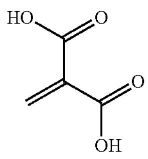
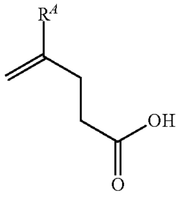
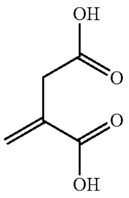
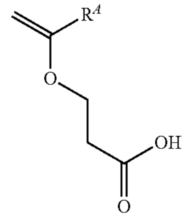
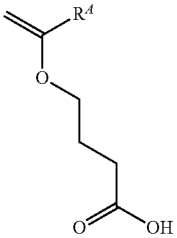
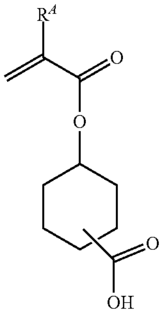
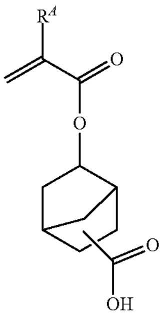
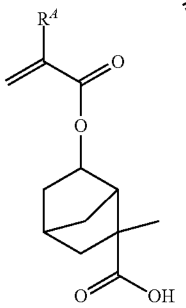
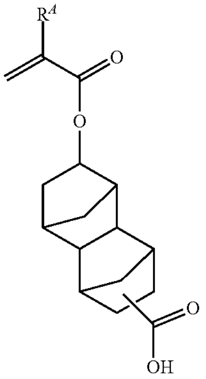
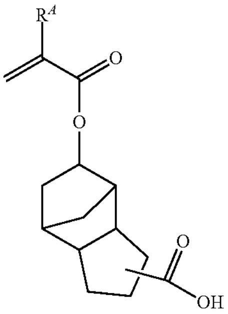
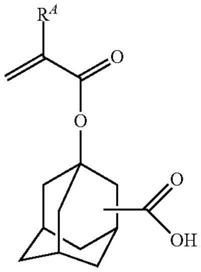
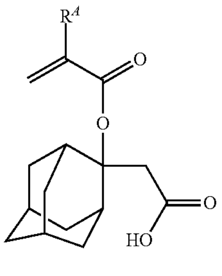
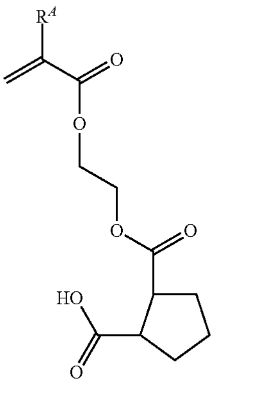

-continued

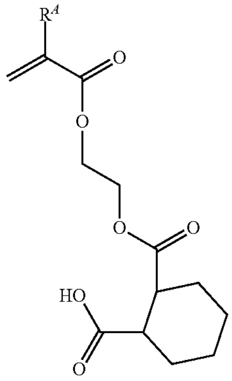
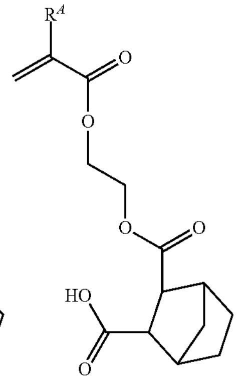
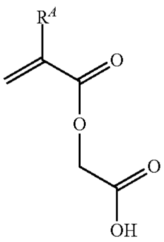
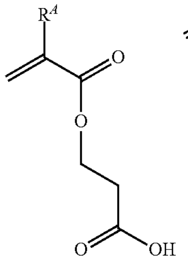
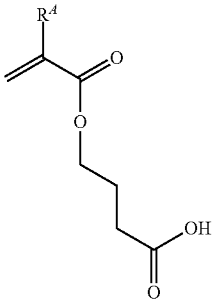
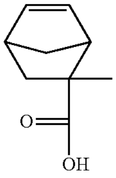
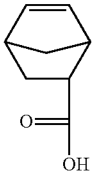
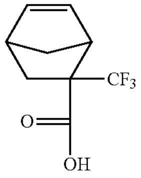
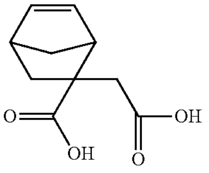
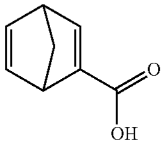
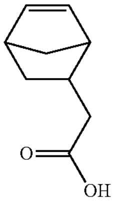

The base polymer may have a repeating unit d derived from indene, benzofuran, benzothiophene, acenaphthylene, chromone, coumarin, norbornadiene, or a derivative thereof. Examples of a monomer to yield the repeating unit d include the following monomers, but the monomer is not limited thereto.

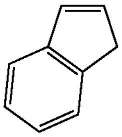
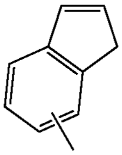
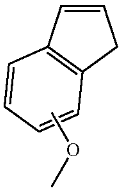
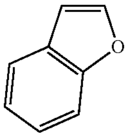
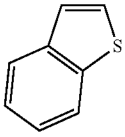
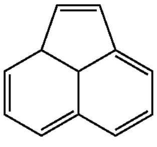
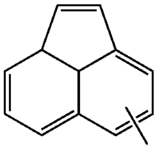

-continued

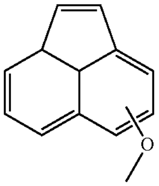
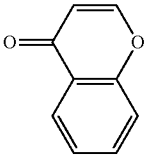
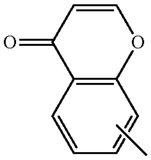
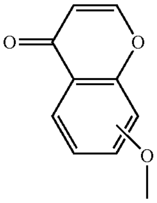
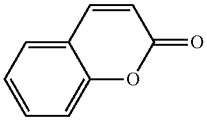
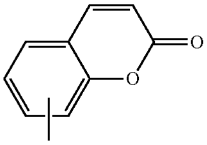
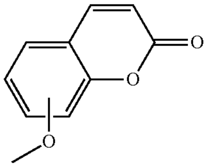
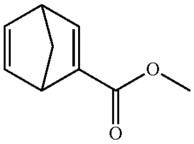

The base polymer may have a repeating unit e derived from styrene, vinylnaphthalene, vinylanthracene, vinylpyrene, methyleneindane, vinylpyridine, or vinylcarbazole.

The base polymer may have a repeating unit f derived from an onium salt having a polymerizable unsaturated bond. Examples of a preferable repeating unit f include a repeating unit represented by the following general formula (f1) (hereinafter, also referred to as the repeating unit f1), a repeating unit represented by the following general formula (f2) (hereinafter, also referred to as the repeating unit f2), and a repeating unit represented by the following general formula (f3) (hereinafter, also referred to as the repeating unit f3). The repeating units f1 to f3 may be used singly, or may be used in combination of two or more kinds thereof.

(f1)

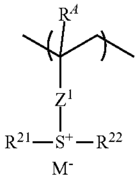

(f2)

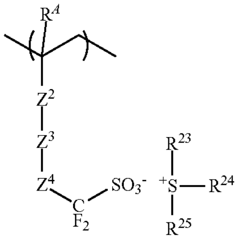

-continued (f3)

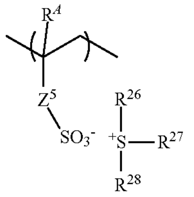

In the general formulae (f1) to (f3), $R^A$ each independently represents a hydrogen atom or a methyl group. $Z^1$ represents a single bond, an aliphatic hydrocarbylene group having 1 to 6 carbon atoms, a phenylene group, a naphthylene group, an ester bond, a group having 7 to 18 carbon atoms obtained by combining these groups, $—O—Z^{11}—$, $—C(=O)—O—Z^{11}—$, or $—C(=O)—NH—Z^{11}—$. $Z^{11}$ represents an aliphatic hydrocarbylene group having 1 to 6 carbon atoms, a phenylene group, a naphthylene group, or a group having 7 to 18 carbon atoms obtained by combining these groups, $Z^{11}$ optionally having a carbonyl group, an ester bond, an ether bond, or a hydroxy group. $Z^2$ represents a single bond or an ester bond. $Z^3$ represents a single bond, $—Z^{31}—C(=O)—O—$, $—Z^{31}—O—$, or $—Z^{31}—O—C(=O)—$. $Z^{31}$ represents a hydrocarbylene group having 1 to 12 carbon atoms, a phenylene group, or a group having 7 to 18 carbon atoms obtained by combining these groups, $Z^{31}$ optionally having a carbonyl group, an ester bond, an ether bond, an iodine atom, or a bromine atom. $Z^4$ represents a methylene group, a 2,2,2-trifluoro-1,1-ethanediyl group, or a carbonyl group. $Z^5$ represents a single bond, a methylene group, an ethylene group, a phenylene group, a fluorinated phenylene group, a phenylene group substituted with a trifluoromethyl group, $—O—Z^{51}—$, $—C(=O)—O—Z^{11}—$, or $—C(=O)—NH—Z^{51}—$. $Z^{51}$ represents an aliphatic hydrocarbylene group having 1 to 6 carbon atoms, a phenylene group, a fluorinated phenylene group, a phenylene group substituted with a trifluoromethyl group, or a combination thereof, $Z^{51}$ optionally having a carbonyl group, an ester bond, an ether bond, a halogen atom, and/or a hydroxy group.

In the general formulae (f1) to (f3), $R^{21}$ to $R^{28}$ each independently represent a halogen atom or a hydrocarbyl group having 1 to 20 carbon atoms and optionally having a heteroatom. The hydrocarbyl group may be a saturated or unsaturated group, and may be any one of linear, branched, and cyclic groups. Specific examples thereof include groups same as those exemplified as the hydrocarbyl group represented by $R^{11'}$ to $R^{19'}$ in the description of the general formulae (Cation-1) to (Cation-3). A part or all of hydrogen atoms in the hydrocarbyl group are optionally substituted with a group having a heteroatom such as an oxygen atom, a sulfur atom, a nitrogen atom, and a halogen atom. A part of carbon atoms in these groups is optionally substituted with a group having a heteroatom such as an oxygen atom, a sulfur atom, and a nitrogen atom. As a result, optionally contained are a hydroxy group, a fluorine atom, a chlorine atom, a bromine atom, an iodine atom, a cyano group, a nitro group, a carbonyl group, an ether bond, an ester bond, a sulfonate ester bond, a carbonate bond, a lactone ring, a sultone ring, a carboxylic anhydride, a haloalkyl group, etc. $R^{23}$ and $R^{24}$ or $R^{26}$ and $R^{27}$ are optionally bonded to each other to form a ring together with the sulfur atom to which these groups are bonded. In this case, examples of the ring include rings same as those exemplified as the rings that can be formed by bonding $R^{11'}$ and $R^{12'}$ together with the sulfur atom to which these groups are bonded, described in the general formula (Cation-1).

In the general formula (f1), $M^-$ represents a non-nucleophilic counterion. Examples of the non-nucleophilic counterion include: halide ions, such as a chloride ion and bromide ion; fluoroalkylsulfonate ions, such as a triflate ion, a 1,1,1-trifluoroethanesulfonate ion, and a nonafluorobutanesulfonate ion; arylsulfonate ions, such as a tosylate ion, a benzenesulfonate ion, a 4-fluorobenzenesulfonate ion, and a 1,2,3,4,5-pentafluorobenzenesulfonate ion; alkylsulfonate ions, such as a mesylate ion and a butanesulfonate ion; imide ions, such as a bis(trifluoromethylsulfonyl)imide ion, a bis(perfluoroethylsulfonyl)imide ion, and a bis(perfluorobutylsulfonyl)imide ion; and methide ions, such as a tris(trifluoromethylsulfonyl)methide ion and a tris(perfluoroethylsulfonyl)methide ion.

Other examples of the non-nucleophilic counterion include: a sulfonate ion in which the α-position is substituted with a fluorine atom, represented by the following general formula (f1-1); and a sulfonate ion in which the α-position is substituted with a fluorine atom and the β-position is substituted with a trifluoromethyl group, represented by the following general formula (f1-2).

(f1-1)

$$R^{31}—CF_2—SO_3^-$$

(f1-2)

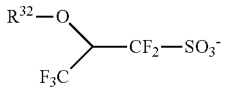

In the general formula (f1-1), $R^{31}$ represents a hydrogen atom or a hydrocarbyl group having 1 to 20 carbon atoms. The hydrocarbyl group optionally has an ether bond, an ester bond, a carbonyl group, a lactone ring, or a fluorine atom. The hydrocarbyl group may be a saturated or unsaturated group, and may be any of linear, branched, and cyclic groups. Specific examples thereof include groups same as those exemplified as a hydrocarbyl group represented by $R^{111}$ in the formula (3A'), described later.

In the general formula (f1-2), $R^{32}$ represents a hydrogen atom, a hydrocarbyl group having 1 to 30 carbon atoms, or a hydrocarbylcarbonyl group having 6 to 20 carbon atoms. The hydrocarbyl group and the hydrocarbylcarbonyl group optionally have an ether bond, an ester bond, a carbonyl group, or a lactone ring. The hydrocarbyl group and the hydrocarbyl part of the hydrocarbylcarbonyl group may be a saturated or unsaturated group, and may be any of linear, branched, and cyclic groups. Specific examples thereof include groups same as those exemplified as a hydrocarbyl group represented by $R^{111}$ in the formula (3A'), described later.

Examples of the cation of a monomer to yield the repeating unit f1 include the following cations, but the cation is not limited thereto. In the following formulae, $R^A$ represents the same as above.

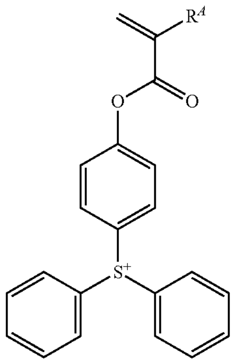
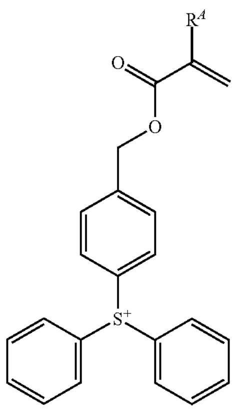
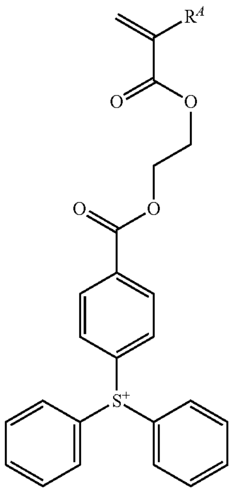
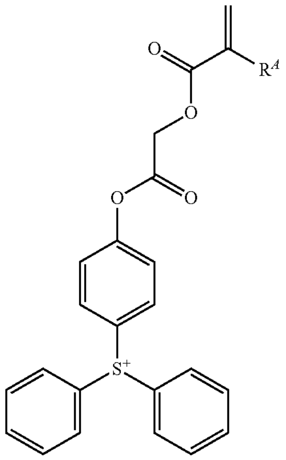
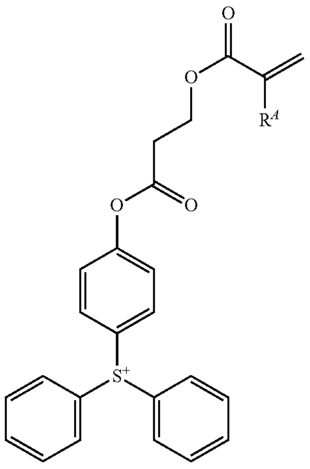
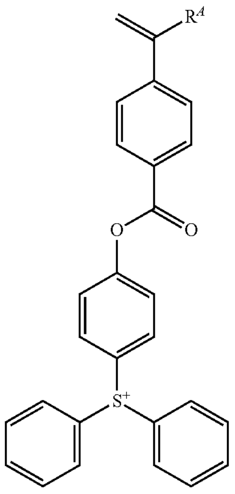
-continued
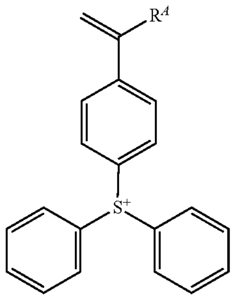
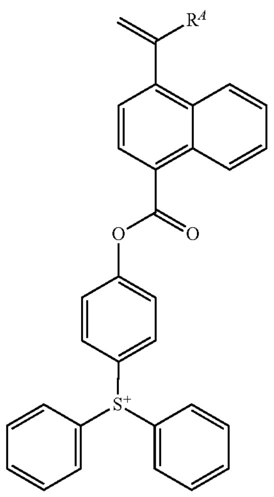
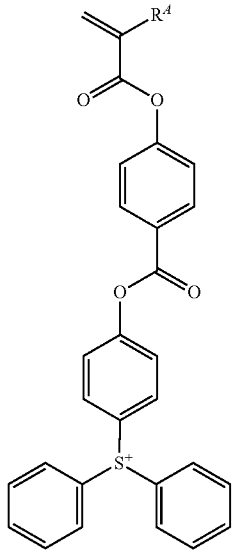
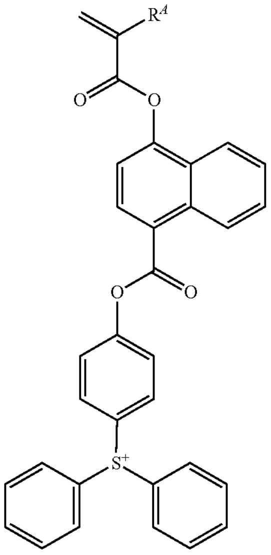
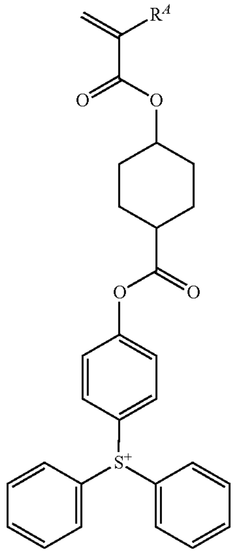
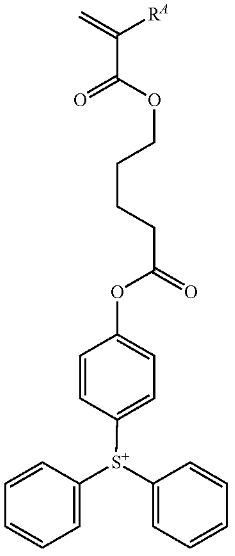

-continued

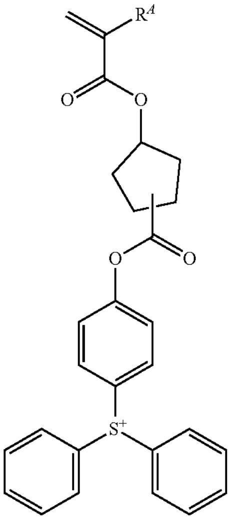

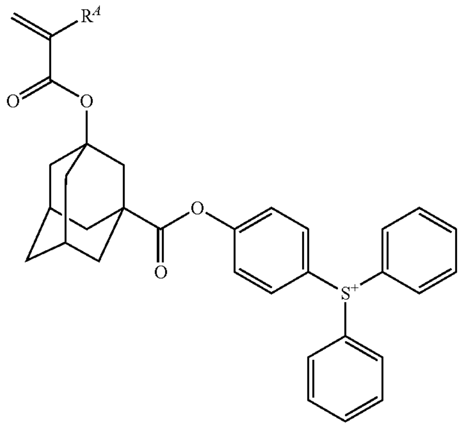

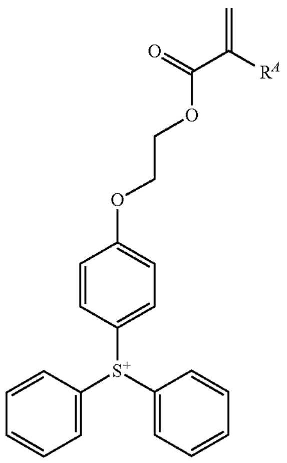

-continued

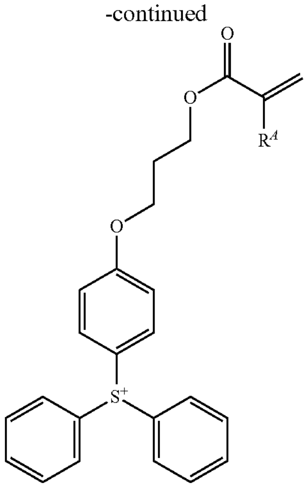

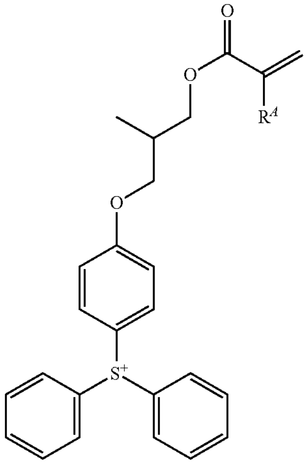

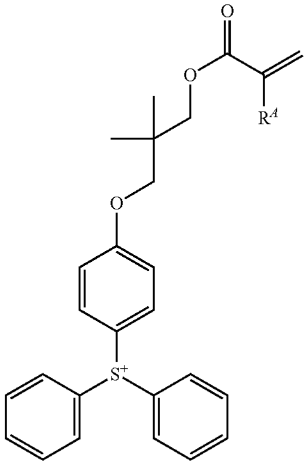

Specific examples of the cation of a monomer to yield the repeating unit f2 or f3 include cations same as those exemplified as the cation of the sulfonium salt represented by the formula (Cation-1).

Examples of the anion of a monomer to yield the repeating unit f2 include the following anions, but the anion is not limited thereto. In the following formulae, $R^A$ represents the same as above.

-continued
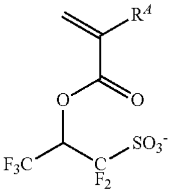
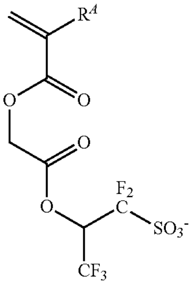
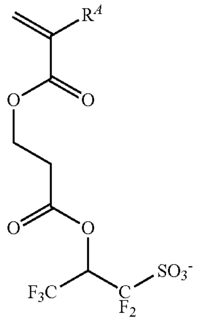
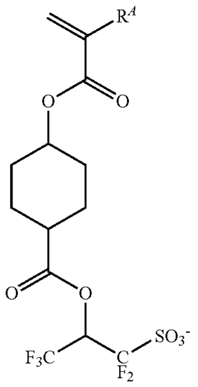
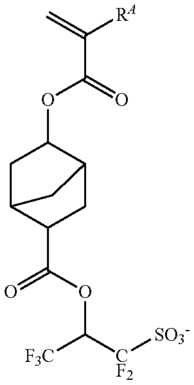
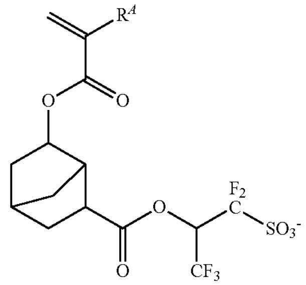
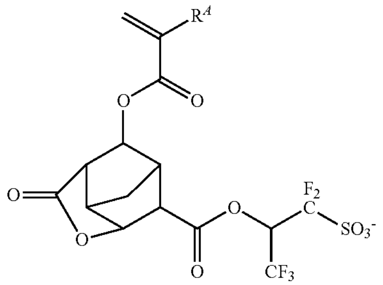
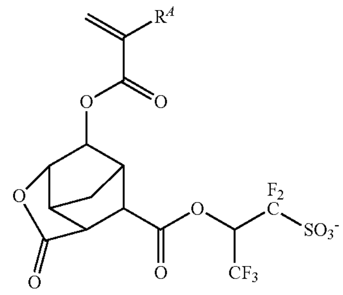
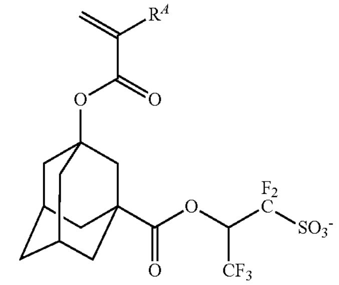
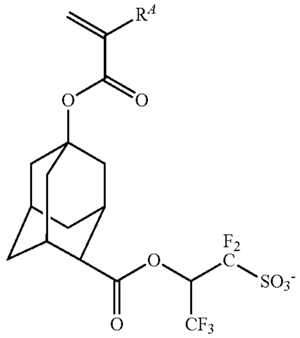
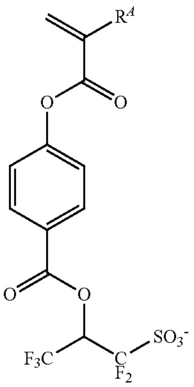
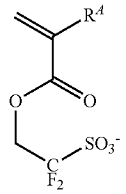
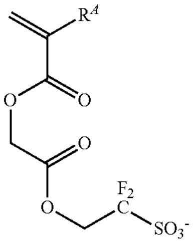
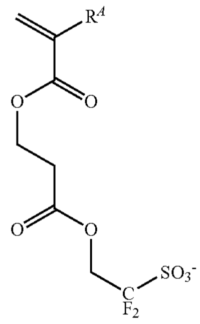
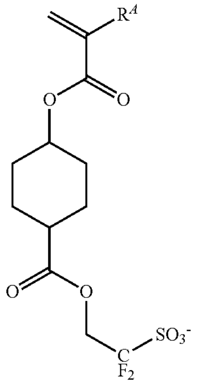

-continued
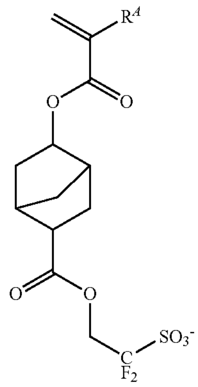
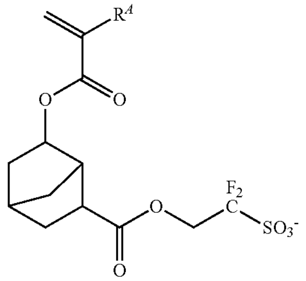
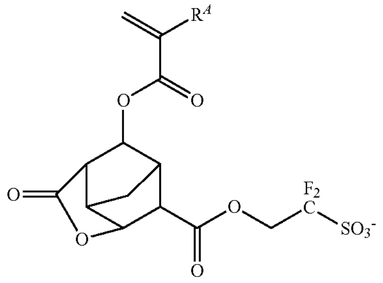
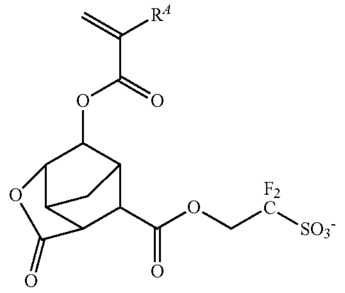
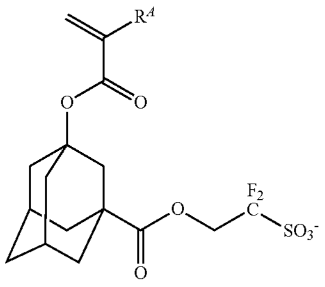
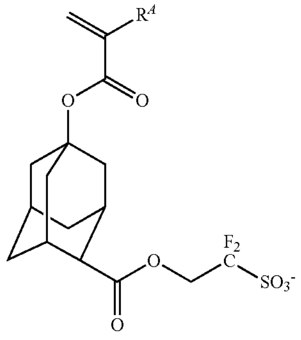
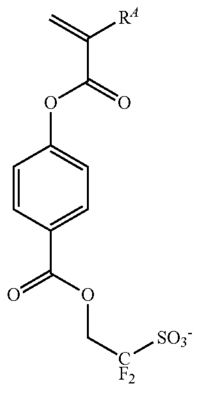
-continued
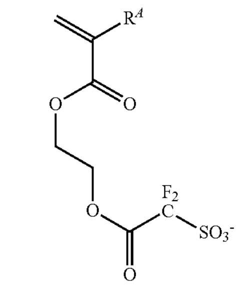
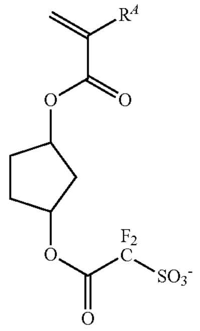
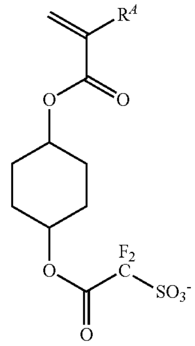
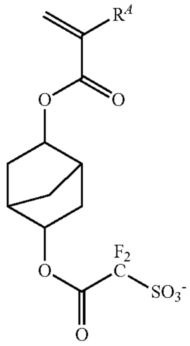
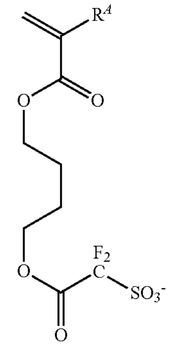
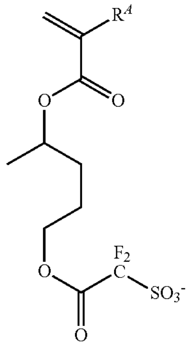
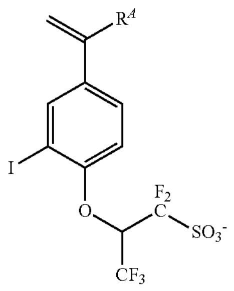
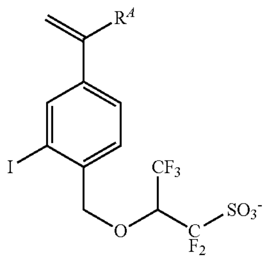
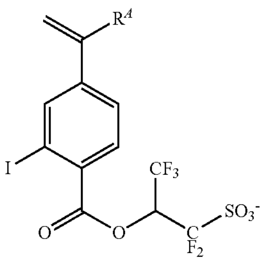
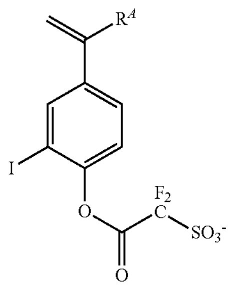

-continued
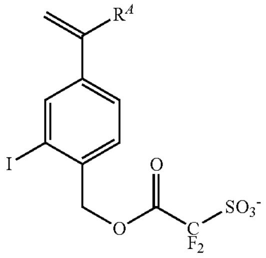
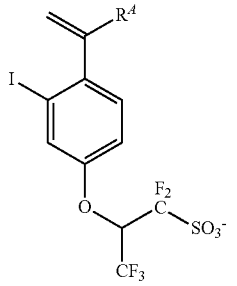
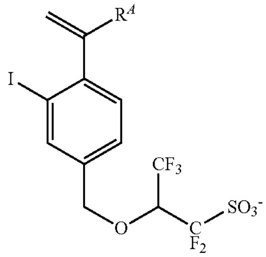
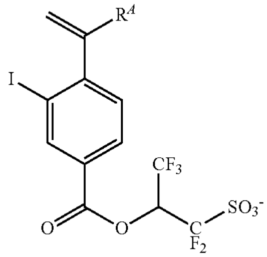
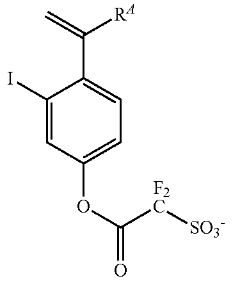
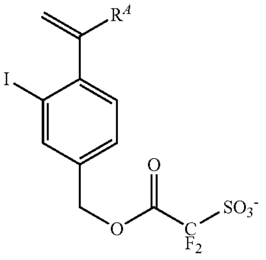
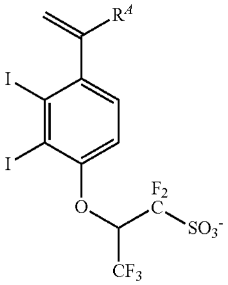
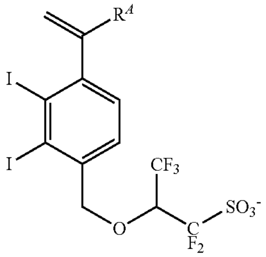
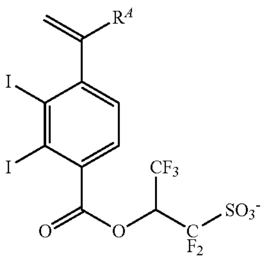
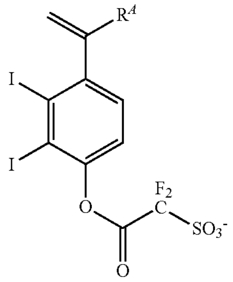
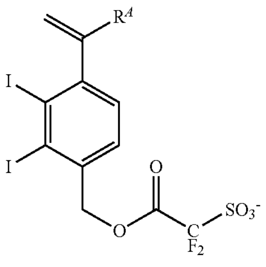
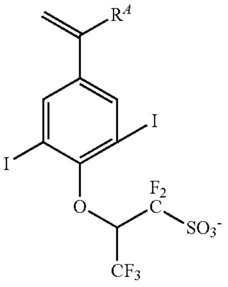
-continued
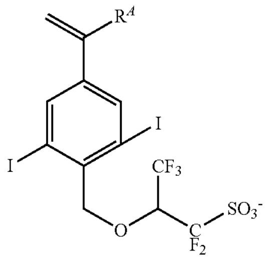
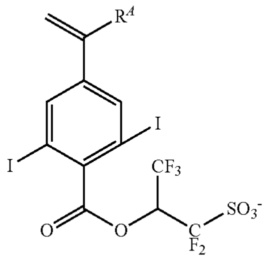
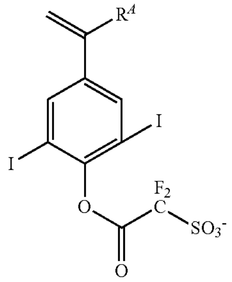
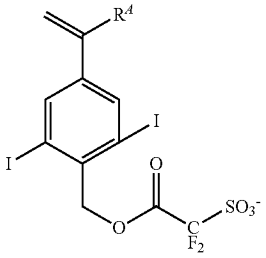
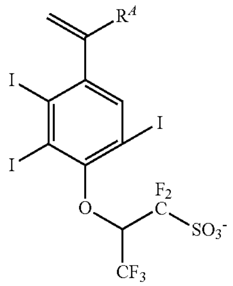
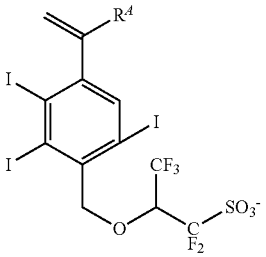
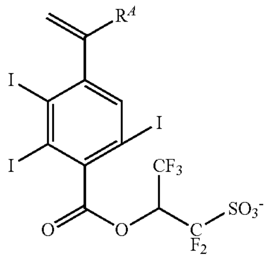
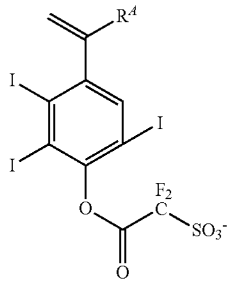
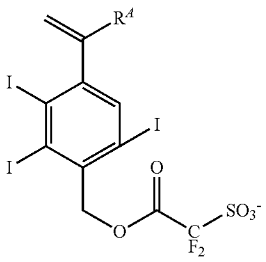
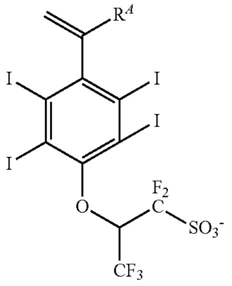
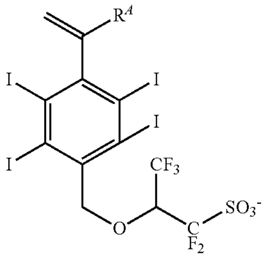
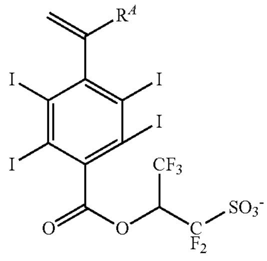

-continued
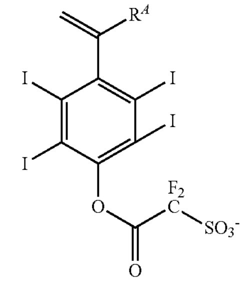
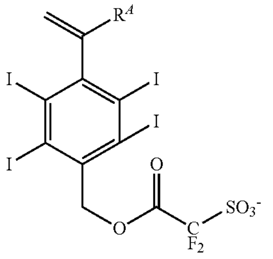
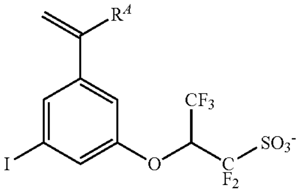
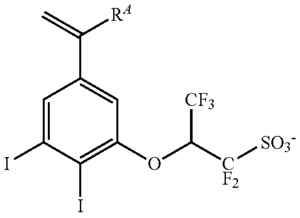
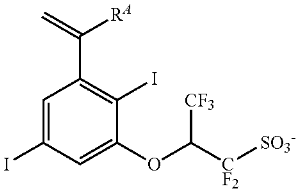
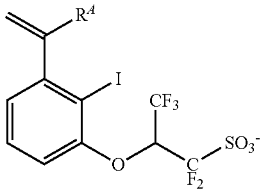
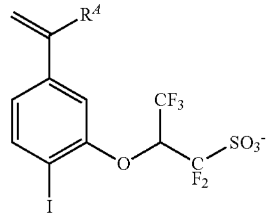
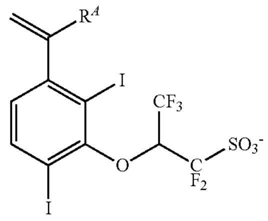
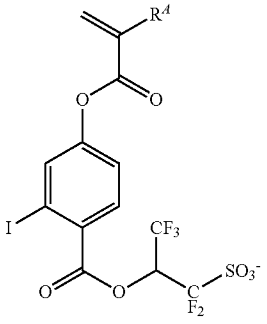
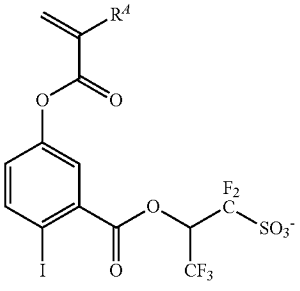
-continued
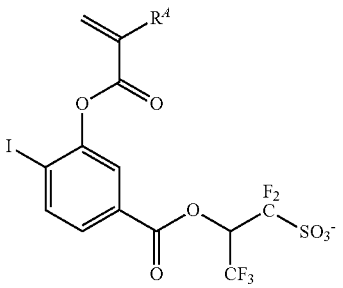
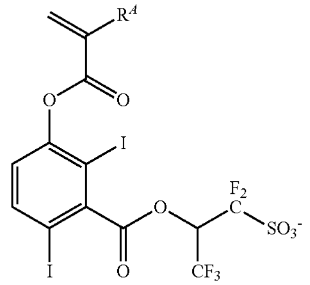
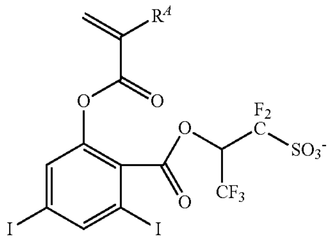
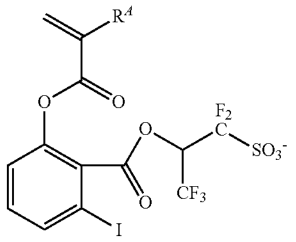
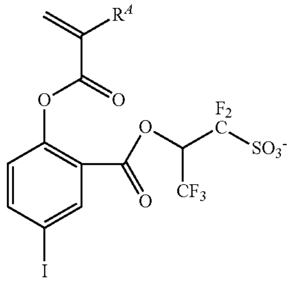
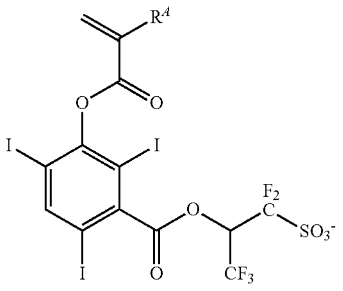

-continued
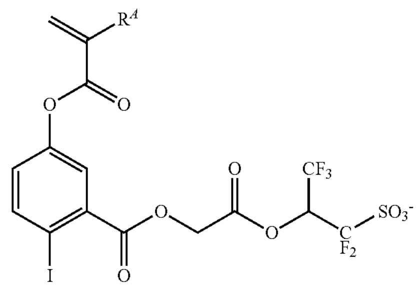
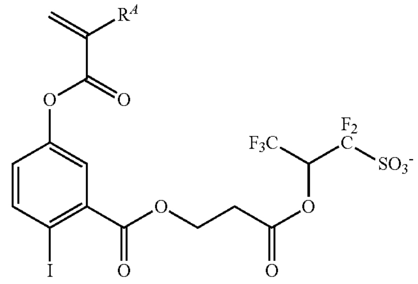
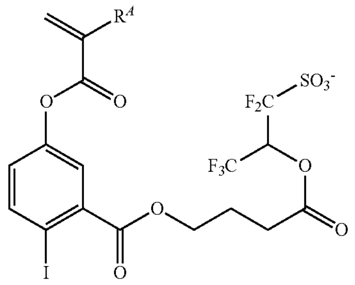
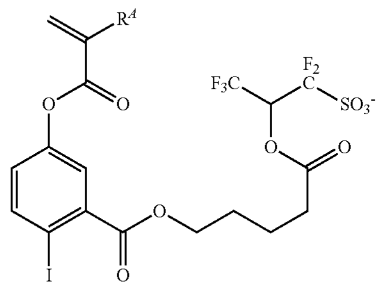
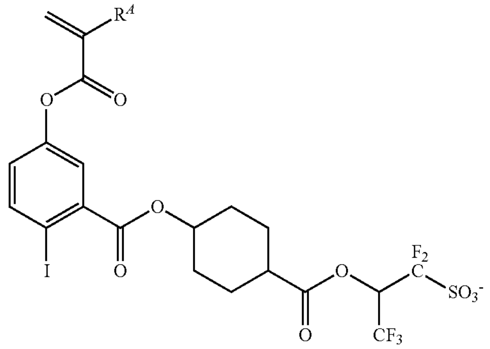
-continued
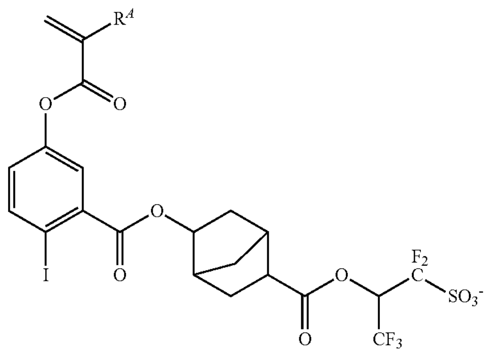
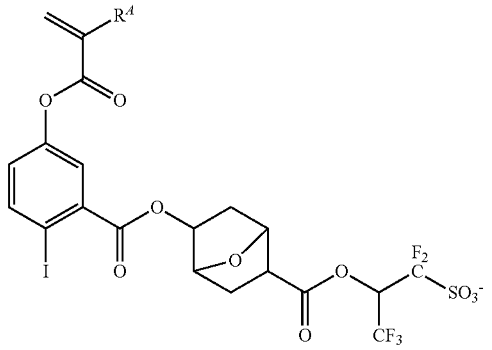
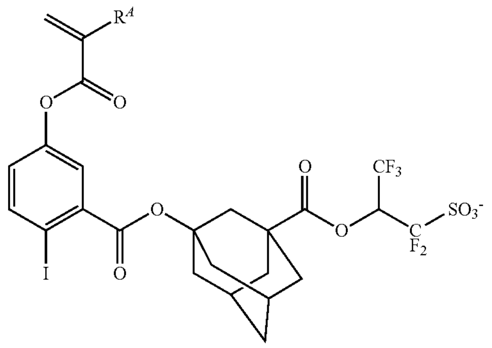
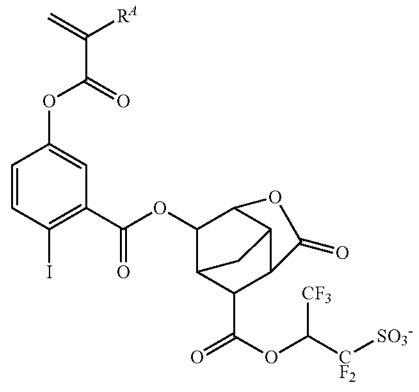

-continued
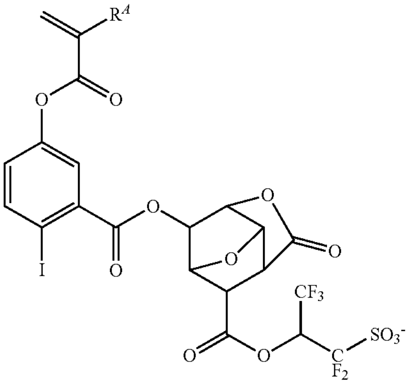
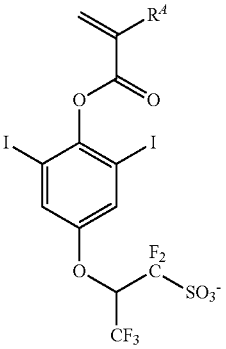
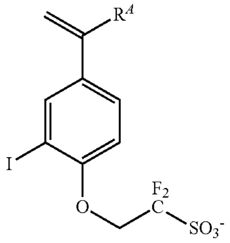
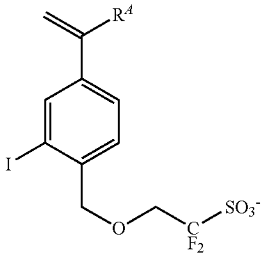
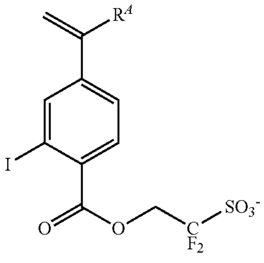
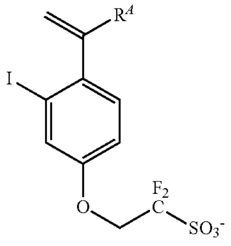
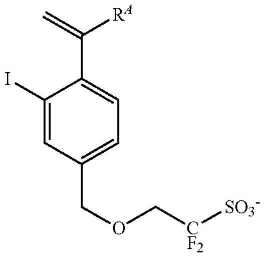
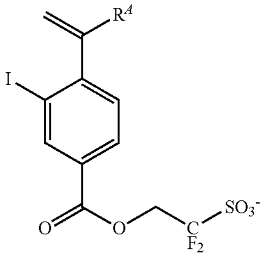
-continued
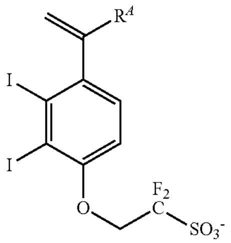
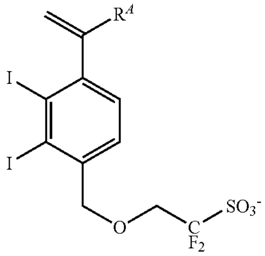
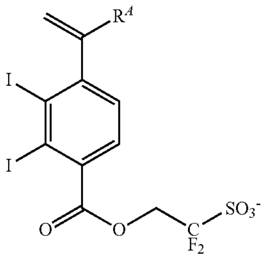
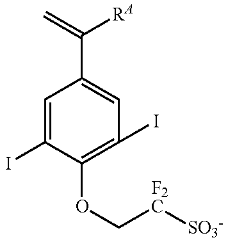
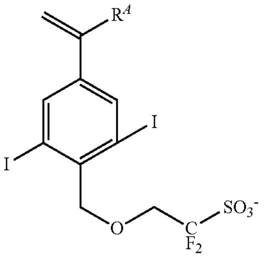
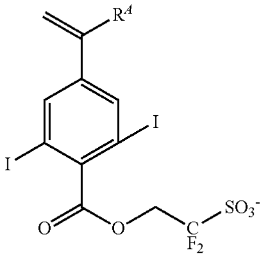
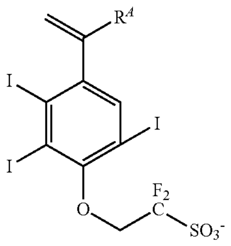
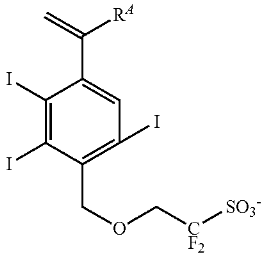
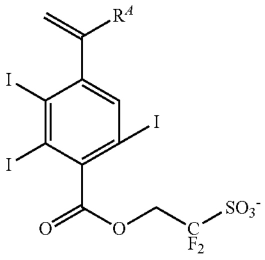
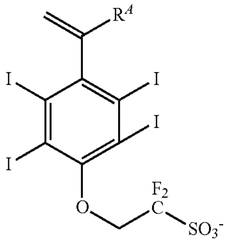
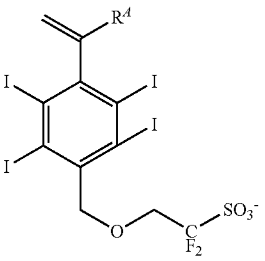
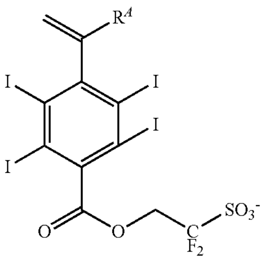

-continued
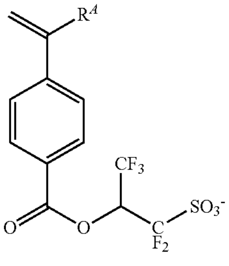
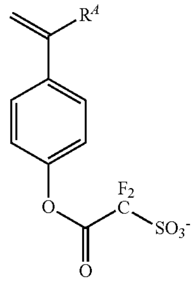
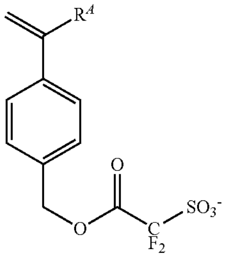
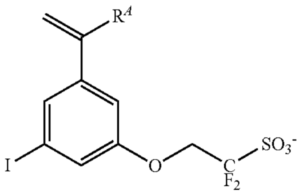
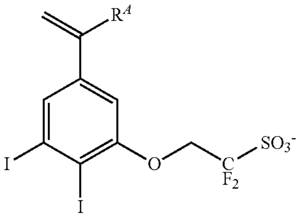
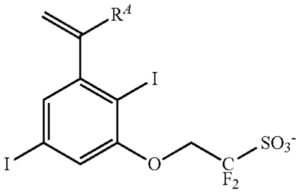
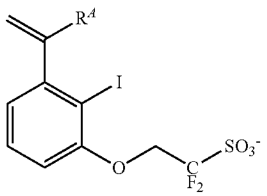
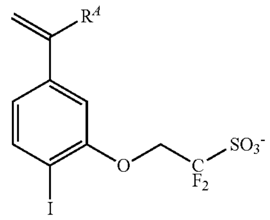
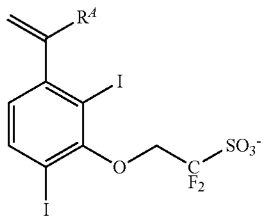
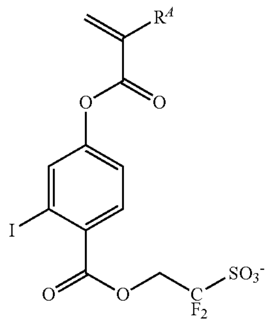
-continued
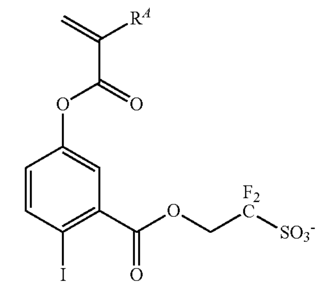
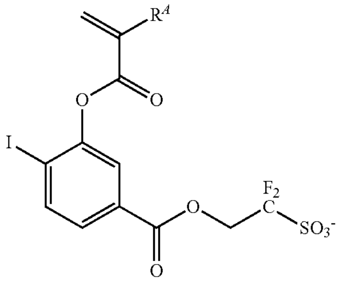
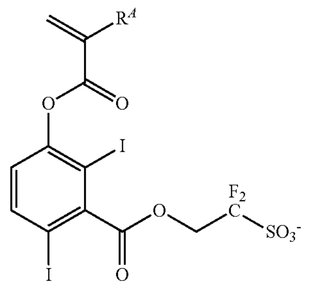
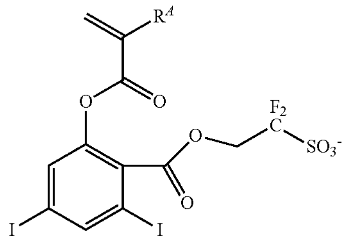
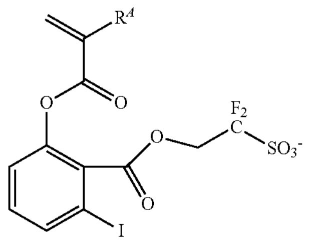
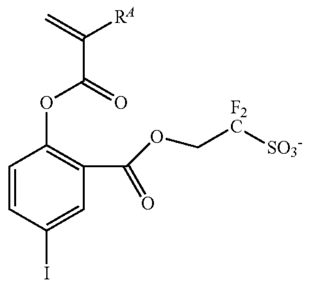

-continued
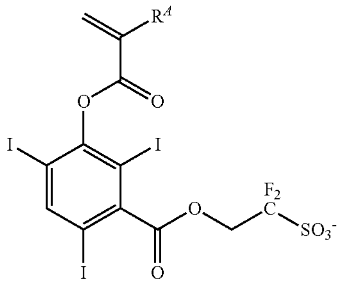
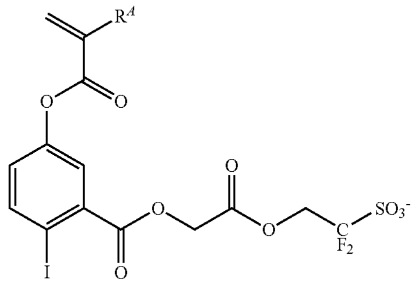
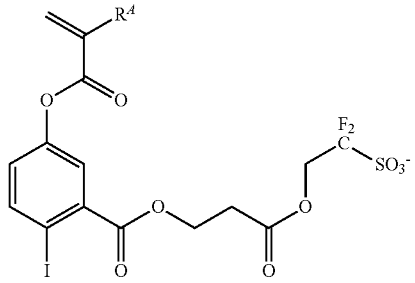
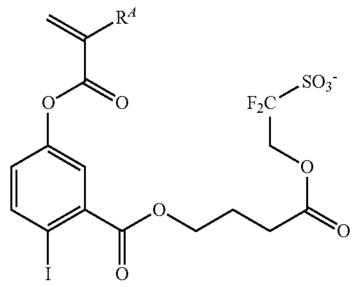
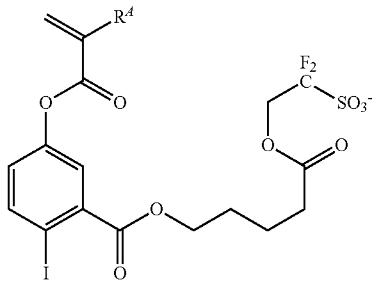
-continued
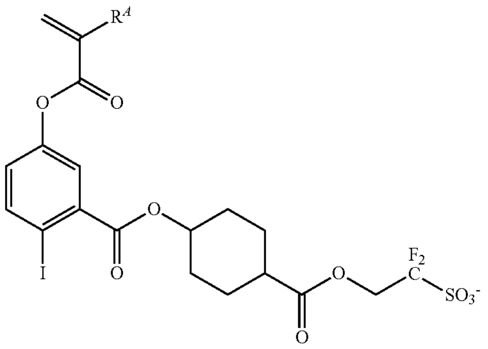
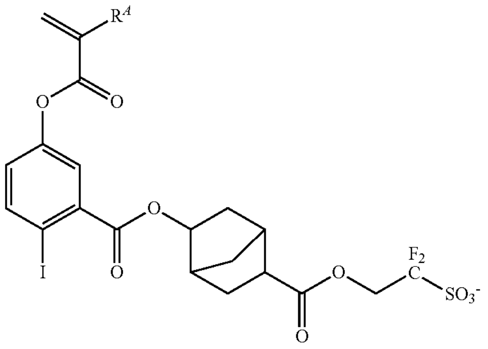
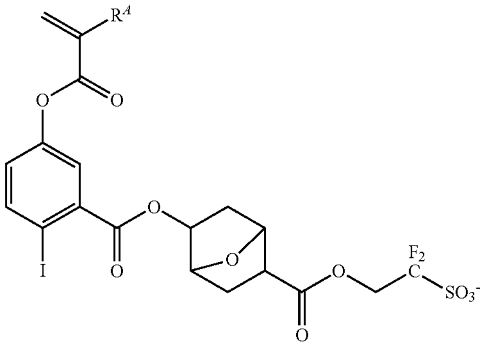
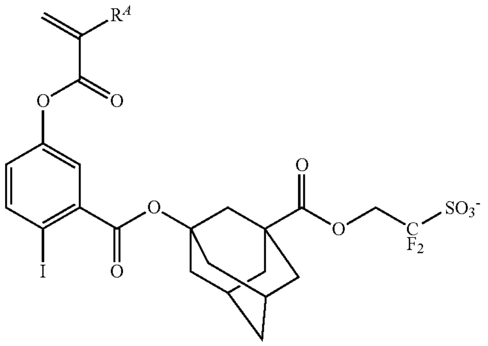

-continued
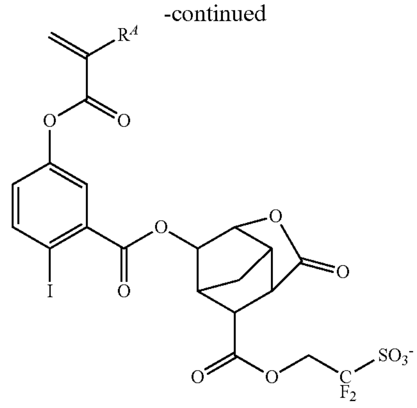
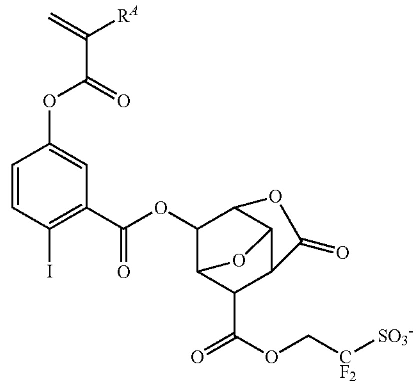
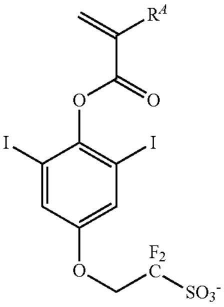
Examples of the anion of a monomer to yield the repeating unit f3 include the following anions, but the anion is not limited thereto. In the following formulae, $R^A$ represents the same as above.
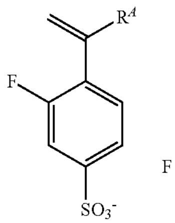
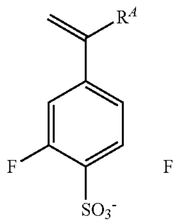
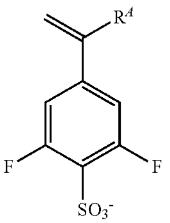
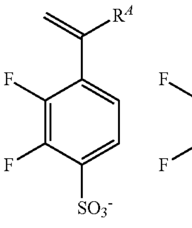
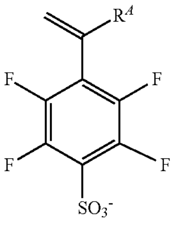
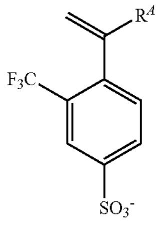
-continued
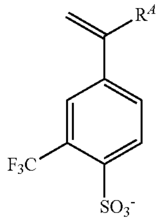
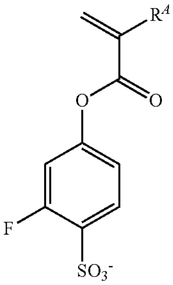
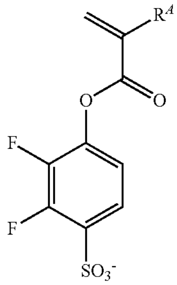
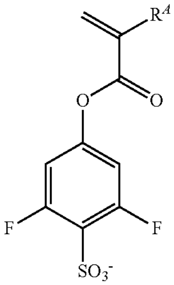
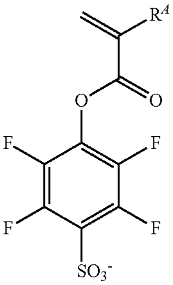
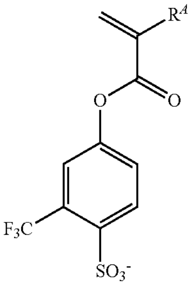
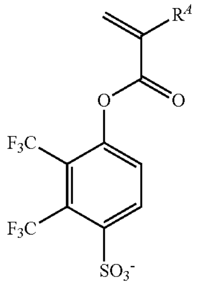
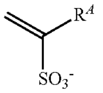
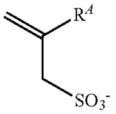
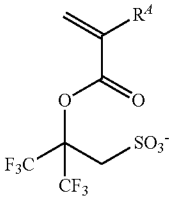
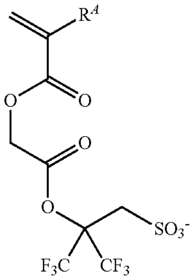
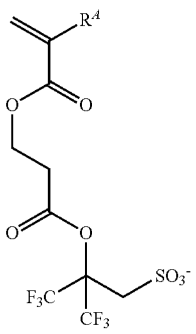
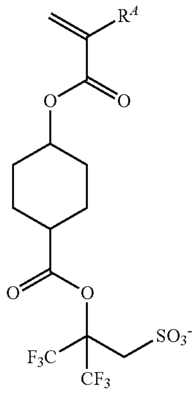

-continued

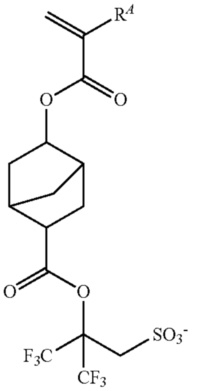

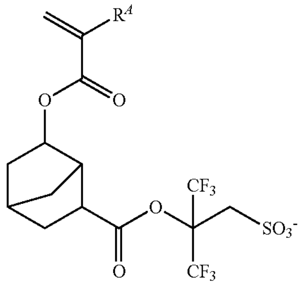

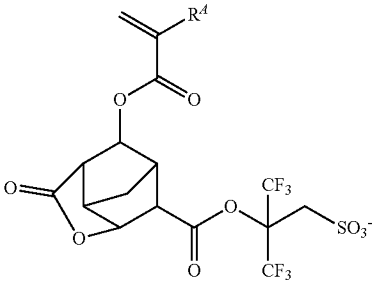

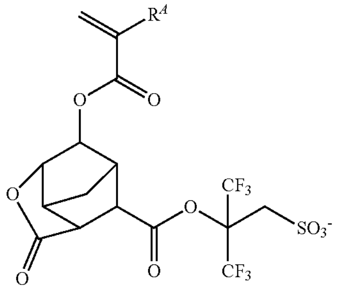

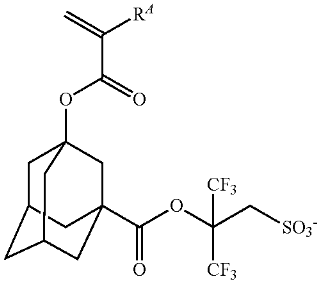

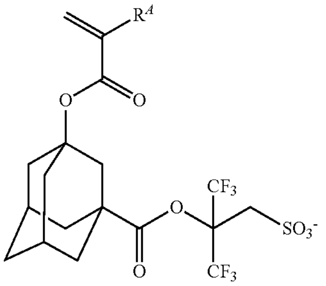

-continued

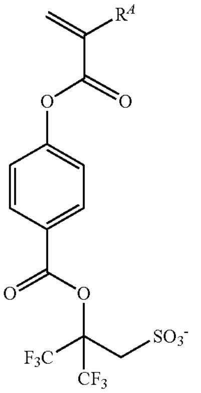

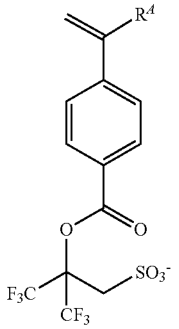

The repeating units f1 to f3 have a function of an acid generator. Binding the acid generator to the polymer main chain reduces the acid diffusion, and can prevent deterioration of resolution due to blur with the acid diffusion. In addition, uniformly dispersing the acid generator improves LWR and CDU. When the base polymer having the repeating unit f is used, blending an additive-type acid generator, described later, can be omitted.

In the base polymer, content rates of the repeating units a1, a2, b, c, d, e, f1, f2, and f3 are preferably $0 \le a1 \le 0.9$, $0 \le a2 \le 0.9$, $0 \le a1+a2 \le 0.9$, $0 \le b \le 0.9$, $0 \le c \le 0.9$, $0 \le d \le 0.5$, $0 \le e \le 0.5$, $0 \le f1 \le 0.5$, $0 \le f2 \le 0.5$, $0 \le f3 \le 0.5$, and $0 \le f1+f2+f3 \le 0.5$, more preferably $0 \le a1 \le 0.8$, $0 \le a2 \le 0.8$, $0 \le a1+a2 \le 0.8$, $0 \le b \le 0.8$, $0 \le c \le 0.8$, $0 \le d \le 0.4$, $0 \le e \le 0.4$, $0 \le f1 \le 0.4$, $0 \le f2 \le 0.4$, $0 \le f3 \le 0.4$, and $0 \le f1+f2+f3 \le 0.4$, and further preferably $0 \le a1 \le 0.7$, $0 \le a2 \le 0.7$, $0 \le a1+a2 \le 0.7$, $0 \le b \le 0.7$, $0 \le c \le 0.7$, $0 \le d \le 0.3$, $0 \le e \le 0.3$, $0 \le f1 \le 0.3$, $0 \le f2 \le 0.3$, $0 \le f3 \le 0.3$, and $0 \le f1+f2+f3 \le 0.3$. Note that, $a1+a2+b+c+d+f1+f2+f3+e=1.0$.

To synthesize the base polymer, the monomers to yield the aforementioned repeating units are heated in an organic solvent with adding a radical polymerization initiator to perform polymerization, for example.

Examples of the organic solvent used for the polymerization include toluene, benzene, tetrahydrofuran (THF), diethyl ether, and dioxane. Examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. The temperature for the polymerization is preferably 50 to 80° C. The reaction time is preferably 2 to 100 hours, and more preferably 5 to 20 hours.

When a monomer having a hydroxy group is copolymerized, the hydroxy group may be substituted with an acetal group easily deprotected by an acid, such as an ethoxyethoxy group, for the polymerization, and the protected hydroxy group may be deprotected by a weak acid and water after the polymerization. Alternatively, the hydroxy group may be substituted with an acetyl group, a formyl group, a pivaloyl group, etc. and hydrolyzed with an alkali after the polymerization.

When hydroxystyrene or hydroxyvinylnaphthalene is copolymerized, acetoxystyrene or acetoxyvinylnaphthalene may be used instead of hydroxystyrene or hydroxyvinylnaphthalene, and the acetoxy group is deprotected with the alkaline hydrolysis after the polymerization to be converted into hydroxystyrene or hydroxyvinylnaphthalene.

As a base in the alkaline hydrolysis, aqueous ammonia, triethylamine, etc. can be used. The reaction temperature is preferably −20 to 100° C., and more preferably 0 to 60° C. The reaction time is preferably 0.2 to 100 hours, and more preferably 0.5 to 20 hours.

The base polymer preferably has a weight-average molecular weight (Mw) of 1,000 to 500,000, and more preferably 2,000 to 30,000. The Mw is in terms of polystyrene by gel permeation chromatography (GPC) using THF as a solvent. Mw within the above range yields good heat resistance of the resist film and solubility in an alkaline developer.

When the base polymer has sufficiently narrow molecular weight distribution (Mw/Mn), a low molecular-weight and high molecular-weight polymers are absent, and thereby there is no risk of foreign matter observed on a pattern and deterioration in a pattern shape after the exposure. Since Mw and Mw/Mn have a larger effect as the pattern rule becomes smaller, the Mw/Mn of the base polymer is preferably 1.0 to 2.0 and particularly preferably 1.0 to 1.5, which indicates narrow distribution, in order to obtain a resist material suitably used for a fine pattern size.

The base polymer may contain two or more kinds of polymers having different composition ratios, Mw, and Mw/Mn.

Acid Generator

The inventive resist material may contain an acid generator to generate a strong acid (hereinafter, also referred to as the additive-type acid generator). The strong acid herein means: a compound having sufficient acidity for causing the deprotection reaction of the acid-labile group in the base polymer in a case of a chemically amplified positive-type resist material; or a compound having sufficient acidity for causing a polarity-changing reaction or crosslinking reaction with the acid in a case of a chemically amplified negative-type resist material. Containing such an acid generator enables the aforementioned onium salt to function as a quencher, and enables the inventive resist material to function as a chemically amplified positive-type resist material or a chemically amplified negative-type resist material.

Examples of the acid generator include a compound to generate an acid by sensitizing with active ray or radiation (photoacid generator). The photoacid generator may be any compound that generates an acid by high-energy ray irradiation, but the photoacid generator preferably generates a sulfonic acid, an imide acid, or a methide acid. Examples of preferable photoacid generators include sulfonium salts, iodonium salts, sulfonyldiazomethanes, N-sulfonyloxyimides, and oxime-O-sulfonate-type acid generators. Specific examples of the photoacid generator include those described in paragraphs [0122] to [0142] of JP 2008-111103 A.

As the photoacid generator, a sulfonium salt represented by the following general formula (3-1) and an iodonium salt represented by the following general formula (3-2) can also be preferably used.

(3-1)

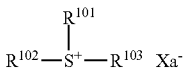

(3-2)

$$R^{104}—I^{+}—R^{105}\ Xa^{-}$$

In the general formulae (3-1) and (3-2), $R^{101}$ to $R^{105}$ each independently represent a halogen atom or a hydrocarbyl group having 1 to 20 carbon atoms and optionally having a heteroatom. The hydrocarbyl group may be a saturated or unsaturated group, and may be any of linear, branched, and cyclic groups. Specific examples thereof include groups same as those exemplified as the hydrocarbyl group represented by $R^{11'}$ to $R^{19'}$ in the description of the formulae (Cation-1) to (Cation-3). $R^{101}$ and $R^{102}$ are optionally bonded to each other to form a ring together with the sulfur atom to which these groups are bonded. In this case, examples of the ring include rings same as those exemplified as the rings that can be formed by bonding $R^{11'}$ and $R^{12'}$ together with the sulfur atom to which these groups are bonded, described in the formula (Cation-1).

Examples of the cation of the sulfonium salt represented by the general formula (3-1) include cations same as those exemplified as the cation of the sulfonium salt represented by the formula (Cation-1), but the cation is not limited thereto.

Examples of the cation of the iodonium salt represented by the general formula (3-2) include cations same as those exemplified as the cation of the iodonium salt represented by the formula (Cation-2), but the cation is not limited thereto.

In the general formulae (3-1) and (3-2), $Xa^{-}$ represents an anion selected from the following formulae (3A) to (3D).

(3A)

$$R^{fa}—CF_2—SO_3^{-}$$

(3B)

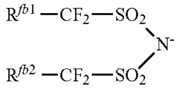

(3C)

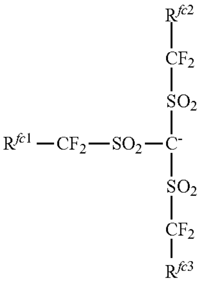

(3D)

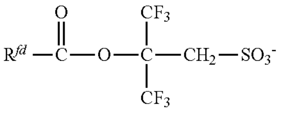

In the general formula (3A), $R^{fa}$ represents a fluorine atom or a hydrocarbyl group having 1 to 40 carbon atoms and optionally having a heteroatom. The hydrocarbyl group may be a saturated or unsaturated group, and may be any of linear, branched, and cyclic groups. Specific examples thereof include groups same as those exemplified as a hydrocarbyl group represented by $R^{111}$ in the formula (3A'), described later.

The anion represented by the formula (3A) is preferably represented by the following general formula (3A').

(3A')

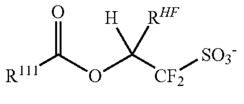

In the general formula (3A'), $R^{HF}$ represents a hydrogen atom or a trifluoromethyl group, and preferably a trifluoromethyl group. $R^{111}$ represents a hydrocarbyl group having 1 to 38 carbon atoms and optionally having a heteroatom. The heteroatom is preferably an oxygen atom, a nitrogen atom, a sulfur atom, a halogen atom, etc., and more preferably an oxygen atom. The hydrocarbyl group particularly preferably has 6 to 30 carbon atoms in terms of obtaining high resolution in fine patterning.

The hydrocarbyl group represented by $R^{111}$ may be a saturated or unsaturated group, and may be any of linear, branched, and cyclic groups. Specific examples thereof include: alkyl groups having 1 to 38 carbon atoms, such as a methyl group, an ethyl group, a propyl group, an isopropyl group, a butyl group, an isobutyl group, a sec-butyl group, a tert-butyl group, a pentyl group, a neopentyl group, a hexyl group, a heptyl group, a 2-ethylhexyl group, a nonyl group, an undecyl group, a tridecyl group, a pentadecyl group, a heptadecyl group, and an icosanyl group; cyclic saturated hydrocarbyl groups having 3 to 38 carbon atoms, such as a cyclopentyl group, a cyclohexyl group, a 1-adamantyl group, a 2-adamantyl group, a 1-adamantylmethyl group, a norbornyl group, a norbornylmethyl group, a tricyclodecanyl group, a tetracyclododecanyl group, a tetracyclododecanylmethyl group, and a dicyclohexylmethyl group; unsaturated aliphatic hydrocarbyl groups having 2 to 38 carbon atoms, such as an allyl group and a 3-cyclohexenyl group; aryl groups having 6 to 38 carbon atoms, such as a phenyl group, a 1-naphthyl group, and a 2-naphthyl group; aralkyl groups having 7 to 38 carbon atoms, such as a benzyl group and a diphenylmethyl group; and groups obtained by combining these groups.

A part or all of hydrogen atoms in these groups are optionally substituted with a group having a heteroatom such as an oxygen atom, a sulfur atom, a nitrogen atom, and a halogen atom. A part of carbon atoms in these groups is optionally substituted with a group having a heteroatom such as an oxygen atom, a sulfur atom, and a nitrogen atom. As a result, optionally contained are a hydroxy group, a fluorine atom, a chlorine atom, a bromine atom, an iodine atom, a cyano group, a nitro group, a carbonyl group, an ether bond, an ester bond, a sulfonate ester bond, a carbonate bond, a lactone ring, a sultone ring, a carboxylic anhydride, a haloalkyl group, etc. Examples of the hydrocarbyl group having a heteroatom include a tetrahydrofuryl group, a methoxymethyl group, an ethoxymethyl group, a methylthiomethyl group, an acetamidomethyl group, a trifluoroethyl group, a (2-methoxyethoxy)methyl group, an acetoxymethyl group, a 2-carboxy-1-cyclohexyl group, a 2-oxopropyl group, a 4-oxo-1-adamantyl group, and a 3-oxocyclohexyl group.

Synthesis of the sulfonium salt having the anion represented by the general formula (3A') is detailed in JP 2007-145797 A, JP 2008-106045 A, JP 2009-7327 A, and JP 2009-258695 A. Sulfonium salts described in JP 2010-215608 A, JP 2012-41320 A, JP 2012-106986 A, JP 2012-153644 A, etc. are also preferably used.

Examples of the anion represented by the general formula (3A) include anions same as those exemplified as the anion represented by the formula (1A) in JP 2018-197853 A.

In the general formula (3B), $R^{fb1}$ and $R^{fb2}$ each independently represent a fluorine atom or a hydrocarbyl group having 1 to 40 carbon atoms and optionally having a heteroatom. The hydrocarbyl group may be a saturated or unsaturated group, and may be any of linear, branched, and cyclic groups. Specific examples thereof include groups same as those exemplified as the hydrocarbyl group represented by $R^{111}$ in the general formula (3A'). $R^{fb1}$ and $R^{fb2}$ preferably represent a fluorine atom or a linear fluorinated alkyl group having 1 to 4 carbon atoms. $R^{fb1}$ and $R^{fb2}$ are optionally bonded to each other to form a ring together with the group to which these groups are bonded ($-CF_2-SO_2-N-SO_2-CF_2-$), and the group obtained in this case by bonding $R^{fb1}$ and $R^{fb2}$ each other is preferably a fluorinated ethylene group or a fluorinated propylene group.

In the general formula (3C), $R^{fc1}$, $R^{fc2}$, and $R^{fc3}$ each independently represent a fluorine atom or a hydrocarbyl group having 1 to 40 carbon atoms and optionally having a heteroatom. The hydrocarbyl group may be a saturated or unsaturated group, and may be any of linear, branched, and cyclic groups. Specific examples thereof include groups same as those exemplified as the hydrocarbyl group represented by $R^{111}$ in the general formula (3A'). $R^{fc1}$, $R^{fc2}$, and $R^{fc3}$ preferably represent a fluorine atom or a linear fluorinated alkyl group having 1 to 4 carbon atoms. $R^{fc1}$ and $R^{fc2}$ are optionally bonded to each other to form a ring together with the group to which these groups are bonded ($-CF_2-SO_2-C^{-}-SO_2-CF_2-$), and the group obtained in this case by bonding $R^{fc1}$ and $R^{fc2}$ each other is preferably a fluorinated ethylene group or a fluorinated propylene group.

In the general formula (3D), $R^{fd}$ represents a hydrocarbyl group having 1 to 40 carbon atoms and optionally having a heteroatom. The hydrocarbyl group may be a saturated or unsaturated group, and may be any of linear, branched, and cyclic groups. Specific examples thereof include groups same as those exemplified as the hydrocarbyl group represented by $R^{111}$ in the formula (3A').

Synthesis of the sulfonium salt having the anion represented by the general formula (3D) is detailed in JP 2010-215608 A and JP 2014-133723 A.

Examples of the anion represented by the general formula (3D) include anions same as those exemplified as the anions represented by the formula (1D) in JP 2018-197853 A.

The photoacid generator having the anion represented by the general formula (3D) has no fluorine atom at the α-position of the sulfo group, but has two trifluoromethyl groups at the β-position, resulting in the photoacid generator having sufficient acidity for cleaving the acid-labile group in the base polymer. Therefore, it can be used as a photoacid generator.

As the photoacid generator, a compound represented by the following general formula (4) can also be preferably used.

(4)

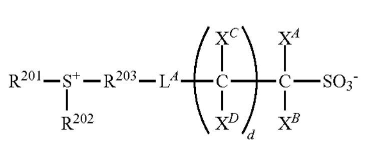

In the general formula (4), $R^{201}$ and $R^{202}$ each independently represent a halogen atom or a hydrocarbyl group having 1 to 30 carbon atoms and optionally having a heteroatom. $R^{203}$ represents a hydrocarbylene group having 1 to 30 carbon atoms and optionally having a heteroatom. Any two of $R^{201}$, $R^{202}$ and $R^{203}$ are optionally bonded to each other to form a ring together with the sulfur atom to which these groups are bonded. In this case, examples of the ring include rings same as those exemplified as the rings that can be formed by bonding $R^{11'}$ and $R^{12'}$ together with the sulfur atom to which these groups are bonded, described in the general formula (Cation-1).

The hydrocarbyl group represented by $R^{201}$ and $R^{202}$ may be a saturated or unsaturated group, and may be any of linear, branched, and cyclic groups. Specific examples thereof include: alkyl groups having 1 to 30 carbon atoms, such as a methyl group, an ethyl group, a propyl group, an isopropyl group, an n-butyl group, a sec-butyl group, a tert-butyl group, an n-pentyl group, a tert-pentyl group, an n-hexyl group, an n-octyl group, a 2-ethylhexyl group, an n-nonyl group, and an n-decyl group; cyclic saturated hydrocarbyl groups having 3 to 30 carbon atoms, such as a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, a norbornyl group, an oxanorbornyl group, a tricyclo[5.2.1.$0^{2,6}$]decanyl group, and an adamantyl group; aryl groups having 6 to 30 carbon atoms, such as a phenyl group, a methylphenyl group, an ethylphenyl group, an n-propylphenyl group, an isopropylphenyl group, an n-butylphenyl group, an isobutylphenyl group, a sec-butylphenyl group, a tert-butylphenyl group, a naphthyl group, a methylnaphthyl group, an ethylnaphthyl group, an n-propylnaphthyl group, an isopropylnaphthyl group, an n-butylnaphthyl group, an isobutylnaphthyl group, a sec-butylnaphthyl group, a tert-butylnaphthyl group, and an anthracenyl group; and groups obtained by combining these groups. A part or all of hydrogen atoms in these groups are optionally substituted with a group having a heteroatom such as an oxygen atom, a sulfur atom, a nitrogen atom, and a halogen atom. A part of carbon atoms in these groups is optionally substituted with a group having a heteroatom such as an oxygen atom, a sulfur atom, and a nitrogen atom. As a result, optionally contained are a hydroxy group, a fluorine atom, a chlorine atom, a bromine atom, an iodine atom, a cyano group, a nitro group, a carbonyl group, an ether bond, an ester bond, a sulfonate ester bond, a carbonate bond, a lactone ring, a sultone ring, a carboxylic anhydride, a haloalkyl group, etc.

The hydrocarbylene group represented by $R^{203}$ may be a saturated or unsaturated group, and may be any of linear, branched, and cyclic groups. Specific examples thereof include: alkanediyl groups having 1 to 30 carbon atoms, such as a methanediyl group, an ethane-1,1-diyl group, an ethane-1,2-diyl group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, and a heptadecane-1,17-diyl group; cyclic saturated hydrocarbylene groups having 3 to 30 carbon atoms, such as a cyclopentanediyl group, a cyclohexanediyl group, a norbornanediyl group, and an adamantanediyl group; arylene groups having 6 to 30 carbon atoms, such as a phenylene group, a methylphenylene group, an ethylphenylene group, an n-propylphenylene group, an isopropylphenylene group, an n-butylphenylene group, an isobutylphenylene group, a sec-butylphenylene group, a tert-butylphenylene group, a naphthylene group, a methylnaphthylene group, an ethylnaphthylene group, an n-propylnaphthylene group, an isopropylnaphthylene group, an n-butylnaphthylene group, an isobutylnaphthylene group, a sec-butylnaphthylene group, and a tert-butylnaphthylene group; and groups obtained by combining these groups. A part or all of hydrogen atoms in these groups are optionally substituted with a group having a heteroatom such as an oxygen atom, a sulfur atom, a nitrogen atom, and a halogen atom. A part of carbon atoms in these groups is optionally substituted with a group having a heteroatom such as an oxygen atom, a sulfur atom, and a nitrogen atom. As a result, optionally contained are a hydroxy group, a fluorine atom, a chlorine atom, a bromine atom, an iodine atom, a cyano group, a nitro group, a carbonyl group, an ether bond, an ester bond, a sulfonate ester bond, a carbonate bond, a lactone ring, a sultone ring, a carboxylic anhydride, a haloalkyl group, etc. The heteroatom is preferably an oxygen atom.

In the general formula (4), $L^A$ represents a single bond, an ether bond, or a hydrocarbylene group having 1 to 20 carbon atoms and optionally having a heteroatom. The hydrocarbylene group may be a saturated or unsaturated group, and may be any of linear, branched, and cyclic groups. Specific examples thereof include groups same as those exemplified as the hydrocarbylene group represented by $R^{203}$.

In the general formula (4), $X^A$, $X^B$, $X^C$, and $X^D$ each independently represent a hydrogen atom, a fluorine atom, or a trifluoromethyl group. Note that, at least one of $X^A$, $X^B$, $X^C$, and $X^D$ represents a fluorine atom or a trifluoromethyl group.

In the general formula (4), "d" represents an integer of 0 to 3.

The photoacid generator represented by the general formula (4) is preferably represented by the following general formula (4').

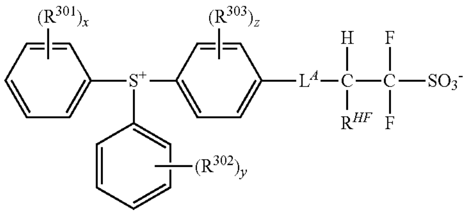
(4')

In the general formula (4'), $L^A$ represents the same as above. $R^{HF}$ represents a hydrogen atom or a trifluoromethyl group, and preferably a trifluoromethyl group. $R^{301}$, $R^{302}$, and $R^{303}$ each independently represent a hydrogen atom or a hydrocarbyl group having 1 to 20 carbon atoms and optionally having a heteroatom. The hydrocarbyl group may be a saturated or unsaturated group, and may be any of linear, branched, and cyclic groups. Specific examples thereof include groups same as those exemplified as the hydrocarbyl group represented by $R^{111}$ in the formula (3A'). "x" and "y" each independently represent an integer of 0 to 5, and "z" represents an integer of 0 to 4.

Examples of the photoacid generator represented by the general formula (4) include photoacid generators same as those exemplified as photoacid generators represented by the formula (2) in JP 2017-026980 A.

Among the above photoacid generators, the photoacid generators having the anion represented by the general formula (3A') or (3D) are particularly preferable since having small acid diffusion and excellent solubility in the solvent. The photoacid generators represented by the formula (4') are particularly preferable since having extremely small acid diffusion.

As the photoacid generator, a sulfonium salt or iodonium salt having an anion having an aromatic ring substituted with an iodine atom or a bromine atom can also be used. Examples of such a salt include salts represented by the following general formula (5-1) or (5-2).

(5-1)

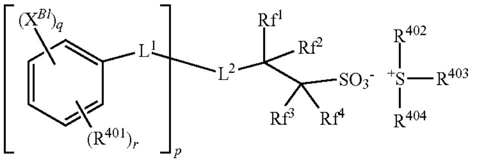

(5-2)

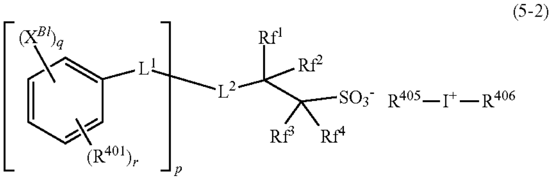

In the general formulae (5-1) and (5-2), "p" represents an integer satisfying 1≤p≤3. "q" and "r" represent an integer satisfying 1≤q≤5, 0≤r≤3, and 1≤q+r≤5. "q" preferably represents an integer satisfying 1≤q≤3, and more preferably 2 or 3. "r" preferably represents an integer satisfying 0≤r≤2.

In the general formulae (5-1) and (5-2), $X^{BI}$ represents an iodine atom or a bromine atom. When "p" and/or "q" represent 2 or more, $X^{BI}$ may be same as or different from each other.

In the general formulae (5-1) and (5-2), $L^1$ represents a single bond, an ether bond, an ester bond, or a saturated hydrocarbylene group having 1 to 6 carbon atoms and optionally having an ether bond or an ester bond. The saturated hydrocarbylene group may be any of linear, branched, and cyclic groups.

In the general formulae (5-1) and (5-2), $L^2$ represents a single bond or a divalent linking group having 1 to 20 carbon atoms when "p" represents 1, and $L^2$ represents a (p+1)-valent linking group having 1 to 20 carbon atoms when "p" represents 2 or 3. The linking group optionally has an oxygen atom, a sulfur atom, or a nitrogen atom.

In the general formulae (5-1) and (5-2), $R^{401}$ represents a hydroxy group, a carboxy group, a fluorine atom, a chlorine atom, a bromine atom, an amino group, a hydrocarbyl group having 1 to 20 carbon atoms, a hydrocarbyloxy group having 1 to 20 carbon atoms, a hydrocarbylcarbonyl group having 2 to 20 carbon atoms, a hydrocarbyloxycarbonyl group having 2 to 20 carbon atoms, a hydrocarbylcarbonyloxy group having 2 to 20 carbon atoms, a hydrocarbylsulfonyloxy group having 1 to 20 carbon atoms, $-N(R^{401A})(R^{401B})$, $-N(R^{401C})-C(=O)-R^{401D}$, or $-N(R^{401C})-C(=O)-O-R^{401D}$. The hydrocarbyl group, the hydrocarbyloxy group, the hydrocarbylcarbonyl group, the hydrocarbyloxycarbonyl group, the hydrocarbylcarbonyloxy group, and the hydrocarbylsulfonyloxy group optionally have a fluorine atom, a chlorine atom, a bromine atom, a hydroxy group, an amino group, an ether bond, an ester bond, or an amide bond. $R^{401A}$ and $R^{401B}$ each independently represent a hydrogen atom or a saturated hydrocarbyl group having 1 to 6 carbon atoms. $R^{401C}$ represents a hydrogen atom or a saturated hydrocarbyl group having 1 to 6 carbon atoms, and optionally having a halogen atom, a hydroxy group, a saturated hydrocarbyloxy group having 1 to 6 carbon atoms, a saturated hydrocarbylcarbonyl group having 2 to 6 carbon atoms, or a saturated hydrocarbylcarbonyloxy group having 2 to 6 carbon atoms. $R^{401D}$ represents an aliphatic hydrocarbyl group having 1 to 16 carbon atoms, an aryl group having 6 to 14 carbon atoms, or an aralkyl group having 7 to 15 carbon atoms, and optionally has a halogen atom, a hydroxy group, a saturated hydrocarbyloxy group having 1 to 6 carbon atoms, a saturated hydrocarbylcarbonyl group having 2 to 6 carbon atoms, or a saturated hydrocarbylcarbonyloxy group having 2 to 6 carbon atoms. The aliphatic hydrocarbyl group may be a saturated or unsaturated group, and may be any of linear, branched, and cyclic groups. The saturated hydrocarbyl group, the saturated hydrocarbyloxy group, the saturated hydrocarbyloxycarbonyl group, the saturated hydrocarbylcarbonyl group, and the saturated hydrocarbylcarbonyloxy group may be any of linear, branched, and cyclic groups. When "p" and/or "r" represent 2 or more, each $R^{401}$ may be same as or different from each other.

Among them, $R^{401}$ preferably represents a hydroxy group, $-N(R^{401C})-C(=O)-R^{401D}$, $-N(R^{401C})-C(=O)-O-R^{401D}$, a fluorine atom, a chlorine atom, a bromine atom, a methyl group, a methoxy group, etc.

In the general formulae (5-1) and (5-2), $Rf^1$ to $Rf^4$ each independently represent a hydrogen atom, a fluorine atom, or a trifluoromethyl group, and at least one of them represents a fluorine atom or a trifluoromethyl group. $Rf^1$ and $Rf^2$ are optionally integrated to form a carbonyl group. In particular, both of $Rf^3$ and $Rf^4$ preferably represent fluorine atoms.

In the general formulae (5-1) and (5-2), $R^{402}$ to $R^{406}$ each independently represent a halogen atom or a hydrocarbyl group having 1 to 20 carbon atoms and optionally having a heteroatom. The hydrocarbyl group may be a saturated or unsaturated group, and may be any of linear, branched, and cyclic groups. Specific examples thereof include groups same as those exemplified as the hydrocarbyl group represented by $R^{11'}$ to $R^{19'}$ in the description of the general formula (Cation-1). A part or all of hydrogen atoms in these groups are optionally substituted with a hydroxy group, a carboxy group, a halogen atom, a cyano group, a nitro group, a mercapto group, a sultone ring, a sulfone group, or a sulfonium-salt-containing group. A part of carbon atoms in these groups is optionally substituted with an ether bond, an ester bond, a carbonyl group, an amide bond, a carbonate bond, or a sulfonate ester bond. Furthermore, $R^{402}$ and $R^{403}$ are optionally bonded to each other to form a ring together with the sulfur atom to which these groups are bonded. In this case, examples of the ring include rings same as those exemplified as the ring that can be formed by bonding $R^{11'}$ and $R^{12'}$ each other together with the sulfur atom to which these groups are bonded, described in the general formula (Cation-1).

Examples of the cation of the sulfonium salt represented by the general formula (5-1) include cations same as those exemplified as the cation of the sulfonium salt represented by the general formula (Cation-1). Examples of the cation of the iodonium salt represented by the general formula (5-2) include cations same as those exemplified as the cation of the iodonium salt represented by the general formula (Cation-2).

Examples of the anion of the onium salt represented by the general formula (5-1) or (5-2) include the following anions, but the anion is not limited thereto. In the following formulae, $X^{BI}$ represents the same as above.

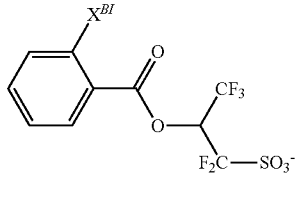

-continued
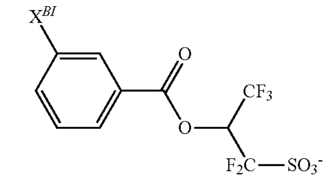
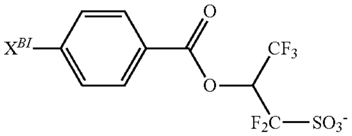
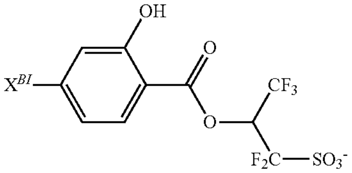
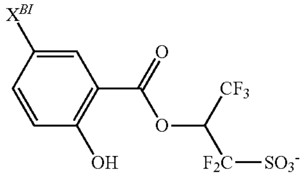
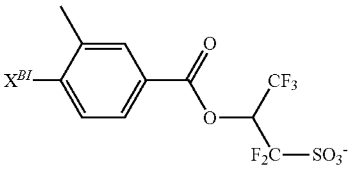
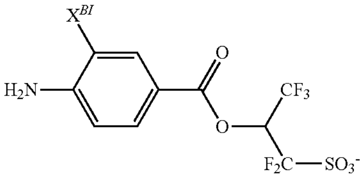
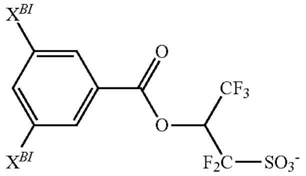
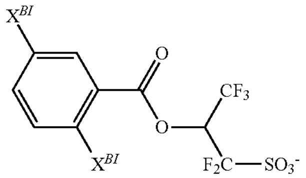
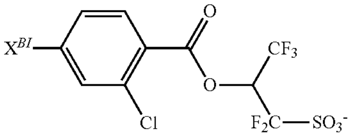
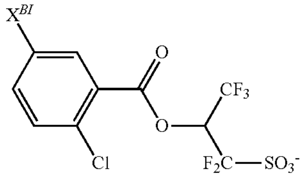
-continued
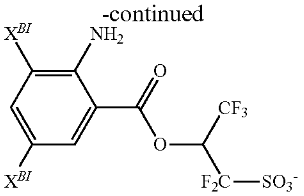
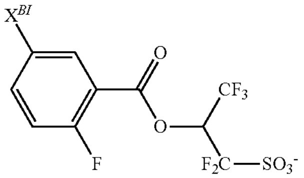
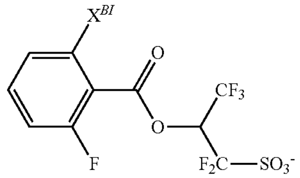
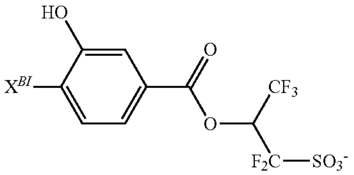
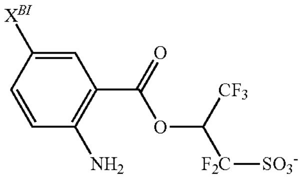
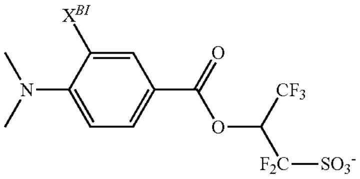
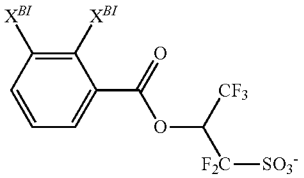
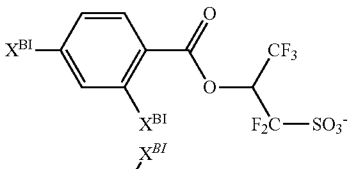
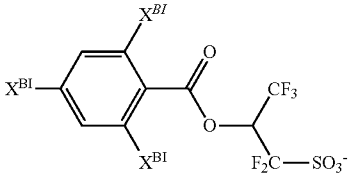
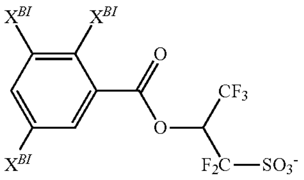

-continued
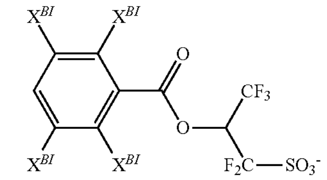
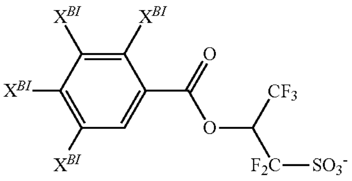
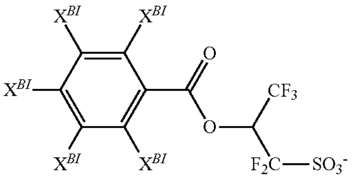
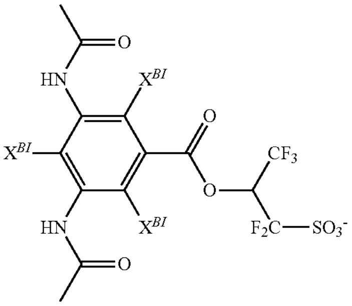
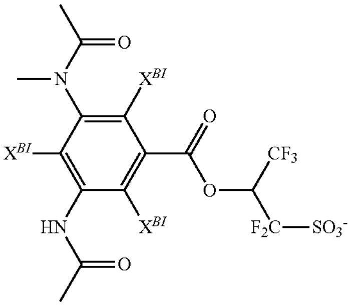
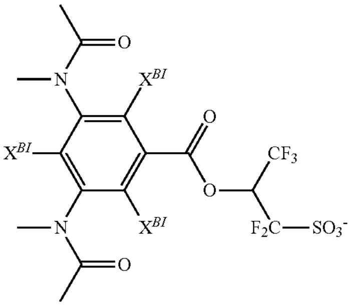
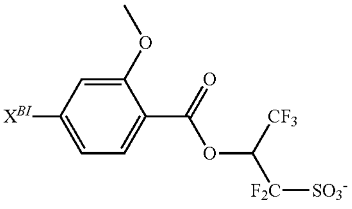
-continued
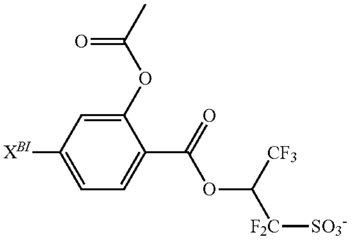
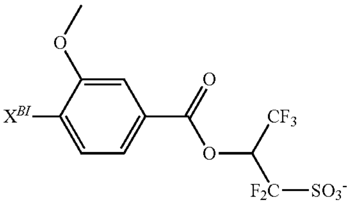
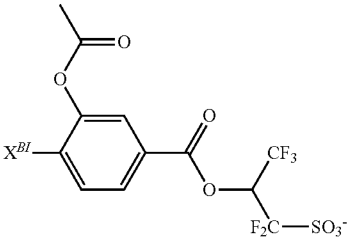
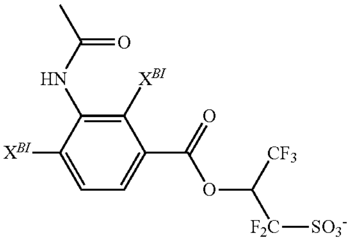
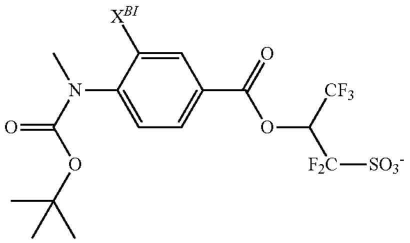
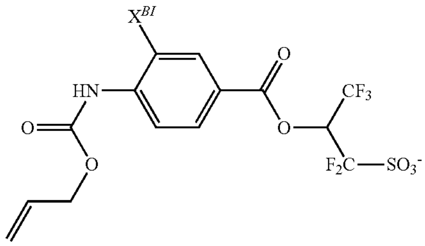
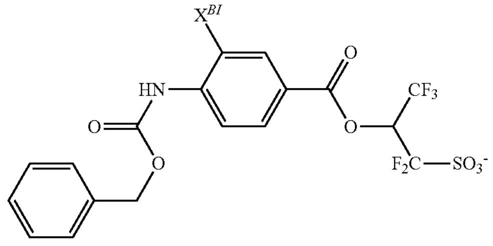

-continued
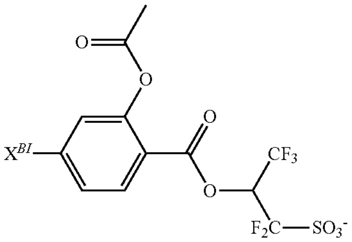
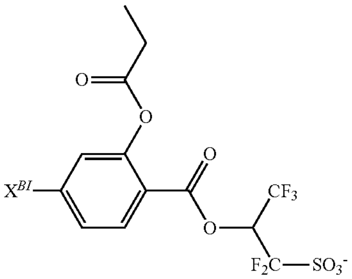
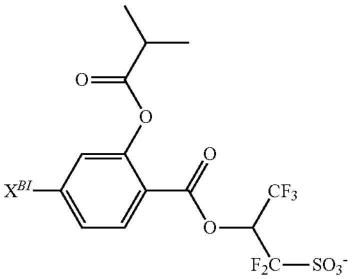
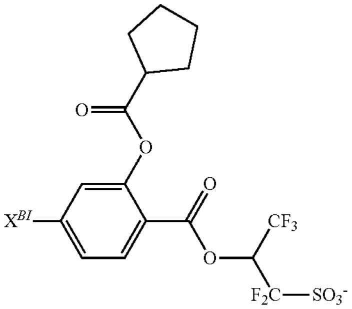
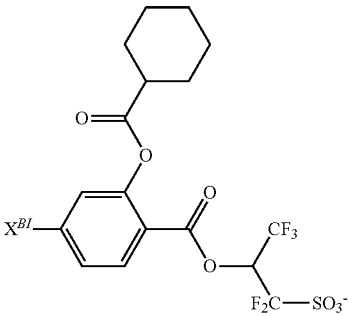
-continued
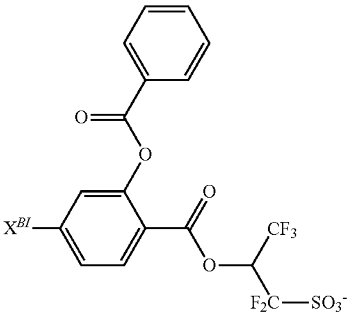
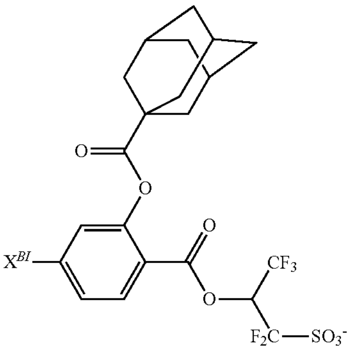
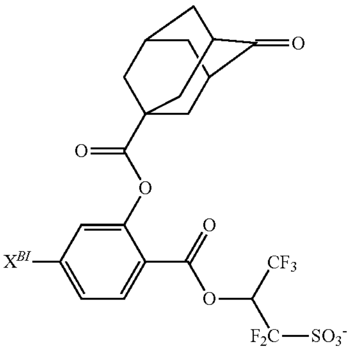
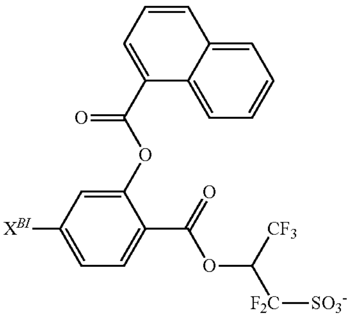
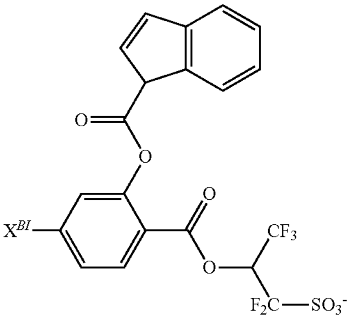

-continued
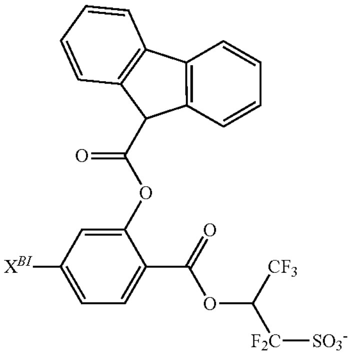
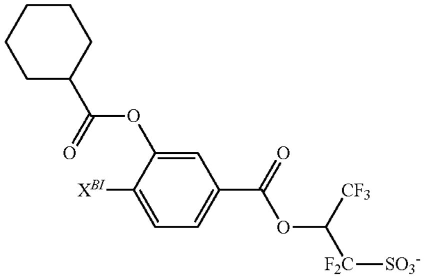
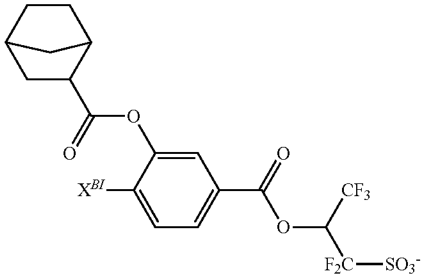
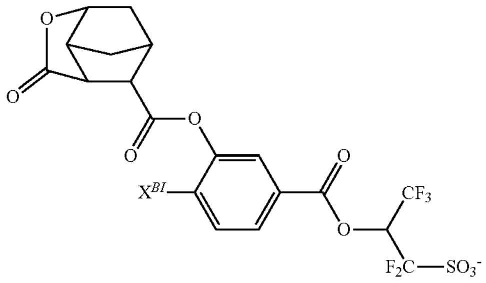
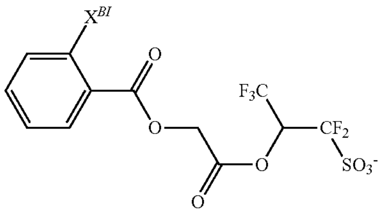
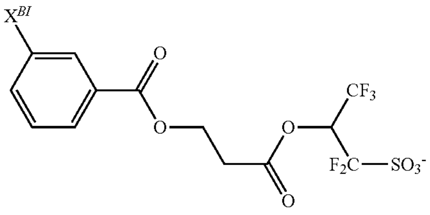
-continued
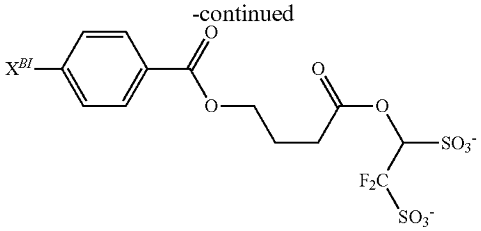
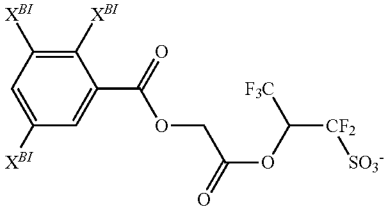
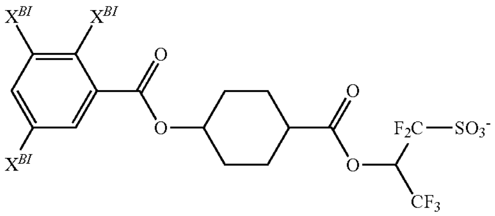
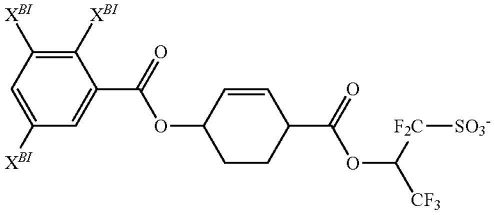
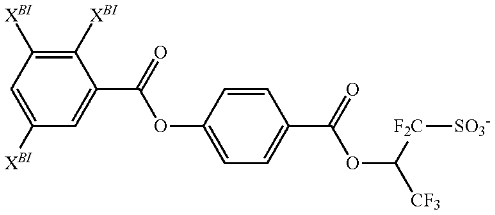
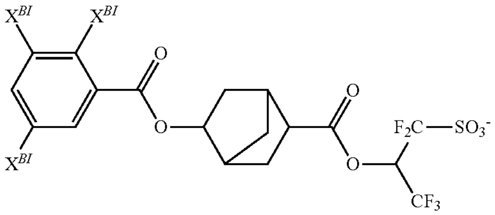
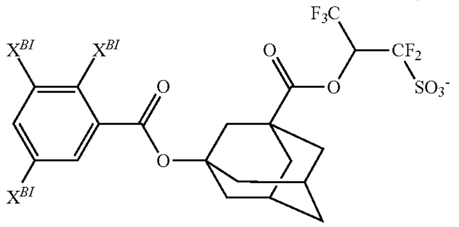
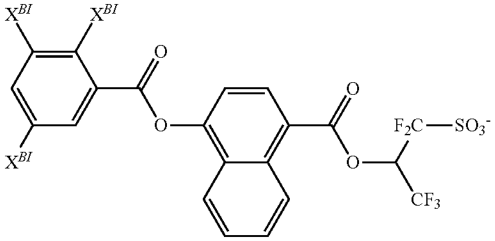

-continued
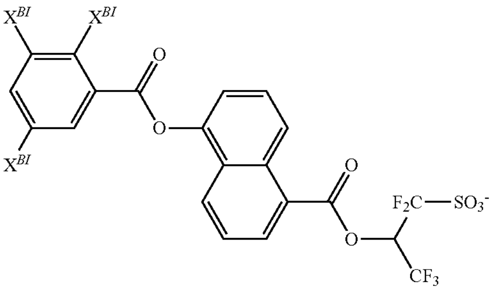
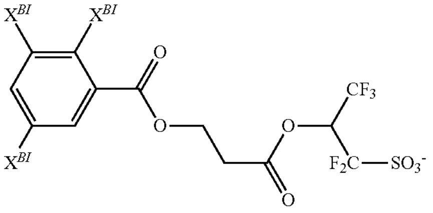
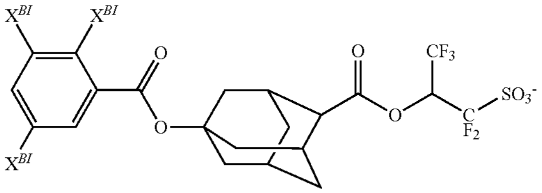
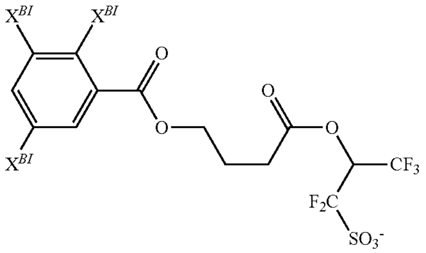
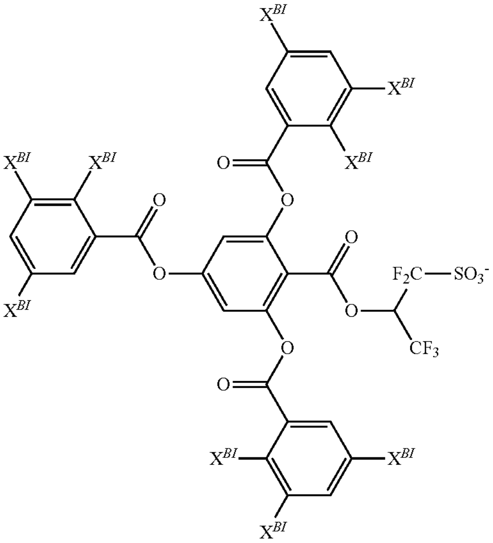
-continued
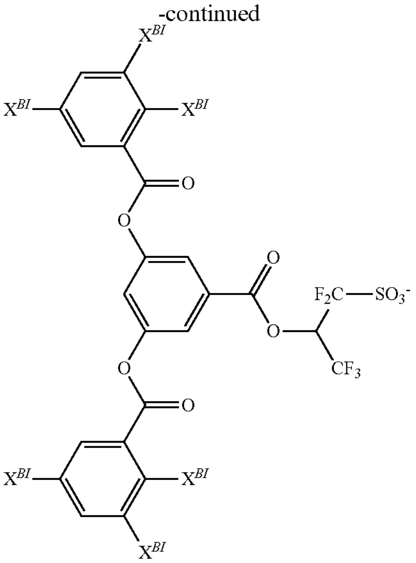
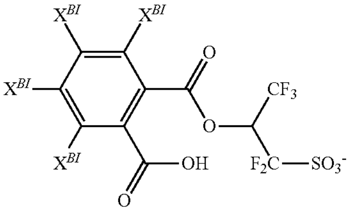
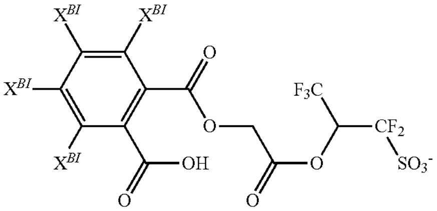
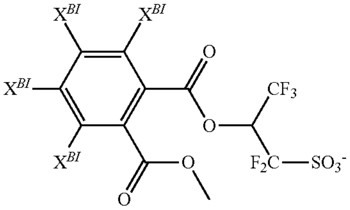
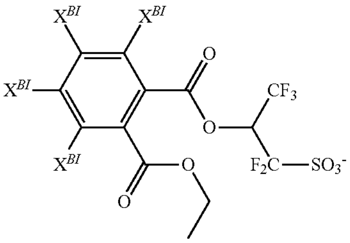
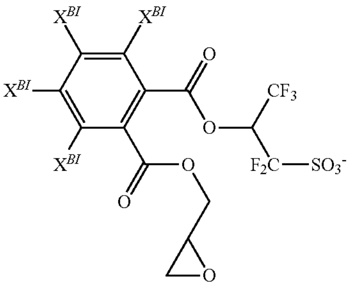

-continued
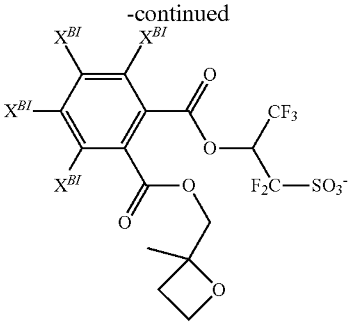
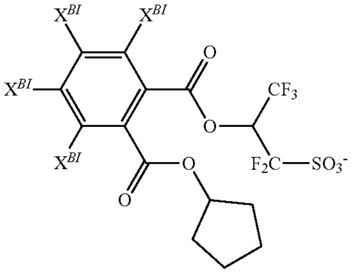
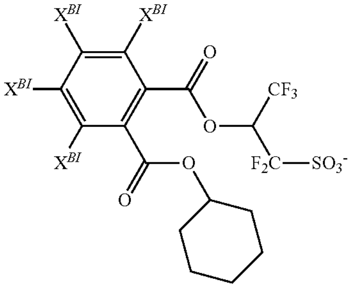
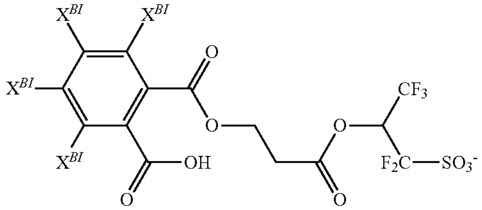
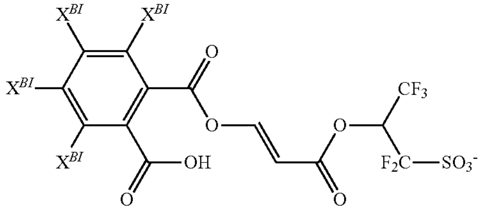
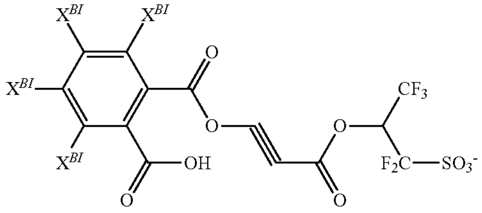
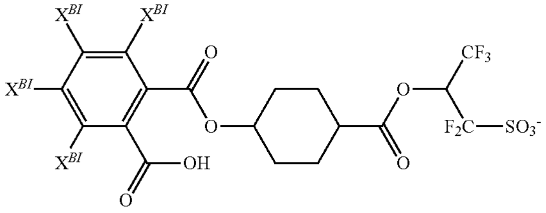
-continued
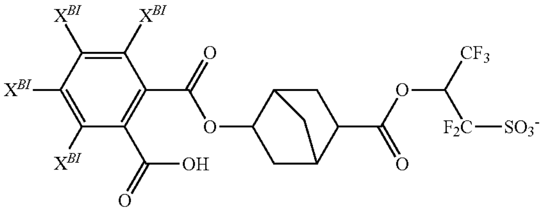
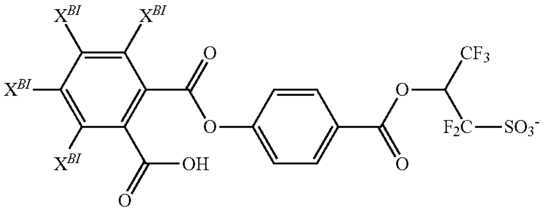
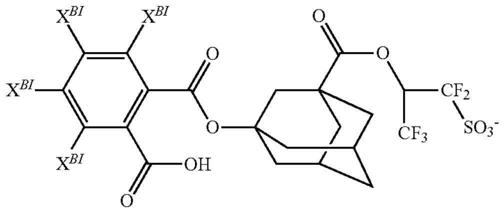
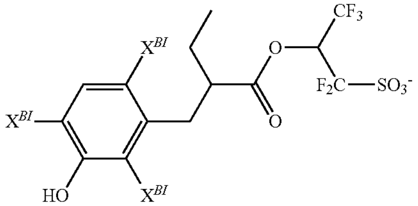
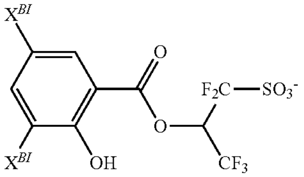
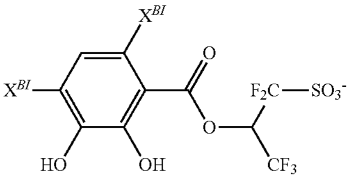
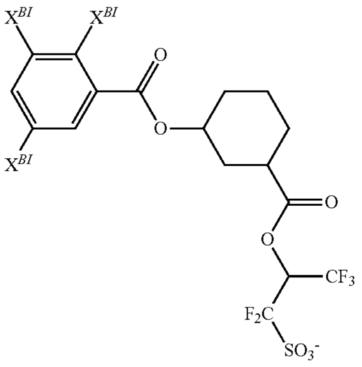

-continued
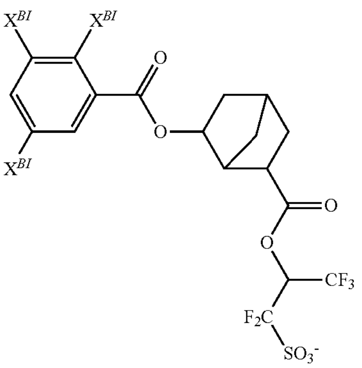
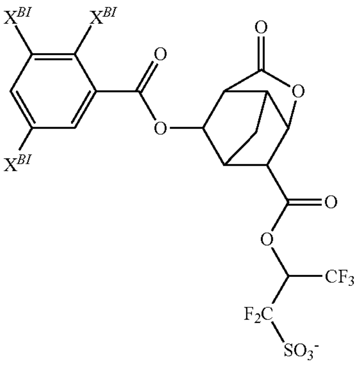
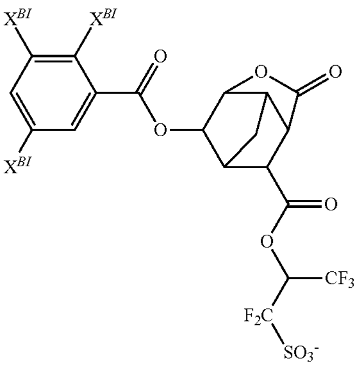
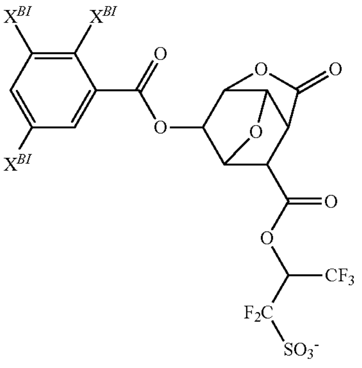
-continued
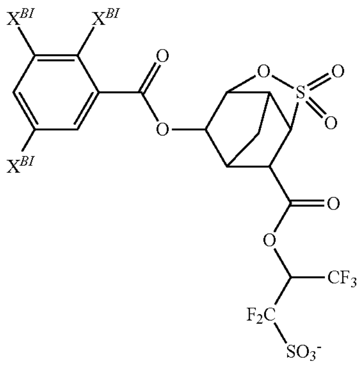
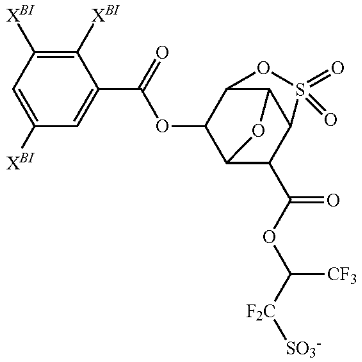
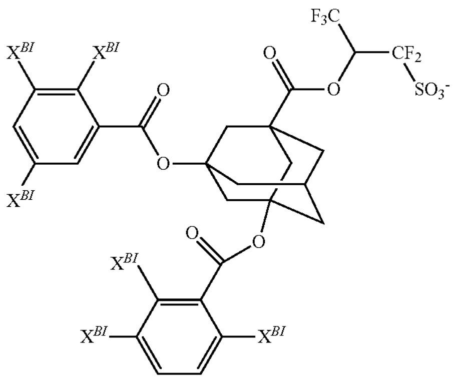
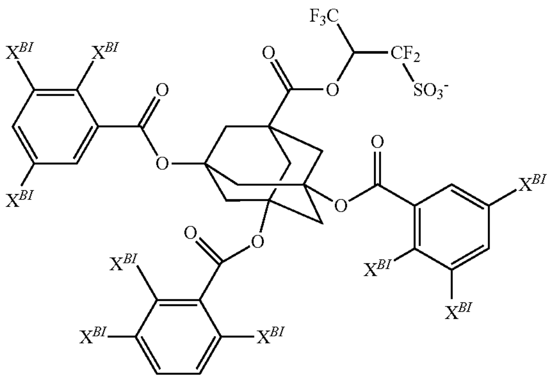

-continued
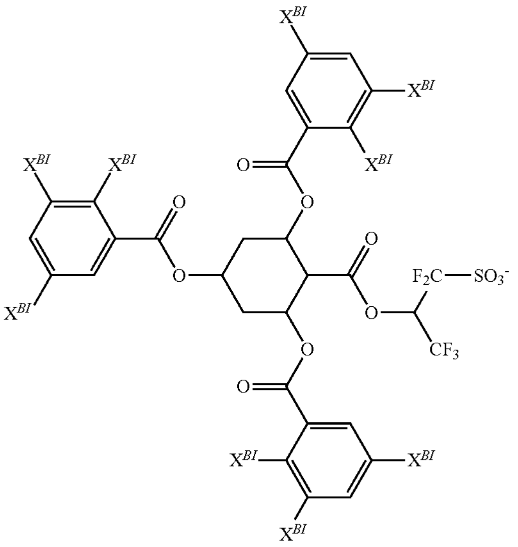
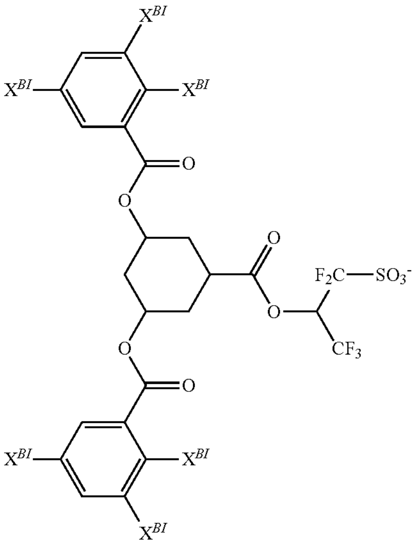
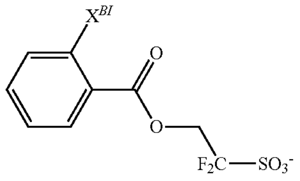
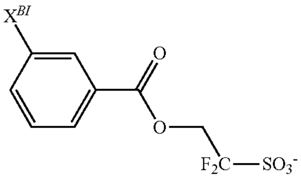
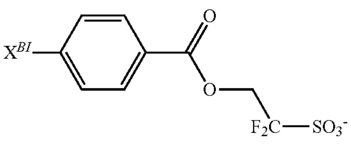
-continued
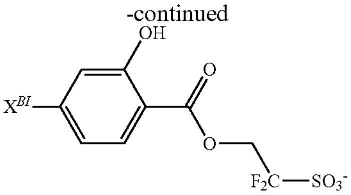
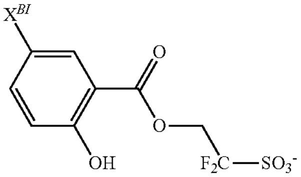
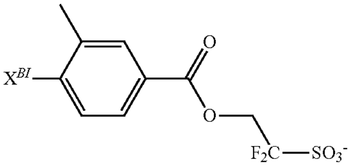
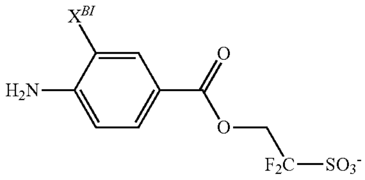
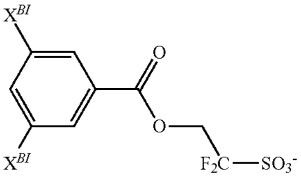
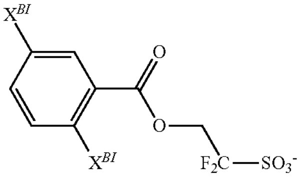
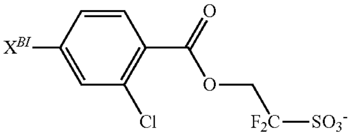
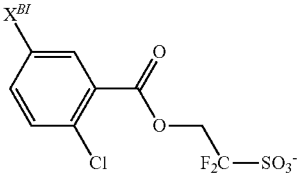
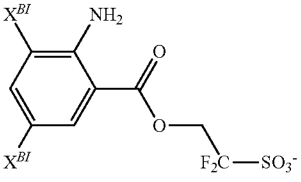
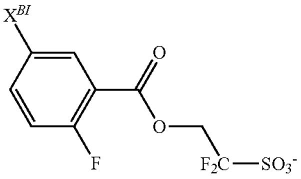

-continued
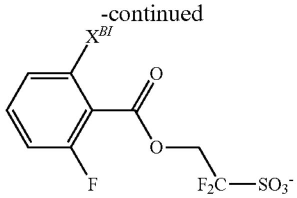
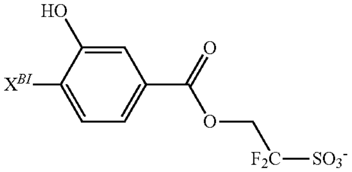
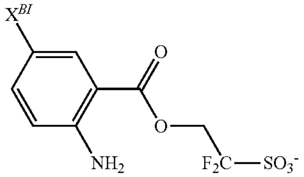
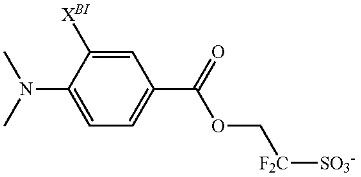
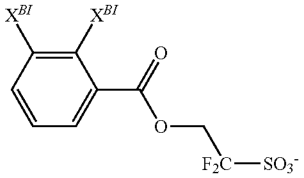
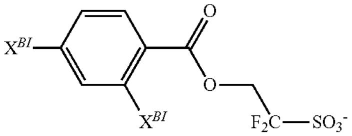
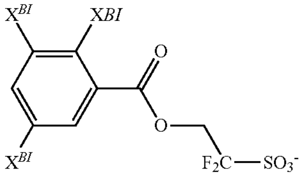
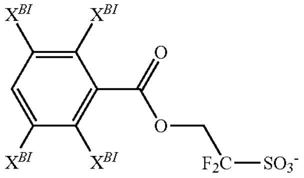
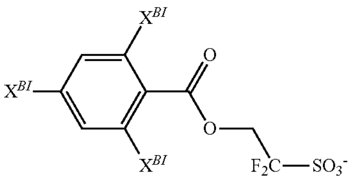
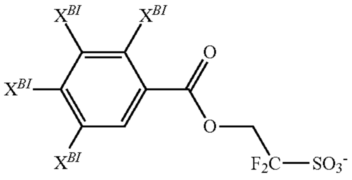
-continued
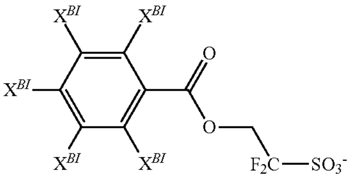
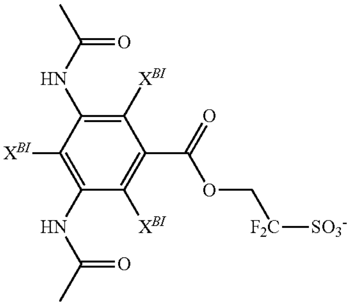
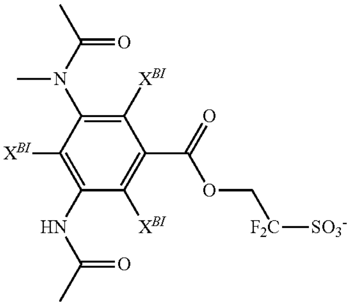
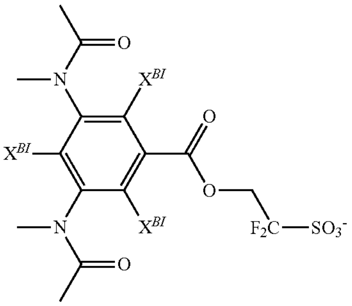
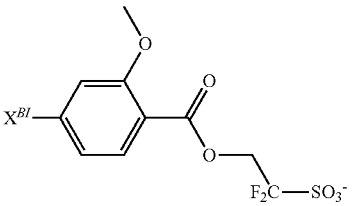
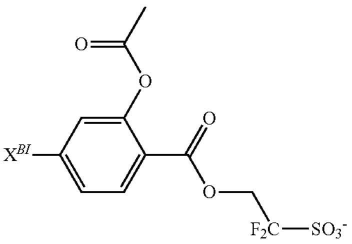

-continued
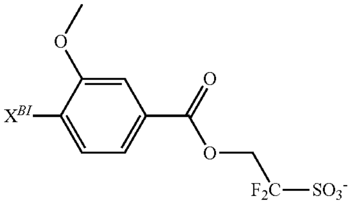
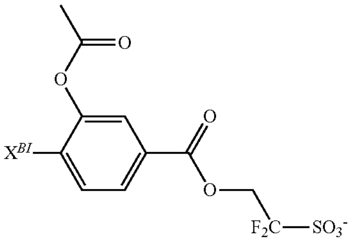
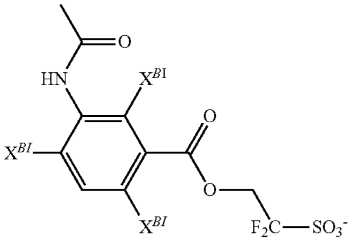
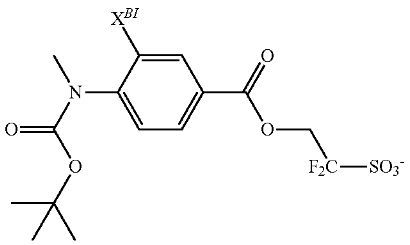
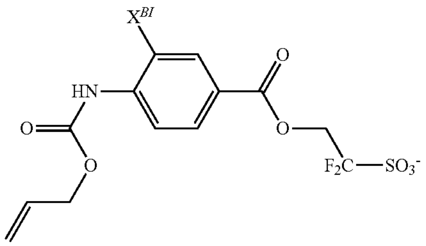
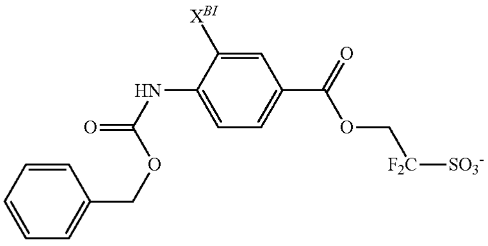
-continued
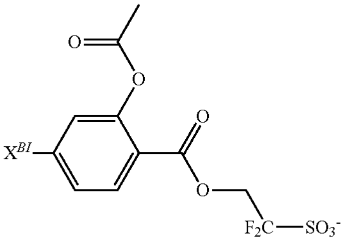
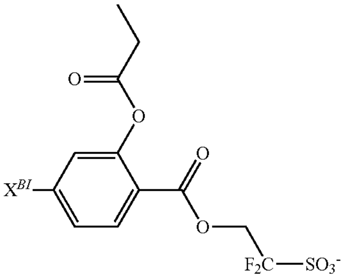
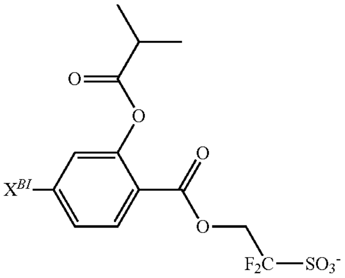
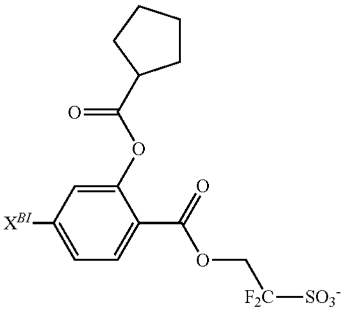
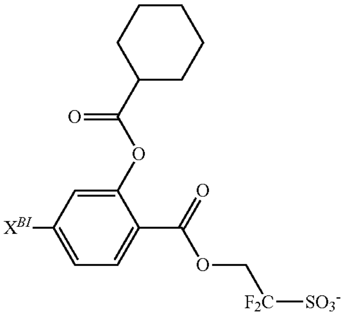

-continued
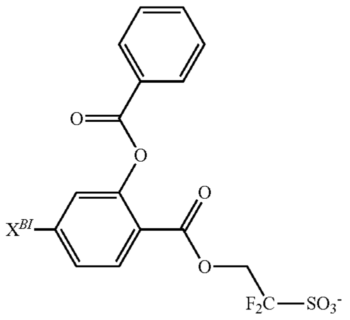
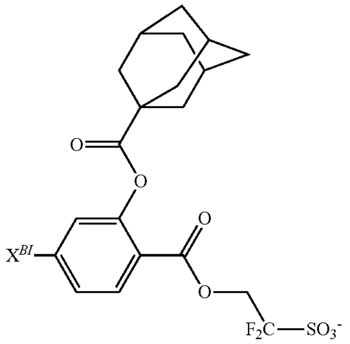
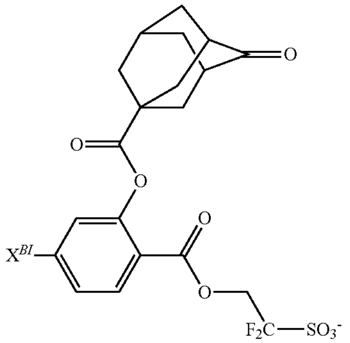
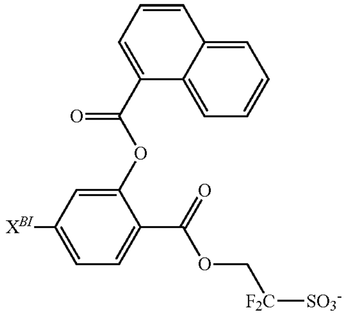
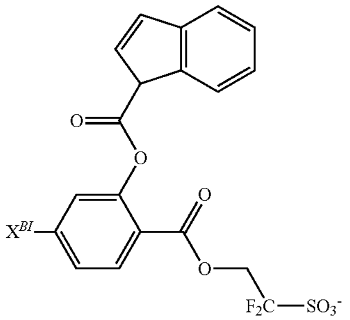
-continued
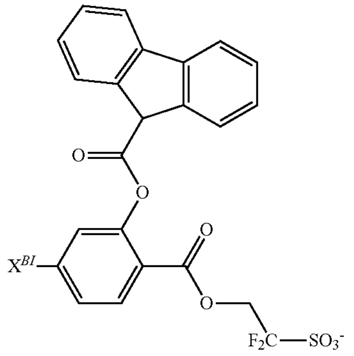
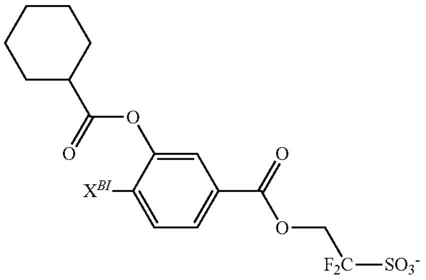
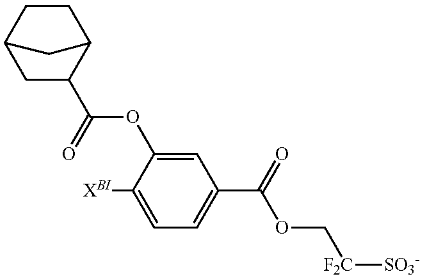
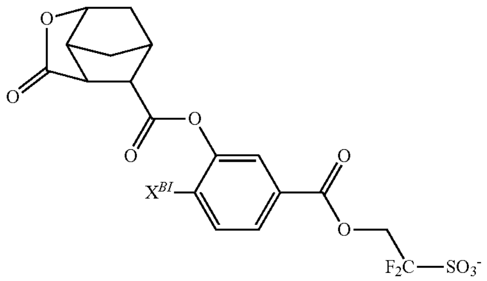
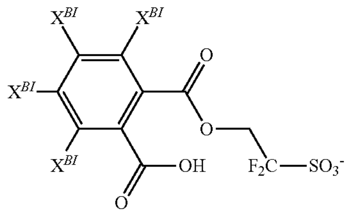
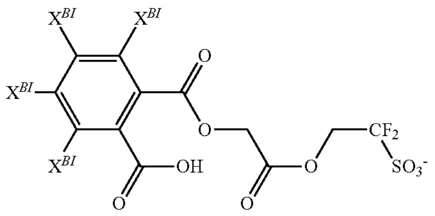

-continued
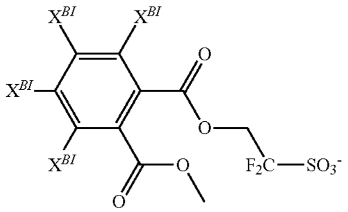
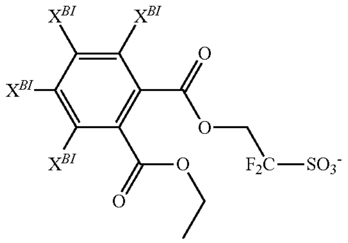
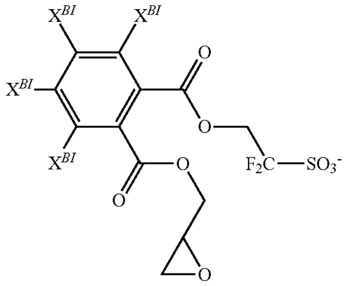
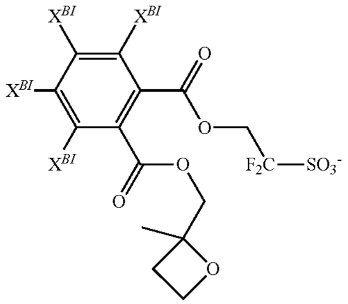
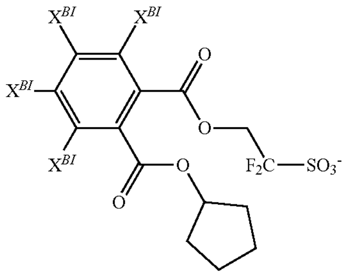
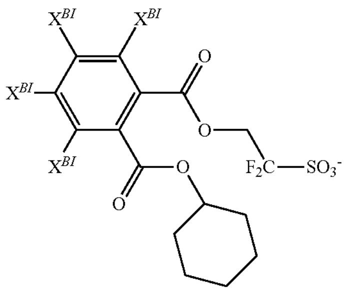
-continued
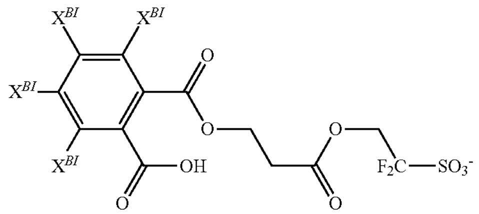
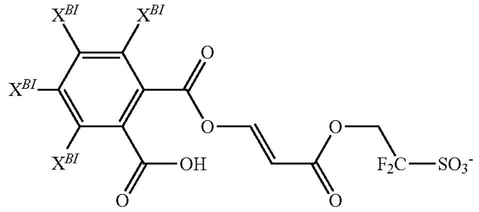
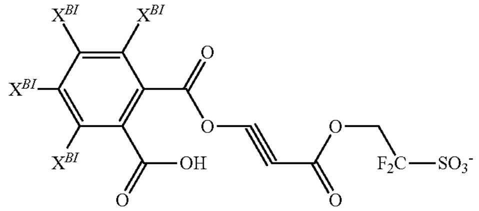
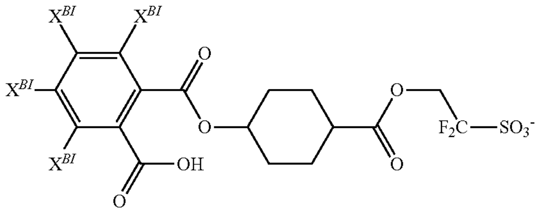
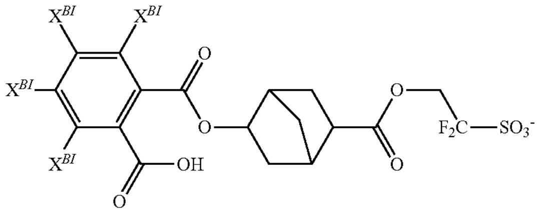
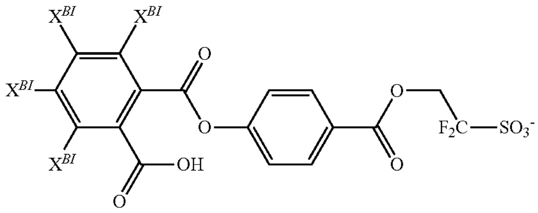
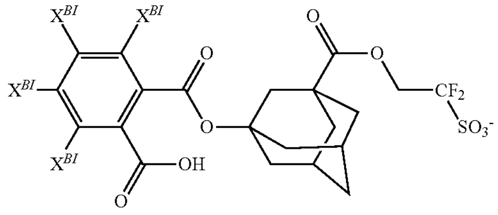
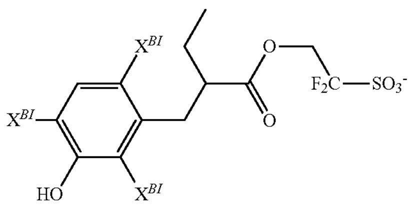

-continued
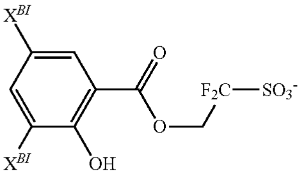
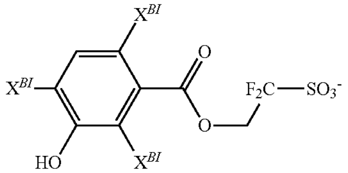
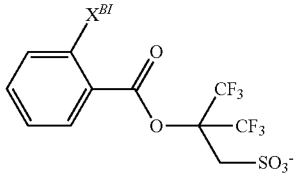
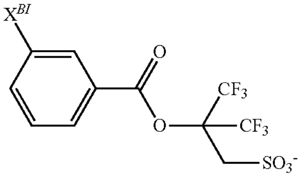
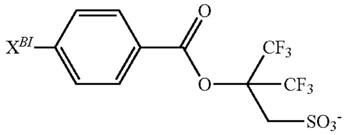
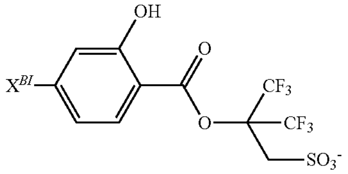
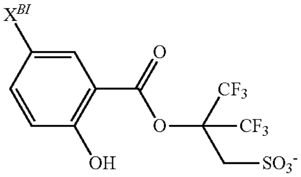
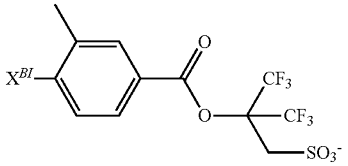
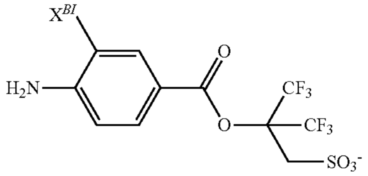
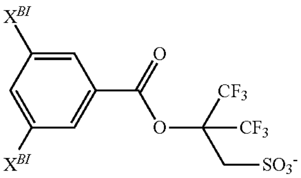
-continued
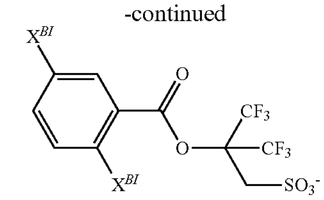
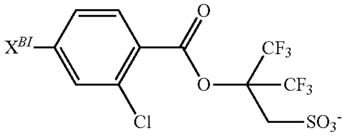
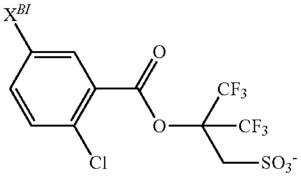
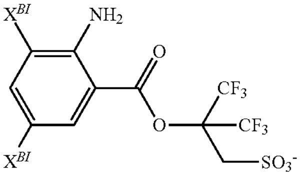
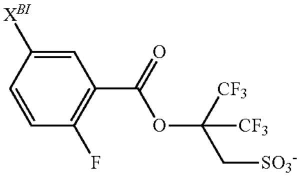
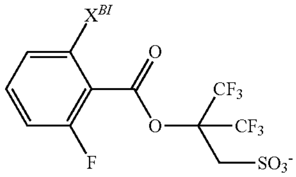
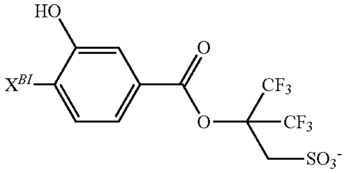
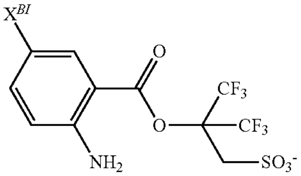
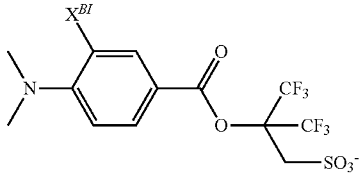
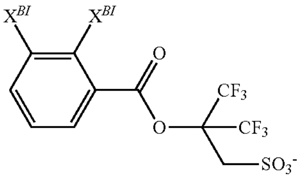

-continued
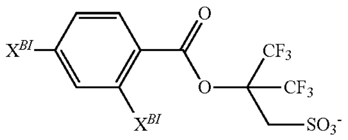
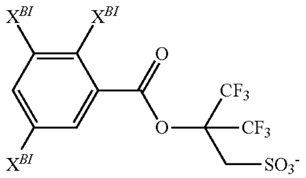
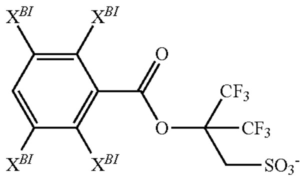
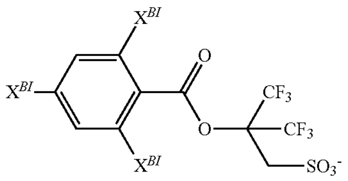
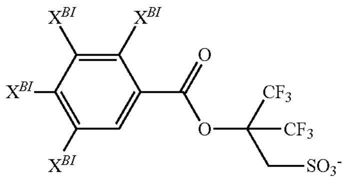
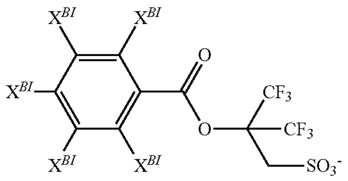
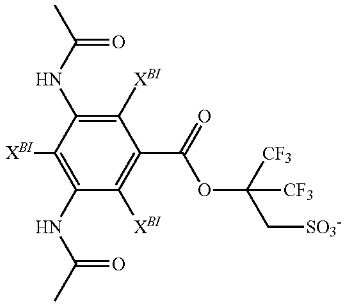
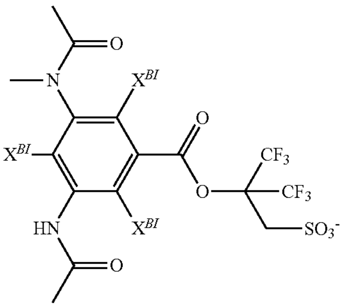
-continued
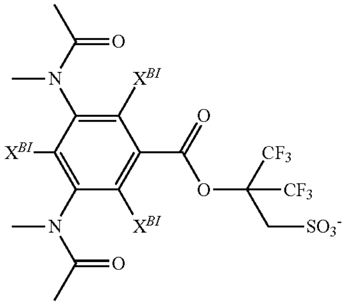
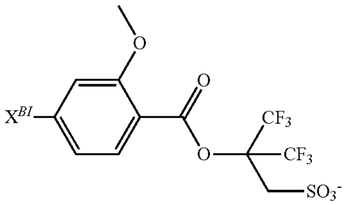
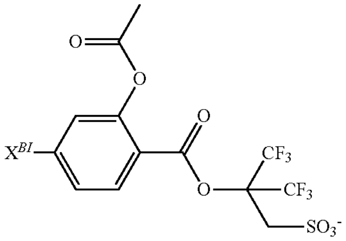
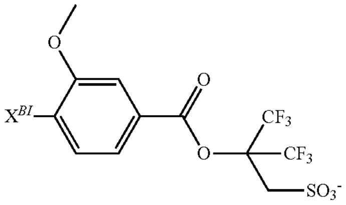
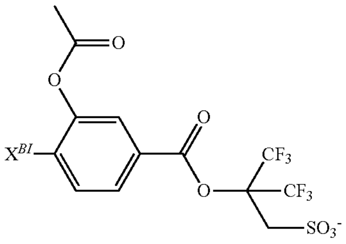
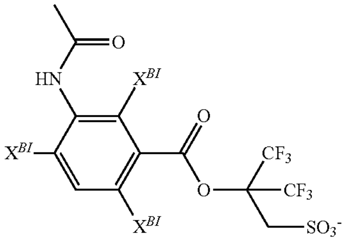
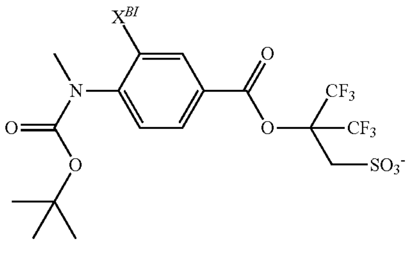

-continued
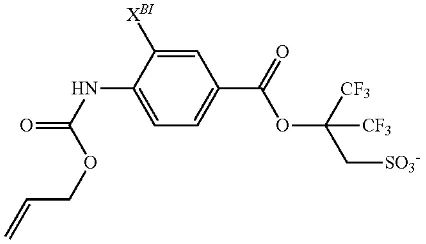
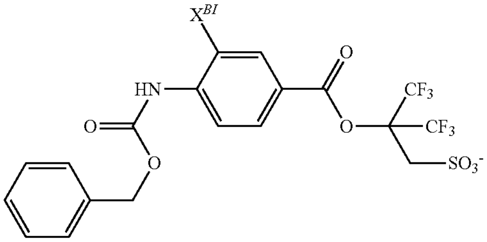
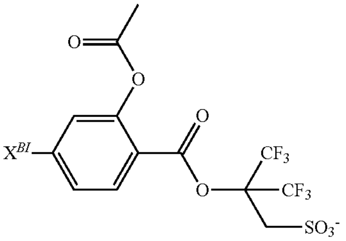
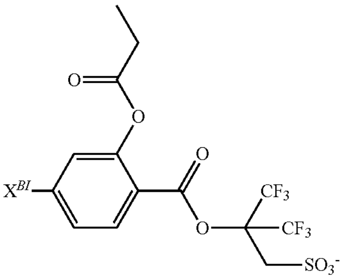
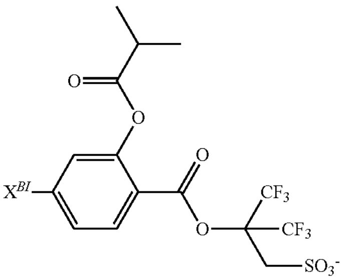
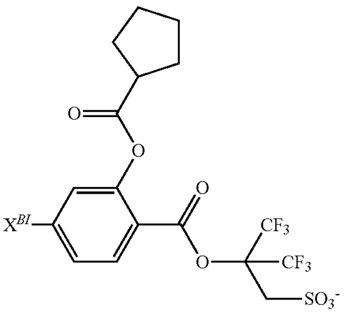
-continued
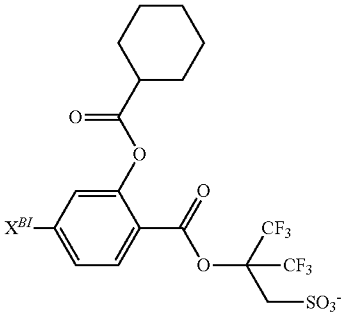
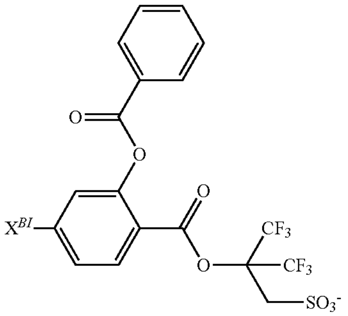
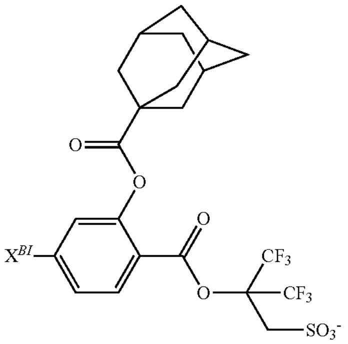
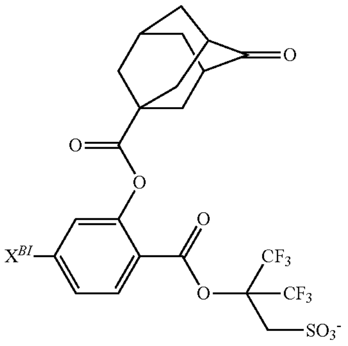
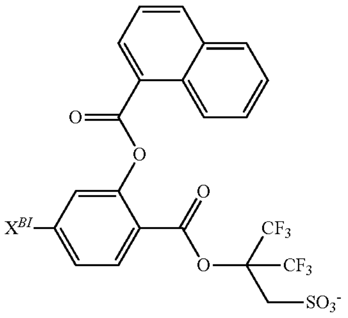

-continued
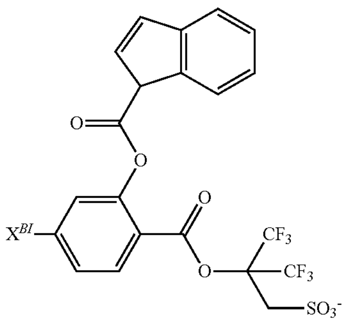
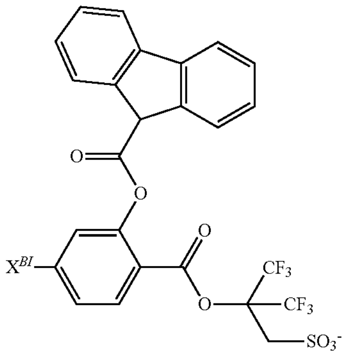
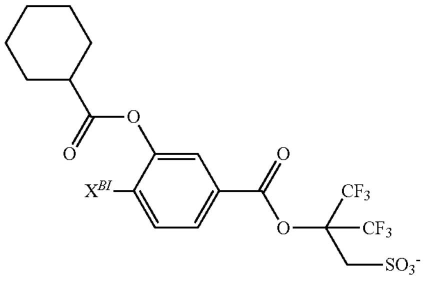
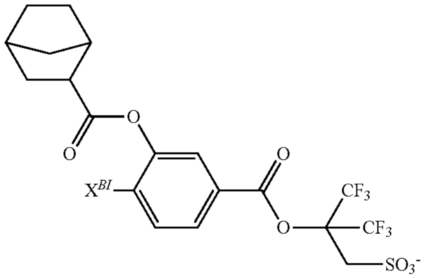
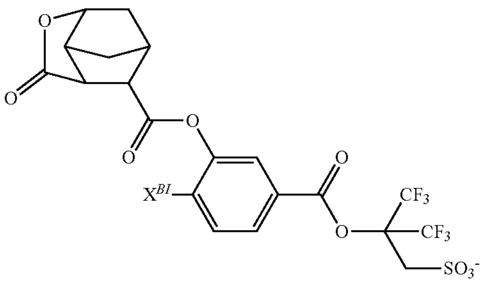
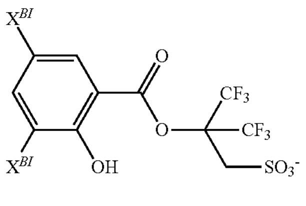
-continued
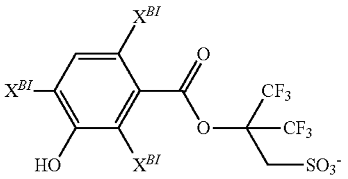
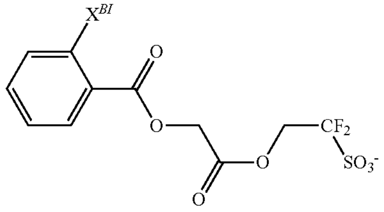
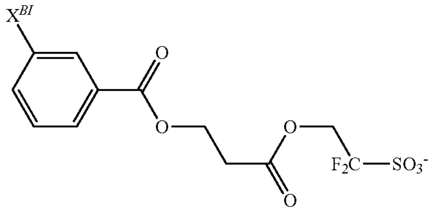
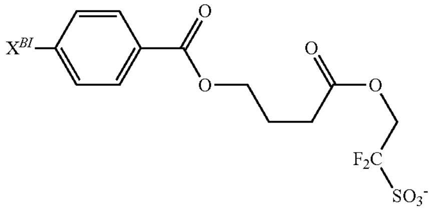
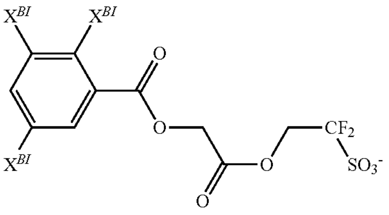
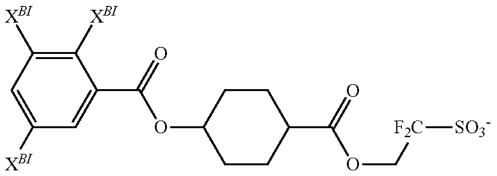
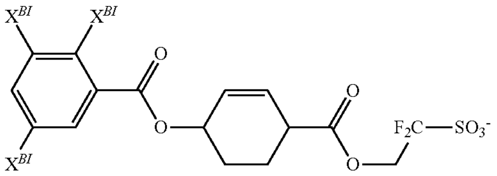
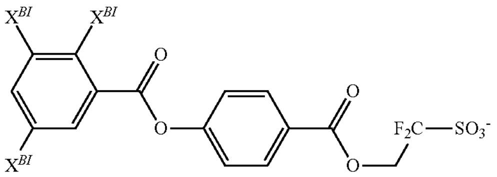
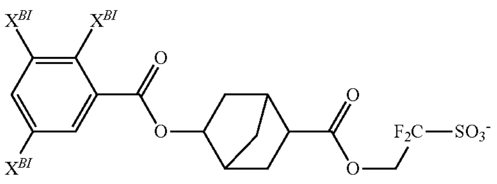

-continued
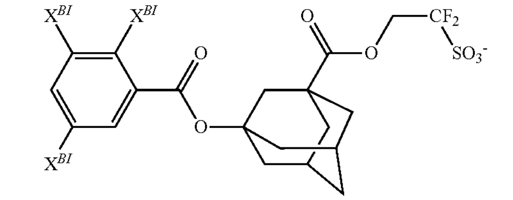
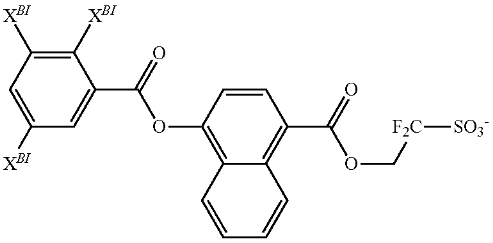
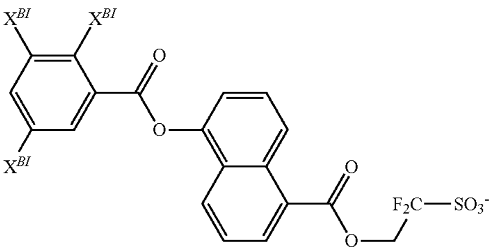
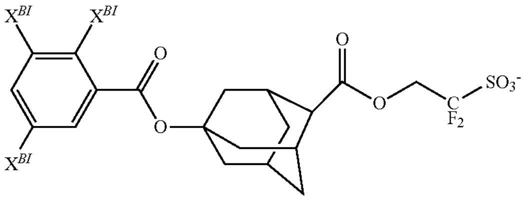
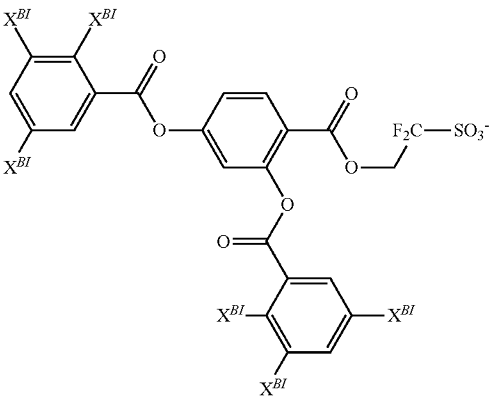
-continued
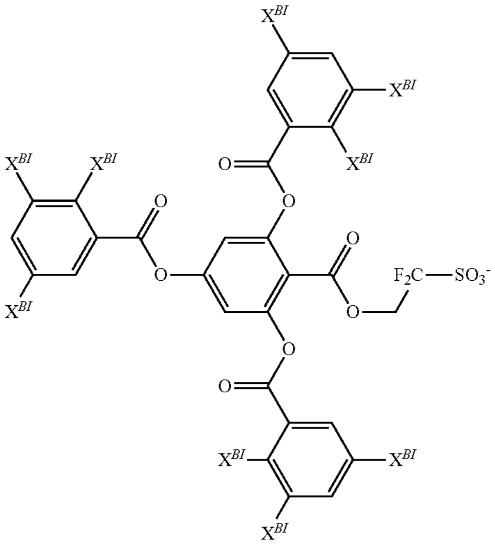
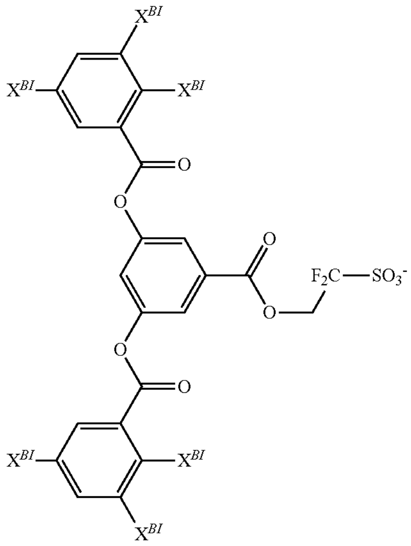
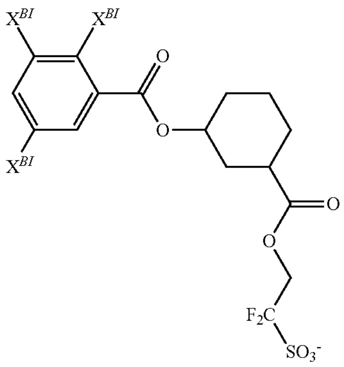

-continued
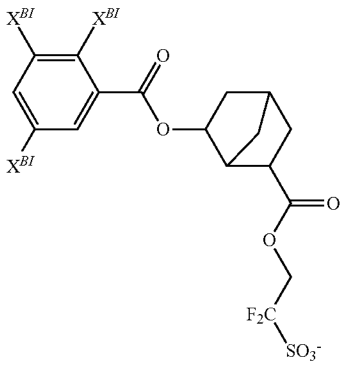
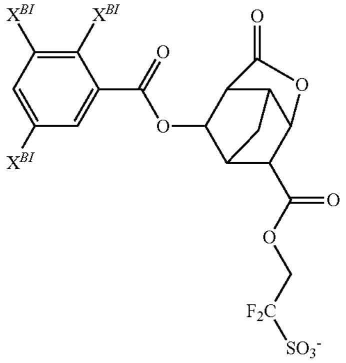
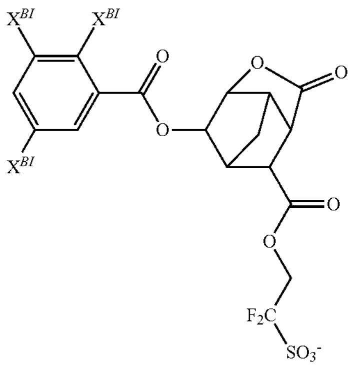
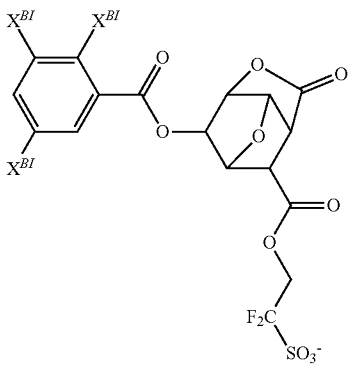
-continued
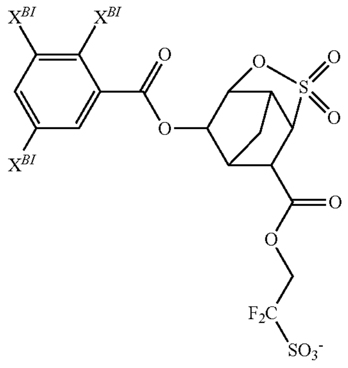
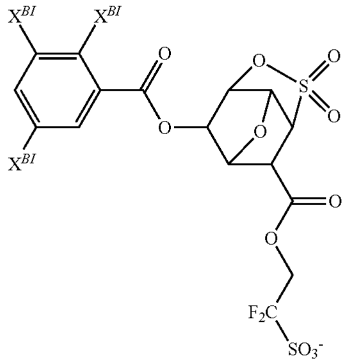
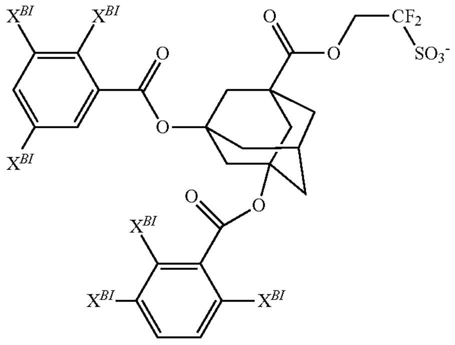
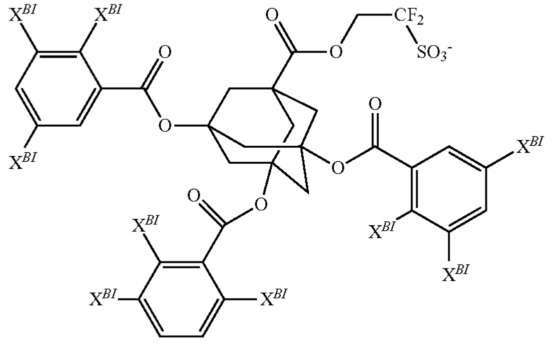

-continued
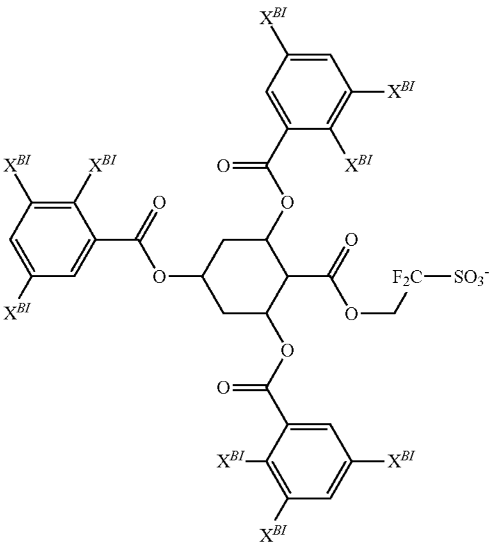
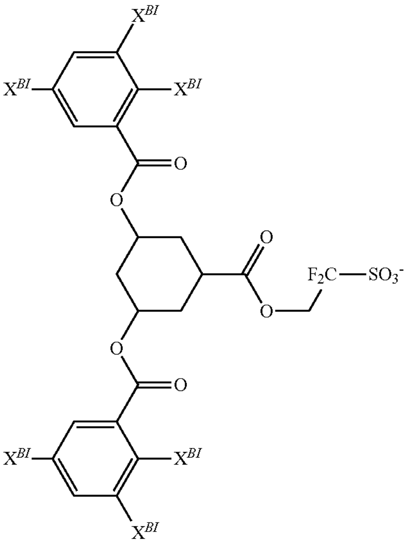
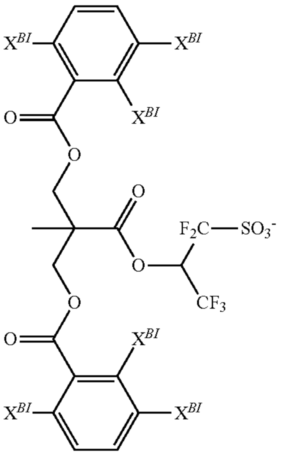
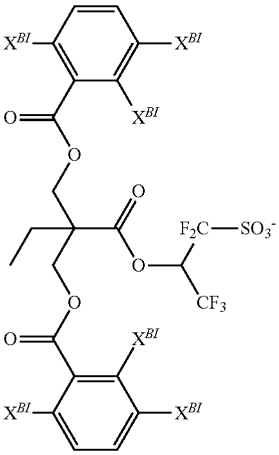
-continued
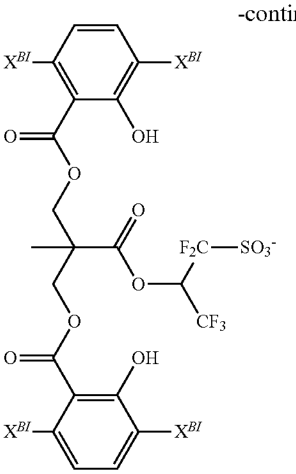
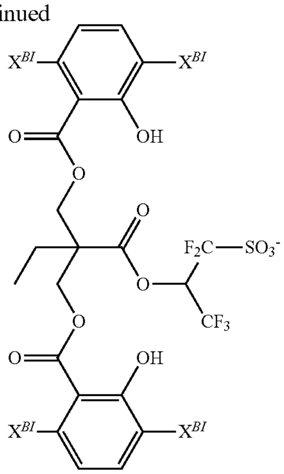
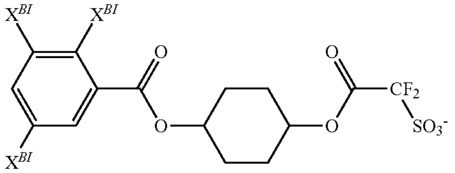
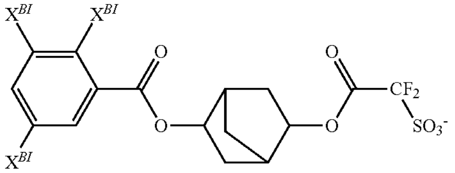
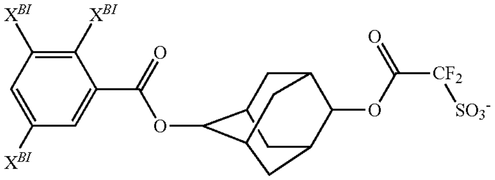
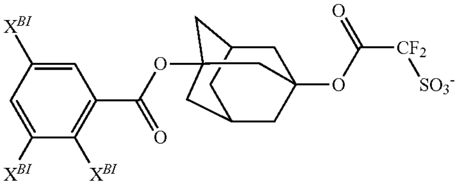
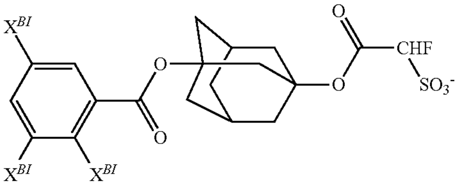
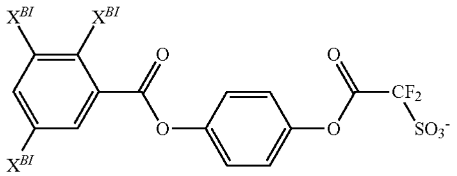
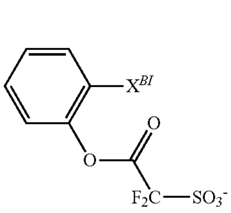
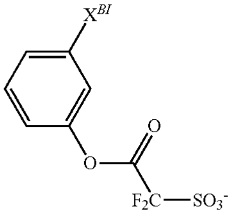

-continued
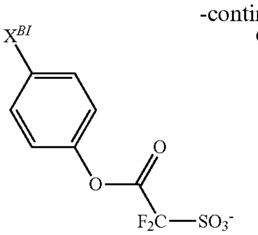
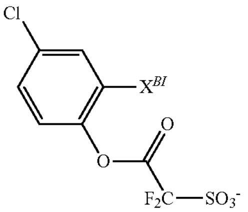
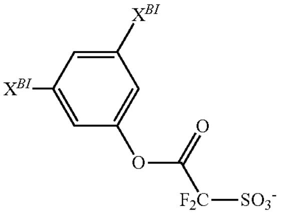
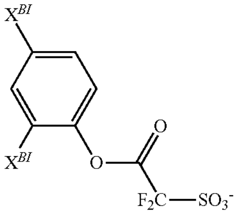
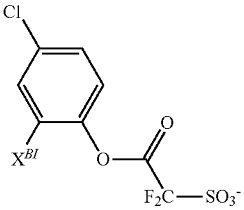
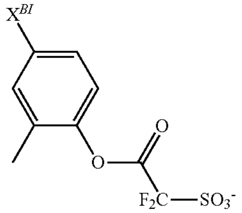
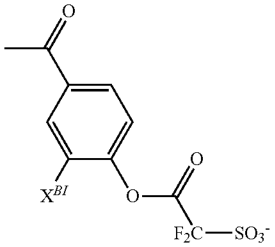
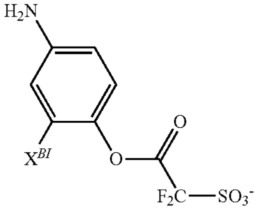
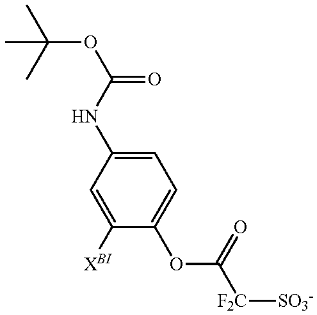
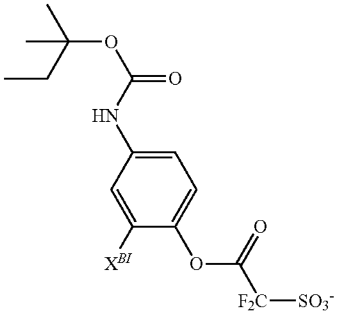
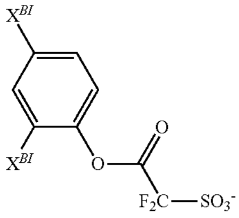
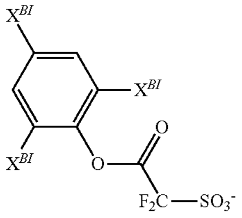
-continued
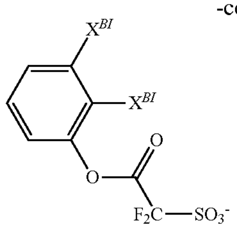
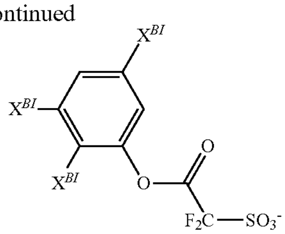
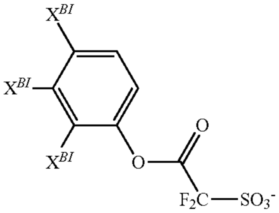
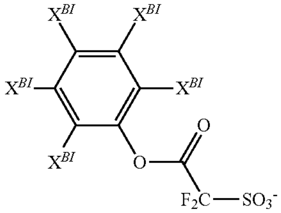
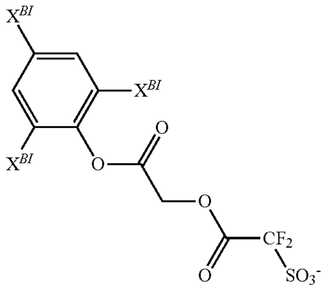
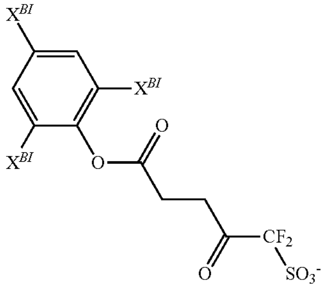
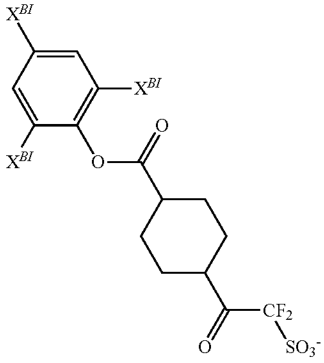
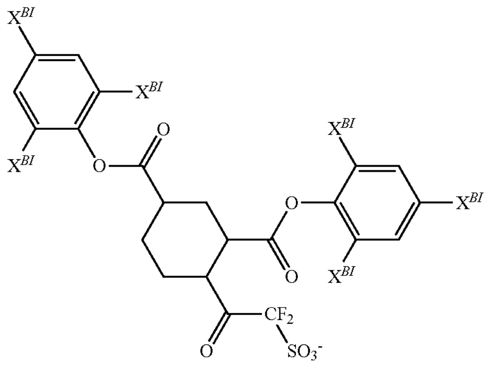

-continued
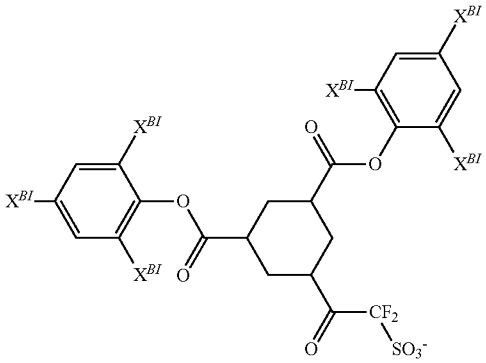
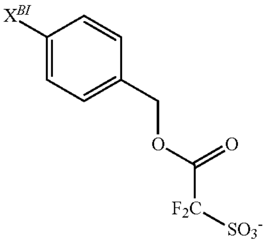
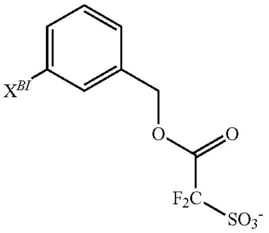
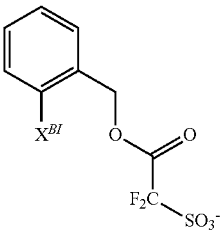
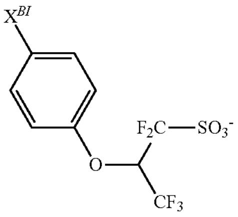
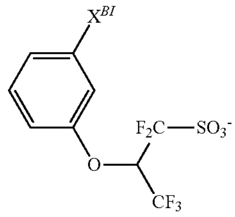
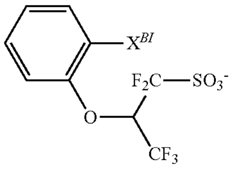
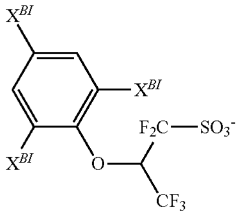
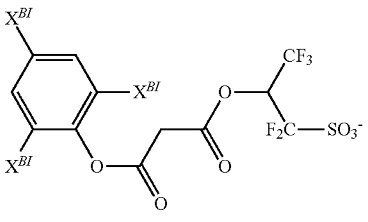
-continued
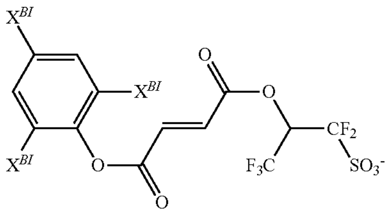
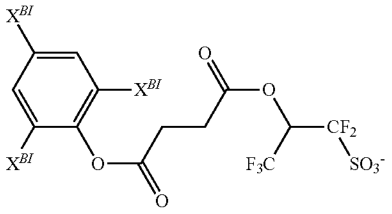
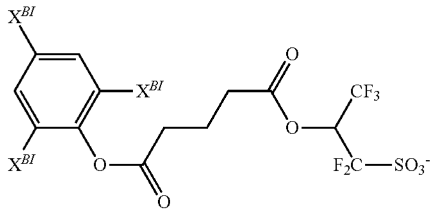
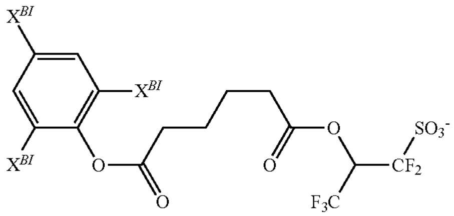
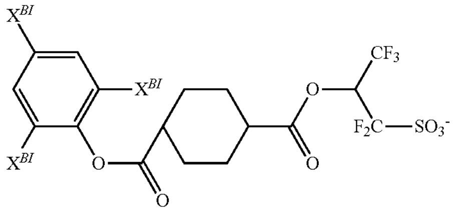
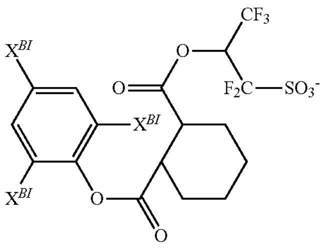
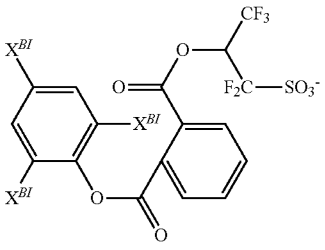

-continued
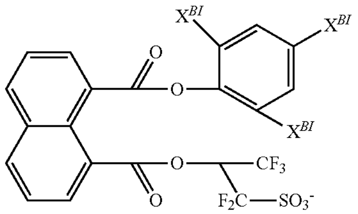
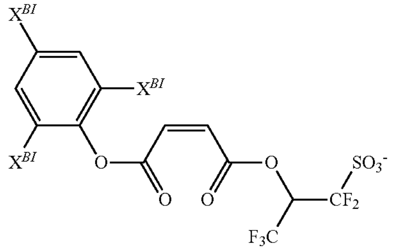
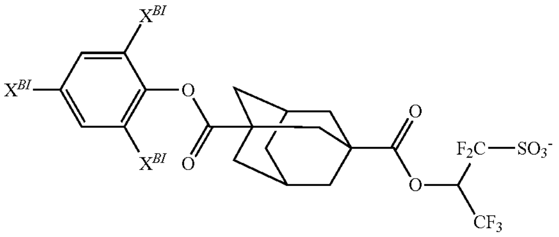
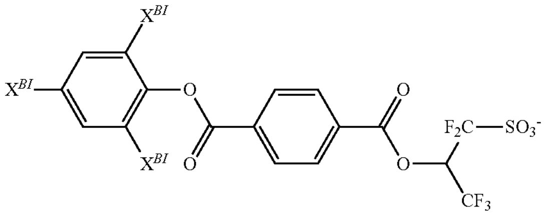
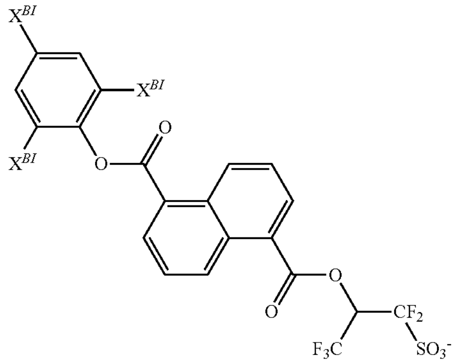
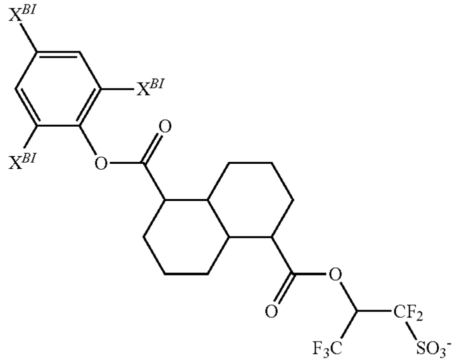
-continued
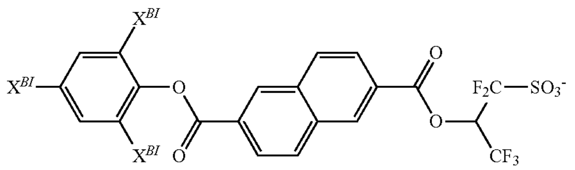
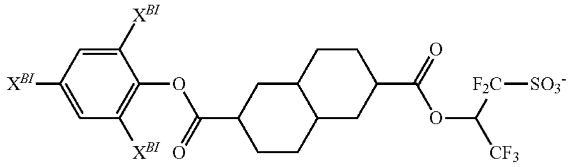
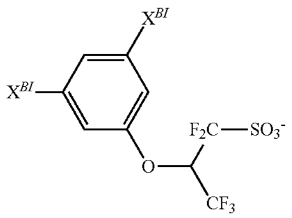
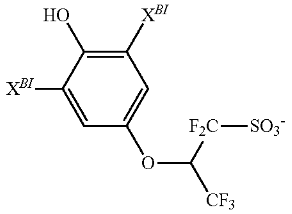
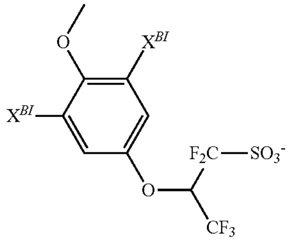
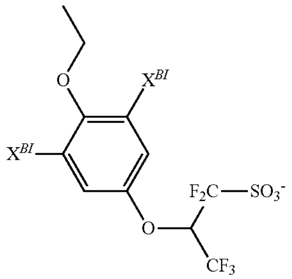
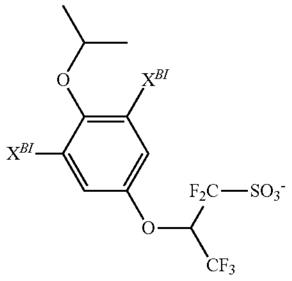

-continued
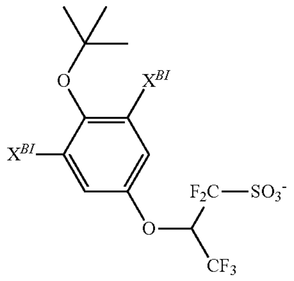
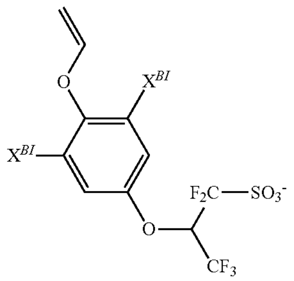
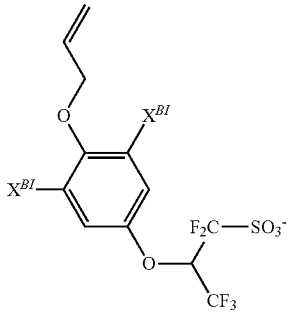
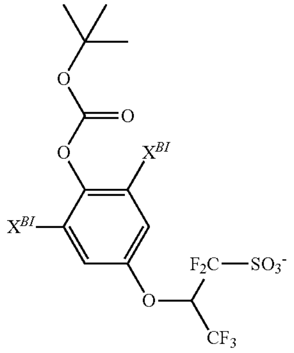
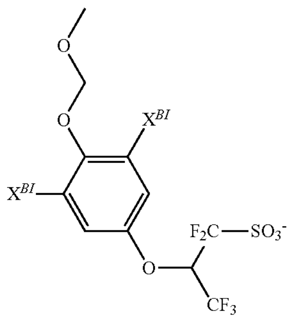
-continued
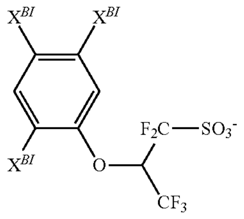
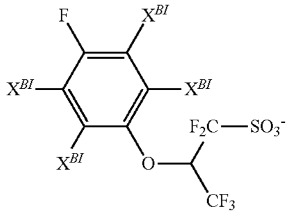
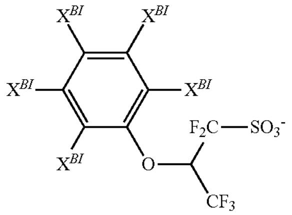
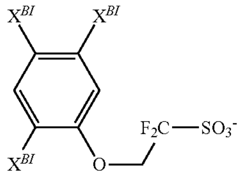
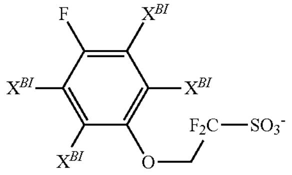
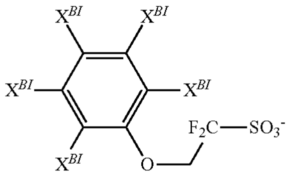
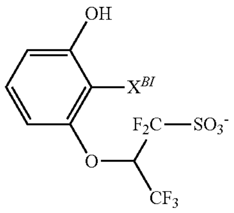
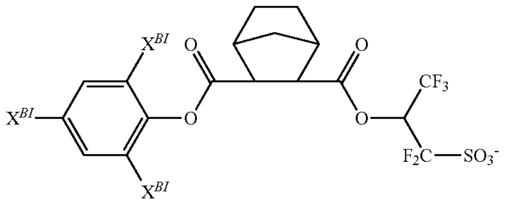
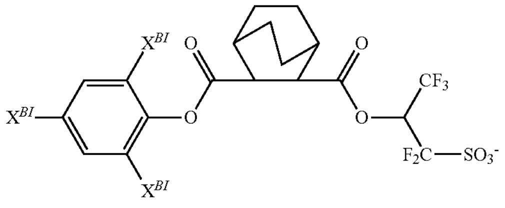

-continued
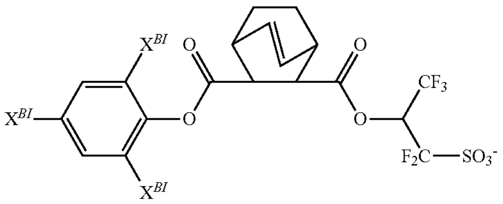
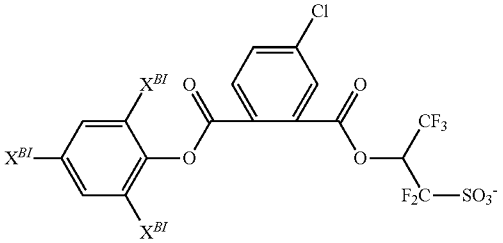
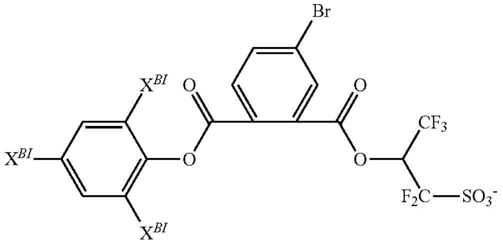
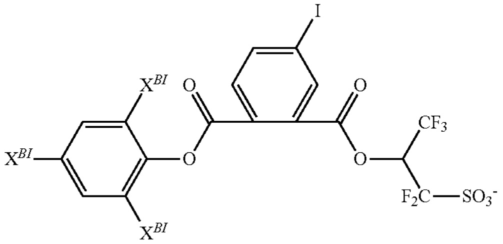
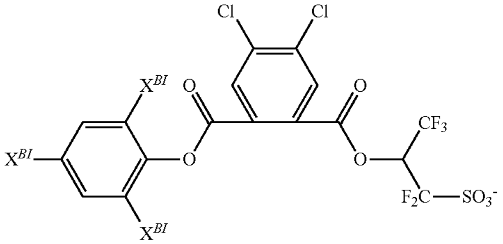
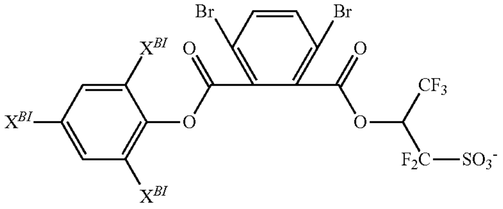
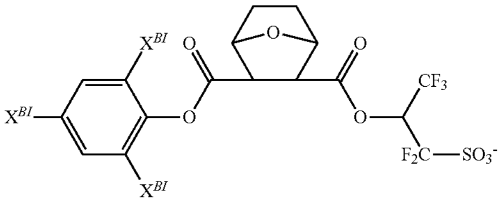
-continued
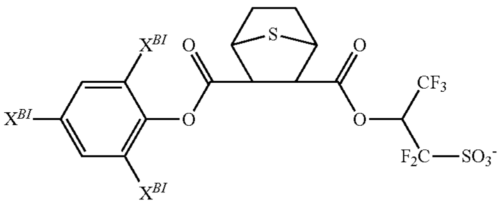
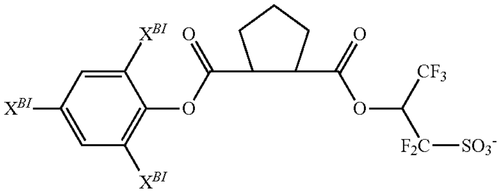
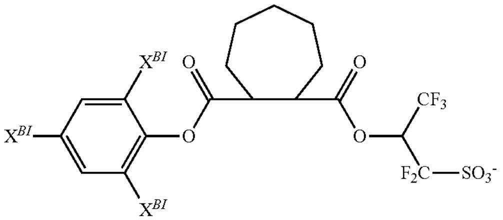
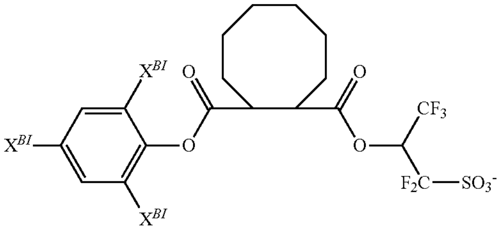
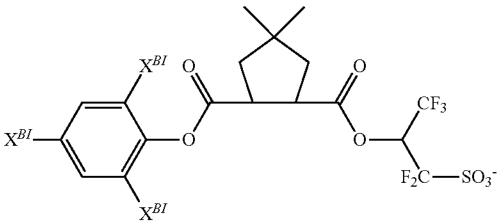
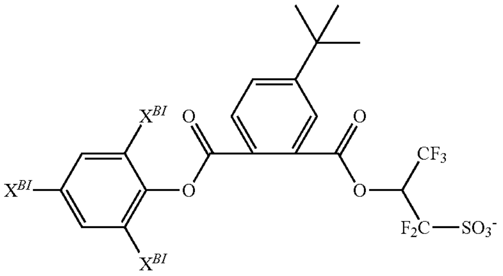

-continued
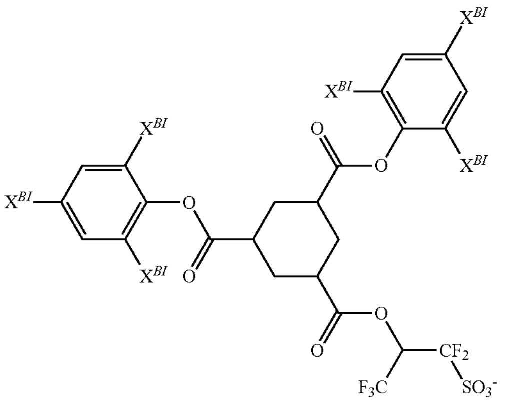
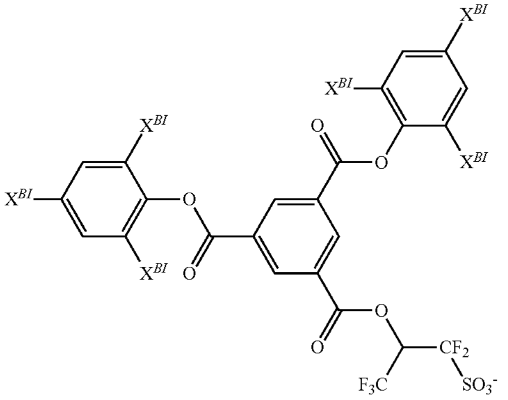
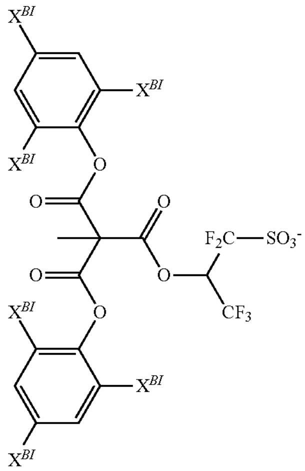
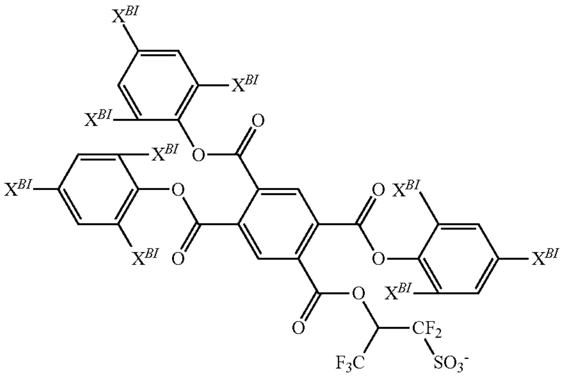
-continued
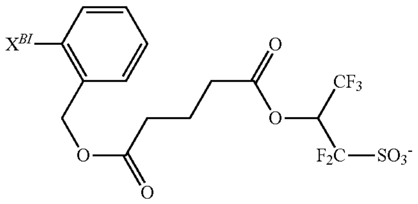
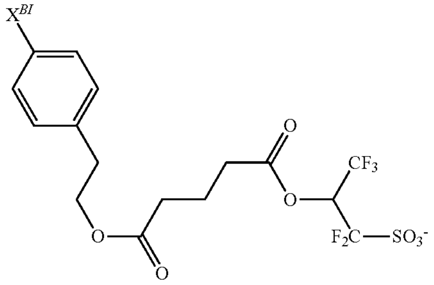
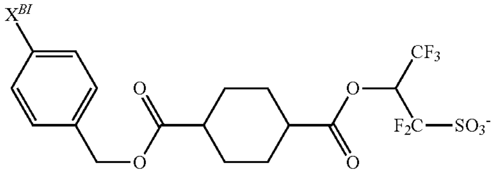
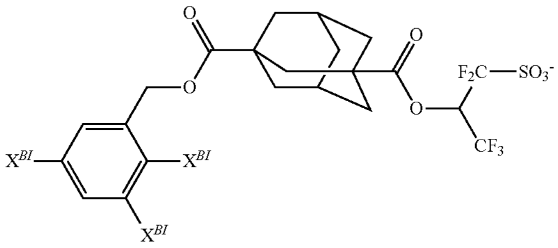
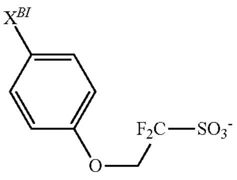
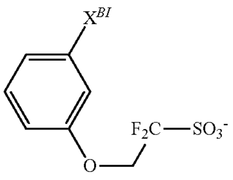
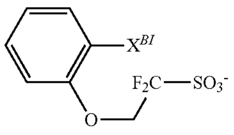
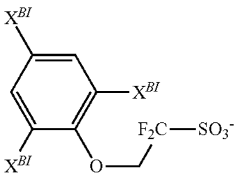
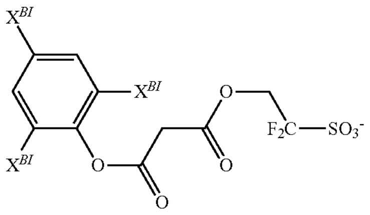
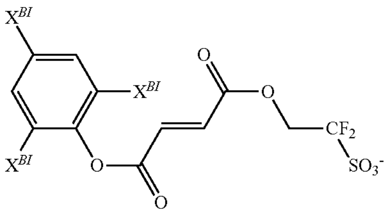

-continued
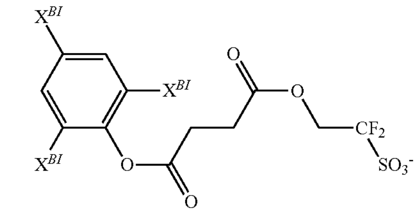
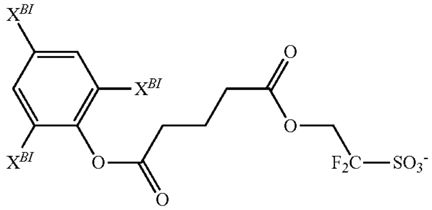
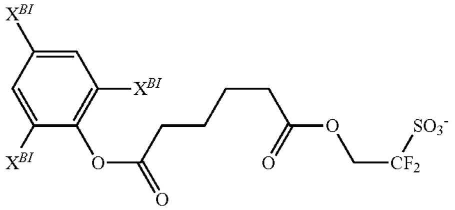
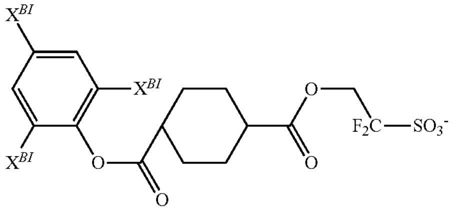
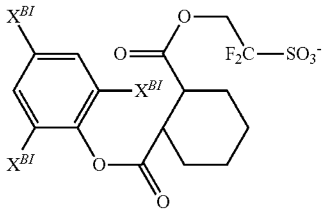
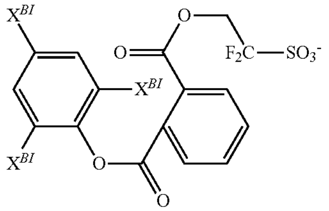
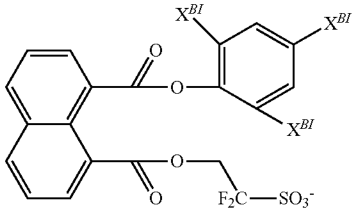
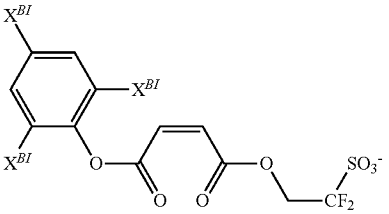
-continued
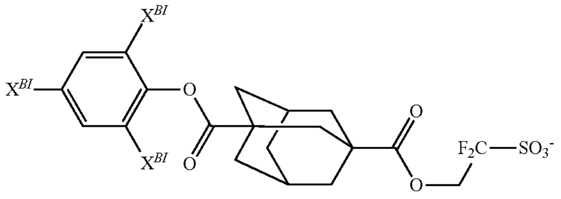
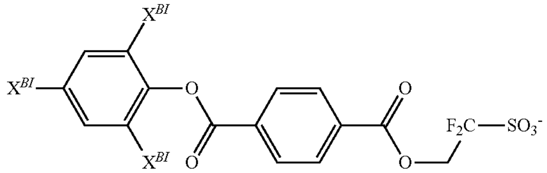
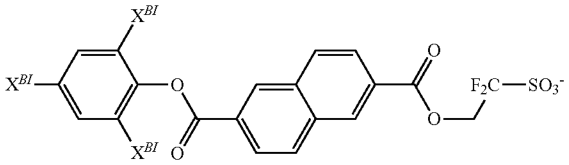
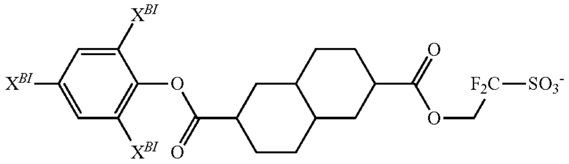
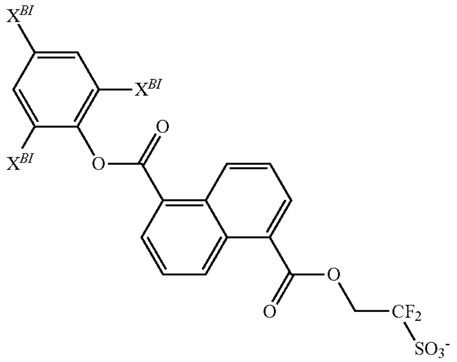
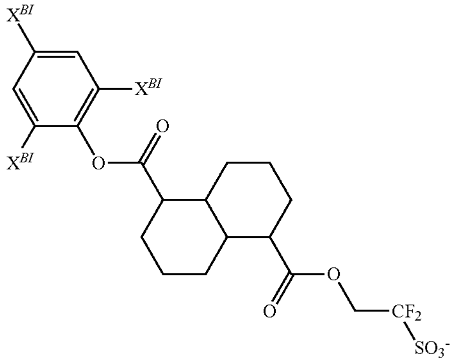

-continued
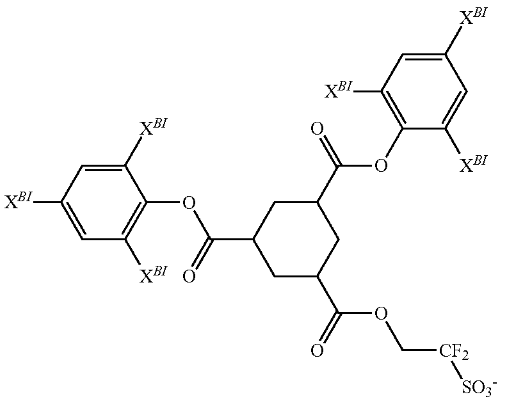
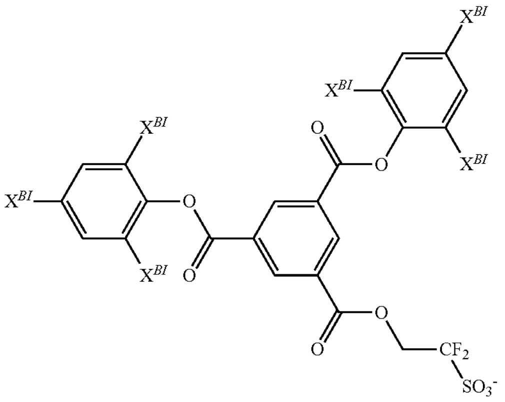
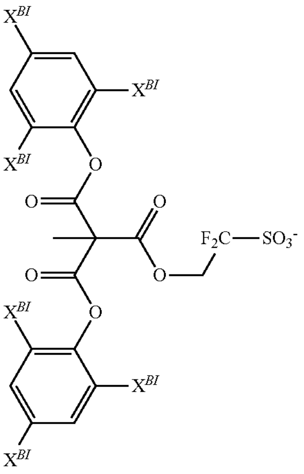
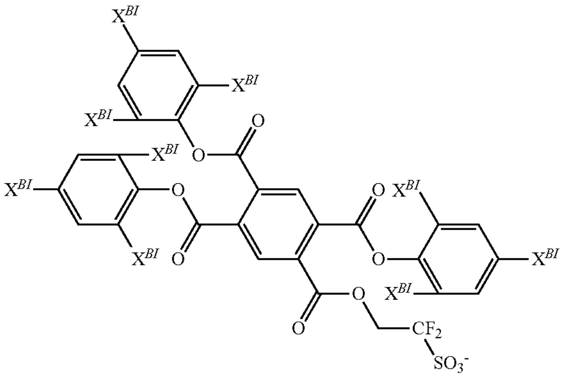
-continued
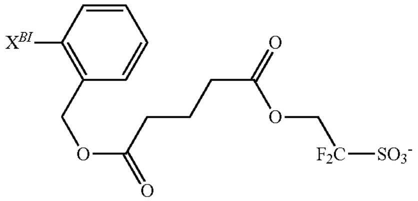
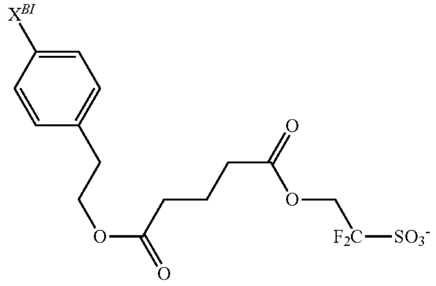
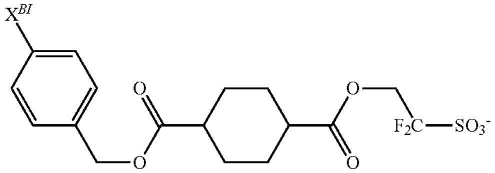
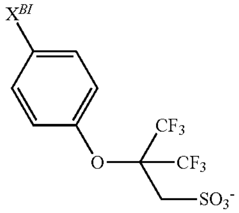
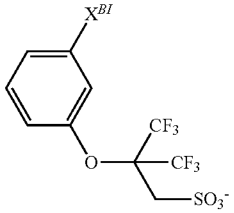
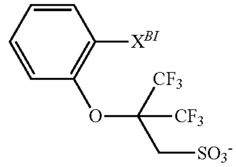
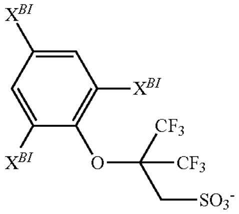
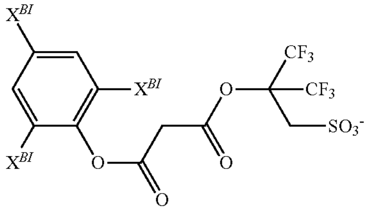
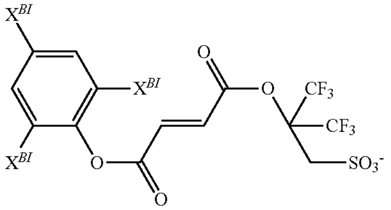
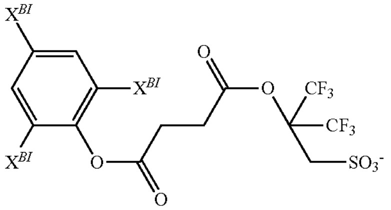

-continued
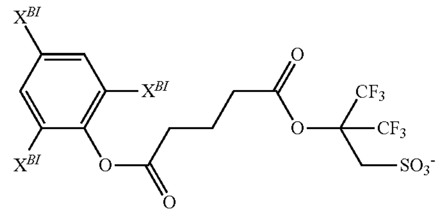
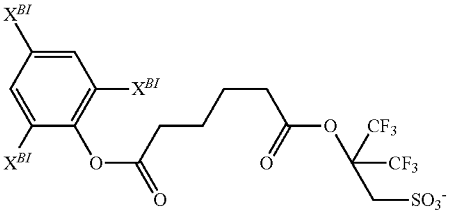
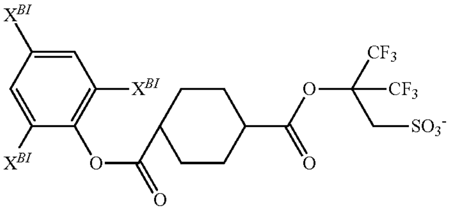
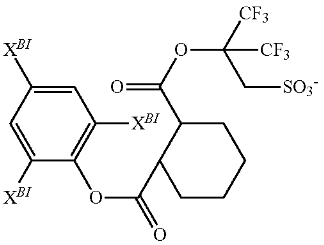
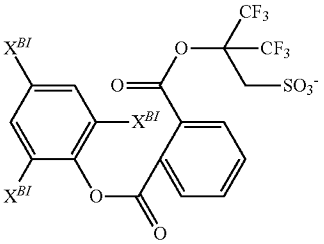
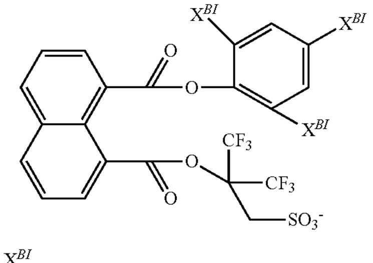
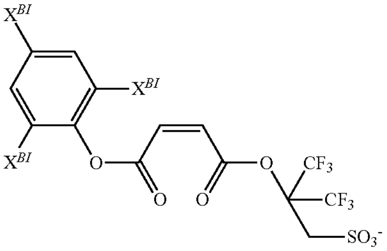
-continued
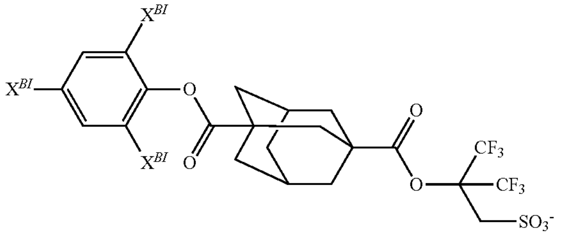
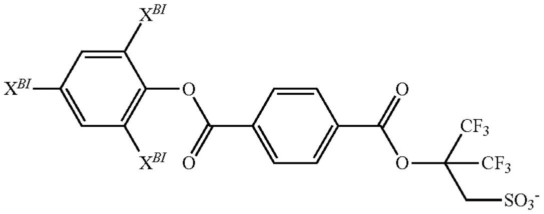
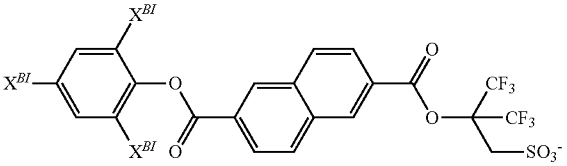
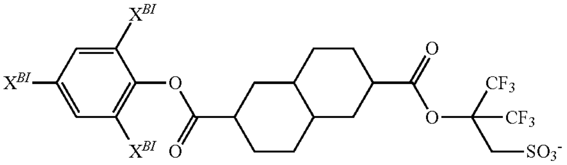
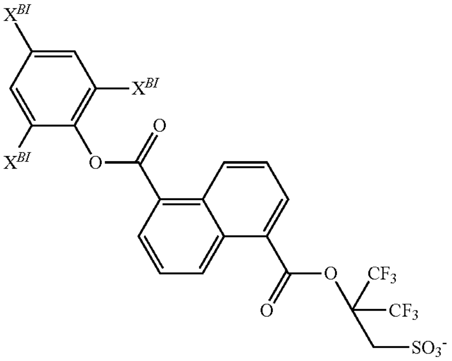
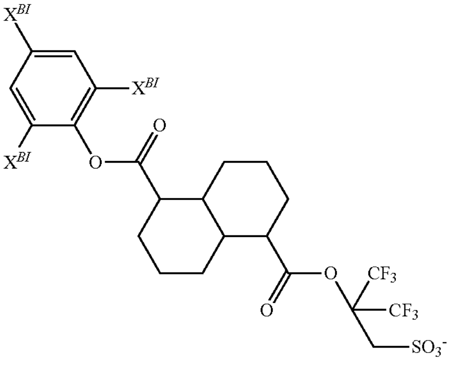

-continued

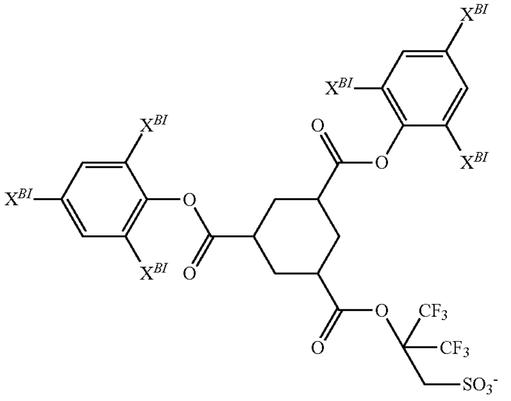

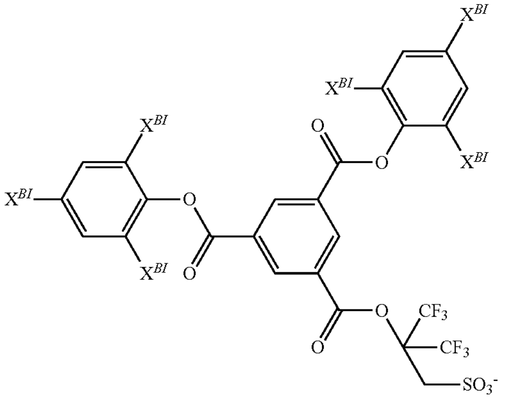

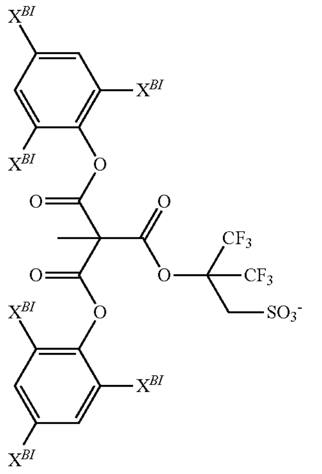

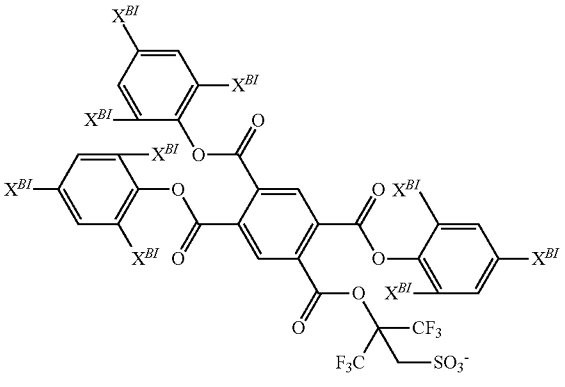

-continued

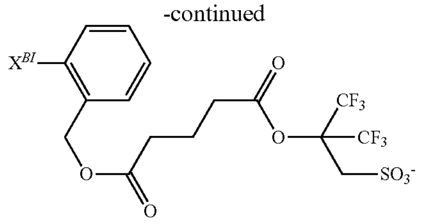

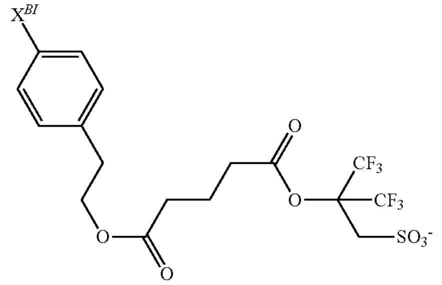

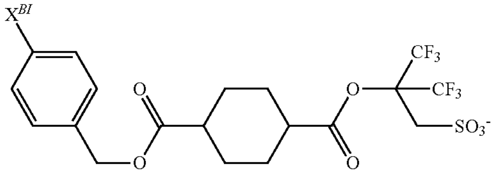

When the inventive resist material contains the additive-type acid generator, the content thereof is preferably 0.1 to 50 parts by mass, and more preferably 1 to 40 parts by mass, relative to 100 parts by mass of the base polymer. The base polymer having any one of the repeating units f1 to f3 and/or the additive-type acid generator enables the inventive resist material to function as the chemically amplified resist composition.

Organic Solvent

The inventive resist material may contain an organic solvent. The organic solvent is not particularly limited as long as the solvent can dissolve each of the aforementioned components and each component described later. Examples of the organic solvent include, as described in paragraphs [0144] to [0145] of JP 2008-111103 A, ketones, such as cyclohexanone, cyclopentanone, methyl-2-n-pentyl ketone, and 2-heptanone; alcohols, such as 3-methoxybutanol, 3-methyl-3-methoxybutanol, 1-methoxy-2-propanol, 1-ethoxy-2-propanol, and diacetone alcohol; ethers, such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones, such as γ-butyrolactone.

The content of the organic solvent in the inventive resist material is preferably 100 to 10,000 parts by mass, and more preferably 200 to 8,000 parts by mass, relative to 100 parts by mass of the base polymer. The organic solvent may be used singly, or may be used with mixing two or more kinds thereof.

Other Components

The inventive resist material may contain, in addition to the aforementioned components, a surfactant, a dissolution inhibitor, a crosslinker, a quencher other than the inventive onium salt (hereinafter, referred to as the other quencher), a water repellency enhancer, acetylene alcohols, and the like.

Examples of the surfactant include surfactants described in paragraphs [0165] to [0166] of JP 2008-111103 A. Adding the surfactant can further improve or regulate the coatability of the resist material. When the inventive resist material contains the surfactant, the content thereof is preferably 0.0001 to 10 parts by mass relative to 100 parts by mass of the base polymer. The surfactant may be used singly, or may be used in combination of two or more kind thereof.

When the inventive resist material is the positive type resist material, blending a dissolution inhibitor can further increase the difference in the dissolution rate between the exposed portion and the unexposed portion to further improve the resolution. Examples of the dissolution inhibitor include: a compound having a molecular weight of preferably 100 to 1,000, more preferably 150 to 800, and having two or more phenolic hydroxy groups in the molecule, wherein 0 to 100 mol % of all the hydrogen atoms in the phenolic hydroxy groups are substituted with an acid-labile group; or a compound having a carboxy group in the molecule, wherein 50 to 100 mol % in average of all the hydrogen atoms of the carboxy groups are substituted with an acid-labile group. Specific examples thereof include compounds in which hydrogen atoms of hydroxy groups or carboxy groups in bisphenol A, trisphenol, phenolphthalein, cresol novolac, naphtharenecarboxylic acid, adamantanecarboxylic acid, and cholic acid are substituted with an acid-labile group. These dissolution inhibitors are described in paragraphs [0155] to [0178] of JP 2008-122932 A, for example.

When the inventive resist material is the positive type resist material and contains the dissolution inhibitor, the content thereof is preferably 0 to 50 parts by mass, and more preferably 5 to 40 parts by mass, relative to 100 parts by mass of the base polymer. The dissolution inhibitor may be used singly, or may be used in combination of two or more kind thereof.

Meanwhile, when the inventive resist material is the negative-type resist material, adding a crosslinker can reduce the dissolution rate in the exposed portion to obtain a negative pattern. Examples of the crosslinker include: epoxy compounds, melamine compounds, guanamine compounds, glycoluril compounds, or urea compounds each of which is substituted with at least one group selected from a methylol group, an alkoxymethyl group, and an acyloxymethyl group; isocyanate compounds; azide compounds; or compounds having a double bond, such as an alkenyloxy group. These compounds may be used as an additive, or may be introduced into the polymer side chain as a pendant group. Compounds having a hydroxy group can also be used as the crosslinker.

Examples of the epoxy compound include tris(2,3-epoxypropyl)isocyanurate, trimethylolmethane triglycidyl ether, trimethylolpropane triglycidyl ether, and triethylolethane triglycidyl ether.

Examples of the melamine compound include hexamethylolmelamine, hexamethoxymethylmelamine, a compound in which 1 to 6 methylol groups in hexamethylolmelamine are methoxymethylated or a mixture thereof, hexamethoxymethylmelamine, hexaacyloxymethylmelamine, and a compound in which 1 to 6 methylol groups in hexamethylolmelamine are acyloxymethylated or a mixture thereof.

Examples of the guanamine compound include tetramethylolguanamine, tetramethoxymethylguanamine, a compound in which 1 to 4 methylol groups in tetramethylolguanamine are methoxymethylated or a mixture thereof, tetramethoxyethylguanamine, tetraacyloxyguanamine, and a compound in which 1 to 4 methylol groups in tetramethylolguanamine are acyloxymethylated or a mixture thereof.

Examples of the glycoluril compound include tetramethylolglycoluril, tetramethoxyglycoluril, tetramethoxymethylglycoluril, a compound in which 1 to 4 methylol groups in tetramethylolglycoluril are methoxymethylated or a mixture thereof, and a compound in which 1 to 4 methylol groups in tetramethylolglycoluril are acyloxymethylated or a mixture thereof.

Examples of the urea compound include tetramethylolurea, tetramethoxymethylurea, a compound in which 1 to 4 methylol groups in tetramethylolurea are methoxymethylated or a mixture thereof, and tetramethoxyethylurea.

Examples of the isocyanate compound include tolylene diisocyanate, diphenylmethane diisocyanate, hexamethylene diisocyanate, and cyclohexane diisocyanate.

Examples of the azide compound include 1,1'-biphenyl-4,4'-bisazide, 4,4'-methylidenebisazide, and 4,4'-oxybisazide.

Examples of the compound having an alkenyloxy group include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

When the inventive resist material is the negative-type resist material and contains the crosslinker, the content thereof is preferably 0.1 to 50 parts by mass, and more preferably 1 to 40 parts by mass, relative to 100 parts by mass of the base polymer. The crosslinker may be used singly, or may be used in combination of two or more kind thereof.

Examples of the other quencher include conventional basic compounds. Examples of the conventional basic compound include primary, secondary, or tertiary aliphatic amines, mixed amines, aromatic amines, heterocyclic amines, nitrogen-containing compounds having a carboxy group, nitrogen-containing compounds having a sulfonyl group, nitrogen-containing compounds having a hydroxy group, nitrogen-containing compounds having a hydroxyphenyl group, alcoholic nitrogen-containing compounds, amides, imides, and carbamates. Specifically, preferable are: primary, secondary, or tertiary amine compounds described in paragraphs [0146] to [0164] in JP 2008-111103 A; particularly, amine compounds having a hydroxy group, an ether bond, an ester bond, a lactone ring, a cyano group, or a sulfonate ester bond; or compounds having a carbamate group described in JP 3790649 B. Adding such a basic compound can further reduce the diffusion rate of the acid in the resist film and modify the shape, for example.

Examples of the other quencher also include onium salts such as sulfonium salts, iodonium salts, and ammonium salts of a sulfonic acid and a carboxylic acid having no-fluorinated α-position, described in JP 2008-158339 A. Although the α-position-fluorinated sulfonic acid, imide acid, or methide acid is required for deprotecting the acid-labile group of the carboxylate ester, a sulfonic acid or a carboxylic acid having no-fluorinated α-position are released through salt exchange with the onium salt having no-fluorinated α-position. Since the sulfonic acid and carboxylic acid having no-fluorinated α-position do not cause deprotection reaction, such onium salts function as a quencher.

Examples of the other quencher further include a polymer quencher described in JP 2008-239918 A. This polymer quencher are segregated on a resist film surface to improve rectangularity of the resist pattern. The polymer quencher also has an effect of preventing film reduction of a pattern and rounding of a pattern top when a protective film for immersion exposure is applied.

When the inventive resist material contains the other quencher, the content thereof is preferably 0 to 5 parts by mass, and more preferably 0 to 4 parts by mass, relative to 100 parts by mass of the base polymer. The other quencher may be used singly, or may be used in combination of two or more kind thereof.

The water repellency enhancer improves water repellency on the resist film surface, and can be used for immersion lithography without a top coating. As the water repellency enhancer, a polymer having a fluorinated alkyl group, a polymer with a specific structure having a 1,1,1,3,3,3-hexafluoro-2-propanol residue, etc. are preferable, and water repellency enhancers exemplified in JP 2007-297590 A, JP 2008-111103 A, etc. are more preferable. The water repellency enhancer is necessarily dissolved in an alkaline developer or an organic solvent developer. The aforementioned specific water repellency enhancer having a 1,1,1,3,3,3-hexafluoro-2-propanol residue has good solubility in the developer. A polymer having a repeating unit having an amino group or an amine salt as a water repellency enhancer is highly effective in preventing evaporation of the acid during post exposure bake (PEB) to prevent the developed hole pattern from failure of opening. When the inventive chemically amplified resist material contains the above water repellency enhancer, the content thereof is preferably 0 to 20 parts by mass, and more preferably 0.5 to 10 parts by mass, relative to 100 parts by mass of the base polymer. The water repellency enhancer may be used singly, or may be used in combination of two or more kind thereof.

Examples of the acetylene alcohols include those described in paragraphs [0179] to [0182] in JP 2008-122932 A. When the inventive chemically amplified resist material contains the acetylene alcohols, the content thereof is preferably 0 to 5 parts by mass relative to 100 parts by mass of the base polymer. The acetylene alcohols may be used singly, or may be used in combination of two or more kind thereof.

Patterning Process

When the inventive resist material is used for manufacturing various integrated circuits, known lithographic technology can be applied. Examples of the patterning process include a method comprising: forming a resist film on a substrate by using the aforementioned chemically amplified resist material; exposing the resist film to high-energy ray; and developing the exposed resist film by using a developer.

First, the inventive resist material is applied on a substrate for integrated circuit manufacturing (such as Si, $SiO_2$, SiN, SiON, TiN, WSi, BPSG, SOG, and an organic anti-reflective film) or a substrate for mask circuit manufacturing (such as Cr, CrO, CrON, $MoSi_2$, and $SiO_2$) by an appropriate coating method such as spin-coating, roll-coating, flow-coating, dip-coating, spray-coating, and doctor-coating so that the coating film thickness is 0.01 to 2 μm. This film is pre-baked on a hot plate at preferably 60 to 150° C. for 10 seconds to 30 minutes, more preferably at 80 to 120° C. for 30 seconds to 20 minutes to form a resist film.

Then, the resist film is exposed by using high-energy ray. Examples of the high-energy ray include ultraviolet ray, far ultraviolet ray, electron beam (EB), extreme ultraviolet ray (EUV) having a wavelength of 3 to 15 nm, X-ray, soft X-ray, excimer laser light, γ-ray, and synchrotron radiation. When ultraviolet ray, far ultraviolet ray, EUV, X-ray, soft X-ray, excimer laser light, γ-ray, synchrotron radiation, etc. is used as the high-energy ray, irradiation is performed directly or using a mask for forming a target pattern so that the exposure dose is preferably approximately 1 to 200 $mJ/cm^2$, more preferably approximately 10 to 100 $mJ/cm^2$. When EB is used as the high-energy ray, writing is performed directly or by using a mask for forming a target pattern at an exposure dose of preferably approximately 0.1 to 300 $\mu C/cm^2$, more preferably approximately 0.5 to 200 $\mu C/cm^2$. The inventive resist material is particularly suitable for fine pattering with, among the high-energy rays, KrF excimer laser light, ArF excimer laser light, EB, EUV, X-ray, soft X-ray, γ-ray, and synchrotron radiation. Among them, KrF excimer laser light, ArF excimer laser light, EB, or EUV having a wavelength of 3 to 15 nm is preferably used, and the inventive resist material is particularly suitable for fine patterning with EB or EUV.

After the exposure, PEB may be performed on a hot plate or in an oven at preferably 30 to 150° C. for 10 seconds to 30 minutes, more preferably 50 to 120° C. for 30 seconds to 20 minutes. The PEB may not be performed.

After the exposure or the PEB, the exposed resist film is developed by a common method such as a dip method, a puddle method, and a spray method for 3 seconds to 3 minutes, preferably 5 seconds to 2 minutes to form a target pattern. For the development, used are a developer of a 0.1 to 10 mass %, preferably 2 to 5 mass %, alkaline aqueous solution such as tetramethylammonium hydroxide (TMAH), tetraethylammonium hydroxide, tetrapropylammonium hydroxide, and tetrabutylammonium hydroxide. In a case of the positive-type resist material, the light-irradiated portion is dissolved in the developer and the unexposed portion is not dissolved to form a target positive-type pattern on the substrate. In a case of the negative-type resist material, in contrast to the case of the positive-type resist material, the light-irradiated portion is insoluble in the developer and the unexposed portion is dissolved.

A negative pattern can also be obtained by using the positive-type resist material containing the base polymer having an acid-labile group with the organic solvent development. Examples of the developer used in this case include 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents can be used singly, or used with mixing two or more kinds thereof.

After the development, rinsing is performed. The rinsing liquid is preferably a solvent that mixes with the developer and does not dissolve the resist film. Preferably used as such a solvent are alcohols having 3 to 10 carbon atoms, ether compounds having 8 to 12 carbon atoms, alkanes, alkenes, or alkynes having 6 to 12 carbon atoms, and aromatic solvents.

Examples of the alcohols having 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol.

Examples of the ether compounds having 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether.

Examples of the alkanes having 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Examples of the alkenes having 6 to 12 carbon atoms include hexene, heptene, octene, cyclohexene, methylcyclohexene, dimethylcyclohexene, cycloheptene, and cyclooctene. Examples of the alkynes having 6 to 12 carbon atoms include hexyne, heptyne, and octyne.

Examples of the aromatic solvents include toluene, xylene, ethylbenzene, isopropylbenzene, tert-butylbenzene, and mesitylene.

The rinsing can reduce collapse of the resist pattern and occurrence of defects. Rinsing is not essential, and no rinsing can reduce the use amount of the solvent.

The hole pattern or trench pattern after the development can be shrunk by thermal flow, RELACS technology, or DSA technology. A shrinking agent is applied on the hole pattern, and during baking, an acid catalyst is diffused from the resist film to cause crosslinking of the shrinking agent on the resist film surface, and the shrinking agent adheres to the side wall of the hole pattern. The baking temperature is preferably 70 to 180° C., and more preferably 80 to 170° C. The baking time is preferably 10 to 300 seconds. The extra shrinking agent is removed to shrink the hole pattern.

EXAMPLE

Hereinafter, the present invention will be specifically described by showing Synthesis Examples, Examples, and Comparative Examples, but the present invention is not limited to the following Examples. Used apparatus was as follows.

MALDI TOF-MS: S3000, manufactured by JEOL Ltd.

[1] Synthesis of Onium Salt

Example 1-1: Synthesis of SQ-1

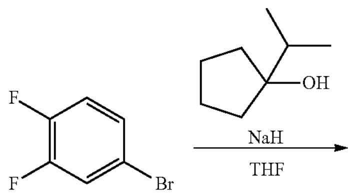

SM-1

-continued

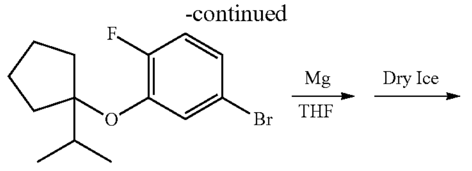

In-1

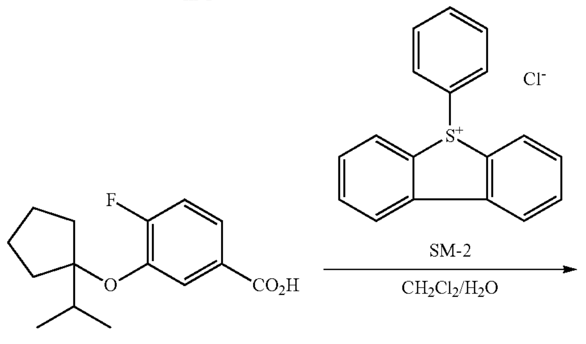

In-2

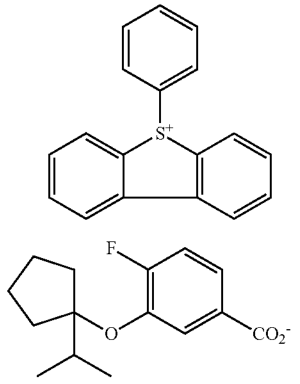

SQ-1

(1) Synthesis of Intermediate In-1

Under a nitrogen atmosphere, sodium hydride (purity: 55 mass %, 10.9 g) was dispersed in THF (60 ml), and a solution composed of 1-isopropylcyclopentanol (35.3 g) and THF (30 ml) was added dropwise thereinto. After the dropwise addition, the mixture was heated with reflux for 4 hours to prepare a metal alkoxide. Then, a starting material SM-1 (48.3 g) was added dropwise, and the mixture was heated with reflux and aged for 18 hours. The reaction liquid was cooled with an ice bath, and the reaction was terminated with water (100 ml). The target product was extracted twice with a solution compose of toluene (100 ml) and hexane (100 ml), common aqueous word-up was performed, the solvent was evaporated, and then purified with distillation to obtain 51.2 g of an intermediate In-1 as a colorless oil (68% yield).

(2) Synthesis of Intermediate In-2

Under a nitrogen atmosphere, a Grignard reagent was prepared from metallic magnesium (4.1 g), the intermediate In-1 (51.2 g), and THF (200 ml). This Grignard reagent was added dropwise into a dispersion of dry ice (200 g) in THF (500 ml). After the dropwise addition, the mixture was aged until the dry ice was sublimated. After the aging, 5 mass % hydrochloric acid (150 g) was added dropwise while maintaining the reaction mixture at 10° C. or lower to terminate the reaction. Thereafter, the target product was extracted with ethyl acetate (600 ml), common aqueous word-up was performed, the solvent was evaporated, and then recrystallization with hexane was performed to obtain an intermediate In-2 as a while crystal (yielded amount: 26.8 g, 58% yield).

(3) Synthesis of Onium Salt SQ-1

Under a nitrogen atmosphere, the intermediate In-2 (4.0 g) and a starting material SM-2 (4.5 g) were dissolved in methylene chloride (50 g) and water (40 g), and the mixture was stirred for 20 minutes. After the reaction liquid was separated to recover the organic layer, common aqueous word-up was performed, and the solvent was evaporated to obtain 5.8 g of an onium salt SQ-1 as a colorless oil (73% yield).

The results of TOF-MS on the onium salt SQ-1 were shown below.

MALDI TOF-MS: POSITIVE $M^+$261 (corresponding to $C_{18}H_{13}S^+$)

NEGATIVE $M^-$265 (corresponding to $C_{15}H_{18}FO_3^-$)

Examples 1-2 to 1-9: Syntheses of SQ-2 to SQ-9

Each onium salt was synthesized with each organic synthesis reaction. The structures of onium salts used for chemically amplified resist compositions are shown below.

SQ-2

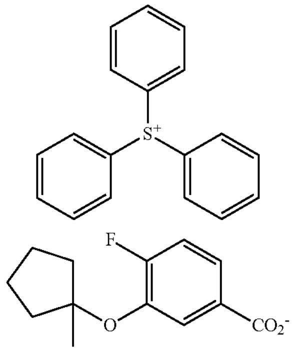

SQ-3

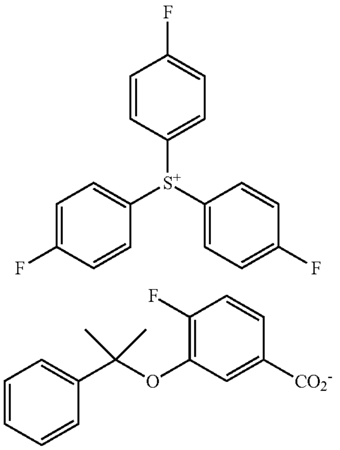

-continued

SQ-4

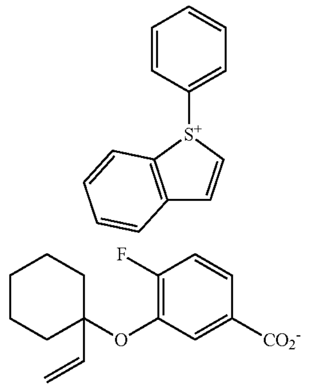

SQ-5

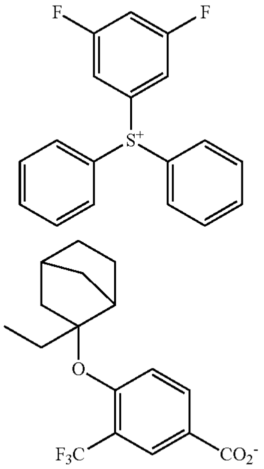

SQ-6

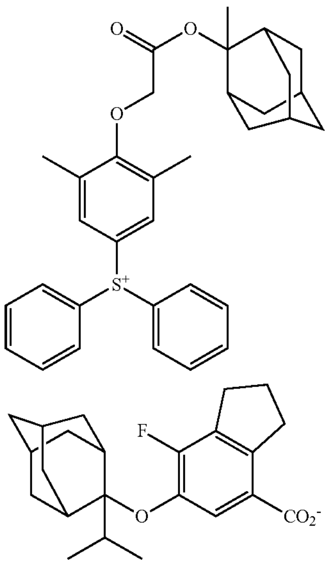

-continued

SQ-7

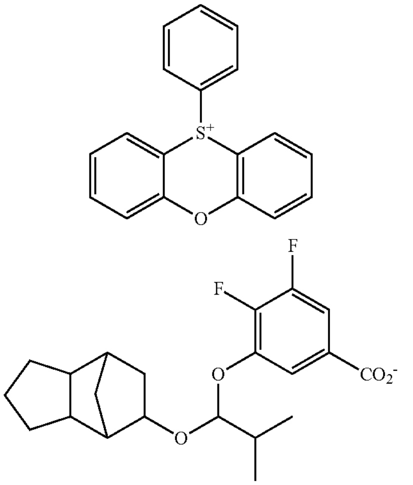

SQ-8

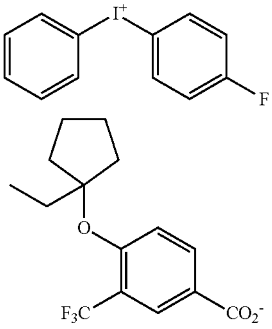

SQ-9

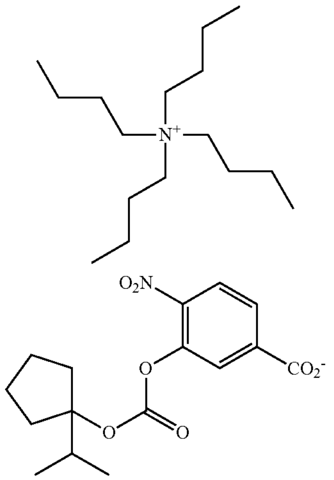

[2] Synthesis Example: Syntheses of Base Polymers (P-1 to 5)

Each of monomers was combined to perform a copolymerization reaction in a THF solvent, the product was precipitated with methanol, further washed repeatedly with hexane, then isolated, and dried to obtain each of base polymers (P-1 to 5) having the following formulation. The formulation of the obtained base polymer was determined by $^1$H-NMR, and Mw and Mw/Mn thereof were determined by GPC (solvent: THF, standard: polystyrene).

P-1

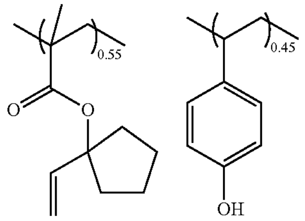

Mw = 4,900
Mw/Mn = 1.51

P-2

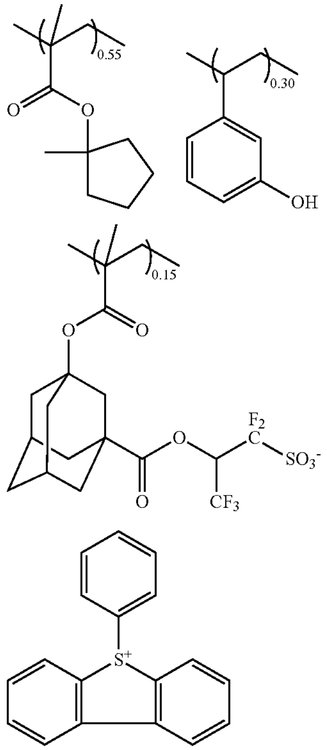

Mw = 8,900
Mw/Mn = 1.89

P-3

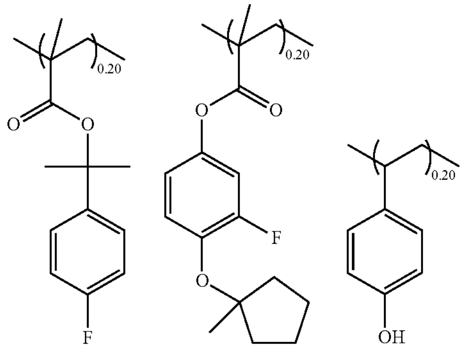

-continued

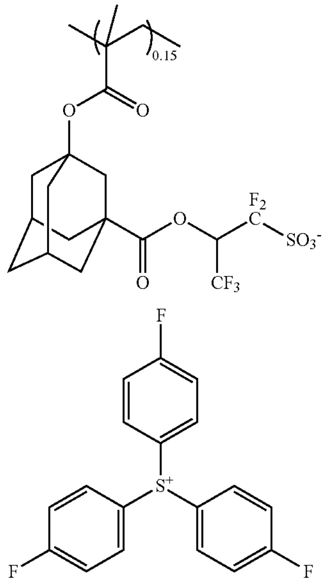

Mw = 7,800
Mw/Mn = 1.75

P-4

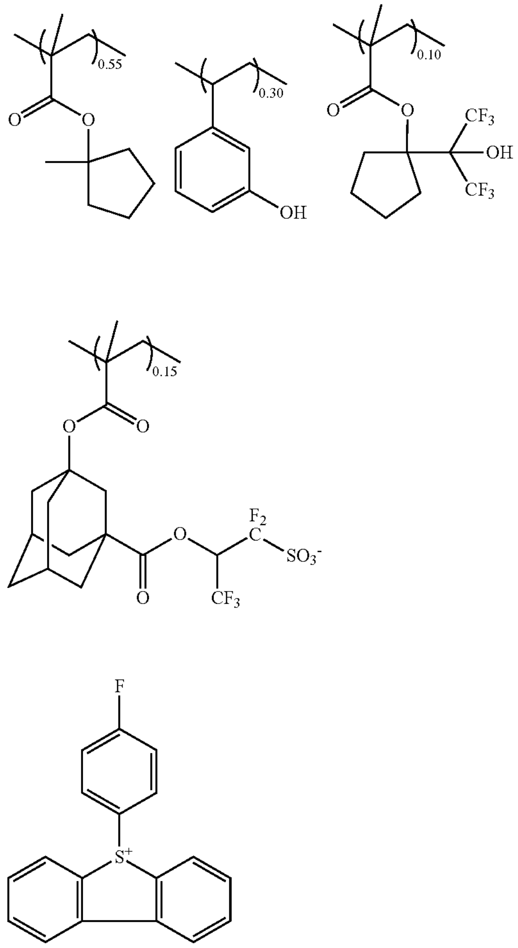

Mw = 8,300
Mw/Mn = 1.81

-continued

P-5

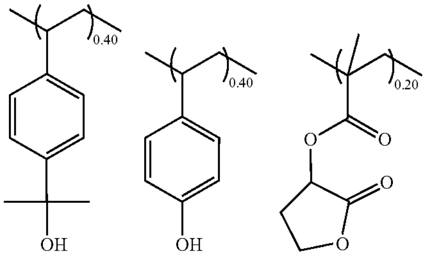

Mw = 6,900
Mw/Mn = 1.62

[3] Examples 2-1 to 2-20 and Comparative Examples 1-1 to 1-12: Preparation of Resist Material (1) Preparation of Resist Material A solution dissolving each component at the formulation shown in Table 1 and Table 2 was filtered with a filter with 0.2 μm in size to prepare a resist material. Resist materials of Examples 2-1 to 2-18 and Comparative Examples 1-1 to 1-10 were positive-type resist materials, and resist materials of Examples 2-19 and 2-20 and Comparative Examples 1-11 and 1-12 were negative-type resist materials.

Each component in Table 1 was as follows.

Organic solvent: PGMEA (propylene glycol monomethyl ether acetate)

DAA (diacetone alcohol)

Photoacid generator: PAG-1 to PAG-5

PAG-1

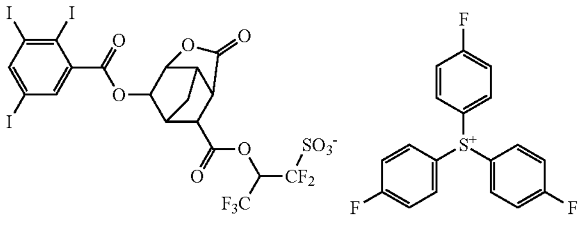

PAG-2

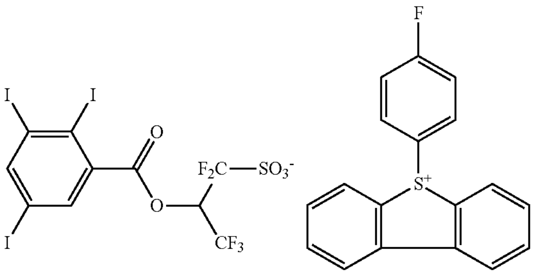

-continued
PAG-3
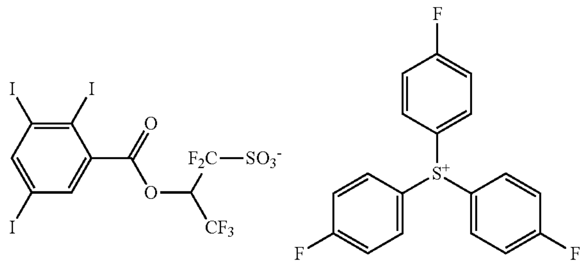
PAG-4
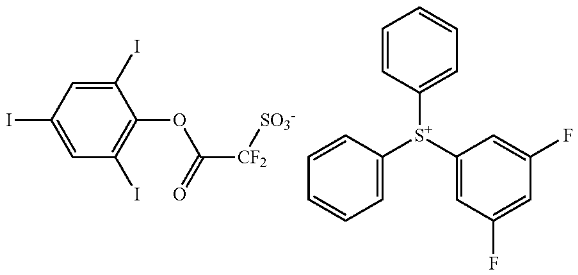
PAG-5
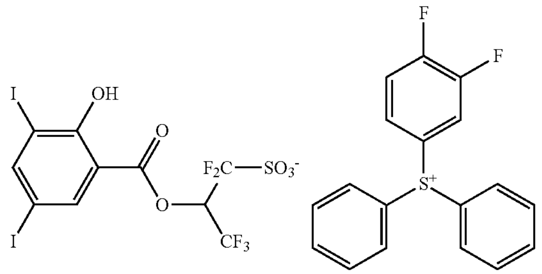
Blended quencher: bQ-1 and bQ-2
bQ-1
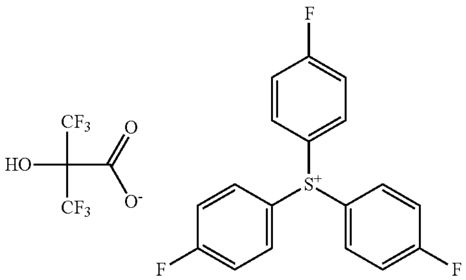
bQ-2
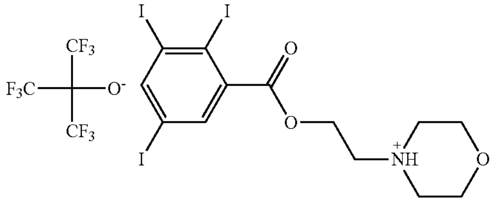
Comparative quencher: cSQ-1 to cSQ-4
cSQ-1
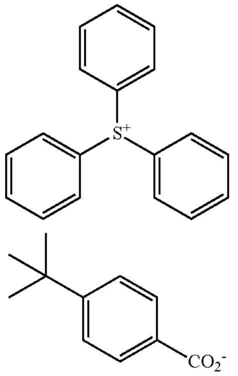
cSQ-2
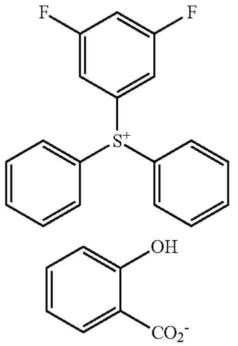
cSQ-3
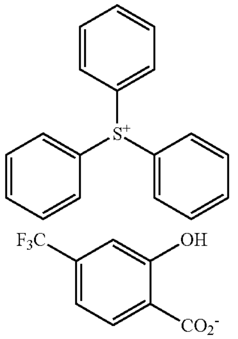
cSQ-4
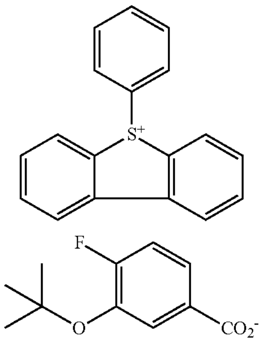

TABLE 1

| | Resist composition | Base polymer (parts by mass) | Photoacid generator (parts by mass) | Quencher (parts by mass) | Organic solvent 1 (parts by mass) | Organic solvent 2 (parts by mass) |
|---|---|---|---|---|---|---|
| Example 2-1 | R-1 | P-1 (100) | PAG-1 (30.2) | SQ-1 (4.8) | PGMEA (3,000) | DAA (500) |
| Example 2-2 | R-2 | P-1 (100) | PAG-2 (24.8) | SQ-2 (4.7) | PGMEA (3,000) | DAA (500) |
| Example 2-3 | R-3 | P-1 (100) | PAG-2 (24.8) | SQ-3 (4.8) | PGMEA (3,000) | DAA (500) |
| Example 2-4 | R-4 | P-1 (100) | PAG-2 (24.8) | SQ-4 (4.7) | PGMEA (3,000) | DAA (500) |
| Example 2-5 | R-5 | P-1 (100) | PAG-2 (24.8) | SQ-5 (4.8) | PGMEA (3,000) | DAA (500) |
| Example 2-6 | R-6 | P-1 (100) | PAG-3 (25.2) | SQ-6 (4.9) | PGMEA (3,000) | DAA (500) |
| Example 2-7 | R-7 | P-1 (100) | PAG-4 (25.2) | SQ-7 (4.8) | PGMEA (3,000) | DAA (500) |
| Example 2-8 | R-8 | P-1 (100) | PAG-3 (25.2) | SQ-8 (4.8) | PGMEA (3,000) | DAA (500) |
| Example 2-9 | R-9 | P-1 (100) | PAG-1 (30.2) | SQ-9 (2.4) bQ-1 (2.4) | PGMEA (3,000) | DAA (500) |
| Example 2-10 | R-10 | P-2 (100) | — | SQ-1 (4.6) | PGMEA (3,000) | DAA (500) |
| Example 2-11 | R-11 | P-2 (100) | — | SQ-2 (4.9) | PGMEA (3,000) | DAA (500) |
| Example 2-12 | R-12 | P-2 (100) | — | SQ-3 (4.8) | PGMEA (3,000) | DAA (500) |
| Example 2-13 | R-13 | P-3 (100) | PAG-3 (10.5) | SQ-4 (4.8) | PGMEA (3,000) | DAA (500) |
| Example 2-14 | R-14 | P-3 (100) | — | SQ-6 (4.7) | PGMEA (2,200) | DAA (900) |
| Example 2-15 | R-15 | P-3 (100) | — | SQ-8 (4.6) | PGMEA (2,200) | DAA (900) |
| Example 2-16 | R-16 | P-4 (100) | — | SQ-1 (2.3) bQ-2 (2.3) | PGMEA (2,200) | DAA (900) |
| Example 2-17 | R-17 | P-4 (100) | — | SQ-5 (4.7) | PGMEA (2,200) | DAA (900) |
| Example 2-18 | R-18 | P-4 (100) | — | SQ-2 (4.7) | PGMEA (2,200) | DAA (900) |
| Example 2-19 | R-19 | P-5 (100) | PAG-1 (30.2) | SQ-1 (4.5) | PGMEA (2,200) | DAA (900) |
| Example 2-20 | R-20 | P-5 (100) | PAG-5 (25.2) | SQ-3 (4.6) | PGMEA (2,200) | DAA (900) |

TABLE 2

| | Resist composition | Base polymer (parts by mass) | Photoacid generator (parts by mass) | Quencher (parts by mass) | Organic solvent 1 (parts by mass) | Organic solvent 2 (parts by mass) |
|---|---|---|---|---|---|---|
| Comparative Example 1-1 | CR-1 | P-1 (100) | PAG-1 (30.2) | cSQ-1 (4.8) | PGMEA (3,000) | DAA (500) |
| Comparative Example 1-2 | CR-2 | P-1 (100) | PAG-2 (24.9) | cSQ-2 (4.6) | PGMEA (3,000) | DAA (500) |
| Comparative Example 1-3 | CR-3 | P-1 (100) | PAG-3 (25.3) | cSQ-3 (4.7) | PGMEA (3,000) | DAA (500) |
| Comparative Example 1-4 | CR-4 | P-1 (100) | PAG-4 (25.1) | cSQ-4 (4.8) | PGMEA (3,000) | DAA (500) |
| Comparative Example 1-5 | CR-5 | P-2 (100) | — | cSQ-4 (4.8) | PGMEA (3,000) | DAA (500) |
| Comparative Example 1-6 | CR-6 | P-2 (100) | — | cSQ-2 (4.6) | PGMEA (3,000) | DAA (500) |
| Comparative Example 1-7 | CR-7 | P-3 (100) | — | cSQ-3 (4.7) | PGMEA (3,000) | DAA (500) |
| Comparative Example 1-8 | CR-8 | P-3 (100) | PAG-3 (10.5) | cSQ-2 (4.6) | PGMEA (3,000) | DAA (500) |
| Comparative Example 1-9 | CR-9 | P-4 (100) | — | cSQ-4 (4.6) | PGMEA (3,000) | DAA (500) |

TABLE 2-continued

| | Resist composition | Base polymer (parts by mass) | Photoacid generator (parts by mass) | Quencher (parts by mass) | Organic solvent 1 (parts by mass) | Organic solvent 2 (parts by mass) |
|---|---|---|---|---|---|---|
| Comparative Example 1-10 | CR-10 | P-4 (100) | — | CSQ-3 (4.7) | PGMEA (3,000) | DAA (500) |
| Comparative Example 1-11 | CR-11 | P-5 (100) | PAG-1 (30.2) | cSQ-2 (4.6) | PGMEA (3,000) | DAA (500) |
| Comparative Example 1-12 | CR-12 | P-5 (100) | PAG-5 (24.6) | cSQ-4 (4.5) | PGMEA (3,000) | DAA (500) |

[4] EUV Lithography Evaluation (1)

Examples 3-1 to 3-20 and Comparative Examples 2-1 to 2-12

Each of the chemically amplified resist compositions (R-1 to R-20 and CR-1 to CR-12) shown in Table 1 and Table 2 was applied by spin-coating on a Si substrate on which a silicon-containing spin-on hard mask SHB-A940 (silicon content of 43 mass %), manufactured by Shin-Etsu Chemical Co., Ltd., was formed with 20 nm in film thickness. Then, the applied composition was prebaked at 100° C. for 60 seconds using a hot plate to produce a resist film with 50 nm in film thickness. This resist film was exposed by using an EUV scanner NXE3300 (NA 0.33, σ0.9/0.6, dipole illumination), manufactured by ASML Holding N.V. The exposure was performed with a LS pattern with 18 nm in on-wafer size and 36 nm in pitch, and with changing an exposure dose and focus (exposure dose pitch: 1 mJ/cm$^2$, focus pitch: 0.020 μm). After the exposure, PEB was performed at a temperature shown in Table 3 and Table 4 for 60 seconds. Thereafter, puddle development with a 2.38 mass % aqueous TMAH solution for 30 seconds, rinsing with a surfactant-containing rinsing material, and spin-drying were performed to obtain a positive-type pattern in Examples 3-1 to 3-18 and Comparative Examples 2-1 to 2-10. In Examples 3-19 and 3-20 and Comparative Examples 2-11 and 2-12, a negative-type pattern was obtained.

The obtained LS pattern was observed with a length-measurement SEM (CG6300), manufactured by Hitachi High-Technologies Corporation, to evaluate sensitivity, exposure latitude (EL), LWR, depth of focus (DOF), and collapse limit in accordance with the following methods. Table 3 and Table 4 show the results.

Sensitivity Evaluation

An optimum exposure dose $E_{op}$(mJ/cm$^2$) to yield the LS pattern with 18 nm in line width and 36 nm in pitch was determined to specify this value as a sensitivity. A smaller sensitivity value indicates higher sensitivity.

EL Evaluation

From exposure doses that formed LS patterns within a range of the 18 nm space width ±10% (16.2 to 19.8 nm), EL (unit: %) was determined by the following equation. The larger the EL value, the better the performance.

$$EL(\%)=(|E_1-E_2|/E_{op})\times 100$$

$E_1$: An optimum exposure dose to yield a LS pattern with 16.2 nm in line width and 36 nm in pitch.

$E_2$: An optimum exposure dose to yield a LS pattern with 19.8 nm in line width and 36 nm in pitch.

$E_{op}$: An optimum exposure dose to yield the LS pattern with 18 nm in line width and 36 nm in pitch.

LWR Evaluation

In the LS pattern obtained by irradiation at $E_{op}$, sizes at 10 positions in the longitudinal direction of the line were measured. From the results, the tripled value (3σ) of the standard variation (σ) was determined as LWR. A smaller LWR value can yield a pattern with smaller roughness and uniform line width.

DOF Evaluation

As evaluation of depth of focus, determined was a focus range that formed LS patterns within a range of the 18 nm size ±10% (16.2 to 19.8 nm). A larger DOF value indicates wider depth of focus.

Evaluation of Collapse Limit of Line Pattern

Line sizes of the LS patterns at each exposure dose with the optimum focus were measured at 10 positions in the longitudinal direction. The narrowest line size obtained without collapse was specified as a collapse limit size. A smaller limit size value indicates excellent collapse limit.

TABLE 3

| | Resist composition | PEB temperature (° C.) | Optimal exposure dose (mJ/cm$^2$) | EL (%) | LWR (nm) | DOF (nm) | Collapse limit |
|---|---|---|---|---|---|---|---|
| Example 3-1 | R-1 | 105 | 32 | 17 | 2.8 | 110 | 10.1 |
| Example 3-2 | R-2 | 100 | 33 | 18 | 2.9 | 120 | 10.4 |
| Example 3-3 | R-3 | 105 | 33 | 17 | 3 | 110 | 10.3 |
| Example 3-4 | R-4 | 100 | 32 | 17 | 2.8 | 110 | 10.2 |
| Example 3-5 | R-5 | 100 | 34 | 18 | 2.7 | 100 | 10.7 |
| Example 3-6 | R-6 | 100 | 33 | 17 | 2.8 | 120 | 10.6 |

TABLE 3-continued

| | Resist composition | PEB temperature (° C.) | Optimal exposure dose (mJ/cm$^2$) | EL (%) | LWR (nm) | DOF (nm) | Collapse limit |
|---|---|---|---|---|---|---|---|
| Example 3-7 | R-7 | 100 | 32 | 18 | 2.9 | 120 | 10.7 |
| Example 3-8 | R-8 | 105 | 32 | 16 | 3 | 110 | 11.1 |
| Example 3-9 | R-9 | 100 | 33 | 18 | 2.9 | 120 | 11.2 |
| Example 3-10 | R-10 | 100 | 28 | 17 | 2.9 | 120 | 10.7 |
| Example 3-11 | R-11 | 105 | 29 | 17 | 2.7 | 120 | 10.5 |
| Example 3-12 | R-12 | 100 | 28 | 18 | 2.8 | 110 | 10.4 |
| Example 3-13 | R-13 | 95 | 26 | 19 | 2.8 | 100 | 10.5 |
| Example 3-14 | R-14 | 100 | 28 | 18 | 3 | 120 | 10.8 |
| Example 3-15 | R-15 | 100 | 29 | 17 | 2.7 | 120 | 10.4 |
| Example 3-16 | R-16 | 100 | 29 | 18 | 2.8 | 110 | 10.8 |
| Example 3-17 | R-17 | 105 | 28 | 19 | 2.9 | 100 | 10.8 |
| Example 3-18 | R-18 | 105 | 28 | 18 | 2.8 | 120 | 10.8 |
| Example 3-19 | R-19 | 110 | 37 | 16 | 3.1 | 120 | 11.1 |
| Example 3-20 | R-20 | 110 | 36 | 17 | 3 | 120 | 11.2 |

TABLE 4

| | Resist composition | PEB temperature (° C.) | Optimal exposure dose (mJ/cm$^2$) | EL (%) | LWR (nm) | DOF (nm) | Collapse limit (nm) |
|---|---|---|---|---|---|---|---|
| Comparative Example 2-1 | CR-1 | 100 | 41 | 16 | 3.4 | 80 | 14.3 |
| Comparative Example 2-2 | CR-2 | 105 | 42 | 15 | 3.4 | 90 | 14.5 |
| Comparative Example 2-3 | CR-3 | 100 | 40 | 15 | 3.3 | 80 | 14.2 |
| Comparative Example 2-4 | CR-4 | 100 | 42 | 15 | 3.2 | 90 | 13.7 |
| Comparative Example 2-5 | CR-5 | 105 | 35 | 14 | 3.3 | 70 | 14.2 |
| Comparative Example 2-6 | CR-6 | 105 | 34 | 16 | 3.4 | 90 | 13.4 |
| Comparative Example 2-7 | CR-7 | 100 | 33 | 15 | 3.5 | 80 | 12.9 |
| Comparative Example 2-8 | CR-8 | 95 | 34 | 16 | 3.2 | 80 | 13.5 |
| Comparative Example 2-9 | CR-9 | 100 | 32 | 16 | 3.6 | 90 | 13.4 |
| Comparative Example 2-10 | CR-10 | 105 | 33 | 15 | 3.5 | 70 | 13.6 |
| Comparative Example 2-11 | CR-11 | 110 | 41 | 16 | 3.6 | 100 | 12.9 |
| Comparative Example 2-12 | CR-12 | 105 | 42 | 15 | 3.6 | 90 | 14.1 |

From the results shown in Table 3 and Table 4, the chemically amplified resist composition containing the inventive quencher has been found to have excellent EL, LWR, and DOF with good sensitivity for both of the positive-type and negative-type resist materials. The composition has a small collapse limit value, and also has been confirmed to hardly cause pattern collapse even in fine patterning.

[5] EUV Lithography Evaluation (2)

Examples 4-1 to 4-20 and Comparative Examples 3-1 to 3-12

Each of the resist materials shown in Table 1 and Table 2 was applied by spin-coating on a Si substrate on which a silicon-containing spin-on hard mask SHB-A940 (silicon content of 43 mass %), manufactured by Shin-Etsu Chemical Co., Ltd., was formed with 20 nm in film thickness. The applied resist material was prebaked at 100° C. for 60 seconds using a hot plate to produce a resist film with 60 nm in film thickness. Then, the resist film was exposed by using an EUV scanner NXE3400 (NA 0.33, σ0.9/0.6, quadrupole illumination, hole pattern mask with 44 nm in pitch as on-wafer size and +20% bias), manufactured by ASML Holding N.V. Then, PEB was performed at a temperature shown in Table 5 and Table 6 for 60 seconds on a hot plate, and development was performed with a 2.38 mass % aqueous TMAH solution for 30 seconds to obtain a hole pattern with 22 nm in size in Examples 4-1 to 4-18 and Comparative Examples 3-1 to 3-10, and a dot pattern with 22 nm in size in Examples 4-19 and 4-20 and Comparative Examples 3-11 and 3-12.

Using a length-measurement SEM (CG6300), manufactured by Hitachi High-Technologies Corporation, an exposure dose when the hole or dot pattern was formed with 22 nm in size was measured to specify this exposure dose as a sensitivity. Sizes of 50 holes or dots in this time were measured, and the tripled value (3σ) of the standard variation (σ) calculated from the results was determined as CDU. Table 5 and Table 6 show the results.

TABLE 5

| | Resist composition | PEB temperature (° C.) | Optimal exposure dose ($mJ/cm^2$) | CDU (nm) |
|---|---|---|---|---|
| Example 4-1 | R-1 | 85 | 32 | 3.2 |
| Example 4-2 | R-2 | 80 | 33 | 3.1 |
| Example 4-3 | R-3 | 85 | 32 | 3.2 |
| Example 4-4 | R-4 | 80 | 31 | 3.2 |
| Example 4-5 | R-5 | 85 | 32 | 3.2 |
| Example 4-6 | R-6 | 80 | 32 | 3.1 |
| Example 4-7 | R-7 | 80 | 31 | 3 |
| Example 4-8 | R-8 | 80 | 33 | 3.1 |
| Example 4-9 | R-9 | 85 | 32 | 3.4 |
| Example 4-10 | R-10 | 80 | 29 | 3.3 |
| Example 4-11 | R-11 | 85 | 28 | 3.1 |
| Example 4-12 | R-12 | 80 | 27 | 3.2 |
| Example 4-13 | R-13 | 80 | 27 | 3.3 |
| Example 4-14 | R-14 | 85 | 28 | 3.2 |
| Example 4-15 | R-15 | 85 | 26 | 3.1 |
| Example 4-16 | R-16 | 80 | 27 | 3.2 |
| Example 4-17 | R-17 | 80 | 28 | 3.1 |
| Example 4-18 | R-18 | 85 | 27 | 3 |
| Example 4-19 | R-19 | 105 | 33 | 3.3 |
| Example 4-20 | R-20 | 110 | 34 | 3.4 |

TABLE 6

| | Resist composition | PEB temperature (° C.) | Optimal exposure dose ($mJ/cm^2$) | CDU (nm) |
|---|---|---|---|---|
| Comparative Example 3-1 | CR-1 | 80 | 35 | 3.6 |
| Comparative Example 3-2 | CR-2 | 85 | 36 | 3.5 |
| Comparative Example 3-3 | CR-3 | 85 | 36 | 3.6 |
| Comparative Example 3-4 | CR-4 | 80 | 35 | 3.4 |
| Comparative Example 3-5 | CR-5 | 80 | 36 | 3.8 |
| Comparative Example 3-6 | CR-6 | 80 | 37 | 3.6 |
| Comparative Example 3-7 | CR-7 | 85 | 35 | 3.7 |
| Comparative Example 3-8 | CR-8 | 80 | 36 | 3.6 |

TABLE 6-continued

| | Resist composition | PEB temperature (° C.) | Optimal exposure dose ($mJ/cm^2$) | CDU (nm) |
|---|---|---|---|---|
| Comparative Example 3-9 | CR-9 | 85 | 35 | 3.7 |
| Comparative Example 3-10 | CR-10 | 80 | 37 | 3.8 |
| Comparative Example 3-11 | CR-11 | 105 | 41 | 4.5 |
| Comparative Example 3-12 | CR-12 | 110 | 39 | 4.9 |

From the results shown in Table 5 and Table 6, the chemically amplified resist composition containing the inventive quencher has been found to have good sensitivity and excellent CDU for both of the positive-type and negative-type resist materials.

The present specification includes the following aspects.

[1]: An onium salt represented by the following general formula (1), (1)

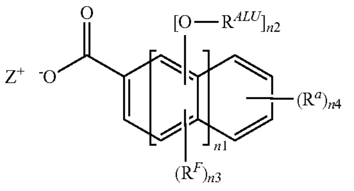

wherein $R^{ALU}$ represents any one of a tertiary ether, tertiary carbonate, or acetal formed together with the adjacent oxygen atom, having a cyclic structure, and optionally having a heteroatom; $R^F$ represents any one of a fluorine atom, a fluorine-containing alkyl group having 1 to 6 carbon atoms, and a nitro group; $R^a$ represents a hydrocarbyl group having 1 to 20 carbon atoms and optionally having a heteroatom; n1 represents an integer of 0 or 1; n2 and n3 represent an integer of 1 or 2; when n2 and n3 represent 1, $R^F$ and —O—$R^{ALU}$ are bonded to carbon atoms adjacent to each other, and when any one or both of n2 and n3 represent 2, one of $R^F$ and one of —O—$R^{ALU}$ are bonded to carbon atoms adjacent to each other; n4 represents an integer of 0 to 3; when n4≥2, a plurality of $R^a$ are optionally bonded to each other to form a cyclic structure together with the carbon atoms to which these are bonded; and $Z^+$ represents an onium cation. [2]: The onium salt according to [1], wherein the structure of $R^{ALU}$ in the general formula (1) is represented by the following general formula (ALU-1) or (ALU-2), (ALU-1)

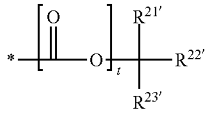

(ALU-2)

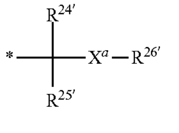

wherein in the formula (ALU-1), $R^{21'}$, $R^{22'}$, and $R^{23'}$ each independently represent a hydrocarbyl group having 1 to 12 carbon atoms and optionally having a heteroatom, any two of $R^{21'}$, $R^{22'}$, and $R^{23'}$ being optionally bonded to each other to form a ring; when $R^{21'}$, $R^{22'}$, and $R^{23'}$ are not bonded to each other to form a ring, at least one of them has a cyclic structure; "t" represents an integer of 0 or 1; in the formula (ALU-2), $R^{24'}$ and $R^{25'}$ each independently represent a hydrogen atom or a hydrocarbyl group having 1 to 10 carbon atoms; $R^{26'}$ represents a hydrocarbyl group having 1 to 20 carbon atoms, or is optionally bonded to $R^{24'}$ or $R^{25'}$ each other to form a heterocyclic group having 3 to 20 carbon atoms together with $X^a$ and the carbon atom to which these groups are bonded; —$CH_2$— contained in the hydrocarbyl group and the heterocyclic group is optionally substituted with —O— or —S—; $X^a$ represents an oxygen atom or a sulfur atom; and "*" represents a bond to the adjacent oxygen atom.

[3]: The onium salt according to [1] or [2], wherein $R^F$ in the general formula (1) represents any one of a fluorine atom or a fluorine-containing alkyl group having 1 to 6 carbon atoms.

[4]: The onium salt according to any one of [1] to [3], wherein $Z^+$ in the general formula (1) represents an onium cation represented by any one of the following general formulae (Cation-1) to (Cation-3), (Cation-1)

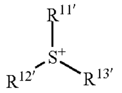

(Cation-2)

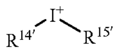

(Cation-3)

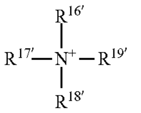

wherein in the formulae (Cation-1) to (Cation-3), $R^{11'}$ to $R^{19'}$ each independently represent a saturated or unsaturated, linear, branched, or cyclic hydrocarbyl group having 1 to 30 carbon atoms and optionally having a heteroatom.

[5]: An acid diffusion inhibitor, comprising the onium salt according to any one of [1] to [4].

[6]: A resist composition, comprising the acid diffusion inhibitor according to [5].

[7]: The resist composition according to [6], further comprising an acid generator to generate an acid.

[8]: The resist composition according to [6] or [7], wherein the acid generator generates a sulfonic acid, an imide acid, or a methide acid.

[9]: The resist composition according to any one of [6] to [8], further comprising an organic solvent.

[10]: The resist composition according to any one of [6] to [9], further comprising a base polymer.

[11]: The resist composition according to [10], wherein the base polymer comprises a repeating unit represented by the following general formula (a1) and/or a repeating unit represented by the general formula (a2), (a1)

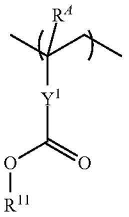

(a2)

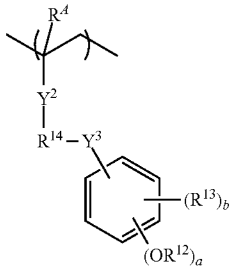

wherein $R^A$ each independently represents a hydrogen atom or a methyl group; $Y^1$ represents a single bond, a phenylene group, a naphthylene group, or a linking group having 1 to 12 carbon atoms and having at least one selected from an ester bond and a lactone ring; $Y^2$ represents a single bond or an ester bond; $Y^3$ represents a single bond, an ether bond, or an ester bond; $R^{11}$ and $R^{12}$ each independently represent an acid-labile group; $R^{13}$ represents a fluorine atom, a trifluoromethyl group, a cyano group, or a saturated hydrocarbyl group having 1 to 6 carbon atoms; $R^{14}$ represents a single bond or an alkanediyl group having 1 to 6 carbon atoms, and a part of carbon atoms therein is optionally substituted with an ether bond or an ester bond; "a" represents 1 or 2; "b" represents an integer of 0 to 4, and $1 \leq a+b \leq 5$.

[12]: The resist composition according to [11], wherein the resist composition is a chemically amplified positive-type resist composition.

[13]: The resist composition according to [10], wherein the base polymer has no acid-labile group.

[14]: The resist composition according to [13], wherein the resist composition is a chemically amplified negative-type resist composition.

[15]: The resist composition according to any one of [10] to [14], wherein the base polymer further comprises at least one selected from repeating units represented by the following general formulae (f1) to (f3), (f1)

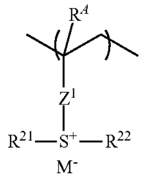

-continued (f2)

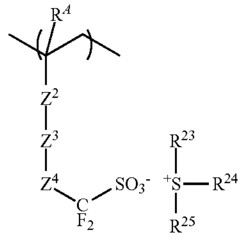

(f3)

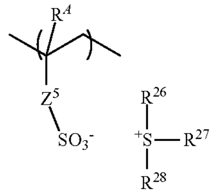

wherein $R^A$ each independently represents a hydrogen atom or a methyl group; $Z^1$ represents a single bond, an aliphatic hydrocarbylene group having 1 to 6 carbon atoms, a phenylene group, a naphthylene group, an ester bond, a group having 7 to 18 carbon atoms obtained by combining these groups, —O—$Z^{11}$—, —C(═O)—O—$Z^{11}$—, or —C(═O)—NH—$Z^{11}$—; $Z^{11}$ represents an aliphatic hydrocarbylene group having 1 to 6 carbon atoms, a phenylene group, a naphthylene group, or a group having 7 to 18 carbon atoms obtained by combining these groups, $Z^{11}$ optionally having a carbonyl group, an ester bond, an ether bond, or a hydroxy group; $Z^2$ represents a single bond or an ester bond; $Z^3$ represents a single bond, —$Z^{31}$—C(═O)—O—, —$Z^{31}$—O—, or —$Z^{31}$—O—C(═O)—; $Z^{31}$ represents a hydrocarbylene group having 1 to 12 carbon atoms, a phenylene group, or a group having 7 to 18 carbon atoms obtained by combining these groups, $Z^{31}$ optionally having a carbonyl group, an ester bond, an ether bond, an iodine atom, or a bromine atom; $Z^4$ represents a methylene group, a 2,2,2-trifluoro-1,1-ethanediyl group, or a carbonyl group; $Z^5$ represents a single bond, a methylene group, an ethylene group, a phenylene group, a fluorinated phenylene group, a phenylene group substituted with a trifluoromethyl group, —O—$Z^{51}$—, —C(═O)—O—$Z^{51}$—, or —C(═O)—NH—$Z^{51}$—; $Z^{51}$ represents an aliphatic hydrocarbylene group having 1 to 6 carbon atoms, a phenylene group, a fluorinated phenylene group, a phenylene group substituted with a trifluoromethyl group, or a combination thereof, $Z^{51}$ optionally having a carbonyl group, an ester bond, an ether bond, a halogen atom, and/or a hydroxy group; $R^{21}$ to $R^{28}$ each independently represent a halogen atom or a hydrocarbyl group having 1 to 20 carbon atoms and optionally having a heteroatom; $R^{23}$ and $R^{24}$ or $R^{26}$ and $R^{21}$ are optionally bonded to each other to form a ring together with the sulfur atom to which these groups are bonded; and $M^-$ represents a non-nucleophilic counterion.

[16]: The resist composition according to any one of [6] to [15], further comprising a surfactant.

[17]: A patterning process, comprising steps of: forming a resist film on a substrate by using the resist composition according to any one of [6] to [16]; exposing the resist film to high-energy ray; and developing the exposed resist film by using a developer.

[18]: The patterning process according to [17], wherein KrF excimer laser light, ArF excimer laser light, electron beam, or extreme ultraviolet ray having a wavelength of 3 to 15 nm is used as the high-energy ray.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. An onium salt represented by the following general formula (1), (1)

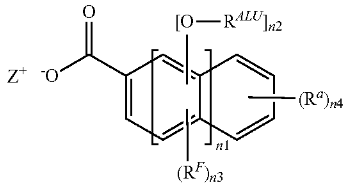

wherein $R^{ALU}$ represents any one of a tertiary ether, tertiary carbonate, or acetal formed together with the adjacent oxygen atom, having a cyclic structure, and optionally having a heteroatom; $R^F$ represents any one of a fluorine atom, a fluorine-containing alkyl group having 1 to 6 carbon atoms, and a nitro group; $R^a$ represents a hydrocarbyl group having 1 to 20 carbon atoms and optionally having a heteroatom; n1 represents an integer of 0 or 1; n2 and n3 represent an integer of 1 or 2; when n2 and n3 represent 1, $R^F$ and —O—$R^{ALU}$ are bonded to carbon atoms adjacent to each other, and when any one or both of n2 and n3 represent 2, one of $R^F$ and one of —O—$R^{ALU}$ are bonded to carbon atoms adjacent to each other; n4 represents an integer of 0 to 3; when n4≥2, a plurality of $R^a$ are optionally bonded to each other to form a cyclic structure together with the carbon atoms to which these are bonded; and $Z^+$ represents an onium cation.

2. The onium salt according to claim 1, wherein the structure of $R^{ALU}$ in the general formula (1) is represented by the following general formula (ALU-1) or (ALU-2), (ALU-1)

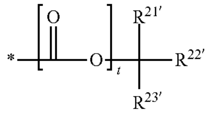

(ALU-2)

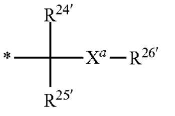

wherein in the formula (ALU-1), $R^{21'}$, $R^{22'}$, and $R^{23'}$ each independently represent a hydrocarbyl group having 1 to 12 carbon atoms and optionally having a heteroatom, any two of $R^{21'}$, $R^{22'}$, and $R^{23'}$ being optionally bonded to each other to form a ring; when $R^{21'}$, $R^{22'}$, and $R^{23'}$ are not bonded to each other to form a ring, at least one of them has a cyclic structure; "t" represents an integer of 0 or 1; in the formula (ALU-2), $R^{24'}$ and $R^{25'}$ each independently represent a hydrogen atom or a hydrocarbyl group having 1 to 10 carbon atoms; $R^{26'}$ represents a hydrocarbyl group having 1 to 20 carbon atoms, or is optionally bonded to $R^{24'}$ or $R^{25'}$ each other to form a heterocyclic group having 3 to 20 carbon atoms together with $X^a$ and the carbon atom to which these groups are bonded; —$CH_2$— contained in the hydrocarbyl group and the heterocyclic group is optionally substituted with —O— or —S—; $X^a$ represents an oxygen atom or a sulfur atom; and "*" represents a bond to the adjacent oxygen atom.

3. The onium salt according to claim 1, wherein $R^F$ in the general formula (1) represents any one of a fluorine atom or a fluorine-containing alkyl group having 1 to 6 carbon atoms.

4. The onium salt according to claim 2, wherein $R^F$ in the general formula (1) represents any one of a fluorine atom or a fluorine-containing alkyl group having 1 to 6 carbon atoms.

5. The onium salt according to claim 1, wherein $Z^+$ in the general formula (1) represents an onium cation represented by any one of the following general formulae (Cation-1) to (Cation-3), (Cation-1)

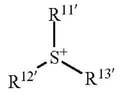

(Cation-2)

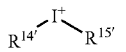

(Cation-3)

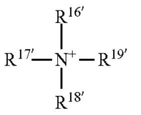

wherein in the formulae (Cation-1) to (Cation-3), $R^{11'}$ to $R^{19'}$ each independently represent a saturated or unsaturated, linear, branched, or cyclic hydrocarbyl group having 1 to 30 carbon atoms and optionally having a heteroatom.

6. The onium salt according to claim 2, wherein $Z^+$ in the general formula (1) represents an onium cation represented by any one of the following general formulae (Cation-1) to (Cation-3), (Cation-1)

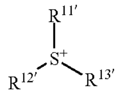

(Cation-2)

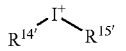

(Cation-3)

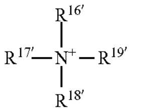

wherein in the formulae (Cation-1) to (Cation-3), $R^{11'}$ to $R^{19'}$ each independently represent a saturated or unsaturated, linear, branched, or cyclic hydrocarbyl group having 1 to 30 carbon atoms and optionally having a heteroatom.

7. An acid diffusion inhibitor, comprising the onium salt according to claim 1.

8. A resist composition, comprising the acid diffusion inhibitor according to claim 7.

9. The resist composition according to claim 8, further comprising an acid generator to generate an acid.

10. The resist composition according to claim 9, wherein the acid generator generates a sulfonic acid, an imide acid, or a methide acid.

11. The resist composition according to claim 8, further comprising an organic solvent.

12. The resist composition according to claim 8, further comprising a base polymer.

13. The resist composition according to claim 12, wherein the base polymer comprises a repeating unit represented by the following general formula (a1) and/or a repeating unit represented by the general formula (a2), (a1)

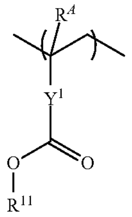

(a2)

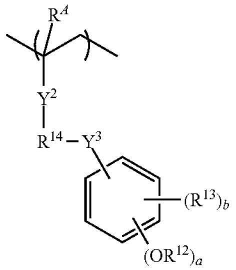

wherein $R^A$ each independently represents a hydrogen atom or a methyl group; $Y^1$ represents a single bond, a phenylene group, a naphthylene group, or a linking group having 1 to 12 carbon atoms and having at least one selected from an ester bond and a lactone ring; $Y^2$ represents a single bond or an ester bond; $Y^3$ represents a single bond, an ether bond, or an ester bond; $R^{11}$ and $R^{12}$ each independently represent an acid-labile group; $R^{13}$ represents a fluorine atom, a trifluoromethyl group, a cyano group, or a saturated hydrocarbyl group having 1 to 6 carbon atoms; $R^{14}$ represents a single bond or an alkanediyl group having 1 to 6 carbon atoms, and a part of carbon atoms therein is optionally substituted with an ether bond or an ester bond; "a" represents 1 or 2; "b" represents an integer of 0 to 4, and $1 \leq a+b \leq 5$.

14. The resist composition according to claim 13, wherein the resist composition is a chemically amplified positive-type resist composition.

15. The resist composition according to claim 12, wherein the base polymer has no acid-labile group.

16. The resist composition according to claim 15, wherein the resist composition is a chemically amplified negative-type resist composition.

17. The resist composition according to claim 12, wherein the base polymer further comprises at least one selected from repeating units represented by the following general formulae (f1) to (f3), (f1)

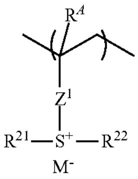

(f2)

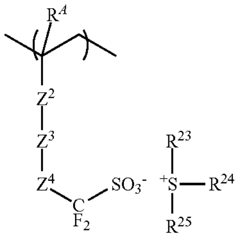

(f3)

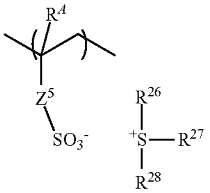

wherein $R^A$ each independently represents a hydrogen atom or a methyl group; $Z^1$ represents a single bond, an aliphatic hydrocarbylene group having 1 to 6 carbon atoms, a phenylene group, a naphthylene group, an ester bond, a group having 7 to 18 carbon atoms obtained by combining these groups, —O—$Z^{11}$—, —C(═O)—O—$Z^{11}$—, or —C(═O)—NH—$Z^{11}$—; $Z^{11}$ represents an aliphatic hydrocarbylene group having 1 to 6 carbon atoms, a phenylene group, a naphthylene group, or a group having 7 to 18 carbon atoms obtained by combining these groups, $Z^{11}$ optionally having a carbonyl group, an ester bond, an ether bond, or a hydroxy group; $Z^2$ represents a single bond or an ester bond; $Z^3$ represents a single bond, —$Z^{31}$—C(═O)—O—, —$Z^{31}$—O—, or —$Z^{31}$—O—C(═O)—; $Z^{31}$ represents a hydrocarbylene group having 1 to 12 carbon atoms, a phenylene group, or a group having 7 to 18 carbon atoms obtained by combining these groups, $Z^{31}$ optionally having a carbonyl group, an ester bond, an ether bond, an iodine atom, or a bromine atom; $Z^4$ represents a methylene group, a 2,2,2-trifluoro-1,1-ethanediyl group, or a carbonyl group; $Z^5$ represents a single bond, a methylene group, an ethylene group, a phenylene group, a fluorinated phenylene group, a phenylene group substituted with a trifluoromethyl group, —O—$Z^{51}$—, —C(═O)—O—$Z^{51}$—, or —C(═O)—NH—$Z^{51}$—; $Z^{51}$ represents an aliphatic hydrocarbylene group having 1 to 6 carbon atoms, a phenylene group, a fluorinated phenylene group, a phenylene group substituted with a trifluoromethyl group, or a combination thereof, $Z^{51}$ optionally having a carbonyl group, an ester bond, an ether bond, a halogen atom, and/or a hydroxy group; $R^{21}$ to $R^{28}$ each independently represent a halogen atom or a hydrocarbyl group having 1 to 20 carbon atoms and optionally having a heteroatom; $R^{23}$ and $R^{24}$ or $R^{26}$ and $R^{27}$ are optionally bonded to each other to form a ring together with the sulfur atom to which these groups are bonded; and $M^-$ represents a non-nucleophilic counterion.

18. The resist composition according to claim 8, further comprising a surfactant.

19. A patterning process, comprising steps of:

forming a resist film on a substrate by using the resist composition according to claim 8;

exposing the resist film to high-energy ray; and developing the exposed resist film by using a developer.

20. The patterning process according to claim 19, wherein KrF excimer laser light, ArF excimer laser light, electron beam, or extreme ultraviolet ray having a wavelength of 3 to 15 nm is used as the high-energy ray.

* * * * *